US 10,408,834 B2

(12) United States Patent
Buening et al.

(10) Patent No.: US 10,408,834 B2
(45) Date of Patent: Sep. 10, 2019

(54) MUTATED PARVOVIRUS STRUCTURAL PROTEINS AS VACCINES

(71) Applicant: Medigene AG, Planegg/Martinsried (DE)

(72) Inventors: Hildegard Buening, Cologne (DE); John Nieland, Aarhus (DK); Luca Perabo, Cologne (DE); Daniela Kuehn, Munich (DE); Kerstin Pinotossi, Munich (DE); Michael Hallek, Cologne (DE); Markus Hoerer, Planegg (DE); Mirko Ritter, Planegg (DE)

(73) Assignees: Medigene AG, Planegg/Martinsried (DE); Ludwig-Maximilians-Universitaet, Munich (DE); Universitaet zu Koeln, Cologne (DE)

( * ) Notice: Subject to any disclaimer, the term of this patent is extended or adjusted under 35 U.S.C. 154(b) by 4 days.

(21) Appl. No.: 14/930,288

(22) Filed: Nov. 2, 2015

(65) Prior Publication Data

US 2016/0153992 A1 Jun. 2, 2016

Related U.S. Application Data

(63) Continuation of application No. 13/937,997, filed on Jul. 9, 2013, now abandoned, which is a continuation of application No. 12/601,639, filed as application No. PCT/EP2008/004366 on Jun. 2, 2008, now abandoned.

(60) Provisional application No. 60/932,446, filed on May 31, 2007.

(30) Foreign Application Priority Data

Jul. 6, 2007 (EP) ..................................... 07013264

(51) Int. Cl.
| | | |
|---|---|---|
| *G01N 33/53* | (2006.01) | |
| *C07K 14/005* | (2006.01) | |
| *C07K 16/10* | (2006.01) | |
| *G01N 33/569* | (2006.01) | |
| *C07K 16/08* | (2006.01) | |
| *C07K 16/42* | (2006.01) | |
| *A61K 39/00* | (2006.01) | |

(52) U.S. Cl.
CPC ..... *G01N 33/56983* (2013.01); *C07K 14/005* (2013.01); *C07K 16/081* (2013.01); *C07K 16/4291* (2013.01); *A61K 39/00* (2013.01); *A61K 2039/5256* (2013.01); *C07K 2317/34* (2013.01); *C07K 2317/76* (2013.01); *C12N 2750/14122* (2013.01); *C12N 2750/14143* (2013.01); *G01N 2333/015* (2013.01); *G01N 2500/04* (2013.01)

(58) Field of Classification Search
None
See application file for complete search history.

(56) References Cited

U.S. PATENT DOCUMENTS

| | | |
|---|---|---|
| 6,491,907 B1 | 12/2002 | Rabinowitz et al. |
| 6,719,978 B2 | 4/2004 | Schiller et al. |
| 6,838,084 B1 | 1/2005 | Jochmus et al. |
| 6,962,815 B2 | 11/2005 | Bartlett |
| 7,875,450 B2 | 1/2011 | Schiller et al. |
| 2002/0081295 A1 | 6/2002 | Schiller et al. |
| 2002/0192823 A1 | 12/2002 | Bartlett |
| 2004/0053410 A1 | 3/2004 | Horer et al. |
| 2004/0087026 A1 | 5/2004 | Bertran et al. |
| 2004/0228798 A1 | 11/2004 | Schiller et al. |

FOREIGN PATENT DOCUMENTS

| | | |
|---|---|---|
| WO | WO-96/02555 A1 | 2/1996 |
| WO | WO-99/67293 A1 | 12/1999 |
| WO | WO-99/67393 A2 | 12/1999 |
| WO | WO-01/05990 A1 | 1/2001 |
| WO | WO-01/05991 A1 | 1/2001 |
| WO | WO-01/54720 A1 | 8/2001 |
| WO | WO-01/93903 A1 | 12/2001 |
| WO | WO-01/93905 A1 | 12/2001 |
| WO | WO-02/13857 A2 | 2/2002 |
| WO | WO-02/32451 A1 | 4/2002 |
| WO | WO-02/095027 A2 | 11/2002 |
| WO | WO-03/054197 A2 | 7/2003 |
| WO | WO-2005/017101 A2 | 2/2005 |
| WO | WO-2006/097416 A1 | 9/2006 |

OTHER PUBLICATIONS

Amexis et al., "Parvovirus B19 empty capsids as antigen carriers for presentation of antigenic determinants of dengue 2 virus," J Infect Dis.194(6):790-4 (2006).

(Continued)

*Primary Examiner* — Stacy B Chen
(74) *Attorney, Agent, or Firm* — Clark & Elbing LLP; Karen L. Elbing

(57) ABSTRACT

The present invention is related to a method for identifying a parvovirus mutated structural protein capable of specifically binding to a binder for an antigen, a parvovirus mutated structural protein which comprises at least one B-cell epitope heterologous to the parvovirus, a multimeric structure comprising the protein, a nucleic acid encoding the protein, a virus or cell comprising the protein, a method of preparing the protein, a medicament comprising the protein, nucleic acid or multimeric structure and its use.

Figure 2:
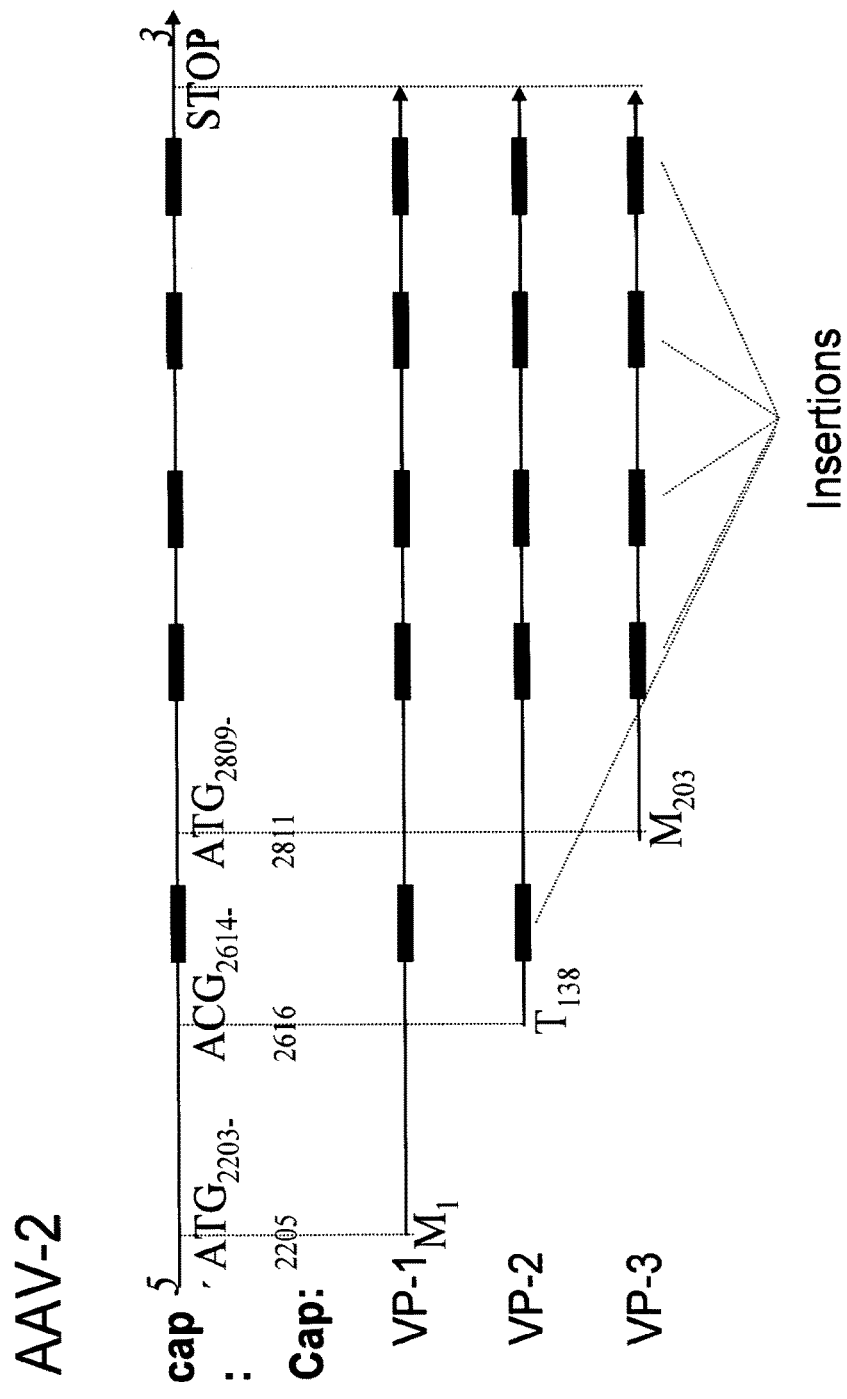

24 Claims, 37 Drawing Sheets
Specification includes a Sequence Listing.

(56) References Cited

OTHER PUBLICATIONS

Arnold et al., "Metabolic biotinylation provides a unique platform for the purification and targeting of multiple AAV vector serotypes," *Mol. Ther.* 14:97-106 (2006).
Asokan and Samulski, "AAV does the shuffle," *Nat. Biotechnol.* 24:158-160 (2006).
Asquith and McInnes, "Emerging cytokine targets in rheumatoid arthritis," *Curr. Opin. Rheumatol.* 19:246-251 (2007).
Aumailley et al., "Identification of the Arg-Gly-Asp Sequence in Laminin A Chain as a Latent Cell-Binding Site Being Exposed in Fragment P1," *FEBS Lett.* 262:82-86 (1990).
Bachmann et al., "The influence of antigen organization on B cell responsiveness," *Science* 262:1448-1451 (1993).
Barassi et al., "Induction of Murine Mucosal CCR5-Reactive Antibodies as an Anti-Human Immunodeficiency Virus Strategy," *J. Virol.* 79:6848-6858 (2005).
Benguric et al., "Phage displayed peptides and anti-idiotype antibodies recognised by a monoclonal antibody directed against a diagnostic antigen of *Mycoplasma capricolum* subsp. *Capripneumoniae*," *Vet. Microbiol.* 81:165-179 (2001).
Bloom and Young, Paroviruses. in Fields, Virology, 4th edition 2001, vol. 2, Chapter 70, Lippincott Williams Wilkins, Philadelphia, pp. 2359-2379 (2001).
Bousquet et al. "The effect of treatment with omalizumab, an anti-IgE antibody, on asthma exacerbations and emergency medical visits in patients with severe persistent asthma," *Allergy* 60:302-308 (2005).
Brown et al., "Chimeric parvovirus B19 capsids for the presentation of foreign epitopes," *Virology* 198:477-488 (1994).
Casal, "Use of parvovirus-like particles for vaccination and induction of multiple immune responses," *Biotechnol. Appl. Biochem*. 29:141-150 (1999).
Chackerian et al., "Conjugation of a self-antigen to papillomavirus-like particles allows for efficient induction of protective autoantibodies," *J. Clin. Invest*. 108:415-423 (2001).
Chackerian et al., "Induction of autoantibodies to mouse CCR5 with recombinant papillomavirus particles," *Proc. Natl. Acad. Sci. U S A*. 96:2373-2378 (1999).
Chapman and Rossmann, "Structure, Sequence, and Function Correlations Among Parvoviruses," *Virology* 194: 491-508 (1993).
Chatterjee et al., "Idiotypic antibody immunotherapy of cancer," *Cancer Immunol. Immunother. CII* 38:75-82 (1994).
Cook et al., "Identification of contact residues in the IgE binding site of human FcepsilonRIalpha," *Biochemistry* 36: 15579-15588 (1997).
Corpet, "Multiple sequence alignment with hierarchical clustering," *Nucleic Acids Res*. 16:10881-10890 (1988).
Database Geneseq "Chemically synthesised BSW17 mimeotope peptide conjugate SAF1-KLH," retrieved from EBI accession No. GSN: AAW27061, database accession No. AAW27061 (1998).
Database Geneseq "Human APP derived immunogenic peptide #9," Retrieved from EBI accession No. GSN: AAB46213, database accession No. AAB46213 (2001).
Database JPO Proteins "Recombinant anti-idiotypic antibodies," retrieved from EBI accession No. JPPOP: BD641916, database accession No. BD641916 (2003).
Dean et al., "Nuclear entry of nonviral vectors," *Gene Ther*. 12:881-890 (2005).
Endell, "Generation of enhanced gene delivery vectors by directed evolution of adeno-associated virus," *Dissertation at the Ludwig-Maximilians-Universiy Munich*, pp. 1-120 (2006).
Escher et al., "Recombinant anti-idiotypic antibodies inhibit human natural anti-glycoprotein (GP) IIb/IIIa autoantibodies," *J. Autoimmun*. 18:71-81 (2002).
Fields, Virology, fourth edition, vol. 2, chapter 69 (Muzycka and Berns), Lippincott Williams Wilkins, Philadelphia (2001).
Fields, Virology, fourth edition, vol. 2, chapter 70 (Bloom and Young), Lippincott Williams Wilkins, Philadelphia (2001).
Gamsjaeger et al., "Sticky fingers: zinc-fingers as protein-recognition motifs," *Trends Biochem. Sci*. 32:63-70 (2007).
Garman et al., "Structure of the Fc fragment of human IgE bound to its high-affinity receptor Fc epsilonRI alpha," *Nature* 406:259-266 (2000).
Girod et al., "Genetic capsid modifications allow efficient re-targeting of adeno-associated virus type 2," *Nat. Med*. 5:1438 (1999).
Gou et al., "Protein Tolerance to Random Amino Acid Change," *Proc. Natl. Acad. Sci. USA* 101:9205-9210 (2004).
Grassi et al., "Quantitative determination of total and specific human IgE with the use of monoclonal antibodies," *J. Allergy Clin. Immunol*. 77:808-822 (1986).
Grifman et al., "Incorporation of tumor-targeting peptides into recombinant adeno-associated virus capsids," *Mol. Ther*. 3:964-975 (2001).
Grimm et al., "Titration of AAV-2 particles via a novel capsid ELISA: packaging of genomes can limit production of recombinant AAV-2," *Gene Ther*. 6:1322-1330 (1999).
Grothaus et al., "Selection of an immunogenic peptide mimic of the capsular polysaccharide of Neisseria meningitidis serogroup A using a peptide display library," *Vaccine* 18:1253-1263 (2000).
Helm et al., "Blocking of passive sensitization of human mast cells and basophil granulocytes with IgE antibodies by a recombinant human epsilon-chain fragment of 76 amino acids," *Proc. Natl. Acad. Sci. U S A*. 86:9465-9946 (1989).
Helm et al., "The mast cell binding site on human immunoglobulin E," *Nature* 331:180-183 (1988).
Huttner et al., "Genetic modifications of the adeno-associated virus type 2 capsid reduce the affinity and the neutralizing effects of human serum antibodies," *Gene Ther*. 10:2139-2147 (2003).
Jefferis, "What is an idiotype?" *Immunol. Today* 14:119-121 (1993).
Jerne et al., "Recurrent idiotypes and internal images," *EMBO J*. 1:243-247 (1982).
Jerne, "Towards a network theory of the immune system," *Ann. Immunol*. (Paris) 125C:373-389 (1974).
Kern et al., "Identification of a Heparin-Binding Motif on Adeno-Associated Virus Type 2 Capsids," *J. Virol*. 77:11072-11081 (2003).
Khare et al., "Epitope selection from an uncensored peptide library displayed on avian leukosis virus," Virology. 315(2):313-21 (2003).
Klenerman et al., "T lymphocyte responses against human parvovirus B19: small virus, big response," *Pathol. Biol*. (Paris) 50:317-325 (2002).
Kricek et al., "IgE-related peptide mimotopes. Basic structures for anti-allergy vaccine development," *Int. Arch. Allergy Immunol*. 118:222-223 (1999).
Kuster et al., "Characterization and Expression of the Gene for the Human Fc Receptor y Subunit," *J. Biol. Chem*. 265:6448-6452 (1990).
Laity et al., "Zinc finger proteins: new insights into structural and functional diversity," *Curr. Opin. Struct. Biol*. 11:309-346 (2001).
Laughlin et al., "Cloning of infectious adeno-associated virus genomes in bacterial plasmids." *Gene* 23:65-73 (1983).
Lesk and Whisstock, "Prediction of Protein Function from Protein Sequence and Structure," pp. 27-28, downloaded Sep. 7, 2007.
Levy and Chen, "Healthy IgE-deficient person," *N. Engl. J. Med*. 283:541-542 (1970).
Li et al., "Overcoming antigen masking of anti-amyloid beta antibodies reveals breaking of B cell tolerance by virus-like particles in amyloidbeta immunized amyloid precursor protein transgenic mice," *BMC Neurosci*. 5:21 (2004).
Lieber, "AAV disply—homing in on the target," *Nat. Biotechnol*. 21:1011-1013 (2003).
Lo-Man et al., "A recombinant virus-like particle system derived from parvovirus as an efficient antigen carrier to elicit a polarized Th1 immune response without adjuvant," Eur J Immunol. 28(4):1401-7 (1998).
Lux et al., "Green Fluorescent Protein-Tagged Adeno-Associated Virus Particles Allow the Study of Cytosolic and Nuclear Trafficking," *J. Virol*. 79:11776-11787 (2005).
Maheshri et al., "Directed evolution of adeno-associated virus yields enhanced gene delivery vectors," *Nat. Biotechnol*. 24:198-204 (2006).

(56) References Cited

OTHER PUBLICATIONS

Martinez et al., "CD4-independent protective cytotoxic T cells induced in early life by a non-replicative delivery system based on virus-like particles," *Virology* 305:428-435 (2003).
Moskalenko et al., "Epitope mapping of human anti-adeno-associated virus type 2 neutralizing antibodies: implications for gene therapy and virus structure," *J. Virol.* 74:1761-1766 (2000).
Muller et al., "Random peptide libraries displayed on adeno-associated virus to select for targeted gene therapy vectors," *Nat. Biotechnol.* 21:1040-1046 (2003).
Muzyczka, "Use of adeno-associated virus as a general transduction vector for mammalian cells," *Curr. Top. Microbiol. Immunol.* 158:97-129 (1992).
Nicklin et al., "Efficient and selective AAV2-mediated gene transfer directed to human vascular endothelial cells," *Mol. Ther.* 4:174-181 (2001).
Nygren and Skerra, "Binding proteins from alternative scaffolds," *J. Immunol. Methods* 290:3-28 (2004).
Office Action for U.S. Appl. No. 12/601,651, dated Apr. 11, 2012 (10 Pages).
Office Action for U.S. Appl. No. 12/628,867, dated Jun. 16, 2011 (22 Pages).
Opie et al., "Identification of Amino Acid Residues in the Capsid Proteins of Adeno-Associated Virus Type 2 that Contribute to Heparan Sulfate Proteoglycan Binding," *J. Virol.* 77:6995-7006 (2003).
Parker et al. "Scheme for ranking potential HLA-A2 binding peptides based on independent binding of individual peptide sidechains," *J. Immunol.* 152:163-175 (1994).
Pennica et al., "Human tumour necrosis factor: precursor structure, expression and homology to lymphotoxin," *Nature* 312:724-729 (1984).
Perabo et al., "Adeno-Associated Virus Display: In Vitro Evolution of AAV Retargeted Vectors," Institut für Biochemie. München, Ludwig-Maximilians-Universität, pp. 1-121 (2003).
Perabo et al., "Combinatorial Engineering of a Gene Therapy Vector: Directed Evolution of Adeno-Associated Virus," *J. Gene Med.* 8:155-162 (2006).
Perabo et al., "Heparan Sulfate Proteoglycan Binding Properties of Adeno-Associated Virus Retargeting Mutants and Consequences for Their in Vivo Tropism," *J. Virol.* 80:7265-7269 (2006).
Perabo et al., "In vitro selection of viral vectors with modified tropism: the adeno-associated virus display," *Mol. Ther.* 8:151-157 (2003).
Presta et al., "The binding site on human immunoglobulin E for its high affinity receptor," *J. Biol. Chem.* 269:26368-26373 (1994).
Prinz et al., "Two different methods result in the selection of peptides that induce a protective antibody response to Neisseria meningitidis serogroup C," *J. Immunol. Methods* 285:1-14 (2004).
Rabinowitz et al., "Insertional mutagenesis of AAV2 capsid and the production of recombinant virus," *Virology* 265:274-285 (1999).
Renschler et al., "Synthetic peptide ligands of the antigen binding receptor induce programmed cell death in a human B-cell lymphoma," *Proc. Natl. Acad. Sci. U S A.* 91:3623-3627 (1994).
Ried et al., "Adeno-associated virus capsids displaying immunoglobulin-binding domains permit antibody-mediated vector retargeting to specific cell surface receptors," *J. Virol.* 76:4559-4566 (2002).
Riemer et al., "Active induction of tumor-specific IgE antibodies by oral mimotope vaccination," *Cancer Res.* 67:3406-3411 (2007).
Rittershaus et al., "Vaccine-induced antibodies inhibit CETP activity in vivo and reduce aortic lesions in a rabbit model of atherosclerosis," *Arterioscler. Thromb. Vasc. Biol.* 20:2106-2112 (2000).
Rudolf et al., "Epitope-Specific Antibody Response to IgE by Mimotope Immunization," *J.Immunol.* 160:3315-3321 (1998).
Rudolf et al., "Molecular Basis for Nonanaphylactogenicity of a Monoclonal Anti-IgE Antibody," *J. Immunol.* 165:813-819 (2000).
Rueda et al., "Engineering parvovirus-like particles for the induction of B-cell, CD4+ and CTL responses," *Vaccine* 18:325-332 (1999).
Rueda et al., "Minor Displacements in the Insertion Site Provoke Major Differences in the Induction of Antibody Responses by Chimeric Parvovirus-like Particles," *Virology* 263: 89-99 (1999).
Ruffing et al., "Mutations in the Carboxy Terminus of Adeno-Associated Virus 2 Capsid Proteins Affect Viral Infectivity: Lack of an RGD Integrin-Binding Motif," *J. Gen. Virol.* 75:3385-3392 (1994).
Sedlik et al., "Recombinant parvovirus-like particles as an antigen carrier: a novel nonreplicative exogenous antigen to elicit protective antiviral cytotoxic T cells," *Proc Natl Acad Sci U S A.* 94(14):7503-8 (1997).
Shi and Bartlett, "RGD inclusion in VP3 provides adeno-associated virus type 2 (AAV2)-based vectors with a heparan sulfate-independent cell entry mechanism," *Mol. Ther.* 7:515-525 (2003).
Shi et al., "Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism," *Hum. Gene Ther.* 17:353-361 (2006).
Shi et al., "Insertional mutagenesis of the adeno-associated virus type 2 (AAV2) capsid gene and generation of AAV2 vectors targeted to alternative cell-surface receptors," *Hum. Gene Ther.* 12:1697-1711 (2001).
Smolen and Steiner, "Therapeutic strategies for rheumatoid arthritis," *Nat. Rev. Drug Discov.* 2:473-488 (2003).
Stachler and Bartlett, "Mosaic vectors comprised of modified AAV1 capsid proteins for efficient vector purification and targeting to vascular endothelial cells," *Gene Ther.* 13:926-931 (2006).
Stadler et al., "Mimotope and anti-idiotypic vaccines to induce an anti-IgE response," *Int. Arch. Allergy Immunol.* 118:119-121 (1999).
Szomolanyi-Tsuda et al., "Antiviral T-cell-independent type 2 antibody responses induced in vivo in the absence of T and NK cells," *Virology* 280:160-168 (2001).
Szomolanyi-Tsuda et al., "T-cell-independent antiviral antibody responses," *Curr. Opin. Immunol.* 10:431-435 (1998).
Szomolanyi-Tsuda et al., "T-Cell-independent immunoglobulin G responses in vivo are elicited by live-virus infection but not by immunization with viral proteins or virus-like particles," *J. Virol.* 72:6665-6670 (1998).
Szomolanyi-Tsuda et al., "The role of CD40-CD154 interaction in antiviral T cell-independent IgG responses," *J. Immunol.* 164:5877-5882 (2000).
Takagi et al., "Application of human Fc epsilon RI alpha-chain-transfected RBL-2H3 cells for estimation of active serum IgE," *Biol. Pharm. Bull.* 26:252-255 (2003).
Theiss et al., "Enhancement of Gene Transfer with Recombinant Adeno-Associated Virus (rAAV) Vectors into Primary B-Cell Chronic Lymphocytic Leukemia Cells by CpG-oligodeoxynucleotides," *Exp. Hematol.* 31:1223-1229 (2003).
Uversky V.N., Fernández A. and Fink A. L. chapter 1, 1-20 in: Protein Reviews vol. 4, editor: M. Zouhair Atassi: Protein Misfolding, Aggregation, and Conformational Disease, Part A: Protein Aggregation and Conformational Disease; Springer (2006).
Varela and Coutinho, "Second generation immune networks," *Immunol. Today* 12:159-166 (1991).
Vogel et al., "A highly conserved interspecies V(H) in the human genome," *J. Mol. Biol.* 341:477-489 (2004).
Vogel et al., "Mimicry of human IgE epitopes by anti-idiotypic antibodies," *J. Mol. Biol.* 298:729-735 (2000).
Wang et al., "Synthetic IgE peptide vaccine for immunotherapy of allergy," *Vaccine* 21:1580-1590 (2003).
Warrington et al., "Adeno-Associated Virus Type 2 VP2 Capsid Protein Is Nonessential and Can Tolerate Large Peptide Insertions at Its N Terminus," *J. Virol.* 78:6595-6609 (2004).
Waterkamp et al., "Isolation of targeted AAV2 vectors from novel virus display libraries," *J. Gene Med.* 8:1307-1319 (2006).
White et al., "Targeted Gene Delivery to Vascular Tissue in Vivo by Tropism-Modified Adeno-Associated Virus Vectors," *Circulation* 109:513-519 (2004).
Wistuba et al., "Subcellular compartmentalization of adeno-associated virus type 2 assembly," *J. VIrol.* 71:1341-1352 (1997).
Wobus et al., "Monoclonal Antibodies against the Adeno-Associated Virus Type 2 (AAV-2) Capsid: Epitope Mapping and

(56) References Cited

OTHER PUBLICATIONS

Identification of Capsid Domains Involved in AAV-2-Cell Interaction and Neutralization of AAV-2 Infection," *J. Virol.* 74:9281-9293 (2000).

Work et al., "Development of Efficient Viral Vectors Selective for Vascular Smooth Muscle Cells," *Mol. Ther.* 9:198-208 (2004).

Work et al., "Vascular Bed-Targeted in Vivo Gene Delivery Using Tropism-Modified Adeno-associated Viruses," *Mol. Ther.* 13:683-693 (2006).

Wu et al., "Mutational Analysis of the Adeno-Associated Virus Type 2 (AAV2) Capsid Gene and Construction of AAV2 Vectors with Altered Tropism," *J. Virol.* 74:8635-8647 (2000).

Xiao et al., "Gene therapy vectors based on adeno-associated virus type 1", *J. Virol.* 73:3994-4003 (1999).

Zinkernagel, "Uncertainties—discrepancies in immunology," *Immunol. Rev.* 185:103-125 (2002).

Fig. 1A

```
              1                                                                  50
    AAV-1     MAADGYLPDW  LEDNLSEGIR  EWWDLKPGAP  KPKANQQKQD  DGRGLVLPGY
    AAV-6     MAADGYLPDW  LEDNLSEGIR  EWWDLKPGAP  KPKANQQKQD  DGRGLVLPGY
    AAV-2     MAADGYLPDW  LEDTLSEGIR  QWWKLKPGPP  PPKPAERHKD  DSRGLVLPGY
    AAV-3B    MAADGYLPDW  LEDNLSEGIR  EWWALKPGVP  QPKANQQHQD  NRRGLVLPGY
    AAV-7     MAADGYLPDW  LEDNLSEGIR  EWWDLKPGAP  KPKANQQKQD  NGRGLVLPGY
    AAV-8     MAADGYLPDW  LEDNLSEGIR  EWWALKPGAP  KPKANQQKQD  DGRGLVLPGY
    AAV-10    MAADGYLPDW  LEDNLSEGIR  EWWDLKPGAP  KPKANQQKQD  DGRGLVLPGY
    AAV-4      MTDGYLPDW  LEDNLSEGVR  EWWALQPGAP  KPKANQQHQD  NARGLVLPGY
    AAV-11    MAADGYLPDW  LEDNLSEGIR  EWWDLKPGAP  KPKANQQKQD  DGRGLVLPGY
    b-AAV     MSFVDHPPDW  LE-SIGDGFR  EFLGLEAGPP  KPKANQQKQD  NARGLVLPGY
    AAV-5     MSFVDHPPDW  LEE-VGEGLR  EFLGLEAGPP  KPKPNQQHQD  QARGLVLPGY
    GPV
    B19
    MVM
    FPV
    CPV
Consensus     ..........  ..........  ..........  ..........  ..........

51                                                                 100
    AAV-1     KYLGPFNGLD  KGEPVNAADA  AALEHDKAYD  QQLKAGDNPY  LRYNHADAEF
    AAV-6     KYLGPFNGLD  KGEPVNAADA  AALEHDKAYD  QQLKAGDNPY  LRYNHADAEF
    AAV-2     KYLGPFNGLD  KGEPVNEADA  AALEHDKAYD  RQLDSGDNPY  LKYNHADAEF
    AAV-3B    KYLGPGNGLD  KGEPVNEADA  AALEHDKAYD  QQLKAGDNPY  LKYNHADAEF
    AAV-7     KYLGPFNGLD  KGEPVNAADA  AALEHDKAYD  QQLKAGDNPY  LRYNHADAEF
    AAV-8     KYLGPFNGLD  KGEPVNAADA  AALEHDKAYD  QQLQAGDNPY  LRYNHADAEF
    AAV-10    KYLGPFNGLD  KGEPVNAADA  AALEHDKAYD  QQLKAGDNPY  LRYNHADAEF
    AAV-4     KYLGPGNGLD  KGEPVNAADA  AALEHDKAYD  QQLKAGDNPY  LKYNHADAEF
    AAV-11    KYLGPFNGLD  KGEPVNAADA  AALEHDKAYD  QQLKAGDNPY  LRYNHADAEF
    b-AAV     KYLGPGNGLD  KGDPVNFADE  VAREHDLSYQ  KQLEAGDNPY  LKYNHADAEF
    AAV-5     NYLGPGNGLD  RGEPVNRADE  VAREHDISYN  EQLEAGDNPY  LKYNHADAEF
    GPV
    B19
    MVM
    FPV
    CPV
Consensus     ..........  ..........  ..........  ..........  ..........

101                                                                150
    AAV-1     QERLQEDTSF  GGNLGRAVFQ  AKKRVLEPLG  LVEEGAKTAP  G-KKRPVEQS
    AAV-6     QERLQEDTSF  GGNLGRAVFQ  AKKRVLEPFG  LVEEGAKTAP  G-KKRPVEQS
    AAV-2     QERLKEDTSF  GGNLGRAVFQ  AKKRVLEPLG  LVEEPVKTAP  G-KKRPVEHS
    AAV-3B    QERLQEDTSF  GGNLGRAVFQ  AKKRILEPLG  LVEEAAKTAP  G-KKRPVDQS
    AAV-7     QERLQEDTSF  GGNLGRAVFQ  AKKRVLEPLG  LVEEGAKTAP  A-KKRPVEPS
    AAV-8     QERLQEDTSF  GGNLGRAVFQ  AKKRVLEPLG  LVEEGAKTAP  G-KKRPVEPS
    AAV-10    QERLQEDTSF  GGNLGRAVFQ  AKKRVLEPLG  LVEEAAKTAP  G-KKRPVEPS
    AAV-4     QQRLQGDTSF  GGNLGRAVFQ  AKKRVLEPLG  LVEQAGETAP  G-KKRPLIES
    AAV-11    QERLQEDTSF  GGNLGRAVFQ  AKKRVLEPLG  LVEEGAKTAP  G-KKRPL-ES
    b-AAV     QEKLASDTSF  GGNLGKAVFQ  AKKRILEPLG  LVETPDKTAP  AAKKRPLEQS
    AAV-5     QEKLADDTSF  GGNLGKAVFQ  AKKRVLEPFG  LVEEGAKTAP  TGKR-----I
    GPV
    B19
    MVM
    FPV
    CPV
Consensus     ..........  ..........  ..........  ..........  ..........
```

Fig. 1B

```
            151                                                              200
    AAV-1   PQE-PDSSSG  IGKTGQQPAK  KRLNFGQTGD  SESVPDPQPL  GEPPATPAAV
    AAV-6   PQE-PDSSSG  IGKTGQQPAK  KRLNFGQTGD  SESVPDPQPL  GEPPATPAAV
    AAV-2   PVE-PDSSSG  TGKAGQQPAR  KRLNFGQTGD  ADSVPDPQPL  GQPPAAPSGL
   AAV-3B   PQE-PDSSSG  VGKSGKQPAR  KRLNFGQTGD  SESVPDPQPL  GEPPAAPTSL
    AAV-7   PQRSPDSSTG  IGKKGQQPAR  KRLNFGQTGD  SESVPDPQPL  GEPPAAPSSV
    AAV-8   PQRSPDSSTG  IGKKGQQPAR  KRLNFGQTGD  SESVPDPQPL  GEPPAAPSGV
   AAV-10   PQRSPDSSTG  IGKKGQQPAK  KRLNFGQTGE  SESVPDPQPI  GEPPAGPSGL
    AAV-4   PQQ-PDSSTG  IGKKGKQPAK  KKLVF----E  DETGAGDGPP  -EGSTSGAMS
   AAV-11   PQE-PDSSSG  IGKKGKQPAR  KRLNF----E  EDTGAGDGPP  -EGSDTSAMS
    b-AAV   PQE-PDSSSG  VGKKGKQPAR  KRLNF----D  DEPGAGDGPP  PEGPSSGAMS
    AAV-5   DDHFPKRKKA  RTEEDSKPST  SS-------D  AEAGPSGSQQ  LQIPAQPASS
      GPV
      B19
      MVM                                       MSDGTSQPD   GGNAVHSAAR
      FPV                                       MSDGAVQPD   GGQP---AVR
      CPV
Consensus   ..........  ..........  ..........  ........p.  ..........

201                                                              250
    AAV-1   -GPTTMASGG  GAPMADNNEG  ADGVGNASGN  WHCDSTWLGD  RVITTSTRTW
    AAV-6   -GPTTMASGG  GAPMADNNEG  ADGVGNASGN  WHCDSTWLGD  RVITTSTRTW
    AAV-2   -GTNTMATGS  GAPMADNNEG  ADGVGNSSGN  WHCDSTWMGD  RVITTSTRTW
   AAV-3B   -GSNTMASGG  GAPMADNNEG  ADGVGNSSGN  WHCDSQWLGD  RVITTSTRTW
    AAV-7   -GSGTVAAGG  GAPMADNNEG  ADGVGNASGN  WHCDSTWLGD  RVITTSTRTW
    AAV-8   -GPNTMAAGG  GAPMADNNEG  ADGVGSSSGN  WHCDSTWLGD  RVITTSTRTW
   AAV-10   -GSGTMAAGG  GAPMADNNEG  ADGVGSSSGN  WHCDSTWLGD  RVITTSTRTW
    AAV-4   -DDSEMRAAA  GGAAVEGGQG  ADGVGNASGD  WHCDSTWSEG  HVTTTSTRTW
   AAV-11   -SDIEMRAAP  GGNAVDAGQG  SDGVGNASGD  WHCDSTWSES  KVTTTSTRTW
    b-AAV   -TETEMRAAA  GNNGGDAGQG  AEGVGNASGD  WHCDSTWSES  HVTTTSTRTW
    AAV-5   LGADTMSAGG  GGPLGDNNQG  ADGVGNASGD  WHCDSTWMGD  RVVTKSTRTW
      GPV         MAEGG  GGAMGDSSGG  ADGVGNASGN  WHCDSQWMGN  TVITKTTRTW
      B19        MTSV   NSAEASTGAG  GGGSNPVKSM  WSEGATFSAN  SVTCTFSRQF
      MVM   VERAADGPGG  SGGGGSGG-G  GVGVSTGSYD  NQTHYRFLGD  GWVEITALAT
      FPV   NERATGSGNG  SGGGGGGGSG  GVGISTGTFN  NQTEFKFLEN  GWVEITANSS
      CPV                           GVGISTGTFN  NQTEFKFLEN  GWVEITANSS
Consensus   ........gg  gg.....g.g  ..Gvg..sg.  whcdstw.g.  .v.t..trtw 251                                                              300
    AAV-1   ALPTYNNHLY  KQISSASTG-  ASND------  ---NHYFGYS  TPWGYFDFNR
    AAV-6   ALPTYNNHLY  KQISSASTG-  ASND------  ---NHYFGYS  TPWGYFDFNR
    AAV-2   ALPTYNNHLY  KQISSQS-G-  ASND------  ---NHYFGYS  TPWGYFDFNR
   AAV-3B   ALPTYNNHLY  KQISSQS-G-  ASND------  ---NHYFGYS  TPWGYFDFNR
    AAV-7   ALPTYNNHLY  KQISSETAG-  STND------  ---NTYFGYS  TPWGYFDFNR
    AAV-8   ALPTYNNHLY  KQISNGTSGG  ATND------  ---NTYFGYS  TPWGYFDFNR
   AAV-10   ALPTYNNHLY  KQISNGTSGG  STND------  ---NTYFGYS  TPWGYFDFNR
    AAV-4   VLPTYNNHLY  KRLGE-----  SLQS------  ---NTYNGFS  TPWGYFDFNR
   AAV-11   VLPTYNNHLY  LRLGT-----  TSSS------  ---NTYNGFS  TPWGYFDFNR
    b-AAV   VLPTYNNHLY  LRLGS-----  SNAS------  ---DTFNGFS  TPWGYFDFNR
    AAV-5   VLPSYNNHQY  REIKSGSVD-  GSNA------  ---NAYFGYS  TPWGYFDFNR
      GPV   VLPSYNNHIY  KAITSGTS--  QDAN------  ---VQYAGYS  TPWGYFDFNR
      B19   LIPYDPEHHY  KVFSPAASSC  HNASGKEAKV  CTISPIMGYS  TPWRYLDFNA
      MVM   RLVHLNMPKS  ENYCRIRVHN  TTDTSVKGNM  AKDDAHEQIW  TPWSLVDANA
      FPV   RLVHLNMPES  ENYKRVVVNN  MDKTAVKGNM  ALDDIHVEIV  TPWSLVDANA
      CPV   RLVHLNMPES  ENYRRVVVNN  MDKTAVNGNM  ALDDIHAQIV  TPWSLVDANA
Consensus   .lp.ynnh.y  ..........  ..........  .......gys  TPWgyfDfNr
```

Fig. 1C

```
              301                                                          350
    AAV-1     FHCHFSPRDW QRLINNNWGF RPKRLNFKLF NIQVKEVTTN DGV-TT---I
    AAV-6     FHCHFSPRDW QRLINNNWGF RPKRLNFKLF NIQVKEVTTN DGV-TT---I
    AAV-2     FHCHFSPRDW QRLINNNWGF RPKRLNFKLF NIQVKEVTQN DGT-TT---I
    AAV-3B    FHCHFSPRDW QRLINNNWGF RPKKLSFKLF NIQVKEVTQN DGT-TT---I
    AAV-7     FHCHFSPRDW QRLINNNWGF RPKKLRFKLF NIQVKEVTTN DGV-TT---I
    AAV-8     FHCHFSPRDW QRLINNNWGF RPKRLSFKLF NIQVKEVTQN EGT-KT---I
    AAV-10    FHCHFSPRDW QRLINNNWGF RPKRLSFKLF NIQVKEVTQN EGT-KT---I
    AAV-4     FHCHFSPRDW QRLINNNWGM RPKAMRVKIF NIQVKEVTTS NGE-TT---V
    AAV-11    FHCHFSPRDW QRLINNNWGL RPKAMRVKIF NIQVKEVTTS NGE-TT---V
    b-AAV     FHCHFSPRDW QRLINNHWGL RPKSMQVRIF NIQVKEVTTS NGE-TT---V
    AAV-5     FHSHWSPRDW QRLINNYWGF RPRSLRVKIF NIQVKEVTVQ DST-TT---I
    GPV       FHCHFSPRDW QRLINNHWGI RPKSLKFKIF NVQVKEVTTQ DQT-KT---I
    B19       LNLFFSPLEF QHLIENYGSI APDALTVTIS EIAVKDVTDK TGGGVQ---V
    MVM       WGVWLQPSDW QYICNTMSQL NLVSLDQEIF NVVLKTVTEQ DSGGQAIKIY
    FPV       WGVWFNPGDW QLIVNTMSEL HLVSFEQEIF NVVLKTVSES ATQPPT-KVY
    CPV       WGVWFNPGDW QLIVNTMSEL HLVSFEQEIF NVVLKTVSES ATQPPT-KVY
Consensus     fh.hfsPr#w Qrli#n.wg. rp.sl...if #!qvKeVt.. .....t....

351                                                          400
    AAV-1     ANNLTSTVQV FSDSEYQLPY VLGSAHQGCL PPFPADVFMI PQYGYLTLN-
    AAV-6     ANNLTSTVQV FSDSEYQLPY VLGSAHQGCL PPFPADVFMI PQYGYLTLN-
    AAV-2     ANNLTSTVQV FTDSEYQLPY VLGSAHQGCL PPFPADVFMV PQYGYLTLN-
    AAV-3B    ANNLTSTVQV FTDSEYQLPY VLGSAHQGCL PPFPADVFMV PQYGYLTLN-
    AAV-7     ANNLTSTIQV FSDSEYQLPY VLGSAHQGCL PPFPADVFMI PQYGYLTLN-
    AAV-8     ANNLTSTIQV FTDSEYQLPY VLGSAHQGCL PPFPADVFMI PQYGYLTLN-
    AAV-10    ANNLTSTIQV FTDSEYQLPY VLGSAHQGCL PPFPADVFMI PQYGYLTLN-
    AAV-4     ANNLTSTVQI FADSSYELPY VMDAGQEGSL PPFPNDVFMV PQYGYCGLV-
    AAV-11    ANNLTSTVQI FADSSYELPY VMDAGQEGSL PPFPNDVFMV PQYGYCGIV-
    b-AAV     SNNLTSTVQI FADSTYELPY VMDAGQEGSL PPFPNDVFMV PQYGYCGLV-
    AAV-5     ANNLTSTVQV FTDDDYQLPY VVGNGTEGCL PAFPPQVFTL PQYGYATLN-
    GPV       ANNLTSTIQV FTDDEHQLPY VLGSATEGTM PPFPSDVYAL PQYGYCTMH-
    B19       TDSTTGRLCM LVDHEYKYPY VLGQGQDTLA PELPIWVYFP PQYAYLTVGD
    MVM       NNDLTACMMV AVDSNNILPY TPAANSMETL GFYPWKPTIA SPYRYYFCVD
    FPV       NNDLTASLMV ALDSNNTMPF TPAAMRSETL GFYPWKPTIP TPWRYYFQWD
    CPV       NNDLTASLMV ALDSNNTMPF TPAAMRSETL GFYPWKPTIP TPWRYYFQWD
Consensus     .#nlTst.qv f.Ds.y.lP% v.g....g.l p.fP..v... pqygY.t...

401                                                          450
    AAV-1     ------NGS- --QAVG---- -----RSSFY CLEYF-PSQM LRTGNNF-TF
    AAV-6     ------NGS- --QAVG---- -----RSSFY CLEYF-PSQM LRTGNNF-TF
    AAV-2     ------NGS- --QAVG---- -----RSSFY CLEYF-PSQM LRTGNNF-TF
    AAV-3B    ------NGS- --QAVG---- -----RSSFY CLEYF-PSQM LRTGNNF-QF
    AAV-7     ------NGS- --QSVG---- -----RSSFY CLEYF-PSQM LRTGNNF-EF
    AAV-8     ------NGS- --QAVG---- -----RSSFY CLEYF-PSQM LRTGNNF-QF
    AAV-10    ------NGS- --QAVG---- -----RSSFY CLEYF-PSQM LRTGNNF-EF
    AAV-4     ------TGNT SQQQTD---- -----RNAFY CLEYF-PSQM LRTGNNF-EI
    AAV-11    ------TGE- NQNQTD---- -----RNAFY CLEYF-PSQM LRTGNNF-EM
    b-AAV     ------TGGS SQNQTD---- -----RNAFY CLEYF-PSQM LRTGNNF-EM
    AAV-5     ------RDN- TENPTE---- -----RSSFF CLEYF-PSKM LRTGNNF-EF
    GPV       ------TNQN GARFND---- -----RSAFY CLEYF-PSQM LRTGNNF-EF
    B19       VNTQGISGDS KKLASE---- -----ESAFY VLEHS-SFQL LGTGGTA-TM
    MVM       RDLSVTYENQ EGTIEHNVMG TPKGMNSQFF TIENTQQITL LRTGDEFATG
    FPV       RTLIPSHTGT SGTPTNVYHG TPDP-DVQFY TIENSVPHL LRTGDEFATG
    CPV       RTLIPSHTGT SGTPTNIYHG TPDP-DVQFY TIENSVPHL LRTGDEFATG
Consensus     .......... .......... .....rs.F% clEyf.psq$ LrTGnnf.t.
```

Fig. 1D

```
                                                            I-453
             451                                            500
    AAV-1    SYTFEEVPFH  SSYAHSQSLD  RLMNPLIDQY  LYYLNRTQ-N  QSGSAQNKDL
    AAV-6    SYTFEDVPFH  SSYAHSQSLD  RLMNPLIDQY  LYYLNRTQ-N  QSGSAQNKDL
    AAV-2    SYTFEDVPFH  SSYAHSQSLD  RLMNPLIDQY  LYYLSRTN-T  PSGTTTQSRL
    AAV-3B   SYTFEDVPFH  SSYAHSQSLD  RLMNPLIDQY  LYYLNRTQGT  TSGTTNQSRL
    AAV-7    SYSFEDVPFH  SSYAHSQSLD  RLMNPLIDQY  LYYLARTQSN  PGGTAGNREL
    AAV-8    TYTFEDVPFH  SSYAHSQSLD  RLMNPLIDQY  LYYLSRTQTT  -GGTANTQTL
    AAV-10   SYTFEDVPFH  SSYAHSQSLD  RLMNPLIDQY  LYYLSRTQST  -GGTQGTQQL
    AAV-4    TYSFEKVPFH  SMYAHSQSLD  RLMNPLIDQY  LWGLQSTTTG  TILNAGTATT
    AAV-11   AYNFEKVPFH  SMYAHSQSLD  RLMNPLLDQY  LWHLQSTTSG  ETLNQGNAAT
    b-AAV    VYKFENVPFH  SMYAHSQSLD  RLMNPLLDQY  LWELQSTTSG  GTLNQGNSAT
    AAV-5    TYNFEEVPFH  SSFAPSQNLF  KLANPLVDQY  LYRFVSTN--  ----NTGGV
    GPV      TFDFEEVPFH  SMFAHSQDLD  RLMNPLVDQY  LWNFNEVD--  ----SSRNA
    B19      SYKFPPVPPE  NLEGCSQHFY  EMYNPLYGSR  LGVPDTL---  ----GGDP
    MVM      TYYFDTNPVK  LTHTWQTNRQ  LGQPPLLSTF  PEAD--TDAG  TI-TAQGSRH
    FPV      TFFFDCKPCR  LTHTWQTNRA  LGLPPFLNSL  PQSEGATNFG  DIGVQQDKRR
    CPV      TFFFDCKPCR  LTHTWQTNRA  LGLPPFLNSL  PQSEGATNFG  DIGVQQDKRR
 Consensus   t%.Fe.vPfh  s...a.sq.l  .l.nPl.dqy  l.....t...  ..].......

501                                            550
    AAV-1    LFSRGSPAGM  SVQPKNWLPG  PCYRQQRVSK  TKTDN-----  NNSNFTWTGA
    AAV-6    LFSRGSPAGM  SVQPKNWLPG  PCYRQQRVSK  TKTDN-----  NNSNFTWTGA
    AAV-2    QFSQAGASDI  RDQSRNWLPG  PCYRQQRVSK  TSADN-----  NNSEYSWTGA
    AAV-3B   LFSQAGPQSM  SLQARNWLPG  PCYRQQRLSK  TANDN-----  NNSNFPWTAA
    AAV-7    QFYQGGPSTM  AEQAKNWLPG  PCFRQQRVSK  TLDQN-----  NNSNFAWTGA
    AAV-8    GFSQGGPNTM  ANQAKNWLPG  PCYRQQRVST  TTGQN-----  NNSNFAWTAG
    AAV-10   LFSQAGPANM  SAQAKNWLPG  PCYRQQRVST  TLSQN-----  NNSNFAWTGA
    AAV-4    NFTKLRPTNF  SNFKKNWLPG  PSIKQQGFSK  TANQNYKIPA  TGSDSLIKYE
    AAV-11   TFGKIRSGDF  AFYRKNWLPG  PCVKQQRFSK  TASQNYKIPA  SGGNALLKYD
    b-AAV    NFAKLTKTNF  SGYRKNWLPG  PMMKQQRFSK  TASQNYKIPQ  GRNNSLLHYE
    AAV-5    QFNKNLAGRY  ANTYKNWFPG  PMGRTQGWNL  GSGVN-----  RASVSAFATT
    GPV      QFKKAVKGAY  GTMGRNWLPG  PKFLDQRVRA  YTGGT---DN  YANWNIWSNG
    B19      KFRSLTHEDH  AIQPQNFMPG  PLVNSVSTKE  GDSFN-----  TGAGKALTGL
    MVM      GATQM-EVNW  VSEAIRTRPA  QVGFCQPHND  FEASR-----  AGPFAAPKVP
    FPV      GVTQMGNTDY  ITEATIMRPA  EVGYSAPYYS  FEAST-----  QGPFKTPIAA
    CPV      GVTQMGNTNY  ITEATIMRPA  EVGYSAPYYS  FEAST-----  QGPFKTPIAA
 Consensus   .f........  .....nw.Pg  p....q....  ....n.....  .g........

551                                            600
    AAV-1    SKYNLNGRES  IINPGTAMAS  HKD-DEDKFF  PMSGVMIFGK  ESAGASNTAL
    AAV-6    SKYNLNGRES  IINPGTAMAS  HKD-DKDKFF  PMSGVMIFGK  ESAGASNTAL
    AAV-2    TKYHLNGRDS  LVNPGPAMAS  HKD-DEEKFF  PQSGVLIFGK  QGSEKTNVDI
    AAV-3B   SKYHLNGRDS  LVNPGPAMAS  HKD-DEEKFF  PMHGNLIFGK  EGTTASNAEL
    AAV-7    TKYHLNGRNS  LVNPGVAMAT  HKD-DEDRFF  PSSGVLIFGK  TGAT-NKTTL
    AAV-8    TKYHLNGRNS  LANPGIAMAT  HKD-DEERFF  PSNGILIFGK  QNAARDNADY
    AAV-10   TKYHLNGRDS  LVNPGVAMAT  HKD-DEERFF  PSSGVLMFGK  QGAGRDNVDY
    AAV-4    THSTLDGRWS  ALTPGPPMAT  AGP-ADSKF-  SNSQLIFAGP  KQNGNTATVP
    AAV-11   THYTLNNRWS  NIAPGPPMAT  AGP-SDGDF-  SNAQLIFPGP  SVTGNTTTSA
    b-AAV    TRTTLDGRWS  NFAPGTAMAT  AAN-DATDF-  SQAQLIFAGP  NITGNTTTDA
    AAV-5    NRMELEGASY  QVPPQPNGMT  NNL-QGSNTY  ALENTMIFNS  QPANPGTTAT
    GPV      NKVNLKDRQY  LLQPGPVSAT  YTE-GEASSL  PAQNILGIAK  DPYRSGSTTA
    B19      STGTSQNTRI  SLRPGPVSQP  YHHWDTDKYV  TGINAISHGQ  TTYGNAEDKE
    MVM      ADVTQGMDRE  --ANGSVRYS  YGKQHGENWA  AHGPAPERYT  WDETNFGSGR
    FPV      GRGGAQTDEN  QAADGDPRYA  FGRQHGQKTT  TTGETPERFT  YI-AHQDTGR
    CPV      GRGGAQTDEN  QAADGNPRYA  FGRQHGQKTT  TTGETPERFT  YI-AHQDTGR
 Consensus   ....l.....  ...pGp....  ..........  ..........  .......t..
```

Fig. 1E

```
                                                                I-587
            601                                                              650
    AAV-1   ---DNVMITD EEEIKATNPV ATERFGTVAV NFQSSSTDPA TGDVHAMGAL
    AAV-6   ---DNVMITD EEEIKATNPV ATERFGTVAV NLQSSSTDPA TGDVHVMGAL
    AAV-2   ---EKVMITD EEEIRTTNPV ATEQYGSVST NLQRGNRQAA TADVNTQGVL
    AAV-3B  ---DNVMITD EEEIRTTNPV ATEQYGTVAN NLQSSNTAPT TRTVNDQGAL
    AAV-7   ---ENVLMTN EEEIRPTNPV ATEEYGIVSS NLQAANTAAQ TQVVNNQGAL
    AAV-8   ---SDVMLTS EEEIKTTNPV ATEEYGIVAD NLQQQNTAPQ IGTVNSQGAL
    AAV-10  ---SSVMLTS EEEIKTTNPV ATEQYGVVAD NLQQANTGPI VGNVNSQGAL
    AAV-4   ---GTLIFTS EEELAATNAT DTDMWGNLPG GDQSNSNLPT VDRLTALGAV
    AAV-11  ---NNLLFTS EEEIAATNPR DTDMFGQIAD NNQNATTAPI TGNVTAMGVL
    b-AAV   ---NNLMFTS EDELRATNPR DTDLFGHLAT NQQNATTVPT VDDVDGVGVY
    AAV-5   YLEGNMLITS ESETQPVNRV AYNVGGQMAT NNQSSTTAPA TGTYNLQEIV
    GPV     GI-SDIMVTE EQEVAPTNGV GWKPYGRTVT NEQNTTTAPT SSDLDVLGAL
    B19     YQQGVGRFPN EKE-----QL KQLQGLNMHT YFPNKGTQQY TDQIE-RPLM
    MVM     DTRDGFIQSA PLVV----PP PLNGILTNAN PIGTKNDIHF SNVFNSYGPL
    FPV     YPEGDWIQNI NFNL----PV TNDNVLLPTD PIGGKTGINY TNIFNTYGPL
    CPV     YPEGDWIQNI NFNL----PV TNDNVLLPTD PIGGKTGINY TNIFNTYGPL
Consensus   ........t. e.e....npv .....g.... ..q..tt... t...n..g.l 651                                                              700
    AAV-1   PGMVWQDRDV YLQGPIWAKI PHTDGHFHPS -PLMGGFGLK NPPPQILIKN
    AAV-6   PGMVWQDRDV YLQGPIWAKI PHTDGHFHPS -PLMGGFGLK HPPPQILIKN
    AAV-2   PGMVWQDRDV YLQGPIWAKI PHTDGHFHPS -PLMGGFGLK HPPPQILIKN
    AAV-3B  PGMVWQDRDV YLQGPIWAKI PHTDGHFHPS -PLMGGFGLK HPPPQIMIKN
    AAV-7   PGMVWQNRDV YLQGPIWAKI PHTDGNFHPS -PLMGGFGLK HPPPQILIKN
    AAV-8   PGMVWQNRDV YLQGPIWAKI PHTDGNFHPS -PLMGGFGLK HPPPQILIKN
    AAV-10  PGMVWQNRDV YLQGPIWAKI PHTDGNFHPS -PLMGGFGLK HPPPQILIKN
    AAV-4   PGMVWQNRDI YYQGPIWAKI PHTDGHFHPS -PLIGGFGLK HPPPQIFIKN
    AAV-11  PGMVWQNRDI YYQGPIWAKI PHADGHFHPS -PLIGGFGLK HPPPQIFIKN
    b-AAV   PGMVWQDRDI YYQGPIWAKI PHTDGHFHPS -PLIGGFGLK SPPPQIFIKN
    AAV-5   PGSVWMERDV YLQGPIWAKI PETGAHFHPS -PAMGGFGLK HPPPMMLIKN
    GPV     PGMVWQNRDI YLQGPIGAKI PKTDGKFHPS -PNLGGFGLH NPPPQVFIKN
    B19     VGSVWNRRAL HYESQLWSKI PNLDDSFKTQ FAALGGWGLH QPPPQIFLKI
    MVM     TTFS-HPSPV YPQGQIWDK- -ELDLEHKPR LHITAPFVCK NNAPGQMLVR
    FPV     TALN-NVPPV YPNGQIWDK- -EFDTDLKPR LHINAPFVCQ NNCPGQLFVK
    CPV     TALN-NVPPV YPNGQIWDK- -EFDTDLKPR LHVNAPFVCQ NNCPGQLFVK
Consensus   pg.vw..rdv y.#gpiwaKi p..D..fhps .p..ggfglk .ppPq..ikn 701                                                              750
    AAV-1   TPVPANPPAE FSATKFASFI TQYSTGQVSV EIEWEL-QKE NSKRWNPEVQ
    AAV-6   TPVPANPPAE FSATKFASFI TQYSTGQVSV EIEWEL-QKE NSKRWNPEVQ
    AAV-2   TPVPANPSTT FSAAKFASFI TQYSTGQVSV EIEWEL-QKE NSKRWNPEIQ
    AAV-3B  TPVPANPPTT FSPAKFASFI TQYSTGQVSV EIEWEL-QKE NSKRWNPEIQ
    AAV-7   TPVPANPPEV FTPAKFASFI TQYSTGQVSV EIEWEL-QKE NSKRWNPEIQ
    AAV-8   TPVPADPPTT FNQSKLNSFI TQYSTGQVSV EIEWEL-QKE NSKRWNPEIQ
    AAV-10  TPVPADPPTT FSQAKLASFI TQYSTGQVSV EIEWEL-QKE NSKRWNPEIQ
    AAV-4   TPVPANPATT FSSTPVNSFI TQYSTGQVSV QIDWEI-QKE RSKRWNPEVQ
    AAV-11  TPVPANPATT FTAARVDSFI TQYSTGQVAV QIEWEI-EKE RSKRWNPEVQ
    b-AAV   TPVPANPATT FSPARINSFI TQYSTGQVAV KIEWEI-QKE RSKRWNPEVQ
    AAV-5   TPVPGN-ITS FSDVPVSSFI TQYSTGQVTV EMEWEL-KKE NSKRWNPEIQ
    GPV     TPVPADPPVE YVHQKWNSYI TQYSTGQCTV EMVWEL-RKE NSKRWNPEIQ
    B19     --LPQSGPIG GIKSMGITTL VQYAVGIMTV TMTFKLGPRK ATGRWNPQPG
    MVM     LGPNLTDQYD PNG-ATLSNI VTYGTFFWKG KLTMRA-KLR ANTTWNPVYQ
    FPV     VAPNLTNQYD PDASANMSRI VTYSDFWWKG KLVFKA-KLR ASHTWNPIQQ
    CPV     VAPNLTNEYD PDASANMSRI VTYSDFWWKG KLVFKA-KLR ASHTWNPIQQ
Consensus   tpvp...... ........s.i tqYstgq..v ...wel..ke .skrWNPe.q
```

Fig. 1F

```
             751                                                        799
   AAV-1    YTSNYAKSAN  V---DFTVDN  NGLYTEPRPI  GTRYLTRPL
   AAV-6    YTSNYAKSAN  V---DFTVDN  NGLYTEPRPI  GTRYLTRPL
   AAV-2    YTSNYNKSVN  V---DFTVDT  NGVYSEPRPI  GTRYLTRNL
   AAV-3B   YTSNYNKSVN  V---DFTVDT  NGVYSEPRPI  GTRYLTRNL
   AAV-7    YTSNFEKQTG  V---DFAVDS  QGVYSEPRPI  GTRYLTRNL
   AAV-8    YTSNYYKSTS  V---DFAVNT  EGVYSEPRPI  GTRYLTRNL
   AAV-10   YTSNYYKSTN  V---DFAVNT  EGTYSEPRPI  GTRYLTRNL
   AAV-4    FTSNYGQQNS  L---LWAPDA  AGKYTEPRAI  GTRYLTHHL
   AAV-11   FTSNYGNQSS  M---LWAPDT  TGKYTEPRVI  GSRYLTNHL
   b-AAV    FTSNYGAQDS  L---LWAPDN  AGAYKEPRAI  GSRYLTNHL
   AAV-5    YTNNYNDPQF  V---DFAPDS  TGEYRTTRPI  GTRYLTRPL
   GPV      FTSNFSNRTS  I---MFAPNE  TGGYVEDRLI  GTRYLTQNL
   B19      VYPPHAAGHL  P---YVLYDP  TATDAKQHHR  HGYEKPEELW  TAKSRVHPL
   MVM      VSVEDNGNSY  MSVTKWLPTA  TGN-MQSVPL  ITRPVARNTY
   FPV      MSINVDNQF-  ----NYVPNN  IGA-MKIVYE  KSQLAPRKLY
   CPV      MSINVDNQF-  ----NYVPSN  IGG-MKIVYE  KSQLAPRKLY
Consensus   .t.n......  .......pd.  tg.y...r.i  gtryltr.l.  .........
```

Fig. 4
A) anti-KLH
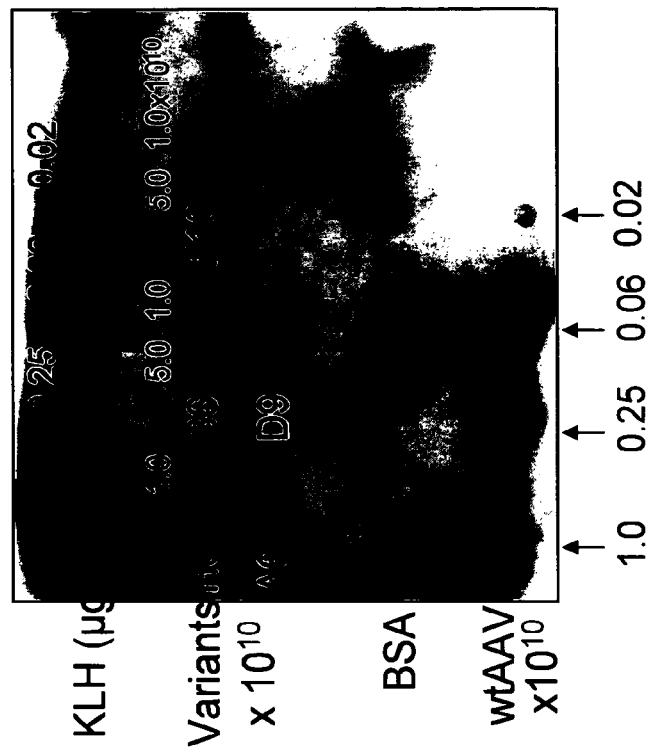
B) anti-AAV2 (A20)
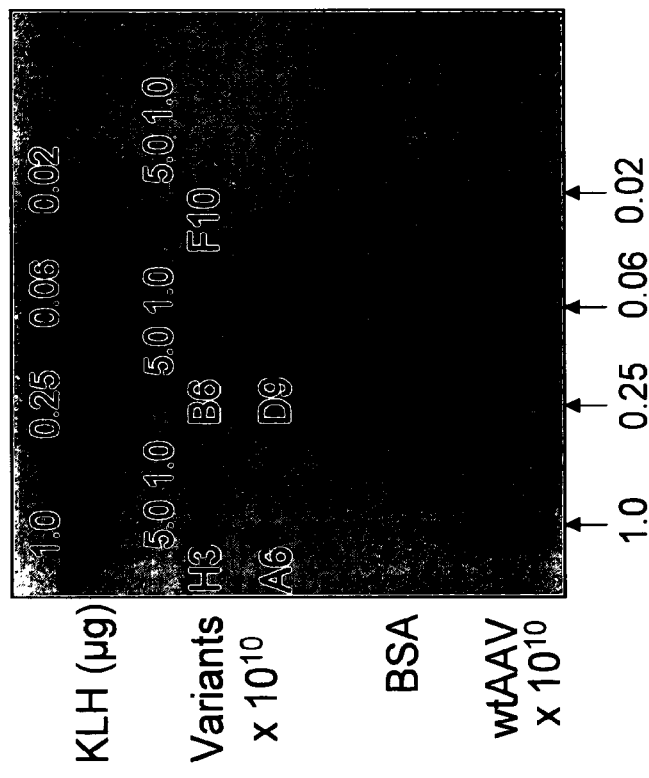

MUTATED PARVOVIRUS STRUCTURAL PROTEINS AS VACCINES

CROSS-REFERENCE TO RELATED APPLICATIONS

This application is a continuation of U.S. application Ser. No. 13/937,997, filed Jul. 9, 2013, which is a continuation of U.S. application Ser. No. 12/601,639, which has a 371(c) date of Mar. 23, 2010, which is a U.S. National Stage of International Application No. PCT/EP2008/004366, filed Jun. 2, 2008, which claims the benefit of U.S. Provisional No. 60/932,446, filed May 31, 2007, and European Patent Application No. 07013264.2, filed Jul. 6, 2007.

BACKGROUND OF THE INVENTION

The present application is related to a method for identifying a parvovirus mutated structural protein capable of specifically binding to a binder for an antigen, a parvovirus mutated structural protein which comprises as least one B-cell epitope heterologous to the parvovirus, a mutlimeric structure comprising the protein, a nucleic acid encoding the protein, a virus or cell comprising the protein, a method of preparing the protein, a medicament comprising the protein, nucleic acid or multimeric structure and its use.

Monoclonal antibody therapies have been one of the most successful therapy forms of new drug developments over the last couple of years in therapeutic fields such as oncology, autoimmune and inflammatory diseases. In monoclonal antibody therapies patients are injected with a specific monoclonal antibody that recognizes the antigen involved in the disease. Antibodies recognize their antigen with the variable domain of the antibody which is also referred to as the idiotype of the antibody.

However, monoclonal antibody therapies also have certain drawbacks. It can be observed that, if the concentration of a specific antibody with one particular idiotype is too high, the patient's immune system develops an antibody response against the idiotype of the therapeutic monoclonal antibody and thereby limits its efficacy. This kind of antibody that recognizes an antibody's idiotype is referred to as an anti-idiotype antibody. In addition, antibodies to monoclonal therapeutic antibodies directed against other parts of the monoclonals often limit efficacy of a passive antibody therapy. Therefore, many of the monoclonal antibody drugs need to be used in combination with the traditional immunosuppression regiments, increasing the overall treatment costs. Furthermore, active suppression of the patient's immune system is detrimental especially, if an intact immune system is required to control the stage of disease such as for oncological indications.

As being a passive vaccination against the target antigen the monoclonal antibody has to be injected frequently depending on the half life of the antibody within the serum of the patient. Therefore, such treatments are expensive and inconvenient for the patients.

An alternative for such monoclonal antibody therapies already exists exemplified by a number of clinical developments using anti-idiotype antibodies as drugs. Such anti-idiotypic antibody therapies are based on the fact (see above) that the patient's immune system can induce an antibody response against the idiotype of an antibody. If one uses a monoclonal antibody expressing a functional imitation of a target epitope (paratope or mimotope) as an idiotype, the patient's immune system will generate a polyclonal antibody response wherein a subset of these antibodies is able to cross-react with the target epitope in the patient. Such antibody expressing a paratope is referred to an anti-idiotypic antibody (based on Jerne's network model of idiotypic relationships (Jerne, 1974, Jerne et al., 1982). Thus, selective immunization with an anti-idiotypic antibody can induce a specific immune response directed against the original antigen (Varela and Coutinho, 1991, Jefferis, 1993, Chatterjee et al., 1994).

Therefore, a vaccination with such an anti-idiotypic antibody actively induces a polyclonal antibody response. As a consequence such anti-idiotypic antibody vaccines have a number of advantages over a passive immunization by a standard monoclonal antibody. There is no antibody response towards the anti-idiotypic antibody that limits its efficacy as exactly this immune response is used as the therapeutic principle. Therefore, it is also not necessary to combine the antibody treatment with an immunosuppression regimen. And further, due to the fact that the anti-idiotypic treatment is an active immunization, the drug only has to be injected from time to time to boost the antibody response generated by the patient himself maintaining a continuous titer of specific antibodies. Additionally, anti-idiotype antibodies induce a polyclonal antibody response against the target antigen that hampers the potential mechanism for resistance to the treatment of e.g. in tumor cells.

However, anti-idiotypic antibody therapies face major disadvantages. The titers of the induced polyclonal antibody response obtained by the vaccination with anti-idiotypic antibodies are often not high enough to establish a beneficial treatment. This is due to the lack of a strong antigen as a vaccine, since antibodies per definition are not very immunogenic. Furthermore, it is difficult to generate specific anti-idiotype vaccines because of this lack of immunogenicity and technical difficulties to identify anti-idiotypic antibodies.

A series of publications describes that an antigen placed in the context of an ordered surface of a viral particle—here a papilloma virus particle—can induce a B cell response that even can abrogate B cell tolerance to such antigen by direct crosslinking the respective B-cell receptor. Bovine papilloma virus-like particles (VLPs) conjugated to an Aβ peptide through biotin were used to generate an immune response against the self antigen Aβ (Li et al., 2004). Further, this group used bovine papilloma virus-like particles having the murine chemokine receptor mCCR5 inserted into an immunodominant site of the viral L1 protein to immunize mice leading to sera with high anti-CCR5 antibody titers despite the fact that CCR5 is a selfantigen. Further, a macaque L1-CCR5 fusion protein was used to immunize pig tail macaques. 4 of the 5 test animals produced CCR5 specific antibodies. In a further approach TNF-α was joined to VLPs by way of a biotin-streptavidin interaction (Chackerian et al., 2001). These VLPs were successful in generating an auto-antibody response in mice, whereas these antibodies bound native TNF-α (U.S. Pat. No. 6,719,978).

Therefore, papilloma VLPs have been shown to be a suitable backbone for the presentation of antigens to the immune system in order to generate strong B cell responses, probably because of their dense, ordered and closely packed array of vaccination epitopes. Due do their exceptionally strong B cell induction papilloma VLPs can be especially useful to overcome B cell tolerance to self antigens.

However, it is questionable if epitopes linked by biotin or inserted by an educated guess can possibly induce the generation of auto-antibodies for a wide range of tolerogens, as advantageous epitopes for vaccination may be threedimensional and inserted epitopes may refold due to the specific environment of the insertion site. This is especially true for small antigens or individual epitopes, where influences of the viral capsid backbone are more relevant than in case of larger insertions.

Therefore, the problem of the instant invention was to find alternative or even superior methods to identify drug candidates useful as vaccines for the treatment of diseases, especially accessible to antibody therapies that avoid one or more of the above mentioned disadvantages (BPV based VLPs with conjugated or manually inserted tolerogen-derived epitopes).

The problem is solved by a screening method for identifying a parvovirus mutated structural protein capable of specifically binding to a binder for an antigen, the method comprising the steps of (a) providing a library of parvovirus virions expressing at least one mutated parvovirus structural protein, (b) providing a binder for an antigen, (c) selecting at least one parvovirus virion specifically binding to the binder, and (d) identifying (i) the parvovirus mutated structural protein or a mutated part thereof, or (ii) the gene or a mutated part thereof encoding the parvovirus mutated structural protein of the parvovirus virion selected in step c).

Parvovirures, especially Adeno-associated virus type 2, are well known in the art as viral vectors for gene therapy (Muzyczka, 1992). Further, the AAV2 structural proteins have been genetically modified to change the cellular tropism of AAV2 and thereby direct the virus to cells or tissues that are under normal conditions not infected by the wild-type AAV2. The first successful retargeting of AAV2 was published by Girod A. et al. (Girod et al., 1999), (WO 99/67393). The authors identified insertion sites for AAV that can be modified e.g. by insertion of short peptide sequences without destroying the capability of the structural proteins to assemble into virions. The insertion of a peptide sequence of choice that is displayed on the surface of the virion then leads to an altered cell tropism that has successfully been tested in vivo (White et al., 2004). The technology has been further developed to be used to reduce the antigenicity of AAV to escape from the immune system of patients that have neutralizing antibodies against AAV (Huttner et al., 2003); (WO 01/05990) and to modify the AAV virion's chromatographic properties to enable the efficient manufacture of AAV vectors for gene therapy (WO 01/05991). This work has been confirmed and further insertion sites have been identified (Shi et al., 2001), especially tables 1-5, page 1708 "Identification of optimal sites for heterologous ligand insertion"; (Shi and Bartlett, 2003), US 2002/0192823; (Wu et al., 2000)).

To improve the technology of retargeting AAV to desired cells or tissues, libraries of mutated structural proteins of AAV have been constructed and successfully used for the selection of AAV clones with altered cell tropism (Perabo et al., 2003, Lieber, 2003, Muller et al., 2003, WO 03/054197).

Parvovirus structural proteins have been known in the past to form virus-like particles that can be used for vaccination purposes. A vaccine containing hybrid recombinant parvovirus-like particles of pig parvovirus (PPV) and canine parvovirus (CPV) containing a CD8+ epitope from the lymphocytic choriomenigitis virus (LCMV) nucleoprotein protected mice against lethal infection with LCMV (Casal, 1999). The same was shown for PPV and CPV virus-like particles (VLPs) containing the C3:T epitope from poliovirus (Casal, 1999). Also B19 structural proteins have been applied in epitope delivery for vaccination purposes. VP-2 capsid proteins of human parvovirus B19 VLPs were used to display linear epitopes of human herpes simplex virus type 1 and mouse hepatitis virus A59 (Brown et al., 1994), U.S. Pat. No. 6,719,978).

However, these attempts have been used only for fairly large pathogenic epitopes and not with tolerogens or small antigens or even individual epitopes, where B cell tolerance has to be broken to have a beneficial effect for the patient.

Screening methods using parvovirus libraries have been previously described in WO 03/054197. Disclosed therein are screening methods to identify parvoviruses with an altered cell tropism. The authors further disclose an immunoselection step using antibodies such as patient sera to remove immunogenic parvoviruses from the pool of viruses (negative selection). However, a selection of a parvovirus virions specifically binding to the binder, e.g. for a virion binding to a therapeutic antibody, was not disclosed, being a positive selection.

Medicaments according to the present invention have numerous advantages over the prior art. The immune system of a mammal is specialized to generate strong antibody responses against viral capsid proteins due to the co-evolution of mammals and their immune system on one hand and viruses on the other hand. Strong antibody responses means titers of 1000 to 100.000 measured in a standard ELISA. Virus-like particles are highly immunogenic due to resemblance of a virus and thereby efficient uptake of such particles by antigen-presenting cells. The size of the virion, the density and symmetric order of B-cell epitopes and the optimal distance of about 50 to 100 Å between any two B-cell epitopes plays a major role regarding very strong T-cell independent B-cell responses mediated by direct cross-linking of the respective B-cell receptor breaking even B-cell tolerance against self-antigens or tolerogens (Szomolanyi-Tsuda and Welsh, 1998, Szomolanyi-Tsuda et al., 1998, Szomolanyi-Tsuda et al., 2000, Szomolanyi-Tsuda et al., 2001, Zinkemagel, 2002, Bachmann et al., 1993).

Taken together, such medicaments are capable of inducing a polyclonal immune response against certain B-cell epitopes that leads to an active immune response resulting in long lasting antibody titers. The multimeric structure of the virion contains a large number of densely packed identical epitopes directly cross-linking the respective receptor on B-cells and, thereby, inducing a T-cell independent B-cell response. The particulate structure of the medicament further supports the immune response via efficient uptake by antigen-presenting cells which activate T-cells finally triggering IgG class switch and hypermutation of activated B-cells, leading to the persistent release of high-affinity IgG antibodies and differentiation of B-cells into memory cells. Using the methods of the current invention such medicaments can easily be screened and produced.

The following definitions explain how the defined terms are to be interpreted in the context of the products, methods and uses of the present invention:

A "structural protein" means a protein that is part of the capsid of the virus. For parvoviruses the structural proteins are generally referred to as VP-1, VP-2 and/or VP-3.

A "mutated structural protein" means a structural protein that has at least one mutation in comparison to the respective structural protein of the wild-type virus.

A "parvovirus" means a member of the family Parvoviridae containing several genera divided between 2 subfamilies Parvovirinae (Parvovirus, Erythrovirus, Dependovirus, Amdovirus, and Bocavirus) and Densovirinae (Densovirus, Iteravirus, Brevidensovirus, Pefudensovirus, and Contravirus) (Fields: Virology, fourth edition 2001, Volume 2, chapters 69 and 70, Lippincott Williams Wilkins, Philadelphia.

Preferred parvoviruses are members of the genus Parvovirus, such as AAV1, AAV2, AAV-3b, AAV-4, AAV-5, AAV-6, AAV-7, AAV-8, AAV-9, AAV10, AAV11, AAV12, bovine AAV (b-AAV), canine AAV (CAAV), canine parvovirus (CPV), mouse parvovirus, minute virus of mice (MVM), B19, H1, avian AAV (AAAV), feline panleukopenia virus (FPV), and goose parvovirus (GPV).

Preferred parvoviruses are adeno-associated virus (AAV), Bovine AAV (b-AAV), canine AAV (CAAV), canine parvovirus (CPV), minute virus of mice (MVM), B19, H1, AAAV, feline panleukopenia virus (FPV) and goose parvovirus (GPV). Especially preferred are AAV1, AAV2, AAV-3b, AAV-4, AAV-5, AAV-6, AAV-7, AAV-8, AAV-9, AAV10, AAV11 or AAV12, especially AAV2.

The term "binder" refers to a molecule that specifically binds to its respective binding partner. Commonly used binders are antibodies, especially monoclonal antibodies, antibody derivatives such as single chain antibodies or antibody fragments. In principle all classes of antibodies can be used, preferred are IgG antibodies. Fragments or multimers of antibodies can equally be used. Commonly used fragments are single chain antibodies, Fab- or (Fab)$_2$-fragments. Examples of other suitable binders are protein scaffolds such as anticalins or lipocalins (Nygren and Skerra, 2004), receptors or parts thereof (e.g. soluble T-cell receptors), ankyrine, microbodies or aptamers. The term "specifically binds" means that two molecules A and B, preferably a proteins, bind to each other thereby generating complex AB with an affinity ($K_D=k_{off}/k_{on}$) of at least $K_D=1\times10^{-5}$ mol/l, preferably $1\times10^{-7}$ mol/l, more preferably $1\times10^{8}$ mol/l, especially $1\times10^{-9}$ mol/l.

The term "antigen" in the context of the products, methods and uses of the present invention refers to any target antigen against which an immune reaction should be induced. Such target antigens are usually antigens that are susceptible to the humoral immune response. They are usually proteins that may be posttranslationally modified, as for example glycosylated proteins. Preferred antigens are serum proteins, proteins that can be found at least under certain conditions (e.g. in a disease state) in the blood (e.g. CETP, IL-6, IL-17, TNF-α), and membrane proteins, especially receptor proteins (e.g. CD20, acetylcholine receptors, IL13R, EGFR). Especially preferred antigens are IgE, tumor-antigens (e.g. Melan A, high molecular weight melanoma associated antigen (HMW MAA), CA125, IL13R, Her2/NEU, L1 cell adhesion molecule), VEGF, EGFR, CD20, IL-9, IL-13, CETP (cholesterol ester transfer protein), TNF-family members (e.g. TNF-α), interleukins (IL-6, IL-17) or misfolded proteins leading to a protein aggregation and, therefore, causing conformational diseases (for an overview see Uversky et al., 2006), e.g. β-amyloid). Excluded from the above definition of "antigen" are parvovirus antigens, i.e. antigens inherent the unmutated parvovirus itself, e.g. derived from B19 (Klenerman et al., 2002).

"Heterologous" in the context of the present invention means a peptide sequence, e.g. an epitope that is not present on the parvovirus wild-type viral capsid and/or structural protein.

A "tolerogen" is a self-antigen that is—in its natural environment—accessible to the humoral immune system. It may be either secreted or otherwise released from a living cell or associated to the outer surface of or integrated into the cellular membrane. Generally speaking tolerogens do—under normal circumstances in contrast to e.g. autoimmune diseases—not evoke a specific immune response due to tolerance against the antigen which results from a previous exposure to the same antigen. Tolerance can occur due to central tolerance or peripheral tolerance. Central tolerance refers to tolerogens which corresponding antigens have been exposed to T cells in the thymus leading to elimination of the specific T cells. Peripheral tolerance occurs when antigens/epitopes/mimotopes/paratopes are presented to T cells without appropriate additional stimuli, commonly provided by inflammation leading to anergy. Still, it has been observed that tolerogens can induce to some extent regulatory B-cell responses (Vogel et al., 2004).

In one preferred embodiment this invention relates to tolerogens due to peripheral tolerance, preferably tolerogens derived from tumor antigens/epitopes/mimotopes/paratopes. Tolerogens encompassed by this invention include peptides, nucleic acids, carbohydrates, and lipids, preferably peptides.

Preferred tolerogens are antigens on the surface of a cell, especially tumor cells, e.g. receptors, especially growth factor receptors, tumor antigens, viral receptors, CD20, acetylcholine receptors, interleukin receptors. Further preferred tolerogens can be blood proteins such as interleukins, IgE, cytokines, immunoglobulins, complement factors, CETP and VEGF.

A "tolerogen-derived epitope" of a specific tolerogen in the context of the products, methods and uses of the present invention refers to a B-cell epitope that
i) is identical to a B-cell epitope of the tolerogen,
ii) a derivative (e.g. a mutant) of a B-cell epitope of the tolerogen that crossreacts with an antibody that binds the B-cell epitope of the tolerogen.
iii) a mimotope of a B-cell epitope of the tolerogen, and/or
iv) a paratope of a B-cell epitope of a tolerogen.

The length of a tolerogen-derived epitope is typically 4-30, preferably 5-20 and most preferably 5-15 amino acids.

The derivative of a B-cell epitope of a tolerogen may be generated by one or more amino acid substitutions, preferably one or more conservative amino acid substitutions, i.e. substitutions that take place within a family of amino acids that are related in their side chains and chemical properties. Examples of such families are amino acids with basic side chains, with acidic side chains, with non-polar aliphatic side chains, with non-polar aromatic side chains, with uncharged polar side chains, with small side chains, with large side chains etc. Further, derivatives may be obtained by one or more single amino acid deletion(s) and/or insertion(s).

"Crossreaction" or "crossreact" of B-cell epitopes with a specific monoclonal antibody means according to this invention that the affinity (Ko) of the epitopes with the antibody are within two magnitudes, preferably within one magnitude when comparing the B-cell epitope to its derivative.

Tolerogen-derived epitopes within the multimeric structure comprising parvovirus mutated structural proteins according to this invention are identical, resemble or mimic antigen stretches of a tolerogen that are—in their natural environment—accessible to the immune system, e.g. epitopes of membrane protein located in the extracellular part, serum proteins, immunoglobulins, plaque proteins. Such antigen stretches are preferably located on the surface of such protein within the body of a mammal, preferably a human.

A "mimotope" is a non-linear structural epitope composed of several amino acids derived from different regions of the linear sequence of the structural protein located in close neighborhood due to the overall tertiary structure of the capsid that is specifically bound by an antibody, or a linear epitope mimicking a discontiuous epitope of the structural protein.

A "paratope" is the antigen binding site that is specifically bound by an antibody.

The mimotope or paratope in the context of the present invention might consist of (parts of) the inserted peptide sequence alone or might be composed of inserted peptide and parvovirus core particle amino acid residues.

An "insertion" of (an) amino acid(s) is generally speaking an insertion of at least one heterologous amino acid into the sequence of—for this invention—a parvovirus structural protein. 'Heterologous' in this context means heterologous as compared to the virus, from which the parvovirus structural protein is derived from. The inserted amino acids can simply be inserted between two given amino acids of the parvovirus structural protein. An insertion of amino acids can also go along with a deletion of given amino acids of the parvovirus sturctural protein at the site of insertion, leading to a complete substitution (e.g. 10 given amino acids are substituted by 10 or more inserted amino acids) or partial substitution (e.g. 10 given amino acids are substituted by 8 inserted amino acids) of amino acids of the parvovirus structural protein.

The invention relates to a method for identifying a parvovirus mutated structural protein capable of specifically binding to a binder for an antigen, the method comprising the steps of (a) providing a library of parvovirus virions expressing at least one mutated parvovirus structural protein, (b) providing a binder for an antigen, (c) selecting at least one parvovirus virion specifically binding to the binder, and (d) identifying (i) the parvovirus mutated structural protein or a mutated part thereof, or (ii) the gene or a mutated part thereof encoding the parvovirus mutated structural protein, of the parvovirus virion selected in step (c). The identified gene or mutated part thereof can then be expressed in a cell to obtain the parvovirus mutated structural protein or mutated part thereof.

For identification the at least one gene or the mutated part thereof encoding the parvovirus mutated structural protein may be transferred into a cell, and a cell producing the parvovirus mutated structural protein capable of binding to the binder can be identified. The gene or the mutated part thereof encoding the parvovirus mutated structural protein can be cloned by transducing the gene into a cell and a cellular clone producing the parvovirus mutated structural protein capable of binding to the binder may be identified. Additionally or alternatively, the gene encoding the parvovirus mutated structural protein may be sequenced comprising the individual steps of obtaining bound virions, optionally amplifying the DNA contained within the virions, and sequencing. Sequencing can be performed by standard methods, e.g. after PCR-amplification of at least the part of the parvoviral structural protein that contains the insert. Amplification products can be cloned into a plasmid, and the plasmids can be transformed into bacteria. Single clones can be sequenced and this sequence information can then be used to generate AAV particles of clonal origin.

In case of AAV the identified capsid sequences can be cloned into a standard AAV helper plasmid or in a plasmid containing the full AAV genome. For example, the 587 insertion site of AAV2 is flanked by NotI/AscI restriction sites which can be used for subcloning of the identified peptide-coding sequences into different VP expression vectors. Alternatively, a large part of VP3 can be subcloned by BsiWI and a second restriction enzyme cutting the vector backbone 3' of the cap ORF (e.g. XmaI in pUC19).

In a preferred embodiment the at least one parvovirus virion selected in step c) of the method of the invention is amplified by viral replication and subsequent packaging in a production cell under suitable conditions, wherein at least steps b) to c) are repeated 1, 2, 3, 4, 5, 6, 7, 8, 9, or 10 times, preferably 1, 2, 3, 4 or 5 times. Optionally, a step for coupling genotype and phenotype of a selected mixture of parvovirus virions can be performed as it is described below for the coupling of a whole library.

The general principle of the identification of such a parvoviral mutated structural protein is that selections are done using a library of viruses displaying a random peptide on the capsid surface. Virus capsid mutants which are able to bind the used binder, e.g. antibody, are selected, can be amplified and are re-used for a new selection round. After each selection round the selected sequences can be analyzed. A selected parvoviral mutated structural protein clone and/or its respective nucleic acid sequence is then used to generate a medicament, i.e. a vaccine.

Preferred binders for the carrying out the identification step of the present invention are Fab or (Fab)$_2$ fragments. If whole IgG antibodies are used, the coupling of the antibody to a support such as a culture plate takes place at random so that the library will be exposed to different parts of the IgG antibody (e.g. the desired idiotype, or the large Fc part which is an undesired event). Therefore, AAV particles which do not only bind the antibody idiotype but which also can bind other parts of the IgG antibodies will be finally isolated. This can be avoided by using only Fab or (Fab)$_2$ fragments. If those fragments are commercially not available for a specific monoclonal antibody, they can be generated from whole IgG antibodies by commercial kits.

There are also alternatives how binding can be performed. In one embodiment the selecting step is performed using a binder that is immobilized on a carrier, preferably directly or via a linker. Such linker can again be linked through a second site of the binder (the first site is the site that is used for screening the library) to a support or surface, e.g. of 12-well plate, e.g. using antibodies as binders through an Fc-specific linker such as protein A or G, sepharose. Fc-specific antibodies or -fragments. The binding of the binder through a linker to the surface has the advantage that the binder is bound in a directed fashion that can avoid unspecific binding of parvovirus mutated structural proteins. By this means, mainly the idiotype of the antibody will be exposed to the particles of the library.

Supports or surfaces used for the method of the invention can either be the surface of Petri dish, 12-well plate or alike, but also suitable chromatography material such CNBr-activated Sepharose. In the latter case a batch method using the chromatography material in suspension can be used.

Alternatively, the selection step is performed using a binder in suspension. Here, binder and parvovirus mutated structural proteins are capable of forming complexes in suspension which reflects the situation in vivo best. Such complexes can be precipitated using standard immune precipitation with Fc-specific antibodies or anti antibody affinity chromatography. Further, binders can be captured by Sepharose A/G columns. Instead of standard immune precipitation magnetic beads coupled to the selection antibody or to any binder which binds to the modified parvoviral particle can be used to isolate the desired modifications out of the library pool.

Specificity of the selection step in either way can be enhanced by addition of at least one washing step to remove unbound or weakly bound parvovirus mutated structural proteins. Suitable washing conditions are e.g. high salt concentrations or use of detergents such as Tween.

Additionally, selected parvovirus virion is further selected for non-binding to a second binder. Such binder might for example be derived from antibodies neutralizing the respective core particle. Another class of binder would be antibodies induced by the same parvovirus virion without inserted peptide sequences. By this means of selection, undesired immunodominant epitopes might be excluded.

Transduction of the gene into a cell is preferably carried out under conditions, where the uptake of the DNA is independent of an infection pathway but occurs through unspecific uptake (e.g. pinocytosis or phagocytosis) further described in more detail below.

Alternatively or additionally, the selection step can be carried out on cells expressing a specific receptor for a binder of choice which is used for selecting the desired parvoviral variant. E.g. cells can be used which express the FcγRI receptor which is specific for any binder comprising an Fc-part of an IgG antibody. For this example, such FcγRI expressing cells can be transduced with a library pool of parvoviruses. First, a negative selection can be performed to avoid unspecific selection of parvoviral candidates which by themselves are able to transduce cells independently from an interaction of a binder with FcγRI. Therefore. FcγRI-expressing cells are incubated with the library pool. The supernatant (pool of parvoviruses which is not able to transduce the cells) is collected and subsequently incubated with the binder of choice (e.g. selection antibody) to perform the positive selection. In the positive selection parvoviruses decorated with the binder will be able to transduce FcγRI expressing cells through attachment of the binder to FcγRI on the surface of the cells. The transduced cells can subsequently be used to amplify the particles.

The specific affinity or avidity of the selected parvovirus mutated structural proteins for the binder can be further enhanced by the additional steps of (e) randomizing the gene encoding the parvovirus mutated structural protein, (f) packaging the randomized genes into a further library of parvoviruses and (g) repeating the steps (a) to (d) of the above selection method.

In a preferred embodiment the parvovirus mutated structural protein further comprises at least one random mutation compared to the respective parvovirus wild type structural protein e.g. with its mutated amino acid residue either directly or indirectly contributing to the overall avidity or affinity of the respective virus particle to the binder of an antigen due to the formation of structural epitopes, mimotopes or paratopes.

Further mutation of the capsid protein might be adequate to e.g. i) introduce additional or even identical B-cell epitopes of the same target antigen, and/or ii) B-cell epitopes of one or more further target protein(s) (multi-target vaccine), T-helper 1 ($T_{H1}$) epitope(s) to further promote the desired $T_{H1}$ immune response, peptide sequence(s) to target antigen-presenting cells, or to obtain capsid mutants with reduced immunogenicity of the core particle. The latter might be one possibility to setup an efficient prime/boost regimen.

In a further preferred embodiment the further mutation might be adequate to introduce at least one cytotoxic T-cell epitope (CTL epitope). For both infectious diseases and cancer it is most useful to combine both humoral and cellular immune responses to fight these diseases. The multimeric structures according to the invention are in principle capable of pseudo-infecting cells. Accordingly these structures—like viruses—are able to enter cells, are processed to peptides, the peptides are loaded onto MHC class I and II molecules and finally presented to CD8- or CD4-positive T cells. The T-cells become stimulated after specific recognition of such processed peptide presented by MHC class I or II molecules. As a consequence of such stimulation CD8 cells may differentiate into cytotoxic T cells and then cause a cellular immune response. CD4 cells may develop into T helper cells which stimulate B cells to provide a humoral immune response or CD8-positive T cells to provide a cytotoxic immune response, which may themselves induce lysis of infected cells and other cells carrying and presenting the same peptide. Suitable CTL epitopes are known in the art for various cancer antigens or viral antigens, or they can be predicted from given antigen sequences using for example the peptide prediction program by Parker. Proposed CTL epitopes can be validated according to the methods as exemplified for HPV-epitopes in U.S. Pat. No. 6,838,084, examples 2-8 (herein incorporated by reference). As processing of CTL epitopes occurs within the cell it is not necessary that such CTL epitopes are located on the surface or are present in a specific conformation.

It is a preferred embodiment of the present invention that an identical B-cell epitope is inserted at two insertion sites, especially in I-587 and I-453, if it is key to have a large number of identical peptides being optimally presented on the surface of a capsid, especially in the case if direct B-cell receptor (BCR) crosslinking is required for T-cell independent priming of B-cells and breaking of tolerance against self-antigens. A higher density of B-cell epitopes increases the likelihood of optimal peptide-specific BCR crosslinking which requires a defined distance between BCRs (e.g. about 5-10 nm), and therefore, respective B-cell epitopes being presented on a parvovirus capsid. As shown in this invention (FIG. 19), identical insertions of—in this case a β-amyloid epitope—into parvovirus capsids at two (or more) different sites at a time can lead to a higher affinity of the capsid to an antibody specifically recognizing the inserted epitope, here the β-amyloid epitope at insertion sites I-453 and I-587. Consequently, in this case it is preferred that the inserted peptide is a B-cell epitope, more preferred a tolerogen-derived epitope. Therefore, it is an especially preferred embodiment of this invention that an identical peptide is inserted at I-453 and I-587 and that this peptide is a B-cell epitope, most preferred a tolerogen-derived epitope.

Further preferred double insertion variants are all possible combinations of I-261, I-453, I-534, I-570, I-573 and I-587, preferably I-261 in combination with I-587 and I-261 in combination with I-453.

Moreover, a larger number of inserted B-cell epitopes decreases the probability for undesired immune reactions against the parvovirus backbone due to i) masking of natural parvovirus B-cell epi/mimotopes and/or ii) slight structural capsid changes rendering these natural B-cell epi/mimotopes less immunogenic. Accordingly, parvovirus structural proteins comprising at least three insertions are especially preferred.

In a preferred embodiment genotype and phenotype of each virion particle of the library is coupled. This means that the genomic mutant of the virion is identical to the phenotypic mutant of the same virion or, in other words, that each structurally modified virus codes for its structural protein mutant.

In contrast to a bacterial transformation, where only one bacteriophage is taken up by one bacterial cell, using transfection methods for eukaryotic cells many DNA copies (up to $1 \times 10^6$) can be taken up per cell (Dean et al., 2005). Therefore, in the case of an AAV library one cell can replicate thousands of AAV genomes at the same time where each may express a different mutated structural protein with a different peptide sequence inserted into VP-1, VP-2, and/or VP-3 of AAV. At least some of these structural proteins can assemble a complete viral capsid (consisting of 5 VP-1, 5 VP-2 and 50 VP-3 proteins) encapsidating only one of the thousands of AAV genomes present in the cell. In case of a geno-/phenotypically coupled library at least 10%, preferably more than 25%, especially more than 50% of the resulting AAV particles have an encapsulated genome which codes for at least 25%, preferably more than 50%, especially more than 80% of the 60 VP proteins of which its capsid is composed. As a consequence, if an uncoupled library was used for a first screening against a target antibody, the chance that screened particles contained the genome coding for this specific peptide sequence might be very low.

In general, geno-/phenotypically coupled virion particles/libraries are obtained when introducing one single copy of the virus genome into each virion production cell entering the cell nucleus. This cell will only produce capsid protein variants encoded of exactly the introduced genome which is replicated and afterwards packaged into the mutant virion particle. Different experimental settings can ensure this:

To obtain a geno-/phenotypically coupled library of parvovirus virions a library of parvovirus virions is produced by transfecting a plasmid library into production cells under suitable conditions whereas a low copy number of viral genomes equal to or less than 100 genomes per cell is used, preferably equal to or less than 10 genomes, more preferably equal to or less than one genome per cell, resulting in geno-/phenotypically coupled virions/library. The overall transfection efficacy will be finally decisive for the ideal number of virus genomes per cell to be transfected.

The required amount of virus plasmid can be quantified, if e.g. autonomous replicating plasmids with similar size as the virus genome encoding a reporter gene such as GFP are used as a model system. Autonomous replicating plasmids are e.g. systems comprising SV40 origin of replication and large T antigen or the EBV (ebstein barr virus) P1 origin and EBNA. Increasing amounts of the self-replicating reporter gene plasmid are cotransfected with carrier DNA such as empty plasmid DNA (e.g. pUC derivates) keeping the amount of total DNA constant. In theory, each cell transfected with the reporter gene plasmid will, due to its self-replication, express sufficient amounts of reporter protein to be detected. At some ratio of reporter gene vector to carrier DNA, a further increase of reporter gene plasmid will lead to a corresponding increase in the number of transfected cells. By this means, the ideal amount of self-replicating reporter gene plasmid can be determined, reflecting the ideal amount of vector genomes.

Similarly, another read-out system for detection of successfully transfected cells are methods such as in-situ PCR to detect the transfected plasmid genome on a single cell level.

Alternatively, the geno-/phenotypically coupled library of parvovirus virions can be produced by transducing a (non- or partially coupled) virion library into production cells under suitable conditions at a ratio of genomes per cell of 5 to 5,000, preferably 10 to 1,000, more preferably 50 to 300, especially approximately 100, and selecting transduction conditions to be independent from infection pathways, particularly through unspecific uptake through pinocytosis and/or phagocytosis, resulting in geno-/phenotypically coupled virions/library. As it is known that a peptide insertion into the I-587 site of AAV2 frequently destroys (dependent of the sequence of the inserted peptide) the heparin binding motif required for efficient infection of HSPG-receptor containing cells such as HeLa or 293 cells, simple infection methods could bias the screening method and lead only to mutants that still can enter HeLa cells specifically through the respective receptor, in case of AAV2 through heparan sulfate proteoglycan (HSPG). Therefore, an unspecific uptake of the virus particle by the production cell is advantageous. Such unspecific uptake can be achieved by seeding production cells on immobilized parvovirus virions. A preferred embodiment relates therefore to a method, whereas the transduction of the parvovirus virion library is performed using production cells seeded on immobilized parvovirus virions. For this method, the virions are directly coated to a support/surface, e.g. a tissue culture plate. Alternatively, first a capsid specific antibody (in case of AAV2 for example A20) is coated to the support/surface and second the capsids are bound to the coated antibodies. The advantage in the latter case is that the antibody/virus particle complex, respectively the virus particle itself is more efficiently detached from the support/surface and thereby internalized by the cell. Importantly, introduction of foreign peptide sequences into I-587 of AAV2 does not destroy the affinity of A20 to the respective mutant particle as the epitopes of A20 are hardly, if at all, affected by the peptide insertion. The cells, e.g. HeLa cells, are finally seeded on the bound capsids. It is expected that this procedure leads to an uptake of the virus, e.g. AAV, by the cell independent of the natural infectious pathway, presumably by pinocytosis and/or phagocytosis.

In a further preferred embodiment a geno-/phenotypically coupled library of parvovirus virions can be obtained by a method where selected virions are specifically taken up by production cells. In this case the library of parvovirus virions is produced by transducing the library into production cells under suitable conditions at a ratio of genomes per cell of 10 to 10,000, preferably 50 to 5,000, more preferably 100 to 3,000, especially approximately 1,000, wherein transduction conditions are selected to be dependent on infection pathways, particularly through specific receptor binding, resulting in geno-/phenotypically coupled virions/library. In order to achieve such receptor-specific uptake the virions of the library are preferably not immobilized but added to the cells in suspension, whereas both cells and virions can be in suspension or cells are immobilized and virions are added in suspension. Therefore, the transfection of the cells is basically dependent on the virus's infection pathway. In this context it is conceivable to transduce FcγRI expressing cells as described above but incubating the selected pool with A20 antibody-decorated AAV particles (instead of incubating the pool with a binder).

Dependence on infection pathways means that virions are taken up by the cells e.g. through receptor-specific uptake, e.g. for AAV2 heparin sulfate proteoglycan (HSPG)-specific uptake (e.g. for virion libraries where natural infection pathways are not blocked or destroyed by the inserted random peptide sequences). For AAV2 particles with peptide sequences being inserted into I-587, infection of cells will work as long as the capsid contains sufficient HSPG binding motifs or binding motifs for secondary receptors expressed on the cell line used for the coupling step. An AAV capsid consists of 60 capsid proteins each containing the I-587 insertion site. Therefore, mosaic capsid virions containing a given percentage of wild-type sequence capsid proteins will still be able to infect cells via HSPG or secondary receptors. Alternatively, virions with peptide insertions partially restoring the affinity to HSPG or secondary receptors will be able to infect cells such as HeLa or 293. Especially peptide sequences containing basic amino acid residues such as lysine or arginine at the correct position have been shown to restore the natural HSPG infection pathway of I-587 AAV capsid mutants. Given the frequency of basic amino acid residues in a 7mer random sequence and given the fact that an AAV capsid consists of 60 capsid proteins, many if not most of the virions of a non-coupled I-587 AAV2 library consisting of particles with a mosaic capsid will still infect cells to a certain degree via HSPG receptor-mediated uptake.

To keep biodiversity of the library during the coupling step (either by transfection of virus genomes or by cell transduction with virion particles by either means, uptake or infection), always an at least 10-fold, preferably 100-fold, especially 500-fold excess of genomic particles compared to the multiplicity of parvoviral mutants should be transduced in order to ensure that each virus variant is amplified. To further ensure that each virus is coupled in the resulting library an at least 2-fold, preferably at least 5-fold excess of cells is to be used compared to total number of genomic particles.

Geno-/phenotype coupling is desired as the genetic information of the packed DNA can easily be used to obtain the sequence of those particles having high affinity or avidity to the respective antigen binder. It is an object of the invention to use for the identification of a parvovirus mutated structural protein such geno-/phenotypically coupled libraries with a coupling of at least 5%, preferably of at least 25% and more preferably of at least 50%, especially at least 90%.

In a preferred embodiment the library has a multiplicity of parvoviral mutants of greater than $10^5$, preferably greater than $10^6$, especially greater than $10^7$. Multiplicity means according to this invention the number of different virions or viral genomes within the library. In principal it is advantageous to use a library of high multiplicity as the likelihood to identify a suitable or even ideal clone increases with the multiplicity of the library.

The multiplicity of the library is generated by insertion of a nucleic acid insert into the coding region of the gene encoding a parvoviral structural protein leading to an amino acids insertion at a particular position within the parvoviral structural protein. It is preferred according to this invention that the insertion(s) is inserted into one or more positions selected from the group consisting of I-1, I-34, I-138, I-139, I-161, I-261, I-266, I-381, I-447, I-448, I-453, I-459, I-471, I-534, I-570, I-573, I-584, I-587, I-588, I-591, I-657, I-664, I-713 and I-716, more preferably I-261, I-453, I-534, I-570, I-573 and I-587, especially I-587.

The used nomenclature I-### refers to the insertion site with ### naming the amino acid number relative to the VP1 protein of AAV2, however meaning that the insertion may be located directly N- or C-terminal, preferably directly C-terminal of one amino acid in the sequence of 5 amino acids N- or C-terminal of the given amino acid, preferably 3, more preferably 2, especially 1 amino acid(s) N- or C-terminal of the given amino acid. For parvoviruses other than AAV2 the corresponding insertion sites can be identified by performing an amino acid alignment or by comparison of the capsid structures, if available. Such alignment has been performed for the parvoviruses AAV1, AAV-6, AAV2, AAV-3b, AAV-7, AAV-8, AAV10, AAV-4, AAV11, b-AAV, AAV-5, GPV, B19, MVM, FPV and CPV (see FIG. 1).

For example the insertion site I-587 corresponds to an insertion before and/or after one of the following amino acids indicated by emphasis

```
SEQ ID NO: 1: FQSSS TDPAT of AAV1,

SEQ ID NO: 2: LQRGN₅₈₇ RQAAT of AAV2,

SEQ ID NO: 3: LQSSN TAPTT of AAV-3b,

SEQ ID NO: 4: LQSSS TDPAT of AAV-6,

SEQ ID NO: 5: LQAAN TAAQT of AAV-7,

SEQ ID NO: 6: LQQQN TAPQI of AAV-8,

SEQ ID NO: 7: LQQAN TGPIV of AAV10,

SEQ ID NO: 8: NQNAT TAPIT of AAV11
and

SEQ ID NO: 9: NQSST TAPAT of AAV-5.
```

Further, the insertion site I-453 corresponds to an insertion directly N- or C-terminal of the following ten amino acids each, preferably directly C-terminal of the amino acid indicated by emphasis

```
SEQ ID NO: 10: QNQSG SAQNK of AAV1,

SEQ ID NO: 11: NTPSG₄₅₃ TTTQS of AAV2,

SEQ ID NO: 12: GTTSG TTNQS of AAV-3b,

SEQ ID NO: 13: QNQSG SAQNK of AAV-6,

SEQ ID NO: 14: SNPGG TAGNR of AAV-7,

SEQ ID NO: 15: QTTGG TANTQ of AAV-8,

SEQ ID NO: 16: QSTGG TQGTQ of AAV10,

SEQ ID NO: 17: SGETL NQGNA of AAV11
and

SEQ ID NO: 18: FVSTN NTGGV of AAV-5.
```

Relating to the AAV2 sequence insertion sites for AAV and other parvoviruses encompassed by this invention are listed in Table 1.

TABLE 1

| Insertion sites for parvoviruses | | | | |
|---|---|---|---|---|
| Insertion site | | corresp. amino acid/sequence of AAV2 | | References |
| I-1 | M₁ | M₁ AADGY | SEQ ID NO: 19 | (Wu et al., 2000) |
| I-34 | P₃₄ | PPPKP₃₄ AERHK | SEQ ID NO: 20 | (Wu et al., 2000) |
| I-138 | T₁₃₈ | EPVKT₁₃₈ APGKK | SEQ ID NO: 21 | (Wu et al., 2000, Warrington et al., 2004, Lux et al., 2005) |

TABLE 1-continued

Insertion sites for parvoviruses

| Insertion site | corresp. amino acid/sequence of AAV2 | | | | References |
|---|---|---|---|---|---|
| I-139 | $A_{139}$ | PVKTA$_{139}$ PGKKR | SEQ ID NO: 22 | | (Shi et al., 2001, Shi and Bartlett, 2003, Arnold et al., 2006) |
| I-161 | $K_{161}$ | SGTGK$_{161}$ AGQQP | SEQ ID NO: 23 | | (Shi et al., 2001, Arnold et al., 2006) |
| I-261 | $S_{261}$ | YKQIS$_{261}$ SQSGA | SEQ ID NO: 24 | | (Girod et al., 1999) |
| I-266 | $A_{266}$ | SQSGA$_{266}$ SNDNH | SEQ ID NO: 25 | | (Wu et al., 2000) |
| I-381 | $N_{381}$ | YLILN$_{381}$ NGSQA | SEQ ID NO: 26 | | (Girod et al., 1999) |
| I-453 | $G_{453}$ | NTPSG$_{453}$ TTTQS | SEQ ID NO: 11 | | data of this invention |
| I-447 | $R_{447}$ | YYLSR$_{447}$ TNTPS | SEQ ID NO: 27 | | (Girod et al., 1999, Wu et al., 2000) |
| I-448 | $T_{448}$ | YLSRT$_{448}$ NTPSG | SEQ ID NO: 28 | | (Grifman et al., 2001) |
| I-459 | $R_{459}$ | TTQSR$_{459}$ LQFSQ | SEQ ID NO: 29 | | (Shi et al., 2001, Arnold et al., 2006) |
| I-471 | $R_{471}$ | ASDIR$_{471}$ DQSRN | SEQ ID NO: 30 | | (Asokan and Samulski, 2006, Moskalenko et al., 2000) |
| I-534 | $F_{534}$ | EEKFF$_{534}$ PQSGV | SEQ ID NO: 31 | | (Girod et al., 1999) |
| I-570 | $P_{570}$ | RTTNP$_{570}$ VATEQ | SEQ ID NO: 202 | | data of this invention for Δ566-575 |
| I-573 | $T_{573}$ | NPVAT$_{573}$ EQYGS | SEQ ID NO: 32 | | (Girod et al., 1999) |
| I-584 | $Q_{584}$ | STNLQ$_{584}$ RGNRQ | SEQ ID NO: 33 | | (Shi et al., 2001, Shi and Bartlett, 2003) |
| I-587 | $N_{587}$ | LQRGN$_{587}$ RQAAT | SEQ ID NO: 2 | | (Girod et al., 1999, Shi et al., 2001, Maheshri et al., 2006, Ried et al., 2002, Grifman et al., 2001, Nicklin et al., 2001, Arnold et al., 2006) |
| I-588 | $R_{588}$ | QRGNR$_{588}$ QAATA | SEQ ID NO: 34 | | (Shi and Bartlett, 2003) |
| I-591 | $A_{591}$ | NRQAA$_{591}$ TADVN | SEQ ID NO: 35 | | (Wu et al., 2000) |
| I-657 | $P_{657}$ | VPANP$_{657}$ STTFS | SEQ ID NO: 36 | | |
| I-664 | $A_{664}$ | TFSAA$_{664}$ KFASF | SEQ ID NO: 37 | | (Wu et al., 2000) |
| I-713 | $T_{713}$ | NVDFT$_{713}$ VDTNG | SEQ ID NO: 38 | | |
| I-716 | $T_{716}$ | FTVDT$_{716}$ NGVYS | SEQ ID NO: 39 | | (Maheshri et al., 2006) |

Amino acid 138 is the N-terminus of VP-2. Preferred embodiments are VP-2 structural proteins with an N-terminal fusion to one of the amino acids within the stretch $T_{138}$ APGKKR (SEQ ID NO: 40) of AAV2 or the corresponding amino acids of other parvoviruses.

I-570 is especially suitable as an insertion site that goes along with a deletion of given amino acids of the parvovirus structural protein at the site of insertion, leading to a complete substitution. In this case the amino acids RTTN PVATEQ can be substituted by an epi- or mimotope.

Further, the inserted nucleic acid sequence may be inserted at any site corresponding to the first amino-terminal amino acids 1 to 50 of VP-1.

Insertions have been successfully made into AAV-serotypes other than AAV2.

TABLE 2

Insertions into AAV-serotypes other than AAV2

| AAV serotype | Sequence | | Ins. site/amino acid relative to AAV2 | | References |
|---|---|---|---|---|---|
| AAV1 | FQSSS$_{588}$ TDPAT | SEQ ID NO: 1 | I-587 | N$_{587}$ | own data |
| AAV1 | SSSTD$_{590}$ PATGD | SEQ ID NO: 41 | I-589 | Q$_{589}$ | (Arnold et al., 2006, Stachler and Bartlett, 2006) |
| AAV-3 | NNLQS$_{586}$-SNTAP | SEQ ID NO: 42 | I-585 | R$_{585}$ | (Arnold et al., 2006) |
| AAV-4 | GGDQS$_{584}$-NSNLP | SEQ ID NO: 43 | I-585 | | (Arnold et al., 2006) |
| AAV-5 | TNNQS$_{575}$-STTAP | SEQ ID NO: 44 | I-585 | | (Arnold et al., 2006) |

The most preferred insertion sites are:
i) I-587 as various insertions have been made in the amino acid stretch around N$_{587}$ (LQRGN$_{587}$ RQAAT, SEQ ID NO: 2) of AAV2. Within this stretch insertions of various peptides were made C-terminal of amino acids Q$_{584}$, N$_{587}$, R$_{588}$ and A$_{591}$ in AAV2 (Table 1) and C-terminal of amino acids of other AAV-serotypes corresponding to R$_{585}$ and Q589 of AAV2 (Table 2).
ii) I-453 as according to this invention epitopes have been successfully inserted C-terminal of G$_{453}$ in AAV2.
iii) FQSSS$_{588}$ TDPAT (SEQ ID NO: 1) or SSSTD$_{590}$ PATGD (SEQ ID NO: 41) of AAV1.
iv) I-261 as according to this invention epitopes have been successfully inserted C-terminal of S$_{261}$ in AAV2.
v) I-534 as according to this invention epitopes have been successfully inserted C-terminal of F$_{34}$ in AAV2.
vi) I-570 as according to this invention epitopes have been successfully inserted C-terminal of P$_{570}$ in AAV2.
vii) I-573 as according to this invention epitopes have been successfully inserted C-terminal of T$_{573}$ in AAV2.

Corresponding amino acids for all insertion sites specified herein for parvoviruses disclosed herein can be retrieved from the alignment in FIG. 1, for those parvoviruses not listed herein an alignment under standard parameters as used herein can be formed with the provided amino acid sequence of such parvovirus and the corresponding amino acids can be retrieved from such alignment.

The amino acid numbers are given relative to the VP-1 amino acid sequence. However, insertions into the structural gene encoding the structural protein may generally also lead to mutated VP-2 and optionally VP-3 proteins comprising an insertion at a site which is corresponding to the VP-1 insertion as VP-2 and VP-3 are generally expressed from the identical structural gene using downstream located start codons for the start of translation leading to—compared to VP-1-N-terminally truncated structural proteins. A schematic organization of the cap gene of AAV2 is provided in FIG. 2. Therefore, the present inventions encompasses structural genes of parvoviruses with corresponding insertions in the VP-1, VP-2 and/or VP-3 proteins. For example for AAV2, insertions into the cap gene between the codons coding for amino acids 1 and 138 lead to an insertion only in VP-1. Insertions between codons coding for amino acids 138 and 203 lead to an insertion in VP-1 and VP-2, whereas insertions after the codon coding for amino acid 203 lead to insertions in VP-1, VP-2 and VP-3.

Preferred insertion sites are the positions following the amino acids that correspond to the AAV2 amino acids number 139, 161, 261, 381, 447, 453, 459, 534, 570, 573, 584, 587, 588, 657 and 713, especially 261, 453, 534, 570, 573, 587, and 588, most preferably 453 and 587. The amino acid numbers are given relative to the VP-1 amino acid sequence of AAV2.

One further embodiment of the present invention are structural proteins of parvoviruses containing insertions within the previously not described insertion sites I-453 and/or I-570.

Using I-453-based libraries may result in the selection of other peptides (as with I-587-based libraries) since adjacent residues may have an influence on the exposure and functionality of the peptides inserted into the structural protein. In addition, the sites (I-587 and I-453) are located on different loops of the AAV capsid. Thus a different mechanism of cell interaction can be assumed. Furthermore, AAV particles derived from I-453 libraries can be purified with heparin affinity chromatography, as the heparin binding site overlapping with I-587 is still intact. The same applies to other insertion sites not overlapping with I-587, preferably insertion sites I-261, I-534, I-570 and I-573.

In one potential embodiment insertions that have been selected in separate screening rounds can be combined with other insertions selected independently. For example one can use a library with an insertion of random peptides at the I-587 site for the screening method and, independently, use a second library with an insertion of random peptides at another site. Selected structural proteins of the two screening methods can then be combined by standard cloning techniques to make one clone that contains the screened insert at the respective two insertion sites.

In a further embodiment, preferred libraries contain multiple insertions at multiple sites of the structural proteins. Especially preferred libraries/structural proteins have insertions in I-453 and I-587.

By designing the sequence of the nucleic acid insert the multiplicity of the library can be controlled. The generation of such a library is for example described in WO 03/054197, hereby incorporated by reference.

The nucleic acid insert has a number of characteristics. It does not, by insertion into the coding region of the parvoviral gene, create a frame shift and thereby a truncated parvoviral structural protein. Therefore, by insertion a multimer of 3 nucleotides is inserted into the coding region of the parvoviral structural gene. The sequence is a randomly or partially randomly generated sequence, thereby generating the multiplicity of the library. A partially random sequence can for example be used to reduce the number of potential stop codons generated by insertion of the sequence and thereby reducing the number of non-functional structural mutant proteins and/or to achieve a more homogeneous distribution of the twenty different amino acids. e.g. by choosing a NNK design (with each N being any nucleotide and K standing for G or T) which in parallel reduces the number of stop codons from three to one.

In a preferred embodiment, the nucleic acid insert may contain, in addition to the randomly or partially randomly generated sequences, a further stretch of at least one codon upstream and/or downstream of the randomized or partially randomized nucleic acid sequences, preferably of 2 to 12 codons coding for small amino acids, preferably Ala, Gly, Ser, Pro, and Cys, especially an insertion of three codons for Ala upstream and two codons for Ala downstream of the randomized or partially randomized nucleic acid sequences, or an insertion of 2-5 glycin residues both, up- and downstream of the randomized or partially randomized nucleic acid sequences. Such additional amino acids do not enlarge the multiplicity of the insertion but may act as spacers to contribute to the proper accessibility of the inserted amino acids at the surface of the virions.

In a further preferred embodiment the insertion comprises linker sequences which enable a circularization of the inserted peptide sequences in order to better present the insertion. Accordingly spacer sequences are selected to form Zinc-fingers (Zn-finger), well known in the art. Preferred Zn-finger motifs are $C_2H_2$, $C_4$, and $C_2HC$ including but not limited to motifs $CX_2CX_nC_2$, $CX_2CX_{10-30}CX_2C$, $CX_5H$ $X_{10-30}CX_2C$, $CX_2CX_{10-30}CX_4H$ (Laity et al., 2001 and Gamsjaeger et al., 2006).

An example of a preferred Zn-finger linker is:

$$X_{(3-5)} CXXCX_{(0-5)} (NNK)_n X_{(0-5)} CXXCX_{(3-5)}$$

(X=Gly or Ala, C=Cys; with each N being any nucleotide and K standing for G or T). Thus the random NNK sequence protrudes from the capsid surface.

As B-cell epitopes are composed of at least 4 amino acids (US 2004/0228798A1), in a preferred embodiment the parvovirus mutant structural protein comprises at least one insertion of 4 to 30 amino acids, preferably 5 to 20 amino acids, especially 5 to 15 amino acids. The B-cell epi-, para- or mimotopes might be composed of the inserted sequence alone, or of amino acid residues of both, the inserted peptide sequence and the viral core protein.

In a further preferred embodiment the insertion comprises within the fixed stretches upstream and downstream of the randomly or partially randomly generated sequences at least one cysteine on each side capable of forming a disulfide bond. Such a disulfide bond would spontaneously form and thereby would stabilize a loop consisting of the inserted amino acids between the two cysteines. Such loop facilitates the optimal exposure of the inserted sequence to the antibodies.

It is also an embodiment of the present invention that the parvovirus mutated structural protein comprises at least one further mutation at a different position. Such further mutation can be used to compose more complex mimotopes, to modify certain properties of the virion, e.g. it can be use to modify its natural antigenicity (e.g. (Huttner et al., 2003); WO 01/05990), to modify its chromatographic properties (e.g. WO 01/05991), to insert a second B-cell epitope, preferably a tolerogen-derived epitope, or to insert a CTL epitope. Such further mutation is selected from a point mutation, an internal or terminal deletion, an insertion and a substitution. Preferably, the further (second) insertion is internally or a N- or C-terminal fusion, whereas the further insertion has a length of 4 to 40, preferably of 5 to 30, most preferably of 7 to 20 amino acids. In one specific embodiment the insertion is a tag useful for binding to a ligand. Such tags are well known in the art, examples for such are listed in Table 3.

TABLE 3

Tags and corresponding ligands

| Tag | Ligand |
|---|---|
| HIS | Nickel |
| GST | Glutathione |
| Protein A | IgG |
| Biotin or Strep | Streptavidin |
| Calmodulin-binding peptide | Calmodulin |
| Fc-Peptide of IgG | Protein A |
| Flag | GLAG- or 3xFLAG peptide |
| HA (hemagglutinin) | HA peptide |

In a further preferred embodiment affinity of a identified parvovirus mutated structural protein for the binder can be modified, preferably enhanced, by generating a library of nucleic acids encoding such parvovirus mutated structural protein having a small number of random mutations per nucleic acid, at other sites than the insertion and or within the insertion, and starting the method of identifying a parvovirus mediated structural protein over again. Such process may be repeated several times, preferably 1 to 5 times, especially 1 to 2 times. A small number of random mutations in this context means an average of at least 10 sequenced clones with 1 to 10, preferably 3 to 8, especially 4 to 6 mutations compared to the starting sequence of the identified parvovirus mutated structural protein. Such random mutations can be inserted by standard techniques known in the art such as error prone PCR and DNA shuffling. In order to achieve that, the viral genomes of the mutants will be isolated and cloned into a suitable plasmid backbone. Random mutations are then inserted by e.g. error prone PCR and/or DNA shuffling. After this, a new packaging is done, followed by a genotype/phenotype coupling step and new selection for binding to a binder of choice, e.g. antibody binding.

Another embodiment of the invention is a parvovirus mutated structural protein obtainable by the methods disclosed above.

A further subject of the present invention relates to a parvovirus mutated structural protein which comprises at least one B-cell epitope heterologous to the parvovirus and not identical to a pathogen, particularly to a B-cell epitope of a pathogen, and wherein the B-cell epitope is located on the surface of the virus.

A preferred embodiment of the invention is a parvovirus mutated structural protein of the invention may be defined as described above in the context of the method of the invention. As used herein the term B-cell epitope is meant to include also mimotopes. Therefore, the epitopes can be both linear or structural. However, especially linear epitopes that are no mimotopes are preferred.

Typically, the size of a B-cell epitope is at least 4 amino acids (US 2004/0228798A1). Therefore, it is a preferred embodiment that the parvovirus mutated structural protein has an insertion consisting of at least one single or multimeric B-cell epitope of 4 to 30 amino acids, preferably 5 to 20 amino acids, especially 5 to 15 amino acids, and a further stretch of at least one amino acid upstream and/or downstream of the B-cell epitope, preferably of 2-12 amino acids selected from the group consisting of Ala, Gly, Ser, Pro, and Cys, especially 3 Ala upstream and 2 downstream of the B-cell epitope, 5 Ala upstream and 5 downstream of the B-cell epitope, or 5 Gly upstream and 5 Gly downstream of the B-cell epitope. It is preferred that such B-cell epitope is not identical to a pathogen, particularly to a B-cell epitope of a pathogen, that—in its natural environment—is accessible to a humoral immune response. Pathogen, according to this invention, means a virus, bacterium and/or eukaryotic parasite.

Such excluded B-cell epitopes of a pathogen can be identified by searching protein databases known to the skilled artisan. If the searched sequence is identical to a sequence present in a protein of a pathogen, such B-cell epitope is, according to this preferred embodiment of the invention, excluded from the invention.

In a further embodiment, the B-cell epitope heterologous to parvovirus is not identical to a mammalian (including human) or pathogen B-cell epitope, but is a functional derivative of a mammalian or pathogen B-cell epitope. A functional derivative is defined as a B-cell epitope that is identifiable e.g. by the methods according to this invention or that crossreacts with a specific monoclonal antibody for such mammalian or pathogen B-cell epitope.

In further embodiments parvovirus mutated structural proteins of the invention are further characterized as defined above, particularly wherein the tolerogen is as defined above.

In an especially preferred embodiment the parvovirus mutated structural protein a comprises a B-cell epitope that is a tolerogen-derived epitope.

Preferably the B-cell epitope is a part of an antigen as defined above. Preferred antigens are IgE, tumor-antigens (e.g. Melan A, high molecular weight melanoma associated antigen (HMW MAA), CA125, IL13R, Her2/NEU, L1 cell adhesion molecule), viral receptors (CCR5), VEGF, EGFR, CD20, IL-6, IL-9, IL-13, IL-17, CETP, TNF-family members (e.g. TNF-α), or β-amyloid.

In a preferred embodiment the B-cell epitope is not a sequence previously inserted into AAV2 at position I-587/I-587 selected from the group consisting of
SEQ ID NO: 45: QAGTFALRGDNPQG.
SEQ ID NO: 46: SIGYPLP,
SEQ ID NO: 47: NGR,
SEQ ID NO: 48: CDCRGDCFC,
SEQ ID NO: 49: RGDAVGV,
SEQ ID NO: 50: RGDTPTS,
SEQ ID NO: 51: GENQARS,
SEQ ID NO: 52: RSNAVVP,
SEQ ID NO: 53: NSSRDLG,
SEQ ID NO: 54: NDVRAVS,
SEQ ID NO: 55: EYHHYNK,
SEQ ID NO: 56: MTPFPTSNEANLGGGS,
SEQ ID NO: 57: QPEHSST,
SEQ ID NO: 58: VNTANST,
SEQ ID NO: 59: NDVRSAN,
SEQ ID NO: 60: NDVRAVS,
SEQ ID NO: 61: VTAGRAP,
SEQ ID NO: 62: APVTRPA,
SEQ ID NO: 63: DLSNLTR and
SEQ ID NO: 64: GQHPRPG, as listed in Table 4.

TABLE 4

Insertions at 587/588 of AAV2, which showed enhanced transduction on target cells (inserted in I-587 or I-588).

| sequence around 587/588 of wt AAV2 QRGN--------------------RQAA SEQ ID NO: 65 | target | enhanced transduction | Ref |
|---|---|---|---|
| QRGN-QAGTFALRGDNPQG------RQAA SEQ ID NO: 45 | β₁ and β₃ integrin | B16F10, RN22 | (Girod et al., 1999) |
| QRGN-ASIGYPLPA----------RQAA SEQ ID NO: 66 | Peptide selected by phage display on HUVEC | HUVEC, HSVEC | (Nicklin et al., 2001) |
| QRGN-NGR----------------RQAA SEQ ID NO: 47 | CD13 | RD, KS1767 | (Grifman et al., 2001) |
| QRGN-ATGCDCRGDCFC--------QAA SEQ ID NO: 67 | αᵥβ₃ and αᵥβ₅ | HeLa, K562, Raji, SKOV-3, local appl. in vivo | (Shi and Bartlett, 2003) |
| QRGN-AAARGDAVGVAA-------RQAA SEQ ID NO: 68 | not known selected by AAV display | MO7e | (Perabo et al., 2003) |
| QRGN-AAARGDTPTSAA-------RQAA SEQ ID NO: 69 | not known selected by AAV display | MO7e | (Perabo et al., 2003) |
| QRGN-AAAGENQARSAA-------RQAA SEQ ID NO: 70 | not known selected by AAV display | Mec1, prim. B-CLL | (Perabo et al., 2003) |

TABLE 4-continued

Insertions at 587/588 of AAV2, which showed enhanced transduction on target cells (inserted in I-587 or I-588).

| sequence around 587/588 of wt AAV2 QRGN--------------------RQAA SEQ ID NO: 65 | target | enhanced transduction | Ref |
|---|---|---|---|
| QRGN-<u>AA</u>ARSNAVVP<u>AA</u>--------RQAA<br>SEQ ID NO: 71 | not known selected by AAV display | Mec1 | (Perabo et al., 2003) |
| QRGQR-<u>G</u>NSSRDLG<u>A</u>-----------QAA<br>SEQ ID NO: 72 | not known selected by AAV display | prim. human coronary endothelial cells; heart after systemic appl. | (Muller et al., 2003) |
| QRGQR-<u>G</u>NDVRAVS<u>A</u>-----------QAA<br>SEQ ID NO: 73 | not known selected by AAV display | prim. human coronary endothelial cells | (Muller et al., 2003) |
| QRGN-<u>AS</u>EYHHYNK<u>A</u>----------RQAA<br>SEQ ID NO: 74 | not known, selected by phage display on primary human saphenous vein SMC | prim. human saphenous vein and arterial SMC | (Work et al., 2004) |
| QRGN-<u>AS</u>MTPFPTSNEANLGGGS<u>A</u>-RQAA<br>SEQ ID NO: 75 | not known, selected by phage display on HUVEC | HUVEC, venous endothelial cells after systemic appl. | (White et al., 2004) |
| QRGN-<u>AS</u>QPEHSST<u>A</u>----------RQAA<br>SEQ ID NO: 76 | not known, selected by in vivo phage display | brain endothelium after systemic appl. | (Work et al., 2006) |
| QRGN-<u>AS</u>VNTANST<u>A</u>----------RQAA<br>SEQ ID NO: 77 | not known, selected by in vivo phage display | lung endothelium after systemic appl. | (Work et al., 2006) |
| QRGQR-<u>G</u>NDVRSAN<u>A</u>-----------QAA<br>SEQ ID NO: 78 | not known selected by AAV display | HSaVEC | (Waterkamp et al., 2006) |
| QRGQR-<u>G</u>NDVRAVS<u>A</u>-----------QAA<br>SEQ ID NO: 79 | not known selected by AAV display | HSaVEC | (Waterkamp et al., 2006) |
| QRGQR-<u>G</u>VTAGRAP<u>A</u>-----------QAA<br>SEQ ID NO: 80 | not known selected by AAV display | Calu6 | (Waterkamp et al., 2006) |
| QRGQR-<u>G</u>APVTRPA<u>A</u>-----------QAA<br>SEQ ID NO: 81 | not known selected by AAV display | Calu6 | (Waterkamp et al., 2006) |
| QRGQR-<u>G</u>DLSNLTR<u>A</u>-----------QAA<br>SEQ ID NO: 82 | not known selected by AAV display | PC3 | (Waterkamp et al., 2006) |

TABLE 4-continued

| Insertions at 587/588 of AAV2, which showed enhanced transduction on target cells (inserted in I-587 or I-588). | | | |
|---|---|---|---|
| sequence around 587/588 of wt AAV2<br>QRGN---------------------RQAA<br>SEQ ID NO: 65 | target | enhanced transduction | Ref |
| QRGQR-GGQHPRPGA-----------QAA<br>SEQ ID NO: 83 | not known selected by AAV display | H9C2 | (Waterkamp et al., 2006) | bold: amino acid sequence of peptide insertion used to target the new receptor;
italic and underlined: amino acid used as linker sequence to flank the targeting peptide;
bold and double underlined: amino acid has been substituted in comparison to wild-type sequence;
B16F10 = mouse melanoma cell line,
RN22 = rat schwannoma,
HUVEC = human umbilical vein endothelial cells,
HSVEC = human saphenous vein endothelial cells,
RD = rhabdomyosarcoma,
KS1767 = Kaposi sarcoma,
HeLa = human cercix carcinoma,
K562 = human chronic myeloid leukemia in blast crisis,
Raji = Burkitt lymphoma cell line,
SKOV-3 = ovarian cancer,
MO7e = megakaryocytic cell line,
Mec1 = derived from B-cell chronic lymphocytic leukemia in prolymphoid transformation,
HSaVEC = primary human venous endothelial cells,
Calu6 = lung carcinoma cell line,
PC3 = prostate carcinoma cell line,
H9C2 = rat cardiomyoblasts In a preferred embodiment the B-cell epitope is not a selected from the group consisting of an integrin, especially a $\beta_1$, $\beta_3$, $a_v\beta_3$ or $a_v\beta_5$ integrin, and CD13.

In a preferred embodiment the epitope is not fused to the N-terminus of the structural protein of the virus, especially not fused to the N-terminus of VP1 or VP2, whereas fusion to the N-terminus of VP3 is envisaged within this invention.

In a preferred embodiment the parvovirus mutated structural protein is capable of inducing an immunoglobulin capable of binding to the antigen the B-cell epitope is derived from.

It is an important feature, that the B-cell epitope is located on the surface of the virus.

In a preferred embodiment of the instant invention the structural protein of a parvovirus as defined above comprises an anti-idiotypic epi-/mimotope of an anti-IgE antibody, and/or an IgE epi-/mimotope.

Vaccines for the Treatment of Asthma and Allergic Diseases

Atopic asthma and allergic rhinitis are caused by adverse immune responses, typified by IgE, against otherwise harmless environmental proteins, allergens. In sensitized individuals, allergen-specific IgE becomes localized in tissues by binding to the high-affinity receptor for IgE, FεRI, expressed by mast cells in various tissues and basophils as well as eosinophils in the blood. Subsequent encounters with the allergen result in cross-linking of IgE/FcRI, which triggers effector cell degranulation and the release of both preformed mediators (histamine, proteolytic enzymes, and proteoglycans) and de novo synthesized mediators (prostaglandin $D_2$, leukotrienes, and cytokines). Together, these mediators are responsible for the clinical manifestations of allergic reactions, including hay fever, asthma, and eczema, as well as life-threatening anaphylactic reactions. Standard therapy includes inhaled corticostreroids (ICS), Beclomethasone Dipropionate (BDP), long-acting β-agonists (LABA) and leukotriene receptor antagonists (LTRAs).

The receptor-binding region of human IgE was previously mapped to the N-terminal region of the CH3 domain (Helm et al., 1988. Helm et al., 1989). Site-directed mutagenesis studies to identify the amino acid residues directly involved in the interaction have been conducted on both IgE (Presta et al., 1994) and FcεRI (Cook et al., 1997). In addition, the crystal structure of the human IgE-FcεRIα complex was recently solved by Garman and colleagues (Garman et al., 2000). The amino acid regions that are involved in receptor binding are localized in three loops and spread over most of the Cε3 domain (Pro-364, Arg-365, Arg-408, Ser-411, Lys-415, Glu-452, Arg-465, and Met-469). Binding is mediated primarily by electrostatic interaction.

Anti-IgE therapy is based on antibodies which bind the receptor-binding target domain Cε3 region of IgE, thereby preventing the binding of IgE to the FcεRI receptor and, therefore, preventing sensitization of mast cells and basophils. However, even if 99% of free IgE were neutralized by the anti-IgE antibody, the therapy still would fail because the few remaining IgE molecules would be sufficient to sensitize the respective cells. Therapeutic efficacy is provided through additional actions: FcεRI expression is regulated by the level of free IgE, in a way that reduced levels of free IgE lead to lowered densities of FcεRI on basophils and mast cells and lowered sensitivities. And, anti-IgE may lead to down-regulation of IgE production by eliminating or down-regulating IgE-expressing B cells, perhaps by cross-linking membrane-bound IgE and causing apoptosis, anergy or most likely also by complement-mediated and cell-mediated cytolysis (Wang et al., 2003). The latter mechanism was, however, not found in clinical trials performed with Omalizumab. For this monoclonal antibody, reduction of IgE production from B-cells (plasma cells) mediated by lowered IgE levels was only observed in animal and in-vitro experiments.

Most of the therapeutic monoclonal antibodies in development can only bind and neutralize free IgE or IgE associated with B-cells. In contrast, FcεRI-bound IgE is not accessible for these anti-IgE antibodies. Anti-IgE antibodies directed against regions of the IgE molecule outside of the receptor binding region (such as the variable, antigen-binding domain of IgE referred to as the IgE idiotype), can bind to an IgE molecule while it is bound to its receptor. This results in cross-linking of receptor-bound IgE, causing an anaphylactic shock in animals treated systemically with such antibodies. Importantly, except for defense mechanisms against parasite infections, IgE seems to play no role in normal physiology and IgE-deficient people are healthy with no apparent sign of pathology (Levy and Chen, 1970).

Omalizumab (XOLAIR®) is a humanized monoclonal anti-IgE antibody for passive immunization, and the first available/approved anti-IgE therapy on the market. A total of 7 phase III clinical trials were performed with this monoclonal anti-IgE antibody, which bind to the Cε3 region of IgE (for a review refer to (Bousquet et al., 2005) without crosslinking the FcεRI receptor. Omalizumab significantly reduced the rate of asthma exacerbations by 38% and the rate of total emergency visits by 47%. The efficacy of Omalizumab was unaffected by patient age, gender, baseline serum IgE or by 2- or 4-weekly dosing schedule, although benefit in absolute terms appeared to be greatest in patients with more severe asthma, defined by a lower value of percentage predicted forced expiratory volume in 1 s ($FEV_1$) at baseline.

As outlined before, one disadvantage of passive immunization with a monoclonal antibody is the requirement of infusions every 2-4 weeks with relatively high antibody doses making such therapies expensive. Therefore, alternative approaches are needed for the treatment of allergic diseases such as atopic allergies or asthma.

According to the present invention this problem is solved by a structural protein of a parvovirus comprising an anti-idiotypic epi-/mimotope of an anti-IgE antibody, and/or an IgE epi-/imimotope. Such structural proteins are preferably capable of forming virus-like particles. They harbor anti-idiotypic epi-/mimotopes of an anti-IgE antibody and/or IgE epi-/mimotopes on the surface of the capsid shell. Therefore, the anti-idiotypic epi-/mimotopes of an anti-IgE antibody, respectively the IgE epi-/mimotopes are accessible to the humoral immune system. Such structural protein can be used in patients to induce specifically an immune response against IgE, meaning antibodies that cross-react with IgE (anti-IgE antibodies), thereby preventing binding of IgE to its high affinity receptor FcRI.

For a lot of the publicly available therapeutic antibodies which can be used as target antibody for AAV selection, the epitopes are not known. To be able to compare the epitopes of the target antibodies and the antibodies induced in e.g. mice after vaccination, epitope mapping can be performed. For example, epitopes recognized by anti mouse or anti human IgE antibodies can be identified from arrays using overlapping peptide scans from the respective IgE spotted on nylon membranes. Preferred antibodies are those with a binding pattern similar to that of Omalizumab, that can be used for selection of mimitopes from the AAV capsid library. Epitopes recognized by antibodies induced in e.g. mice after vaccination can be identified from arrays spotted on glass slides. Cross-reactivity of anti human IgE antibodies or antibodies induced in mice after vaccination with the constant chain regions of other Ig's can be monitored in Westernblot experiments.

Especially preferred embodiments of the invention are structural proteins of parvoviruses, especially AAV, that contain IgE epitopes or mimotopes, preferably previously known epitopes or mimotopes. As described by Rudolf, Stadler, Vogel and colleagues (Rudolf et al., 1998, Rudolf et al., 2000, Stadler et al., 1999, Vogel et al., 2000), one can develop so-called mimotope immunization vaccines based on peptide phage display libraries screened for particles recognizing BSW17, a mouse monoclonal anti-human IgE antibody. Peptide sequences best recognized by BSW17 are the mimotope sequences EFCINHRGYWVCGD ('Rudolf' (Rudolf et al., 2000)), and (SEQ ID NO: 84)

INHRGYWV ('C4M', {Rudolf, 2000 #52}) (SEQ ID NO: 203)

with G, W and V (underlined) being conserved among all sequences identified (the cysteine residues (in bold) mediate a circular form of the peptide via disulfide bridging) and the epitope VNLTWSRASG (Kricek et al., 1999). (SEQ ID NO: 85)

In the course of this invention previously novel epitopes that are especially suitable for vaccination purposes against allergic diseases like asthma have been identified:

```
                                  (SEQ ID NO: 204)
EKQRNGTLT ('Bind2')

(SEQ ID NO: 205)
EDGQVMDVDLS ('Flex')

(SEQ ID NO: 206)
TYQCRVTHPHLPRALMR ("3DEpi1")

(SEQ ID NO: 207)
RHSTTQPRKTKGSG ("3DEpi2")

(SEQ ID NO: 208)
DSNPRGVSAYLSR ("3DEpi3")

(SEQ ID NO: 209)
TITCLVVDLAPSK ("3DEpi4")

(SEQ ID NO: 210)
KTKGSGFFVF ("C4E")

(SEQ ID NO: 211)
THPHLPRALMRS ("Wang-CS")

(SEQ ID NO: 212)
GETYQCRVTHPHLPRALMRSTTK ("Wang")

(SEQ ID NO: 213)
LPRALMRS (C21)
```

Accordingly, the present invention further relates to novel IgE B-cell epitopes Bind2, Flex, 3DEpi1, 3DEpi2, 3DEpi3, 3DEpi4, C4E, Wang-CS, Wang, and C21 and/or to a functionally active variant thereof. A functionally active variant of these epitopes means a B-cell epitope which generates in a rabbit vaccination experiment according to example 10.9 a B-cell response measurable as titer of specific antibodies binding to human IgE. The invention further relates to medicaments in general comprising such epitopes or functionally active variants thereof, preferably vaccines comprising such epitopes or functionally active variants thereof for the treatment or prevention of allergic diseases, especially asthma.

Such functionally active variants can either be single peptides or mixtures of single peptides consisting of peptide sequences of up to 40 amino acids, preferably up to 25 amino acids, more preferably 15 amino acids, especially 9 amino acids of the given sequence, or a fusion of such functionally active variant to a carrier. Such carrier is meant to be any molecule except for the naturally occurring IgE protein or part thereof (larger than the functionally active variant), preferably a parvoviral particle, but also a different virus- or bacteriophage particle, a polymer (e.g. LPH) or a fusion protein, capable of generating a B cell response (as defined above) against such functionally active variant. Such fusion to a carrier can i.e. be obtained by chemically linking the variant to the carrier or by genetically making fusion proteins or insertion variants.

Figure 14:
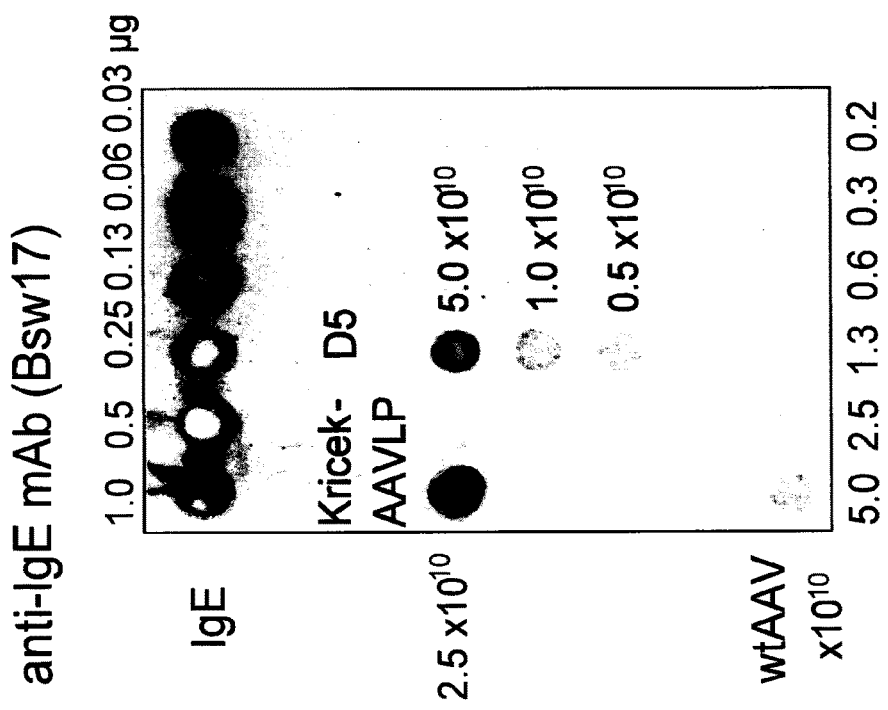

These and similar sequences or parts therefore including or excluding the cysteine residues and flanking sequences can be introduced into positions I-587 and others of AAV VP as described in FIG. 14. The corresponding AAV particles can be manufactured (initially as genome-containing infectious AAV), purified and characterized. Although AAV capsids have a different conformational structure than phages, the chance that a similar structure of the mimotope sequence EFCINHRGYWVCGD (SEQ ID NO: 84) is present on both, phages and AAV, is high due to the cysteine residues building up a loop structure of the peptide sequence. For linear epitopes such as VNLTWSRASG (SEQ ID NO: 85), interchangeability should also be possible. If these AAV particles bind BSW17 (the anti-IgE antibody used for phage display), they can be used as an anti-IgE vaccine that can be used with and without co-formulation in a suitable adjuvant.

Especially preferred embodiments of the invention are structural proteins of parvoviruses that contain IgE epi-/mimotopes that, once injected into an immunocompetent mammal, induce anti-IgE specific antibodies with therapeutic efficacy without cross-linking properties. Cross-linking properties means that in an immunocompetent mammal the generated anti-IgE antibodies are binding IgE molecules in a way that IgE/FcεRI binding is still possible. By such way, and if one antibody binds several IgE molecules at a time, the high-affinity FcεRI receptor is crosslinked on effector cells leading to its degranulation. This would induce a systemic anaphylactic shock. On the other hand, the structural proteins of parvoviruses should be able to directly crosslink the respective B-cell receptor (binding the IgE epi-/mimotopes or the anti-idiotype epi-/mimotope of an anti-IgE antibody) to activate the corresponding B-cells and to induce anti-IgE antibody production independent of a T-cell response.

Vaccines for the Treatment of Alzheimer's Disease

Especially preferred embodiments of the invention are structural proteins of parvoviruses, especially AAV, that contain β-amyloid epitopes or mimotopes, preferably known epitopes or mimotopes, that can be used for the treatment of Alzheimer disease. In the context of the present invention a B-cell epitope of f-amyloid was inserted into a parvovirus capsid and displayed on the surface of the capsid. In a preferred embodiment the B-cell epitope is a human epitope. Preferably it is inserted into I-453 and/or I-587, especially into I-453 and/or I-587 of AAV1, AAV2 or AAV-6. In an especially preferred embodiment the B-cell epitope has the sequence DAEFRHDSG (SEQ ID NO: 158).

In general, misfolded proteins leading to a protein aggregation and, therefore, causing conformational diseases, are good candidate targets for an active immunization approach with AAV vaccines. Ideally, B-cell epitopes represented by misfolded proteins or protein aggregates only are chosen for presentation on AAV particles (for an overview, please refer to Uversky et al., 2006, especially; table 1-1).

Vaccines for the Treatment of Atherosclerosis

Atherosclerosis is a disease affecting arterial blood vessels. It is a chronic inflammatory response in the walls of arteries, in large part due to the accumulation of macrophage white blood cells and promoted by low density (especially small particle) lipoproteins (plasma proteins that carry cholesterol and triglycerides) without adequate removal of fats and cholesterol from the macrophages by functional high density lipoproteins (HDL). It is commonly referred to as a "hardening" or "furring" of the arteries. It is caused by the formation of multiple plaques within the arteries. There is a strong inverse relationship between the plasma concentration of cholesterol in HDLs (HDL-C) and the development of coronary heart disease (CHD). Plasma concentration of HDL-C is a powerful predictor of CHD. Although 33% of patients with CHD have low plasma levels of HDL-C as their primary lipid abnormality, there is currently no effective therapy for increasing the plasma concentration of HDL-C. Diet and moderate exercise are ineffective, statins afford only a modest 5% to 7% increase in HDL-C, and niacin has side effects and compliance profiles that limit its use.

One therapeutic approach that has been suggested for increasing plasma HDL-C concentrations is the inhibition of cholesteryl ester transfer protein (CETP) activity. CETP is a 74-kDa plasma glycoprotein that facilitates transfer of neutral lipids and phospholipids between lipoproteins and contributes to the regulation of plasma concentration of HDL-C. CETP functions in the plasma to lower the concentration of HDL-C by moving cholesteryl esters from HDLs to VLDLs and LDLs (Rittershaus et al., 2000).

Accordingly it is one embodiment of the invention to provide structural proteins of parvoviruses, especially AAV, that contain CETP epitopes or mimotopes that can be used for the treatment of atherosclerosis. Suitable epitopes or mimotopes are the human CETP derived peptides hTP10, hTP11, hTP12, hTP13, hTP18 and hTP20, hRitsch-1, hRitsch-2, hRitsch-3, hCETP-intern and hCETP C-Term:

```
                                        (SEQ ID NO: 214)
     PKTVSNLTESSSESVQS (hTP10)

(SEQ ID NO: 215)
     SLMGDEFKAVLET (hTP11)

(SEQ ID NO: 216)
     QHSVAYTFEED (hTP12)

(SEQ ID NO: 217)
     INPEIITRDG (hTP13)

(SEQ ID NO: 218)
     DISLTGDPVITASYL (hTP18)

(SEQ ID NO: 219)
     DISLTGDPVITA (hTP20)

(SEQ ID NO: 220)
     DQSIDFEIDSA (hRitsch-1)

(SEQ ID NO: 221)
     KNVSEDLPLPTFSPTLLGDS (hRitsch-2)

(SEQ ID NO: 222)
     KNVSEDLPLPT (hRitsch-3)

(SEQ ID NO: 223)
     CDSGRVRTDAPD (hCETP-intern)

(SEQ ID NO: 224)
     FPEHLLVDFLQSLS (hCETP C-Term)
```

The present invention further relates to novel CETP B-cell epitopes hTP10, hTP11, hTP12, hTP13, hTP18, hTP20, hRitsch-1, hRitsch-2, hRitsch-3, hCETP-intern and hCETP C-Term and/or to a functionally active variant thereof. The invention further relates to medicaments in general comprising such epitopes or functionally active variants thereof, preferably vaccines comprising such epitopes or functionally active variants thereof for the treatment or prevention of atherosclerosis.

Vaccines for the Treatment of Tumor Diseases

Antibody therapies such as Herceptin, Avastin, Erbitux, Omnitarg, Rituxan, Campath, Zevalin, Mylotarg, Bexxar or Panitumumab play an increasing role in fighting various types of tumor diseases. These antibodies specifically bind epitopes of factors causing uncontrolled cellular growth, such as growth factor receptors or growth factors. Accordingly, it is a further embodiment of this invention to provide structural proteins of parvoviruses, especially AAV, that contain epitopes of such factors causing uncontrolled cellular growth.

HER2/neu (also known as ErbB-2, ERBB2) is a protein giving higher aggressiveness in breast cancers. It is a member of the ErbB protein family, more commonly known as the epidermal growth factor receptor family. HER2/neu has also been designated as CD340. HER2/neu is notable for its role in the pathogenesis of breast cancer and as a target of treatment. It is a cell membrane surface-bound receptor tyrosine kinase and is normally involved in the signal transduction pathways leading to cell growth and differentiation. Approximately 25-35 percent of breast cancers have an amplification of the HER2/neu gene or overexpression of its protein product. Overexpression also occurs in other cancer such as ovarian cancer and stomach cancer. Clinically, HER2/neu is important as the target of the monoclonal antibody trastuzumab (marketed as Herceptin).

As for an active vaccination approach, the epitope sequence QMWAPQWGPD (SEQ ID NO: 225) presented in a circular way has been shown to induce polyclonal antibodies with therapeutic effectiveness. Therefore, an Her2/NEU-AAV vaccine can be generated by insertion of the peptide

QMWAPQWGPD (SEQ ID NO: 225)

into AAV using suitable adaptor sequences (Riemer et al., 2007).

Vaccines for the Treatment of Autoimmune Diseases and Chronic Inflammatory Diseases Autoimmune diseases as well as inflammatory diseases arise from an overactive immune response of the body against substances and tissues normally present in the body. In other words, the body attacks its own cells.

Rheumatoid arthritis (RA) is an autoimmune disease which causes chronic inflammation of the joints, the tissue around the joints, as well as other organs in the body affecting 0.5-1.0% of the population in the industrialized world. It commonly leads to significant disability and consequently to a significant reduction of quality of life. If not treated appropriately, RA leads to a reduction of life expectancy (Smolen and Steiner, 2003).

Psoriasis is a chronic inflammatory disease of the skin characterized by overgrowth of epidermal cells, angiogenesis, infiltration of immune cells, and increased production of cytokines.

Similar activation of immune cells and increased production of cytokines is associated with autoimmune diseases and (chronic) inflammatory diseases as further listed below.

In order to limit or control such disease causing/related immune responses it has become an established therapeutic modality to neutralize cytokines involved in the pathogenesis of autoimmune and inflammatory diseases. Antibodies (infliximab, adalimumab) and a soluble receptor construct neutralizing the action of TNF-α (etanercept) have been established in the treatment of RA and other disease. Now there is evidence implicating several novel cytokines, including IL-32 and IL-17, in the pathogenesis of RA. In addition we assess the development of existing targets as they move towards clinical evaluation, particularly IL-1, IL-6, IL-15, IL-18 and the IL-12 superfamily (Asquith et al., 2007).

Vaccines for the Treatment of Infectious Diseases

Blocking of viral infection by induction of auto-antibodies against the cellular receptor of the virus is a suggested mechanism of a preventive or therapeutic vaccination against viruses, preferably for viruses where classical vaccination attemps have failed like HIV using CCR5 as the target receptor (Chackerian, 1999).

Accordingly, preferred embodiments of the invention are structural proteins of parvoviruses, especially AAV, that contain epitopes or mimotopes of viral receptors, preferably of CCR5, preferably known epitopes or mimotopes that can be used as vaccines for the treatment of such viral infection and associated diseases, preferably HIV infection/AIDS. In a preferred embodiment the B-cell epitope is a human epitope.

Preferred B-cell epitopes are HYAAAQWDFGNTMCQL (SEQ ID NO: 357), YAAQWDFGNTMCQ (SEQ ID NO: 358), RSQKEGLHYT (SEQ ID NO: 359) or a functionally active variant thereof.

Accordingly, preferred embodiments of the invention are structural proteins of parvoviruses, especially AAV, that contain epitopes or mimotopes of cytokines, preferably of TNF-α, IL-6 and/or IL-17, preferably known epitopes or mimotopes, that can be used for the treatment of autoimmune diseases and/or chronic inflammatory diseases, preferably rheumatoid arthritis and/or Crohn's disease. In a preferred embodiment the B-cell epitope is a human epitope. Preferably it is inserted into I-453 and/or I-587, especially into I-453 and/or I-587 of AAV1, AAV2 or AAV-6. Preferred B-cell epitopes are the human epitopes:

```
                                    (SEQ ID NO: 226)
         SSRTPSDKPVAHVVANPQAE (TNF-α V1)

(SEQ ID NO: 227)
         SRTPSDKPVAHVVANP (TNF-α V2)

(SEQ ID NO: 228)
         SSRTPSDKP (TNF-α V3)

(SEQ ID NO: 229)
         NADGNVDYHMNSVP (IL-17 V1)

(SEQ ID NO: 230)
         DGNVDYHMNSV (IL-17 V2)

(SEQ ID NO: 231)
         RSFKEFLQSSLRALRQ (IL-6 V1)

(SEQ ID NO: 232)
         FKEFLQSSLRA (IL-6 V2)
```

The present invention further relates to novel cytokine B-cell epitopes TNF-α V1, TNF-αV2, TNF-α V3, IL-17 V1, IL-17 V2, IL-6 V1 and IL-6 V2 and/or to a functionally active variant thereof. The invention further relates to medicaments in general comprising such epitopes or functionally active variants thereof, preferably vaccines comprising such epitopes or functionally active variants thereof for the treatment or prevention of autoimmune diseases and/or chronic inflammatory diseases, preferably rheumatoid arthritis, Crohn's disease or psoriasis.

According to this invention the structural proteins of parvoviruses are the viral capsid proteins that are referred to as VP-1, VP-2 and in many instances VP-3 for most of the known parvoviruses, especially the AAV. In principal the recombinant parvoviruses made from a mutant cap gene can be used directly for vaccination in animal models or even in humans. However, as such a vaccination is a gene therapy it is preferred to use inactivated (e.g. by gamma or UV-irradiation) genome-containing AAV particles, or virus-like particles of the respective parvovirus for vaccination purposes. Such virus-like particles are capsid-like structures that are composed of the structural proteins of the respective parvovirus, e.g. VP-1, VP-2 and/or VP-3, or parts thereof such as N- or C-terminal truncated structural proteins but do not contain a viral genome. VP-2 alone has been shown to assemble into virus-like particles and can be expressed in various expression systems such as bacteria e.g. *E. coli*, yeasts, e.g. *Saccharomyces cerevisiae, hansenula polymorpha, Pichla pastoris*, in insect cells, e.g. the baculovirus expression system (SF9, SF+ or High Five cells), or in mammalian cells (such as CHO, HeLa, 293, BHK, or PerC6).

Another preferred embodiment are structural proteins of parvoviruses that do not form regular virus-like particles but capsomers or other regular or amorphous aggregates that present the foreign epi-/mimotopes in a highly structured and/or dense manner.

The parvoviral mutated structural protein can further be fused to a second protein or peptide. Such second proteins can be tags, such as provided in Table 3. Tags can for example be used for purification purposes.

Preferably the parvoviral mutated structural protein is capable of forming a multimeric structure. Accordingly, another subject of the invention relates to a multimeric structure comprising parvovirus mutated structural proteins according to the invention. Such multimeric structure can be a capsomer, a virus-like particle or a virus. Capsomers are multimeric subunits of a viral capsid, typically consisting of 5-6 capsid proteins (pentamers and hexamers). Virus-like particles are empty viruses, meaning that they do not comprise genetic material such as a viral genome or relevant part thereof.

The multimeric structure may also be an aggregate of at least 5, preferably at least 10, more preferably at least 30, most preferably at least 60 structural proteins. Compared to capsomers or virus-like particles aggregates are amorphous structures with no symmetric order.

Preferably the B-cell epitope heterologous to the parvovirus is located on the surface of the multimeric structure.

A further embodiment of the present invention is a nucleic acid coding for a parvovirus mutated structural protein of the invention such as DNA, RNA, mRNA etc.

A further embodiment of the present invention is a virus that comprises a parvovirus mutated structural protein of the invention and or nucleic acid coding for a parvovirus mutated structural protein of the invention. Such virus may be active or inactive, for example it may have been inactivated through standard techniques such as attenuation or irradiation.

A further embodiment of the present invention is a cell comprising a nucleic acid coding for the parvovirus mutated structural protein. Such cell can be a bacterium, preferably *E. coli*, a yeast cell, preferably *s. cerevisiae, hansenula polymorpha* or *pichia pastoris*, an insect cell, preferably SF-9, SF+ or High5, or a mammalian cell, preferably HeLa, 293, VERO, PERC6, BHK or CHO.

The parvovirus mutated structural proteins of the invention can be prepared by the method comprising the steps of (a) expressing the nucleic acid coding for the parvovirus mutated structural protein by cultivating the cell as defined above under suitable conditions, and (b) isolating the expressed parvovirus mutated structural protein of step (a).

Another subject of the invention relates to a medicament, particularly a vaccine comprising at least one parvovirus mutated structural protein of the invention and/or a nucleic acid of the invention, preferably at least one multimeric structure of the invention. Preferably, the medicament is a vaccine.

In a preferred embodiment of the invention a vaccine is a mixture of more than one multimeric structures comprising parvovirus mutated structural proteins as further defined herein. Preferably two to three virus-like particles of a parvovirus displaying different B-cell epitopes as further defined herein are combined for the vaccination of a patient. Further, it is envisaged that a vaccine according to this invention is combined with some other type of vaccine for convenience of the patient.

The medicament of the present invention may further encompass pharmaceutically acceptable carriers and/or excipients. The pharmaceutically acceptable carriers and/or excipients useful in this invention are conventional and may include buffers, stabilizers, diluents, preservatives, and solubilizers. Remington's Pharmaceutical Sciences, by E. W. Martin, Mack Publishing Co., Easton, Pa., 15th Edition (1975), describes compositions and formulations suitable for pharmaceutical delivery of the (poly)peptides herein disclosed. In general, the nature of the carrier or excipients will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e. g. powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In a preferred embodiment the medicament further comprises an immunostimulatory substance such as an adjuvant. The adjuvant can be selected based on the method of administration and may include mineral oil-based adjuvants such as Freund's complete and incomplete adjuvant, Montanide incomplete Seppic adjuvant such as ISA, oil in water emulsion adjuvants such as the Ribi adjuvant system, syntax adjuvant formulation containing muramyl dipeptide, or aluminum salt adjuvants. Preferably, the adjuvant is a mineral oil-based adjuvant, especially ISA206 (SEPPIC, Paris, France), most preferably ISA51 (SEPPIC, Paris, France). In another preferred embodiment the parvovirus mutated structural protein is co-formulated with at least one suitable adjuvant such as CpG, Imidazoquinolines, MPL, MDP, MALP; flagellin, LPS, LTA, or cholera toxin or derivative thereof, HSP60, HSP70, HSP90, saponins, QS21, ISCOMs, CFA, SAF, MF59, adamantanes, aluminum hydroxide, aluminum phosphate or a cytokine.

In a more preferred embodiment the immunostimulatory substance is selected from the group comprising polycationic polymers, especially polycationic peptides such as polyarginine, immunostimulatory deoxynucleotides (ODNs), peptides containing at least two LysLeuLys motifs, especially KLKLLLLLKLK, neuroactive compounds, especially human growth hormone, alumn, adjuvants or combinations thereof. Preferably, the combination is either a polycationic polymer and immunostimulatory deoxynucleotides or of a peptide containing at least two LysLeuLys motifs and immunostimulatory deoxynucleotides. In a still more preferred embodiment the polycationic polymer is a polycationic peptide.

In an even more preferred embodiment of the invention the immunostimulatory substance is at least one immunostimulatory nucleic acid. Immunostimulatory nucleic acids are e.g. neutral or artificial CpG containing nucleic acids, short stretches of nucleic acids derived from non-vertebrates or in form of short oligonucleotides (ODNs) containing non-methylated cytosine-guanine dinucleotides (CpG) in a defined base context (e.g. as described in WO 96/02555). Alternatively, also nucleic acids based on inosine and cytidine as e.g. described in WO 01/93903, or deoxynucleic acids containing deoxy-inosine and/or deoxyuridine residues (described in WO 01/93905 and WO 02/095027) may preferably be used as immunostimulatory nucleic acids in the present invention. Preferably, mixtures of different immunostimulatory nucleic acids are used in the present invention. Additionally, the aforementioned polycationic compounds may be combined with any of the immunostimulatory nucleic acids as aforementioned. Preferably, such combinations are according to the ones described in WO 01/93905, WO 02/32451, WO 01/54720, WO 01/93903, WO 02/13857 and WO 02/095027 and the AU application A 1924/2001.

In a further embodiment the medicament comprising the parvovirus mutated structural protein comprising at least one B-cell epitope heterologous to the parvovirus is (used for the manufacture of) a vaccine, preferably for preventing or treating an autoimmune disease (e.g. diabetes type 1), a tumor disease (examples are: melanoma: e.g. HMW MAA, glioblastome multiforme: e.g. CA125, anti-IL13R, colon cancer: e.g. CA125 or anti-EGF(R), breast cancer: e.g. Her2/NEU, ovarian cancer e.g. L1 adhesion molecule, B-cell lymphoma: e.g. CD20), an allergic disease (asthma, allergies such as allergic rhinitis, examples for targets are IgE, IL-4, IL-9, IL-13), a metabolic disease (e.g. high cholesterol, intervention into the cholesterol metabolism (target example: CETP), obesity, hypertension (target example: angiotensin II), an inflammatory disease (e.g. rheumatoid arthritis, Crohn's disease; target examples: IL-6, IL-17 and TNF-α), a neurological disease (e.g. Alzheimer's disease; target example: β-Amyloid) or to be used in ophthalmology (e.g. AMD; target example: VEGF).

Also encompassed by the present inventions are methods for vaccination and/or for treating or preventing the diseases specified herein by administering to a patient an effective amount of a parvovirus mutated structural protein of the invention and or nucleic acid coding for a parvovirus mutated structural protein of the invention.

Accordingly, a further aspect of the present invention relates to a medicament of of the invention for the treatment and/or prevention of a) an allergic disease and/or asthma whereas the B cell epitope comprises an anti-idiotypic epi-/mimotope of an anti-IgE antibody, and/or an IgE epi-/mimotope, particularly a mimotope of sequence of EFCINHRGYWVCGD or INHRGYWV, with the first G, W and V being conserved and cysteine residues C mediating a circular form of the peptide via disulfide bridging, or particularly an epitope selected from the group consisting of EKQRNGTLT (SEQ ID NO: 204), EDGQVMDVDLS (SEQ ID NO: 205), TYQCRVTHPHLPRALMR (SEQ ID NO: 206), RHSTTQPRKTKGSG (SEQ ID NO: 207), DSNPRGVSAYLSR (SEQ ID NO: 208), TITCLVVDLAPSK (SEQ ID NO: 209), KTKGSGFFVF (SEQ ID NO: 210), THPHLPRALMRS (SEQ ID NO: 211), GETYQCRVTHPHLPRALMRSTTK (SEQ ID NO: 212), LPRALMRS (SEQ ID NO: 213) and a functionally active variant thereof;

b) Alzheimer's disease whereas the B cell epitope comprises a β-amyloid epitope or mimotope, particularly comprising or having the sequence DAEFRHDSG (SEQ ID NO: 158) or a functionally active variant thereof;

c) atherosclerosis whereas the B cell epitope comprises a CETP epitope or mimotope, particularly an epitope selected from the group consisting of PKTVSNLTESSSESVQS (SEQ ID NO: 214), SLMGDEFKAVLET (SEQ ID NO: 215), QHSVAYTFEED (SEQ ID NO: 216), INPEIITRDG (SEQ ID NO: 217). DISLTGDPVITASYL (SEQ ID NO: 218), DISLTGDPVITA (SEQ ID NO: 219), DQSIDFEIDSA (SEQ ID NO: 220), KNVSEDLPLPTFSPTLLGDS (SEQ ID NO: 221), KNVSEDLPLPT (SEQ ID NO: 222), CDSGRVRTDAPD (SEQ ID NO: 223), FPEHLLVDFLQSLS (SEQ ID NO: 224) and a functionally active variant thereof;

d) a tumor disease whereas the B cell epitope comprises a growth factor receptors or growth factors epitope or mimotope, particularly a HER2/neu epitope or mimotope, especially the epitope QMWAPQWGPD (SEQ ID NO: 225) or a functionally active variant thereof;

e) an autoimmune disease and/or chronic an inflammatory disease, preferably rheumatoid arthritis and/or Crohn's disease, whereas the κ cell epitope comprises an epitope or mimotope of a cytokine, preferably of TNF-α, IL-6 and/or IL-17, especially an epitope selected from the group consisting of SSRTPSDKPVAHVVANPQAE (SEQ ID NO: 226), SRTPSDKPVAHVVANP (SEQ ID NO: 227), SSRTPSDKP (SEQ ID NO: 228), NADGNVDYHMNSVP (SEQ ID NO: 229), DGNVDYHMNSV (SEQ ID NO: 230), RSFKEFLQSSLRALRQ (SEQ ID NO: 231), FKEFLQSSLRA (SEQ ID NO: 232) and a functionally active variant thereof; or f) an infectious disease, preferably HIV infection, whereas the B cell epitope comprises an epitope or mimotope of a viral receptor, preferably of CCR5, especially an epitope selected from the group consisting of HYAAAQWDFGNTMCQL (SEQ ID NO: 357), YAAQWDFGNTMCQ (SEQ ID NO: 358), RSQKEGLHYT (SEQ ID NO: 359) and a functionally active variant thereof.

In a still further aspect of the present invention the medicament of the invention as specifid herein is used in a method of treating or preventing a) an allergic disease and/or asthma whereas the B cell epitope comprises an anti-idiotypic epi-/mimotope of an anti-IgE antibody, and/or an IgE epi-/mimotope, particularly a mimotope of sequence of EFCINHRGYWVCGD or INHRGYWV, with the first G, W and V being conserved and cysteine residues C mediating a circular form of the peptide via disulfide bridging, or particularly an epitope selected from the group consisting of EKQRNGTLT (SEQ ID NO: 204), EDGQVMDVDLS (SEQ ID NO: 205), TYQCRVTHPHLPRALMR (SEQ ID NO: 206). RHSTTQPRKTKGSG (SEQ ID NO: 207), DSNPRGVSAYLSR (SEQ ID NO: 208), TITCLVVDLAPSK (SEQ ID NO: 209), KTKGSGFFVF (SEQ ID NO: 210), THPHLPRALMRS (SEQ ID NO: 211), GETYQCRVTHPHLPRALMRSTTK (SEQ ID NO: 212), LPRALMRS (SEQ ID NO: 213) and a functionally active variant thereof;

b) Alzheimer's disease whereas the B cell epitope comprises a β-amyloid epitope or mimotope, particularly comprising or having the sequence DAEFRHDSG (SEQ ID NO: 158) or a functionally active variant thereof;
c) atherosclerosis whereas the B cell epitope comprises a CETP epitope or mimotope, particularly an epitope selected from the group consisting of PKTVSNLTESSS-ESVQS (SEQ ID NO: 214), SLMGDEFKAVLET (SEQ ID NO: 215), QHSVAYTFEED (SEQ ID NO: 216), INPEIITRDG (SEQ ID NO: 217), DISLTGDPVITASYL (SEQ ID NO: 218), DISLTGDPVITA (SEQ ID NO: 219), DQSIDFEIDSA (SEQ ID NO: 220), KNVSEDLPLPTF-SPTLLGDS (SEQ ID NO: 221), KNVSEDLPLPT (SEQ ID NO: 222), CDSGRVRTDAPD (SEQ ID NO: 223), FPEHLLVDFLQSLS (SEQ ID NO: 224) and a functionally active variant thereof;
d) a tumor disease whereas the B cell epitope comprises a growth factor receptors or growth factors epitope or mimotope, particularly a HER2/neu epitope or mimotope, especially the epitope QMWAPQWGPD (SEQ ID NO: 225) or a functionally active variant thereof;
e) an autoimmune disease and/or chronic an inflammatory disease, preferably rheumatoid arthritis and/or Crohn's disease, whereas the B cell epitope comprises an epitope or mimotope of a cytokine, preferably of TNF-α, IL-6 and/or IL-17, especially an epitope selected from the group consisting of SSRTPSDKPVAHVVANPQAE (SEQ ID NO: 226), SRTPSDKPVAHVVANP (SEQ ID NO: 227), SSRTPSDKP (SEQ ID NO: 228), NADGN-VDYHMNSVP (SEQ ID NO: 229), DGNVDYHMNSV (SEQ ID NO: 230), RSFKEFLQSSLRALRQ (SEQ ID NO: 231), FKEFLQSSLRA (SEQ ID NO: 232) and a functionally active variant thereof; or
f) an infectious disease, preferably HIV infection, whereas the B cell epitope comprises an epitope or mimotope of a viral receptor, preferably of CCR5, especially an epitope selected from the group consisting of HYAAAQWDF-GNTMCQL (SEQ ID NO: 357), YAAQWDFGNTMCQ (SEQ ID NO: 358), RSQKEGLHYT (SEQ ID NO: 359) and a functionally active variant thereof, wherein an effective amount of the medicament is administered to a patient in need of the prevention or treatment.

The vaccine used for immunization may be administered to a subject in need thereof, preferably mammals, and still more preferably humans, in any conventional manner, Including oral, intranasal, intramuscular (i.m.), intra-lymph node, intradermal, intraperitoneal, subcutaneous (s.c.), and combinations thereof, but most preferably through intramuscular injection.

The volume of each dose for administration is preferably up to about 5 ml, still more preferably between 1 ml and 3 ml, and most preferably about 2 ml. The volume of the dose when intramuscular injection is the selected administration route is preferably up to about 5 ml, preferably up to 3 ml, preferably between 1 ml and 3 ml, more preferably between 0.5 ml and 2 ml, and most preferably about 1 ml. The amount of vaccine in each dose should be enough to confer effective immunity against and decrease the risk of developing clinical signs to a subject receiving a vaccination therewith.

Preferably, the unit dose of protein or nucleic acid should be up to about 5 μg protein/kg body weight, more preferably between about 0.2 to 3 μg, still more preferably between about 0.3 to 1.5 μg, more preferably between about 0.4 to 0.8 μg, and still more preferably about 0.6 μg. Alternative preferred unit doses could be up to about 6 μg protein or nucleic acid/kg body weight, more preferably between about 0.05 to 5 μg, still more preferably between about 0.1 to 4 μg.

The dose is preferably administered 1 to 4 times, especially 1 to 3 times, e.g. with an interval of 1 to 3 weeks. Preferred amounts of protein per dose are from approximately 1 μg to approximately 1 mg, more preferably from approximately 5 μg to approximately 500 μg, still more preferably from approximately 10 μg to approximately 250 μg and most preferably from approximately 25 μg to approximately 100 μg.

Nucleic acid delivery compositions and methods are known to those of skill in the art. The nucleic acid of the invention may be employed in the methods of this invention or in the compositions described herein as DNA sequences, either administered as naked DNA, associated with a pharmaceutically acceptable carrier or comprised in a vector. The nucleic may be administered therapeutically or as part of the vaccine composition e.g., by injection.

An "effective amount" of a nucleic acid composition may be calculated as that amount capable of exhibiting an in vivo effect, e.g. preventing or ameliorating a sign or symptoms. Such amounts may be determined by one of skill in the art. Preferably, such a composition is administered parenterally, preferably intramuscularly or subcutaneously. However, it may also be formulated to be administered by any other suitable route, including intra-nasally, orally or topically. The selection of the route of delivery and dosage of such therapeutic compositions is within the skill of the art.

Treatment in the context of the present invention refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Examples for autoimmune disease that are especially suitable for this invention are listed in Table 5.

TABLE 5

Autoimmune diseases and suitable antibody targets/antigens

| Disease | antibody target/antigen |
|---|---|
| Myasthenia gravis | Acetylcholine receptors |
| Graves's disease | Thyroid-stimulating hormone receptor |
| Thyroiditis | Thyroid |
| Insulin-resistant diabetes | Insulin receptor |
| Asthma | Beta-2 adrenergic receptors |
| Juvenile insulin-dependent diabetes | Pancreatic islet cells |
| Pernicious anemia | Gastric parietal cells |
| Addison's disease | Adrenal cells |
| Idiopathic hypoparathyroidism | Parathyroid cells |
| Spontaneous infertility | Sperm |
| Premature ovarian failure | Interstitial cells, corpus luteum cells |
| Pemphigus | Intercellular substance of skin |
| Primary biliary cirrhosis | Mitochondria |
| Autoimmune hemolytic anemia | Erythrocytes |
| Idiopathic thrombocytopenic purpura | Platelets |
| Idiopathic neutropenia | Neutrophils |
| Vitiligo | Melanocytes |
| Osteosclerosis and Meniere's disease | Type-II collagen |
| Chronic active hepatitis | Nuclei of hepatocytes |
| Goodpasture's syndrome | Basement membranes |
| Rheumatoid arthritis | Gamma globulin, virus-related antigens, IL-6, IL-17, TNF-α |
| Sjogren's syndrome | Nuclei and centromeres |
| Systemic lupus erythematosus | Nuclei, DNA, RNA, erythrocytes, etc. |

TABLE 5-continued

Autoimmune diseases and suitable antibody targets/antigens

| Disease | antibody target/antigen |
|---|---|
| Scleroderma | Nuclei and centromeres |
| Polymyositis | Nuclei, RNA |

Preferred autoimmune diseases are asthma, Juvenile insulin-dependent diabetes (diabetes type 1) and rheumatoid arthritis. Therefore, preferred antigens are the corresponding antigens of Beta-2 adrenergic receptors, Pancreatic islet cells, Gamma globulin E, virus-related antigens IL-6, IL-17, and TNF-α.

Examples for tumor diseases that are especially suitable for this invention are listed in Table 6.

TABLE 6

Tumor diseases and suitable antibody targets/antigens

| Disease | antibody target/antigen |
|---|---|
| Melanoma | HMW MAA (=high molecular weight melanoma associated antigen), BAGE, GAGE, MAGE-3, Melan A, MART-1, NY ESO, gp 100, tyrosinase |
| Colon cancer | CA125, EGFR |
| Gliobastome multiforme (GBM) | CA125, IL13R |
| Breast cancer | Her2/NEU |
| Ovarian cancer | L1 cell adhesion molecule |
| various cancers (e.g. for colon cancer, small lung cell carcinoma) | VEGF |
| B-cell lymphoma, e.g. Non-Hodgkin Lymphoma | CD20 |

Examples for allergic diseases are asthma, especially atopic asthma, and all types of allergies. The preferred target antigens for vaccination against allergic diseases are IgE, IL9, and IL13, especially IgE.

An example for a metabolic disease is a disorder in the cholesterol metabolism (e.g. atherosclerosis), a preferred target antigen is CETP.

Examples for inflammatory diseases that are especially suitable for this invention are listed in Table 7.

TABLE 7

(Chronic) Inflammatory diseases
Disease

COPD (chronic obstructive pulmonary disease)
OA (osteoarthritis)
Rheumatoid arthritis
Polymyalgia rheumatica
Gouty arthritis, Gout, Pseudogout
Atherosclerosis
Crohn's disease (inflammatory bowel disease)
Shoulder tendinitis, Bursitis
Colitis
Multiple Sclerosis
Systemic Lupus Erythematosus
Psoriasis
Juvenile diabetes
Type I diabetes mellitus (insulin-resistant diabetes)
Hypothyroidism
Chronic fatigue syndrome
Kawasaki's disease
Cardiovascular disease
Pericarditis
Lymph adenopathy
Raynaud's phenomenon TABLE 7-continued (Chronic) Inflammatory diseases
Disease Sarcoidosis
Sjogren's syndrome
Spondyloarthropathies
Vasculitides
Scleroderma
Goodpasture's syndrome
Wegener's granulomatosis
temporal = Giant cell arteritis
Celiac disease
Addison's disease
Autoimmune hepatitis
Grave's disease
Graft-vs-host disease Preferred target antigens are IL-6, IL-17, TNF-α and CD20.

Examples for diseases in ophthalmology are age-related macular degeneration (AMD) and diabetic retinopathy, a preferred target in these indications is VEGF.

Other preferred diseases are Alzheimer disease with the target antigen β-amyloid.

The parvovirus mutated structural protein comprising at least one B-cell epitope heterologous to the parvovirus can be especially useful for manufacture of a medicament for breaking immune tolerance.

In the context of the uses of the invention, the features of the parvovirus mutated structural protein are as defined above.

In a preferred embodiment the disease is not an infectious disease, meaning a disease caused by a virus, a bacterium, a fungus or a eukaryotic parasite.

In a further embodiment parvovirus mutated structural protein is not used to make a vector that is used in gene therapy.

In this document, the content of all cited documents is included by reference.

The following examples and figures are intended to explain the invention in detail without restricting it.

FIGURES

FIG. 1: Amino acid sequence alignment of parvovirus AAV1 (SEQ ID NO:185), AAV-6 (SEQ ID NO. 186), AAV2 (SEQ ID NO:187), AAV-3b (SEQ ID NO:188), AAV-7 (SEQ ID NO:189), AAV-8 (SEQ ID NO. 190), AAV10 (SEQ ID NO:191), AAV-4 (SEQ ID NO:192), AAV11 (SEQ ID NO:193), b-AAV (SEQ ID NO. 194), AAV-5 (SEQ ID NO:195), GPV (SEQ ID NO:196), B19 (SEQ ID NO:197), MVM (SEQ ID NO:198), FPV (SEQ ID NO. 199), and CPV (SEQ ID NO:200).

Alignment was made using Multalin version 5.4.1 (Corpet, 1988). Symbol comparison table: blosum62, Gap weight: 12, Gap length weight: 2, Consensus levels: high=90% low=50%. Consensus symbols: ! is anyone of IV; $ is anyone of LM; % is anyone of FY; # is anyone of NDQEBZ.

The corresponding amino acids to $G_{453}$ and $N_{587}$ of AAV2 and the preferred insertion range for I-453 and I-587 are boxed.

| Name | Length | Check | Weight | Seq. GP-No. |
|---|---|---|---|---|
| AAV1 | 799 | 4900 | 0.26 | 9632548 |
| AAV-6 | 799 | 5176 | 0.26 | 2766607 |
| AAV2 | 799 | 2359 | 0.50 | 2906023 |
| AAV-3b | 799 | 3639 | 0.50 | 2766610 |
| AAV-7 | 799 | 132 | 0.50 | 22652859 |
| AAV-8 | 799 | 3007 | 0.37 | 22652862 |
| AAV10 | 799 | 4671 | 0.37 | 48728343 |
| AAV-4 | 799 | 7292 | 0.74 | 2337940 |
| AAV11 | 799 | 2546 | 0.74 | 48728346 |
| b-AAV | 799 | 5299 | 0.79 | 48696559 |
| AAV-5 | 799 | 5950 | 1.34 | 91134730 |
| GPV | 799 | 3208 | 1.92 | 9628653 |
| B19 | 799 | 1920 | 2.45 | 4092542 |
| MVM | 799 | 332 | 2.05 | 2982110 |
| FPV | 799 | 7156 | 1.61 | 494031 |
| CPV | 799 | 7674 | 1.61 | 494746 |
| consensus | 799 | 6436 | 0.00 | |

Further parvoviruses can be found at the NCBI website.

FIG. 2: Schematic organization of the cap gene of AAV2

Figure 3:
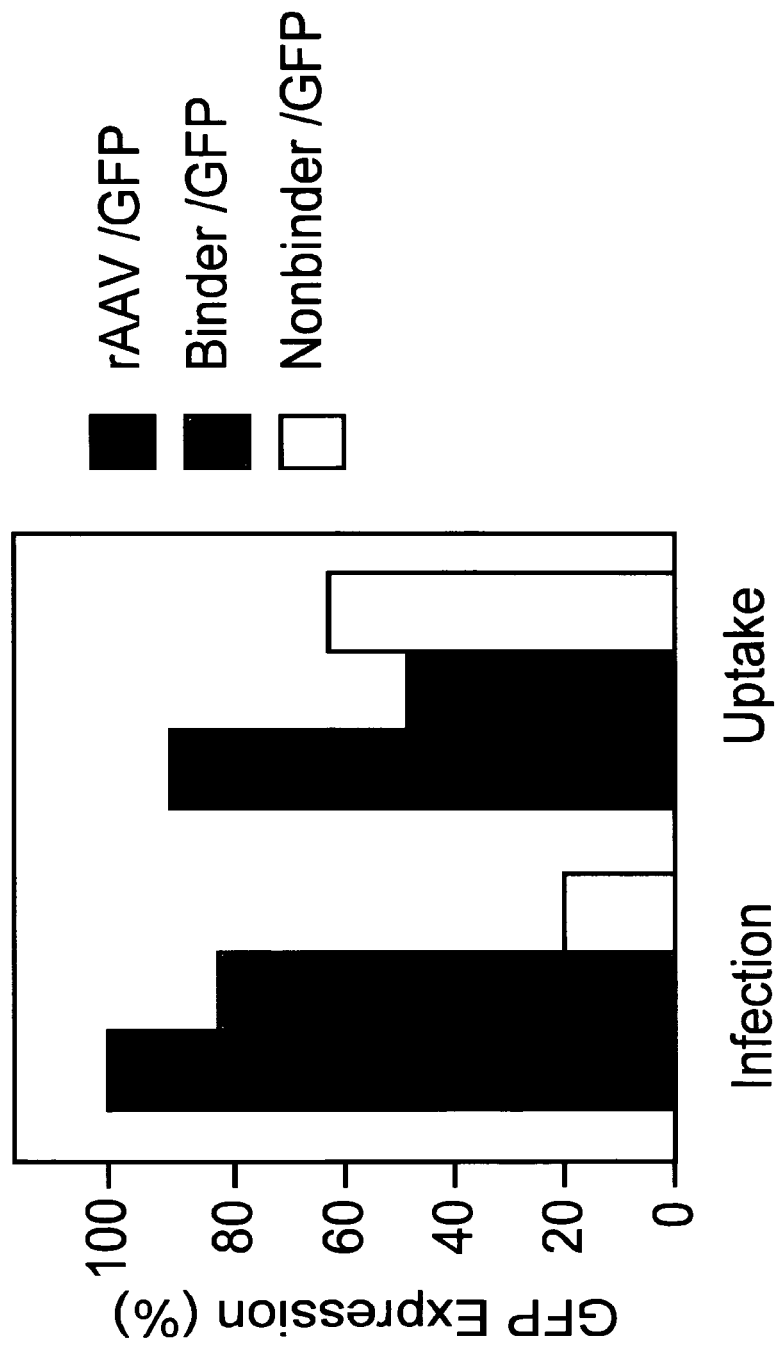

FIG. 3: Infection and Uptake experiment with Binder and Nonbinder Pools

For uptake wells were coated with A20 antibody and incubated with rAAV/GFP, the Binder or the Nonbinder pool (GPC of $1 \times 10^3$). After removing of unbound virus, HeLa cells were seeded into the wells. After 48 h of cultivation GFP expression of the cells was analyzed by flow-cytometry. For infection HeLa cells were seeded into wells and infected with rAAV/GFP, the Binder or the Nonbinder pool (GPC of $1 \times 10^3$). After 48 h of cultivation GFP expression of the cells was analyzed by flow-cytometry.

FIG. 4: Interaction of AAV variants with anti-KLH antibody (A) $5.0 \times 10^{10}$ and $1.0 \times 10^{10}$ capsids of the AAV variants (H3, B6, F10, A6, D9) isolated by the screening of the AAV library with the anti-KLH mAb were dotted onto a nitrocellulose membrane. As negative control wtAAV was spotted in serial dilution ranging from $1.0 \times 10^{10}$ to $1.6 \times 10^8$ capsids per dot (lower lane). Likewise serial dilutions of BSA (1.0 µg-0.03 µg) were spotted on the membrane as a negative control. As positive control different dilutions of KLH protein were spotted (1.0 µg-0.02 µg) (upper lane). The membrane was incubated with the anti-KLH antibody used for the screening of the AAV library and binding of the anti-KLH antibody to the spotted AAV variants was detected with an anti-mouse IgG (γ) HRP conjugate.

(B) After stripping of the membrane, binding of equal amounts of the AAV variants to the membrane was demonstrated using the A20 mAb and binding of the A20 mAb to the spotted AAVLPs was detected with an anti-mouse IgG (γ) HRP conjugate.

Figure 5:
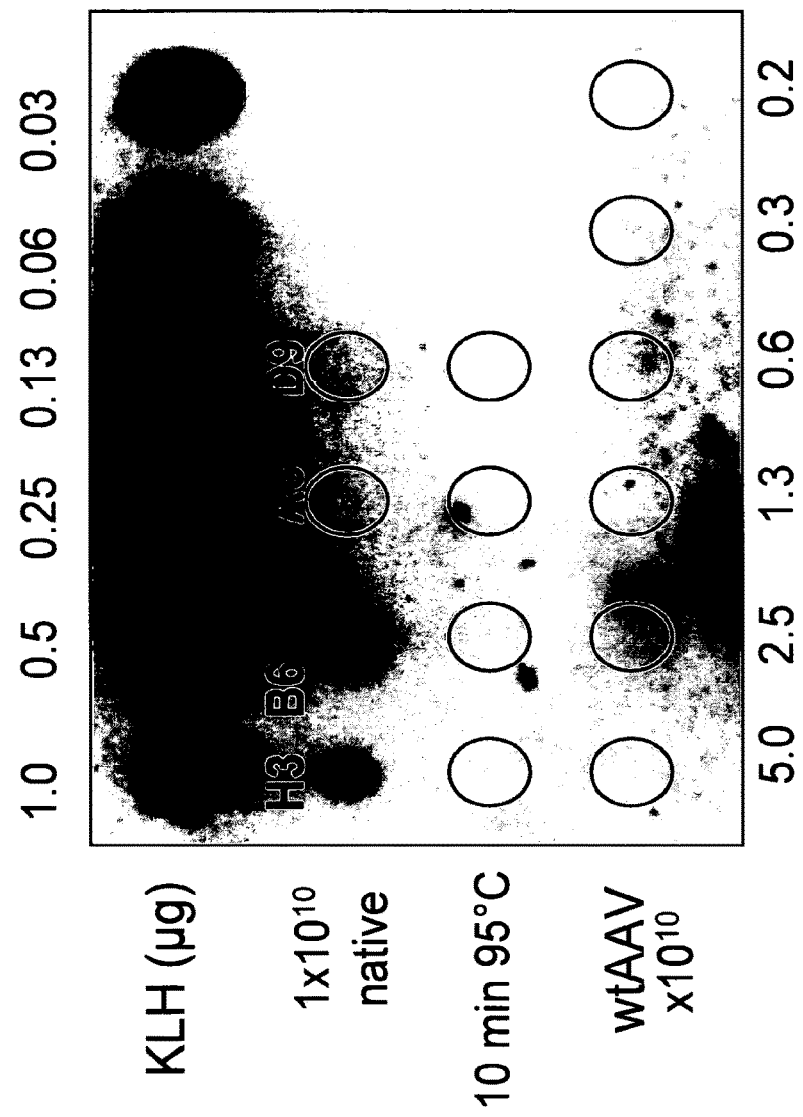

FIG. 5: Interaction of the anti-KLH antibody with a structural motif of the AAV variants $1 \times 10^{10}$ native or heat-inactivated (10 min, 95° C.) capsids were spotted onto a nitrocellulose membrane. As negative control wtAAV was spotted ranging from $5.0 \times 10^{10}$ to $1.6 \times 10^9$ capsids per dot (lower lane). As a positive control different dilutions of KLH protein were spotted (1.0 µg-0.03 µg) (upper lane). The membrane was incubated with the anti-KLH antibody used for the screening of the AAV library and binding of the anti-KLH antibody to the spotted AAV variants was detected with an anti-mouse IgG HRP conjugate.

Figure 6:
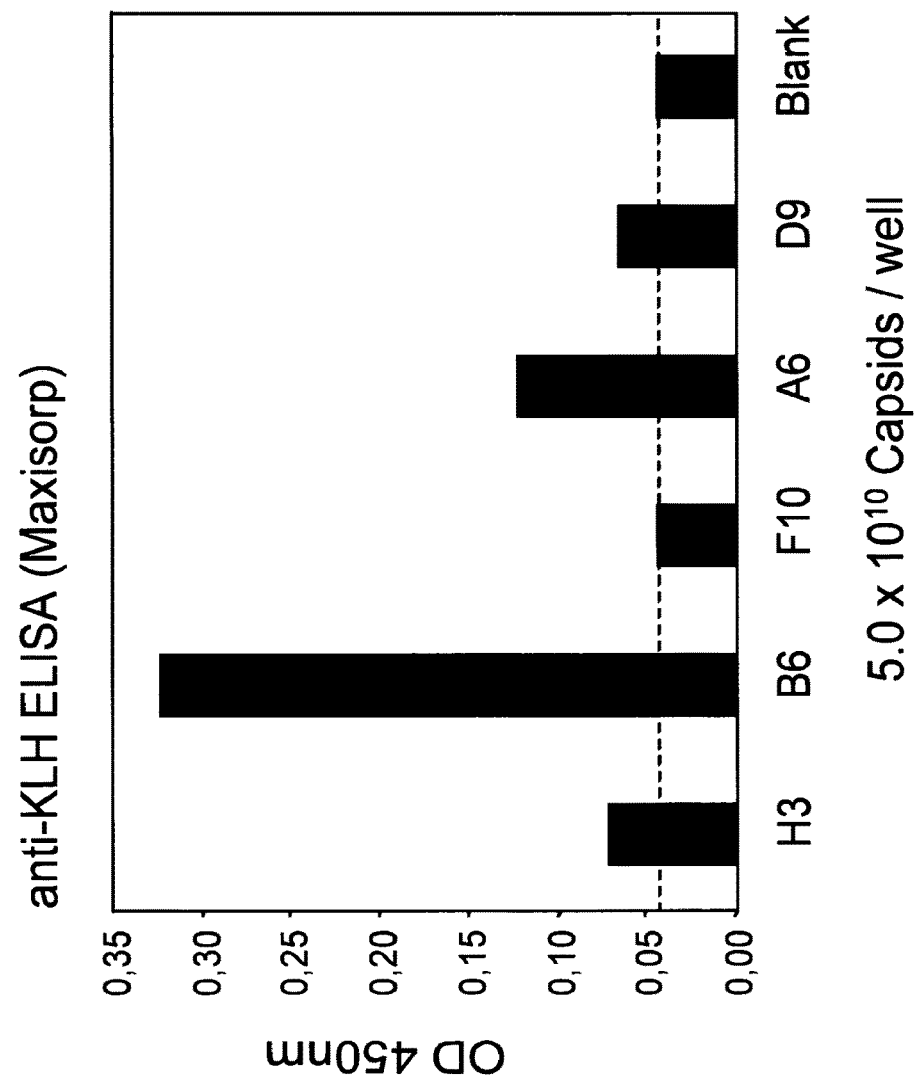

FIG. 6: Interaction of AAV variants with anti-KLH antibody (ELISA)

$5 \times 10^{10}$ AAV particles (H3, F10, B6, A6, D9) were coated onto a Maxisorp microtiter plate. As negative control wtAAV was coated ranging from $5.0 \times 10^{10}$ to $7.8 \times 10^8$ capsids per well (not shown). The coated particles were incubated with the anti-KLH antibody used for the screening of the AAV library. Binding of the anti-KLH antibody to the immobilized AAV variants was detected with an anti-mouse IgG HRP (horse radish peroxidase) conjugate using TMB (tetramethylbenzidine) as substrate and the absorbance was read at 450 nm. The threshold of the assay is shown as a dotted line.

Figure 7:
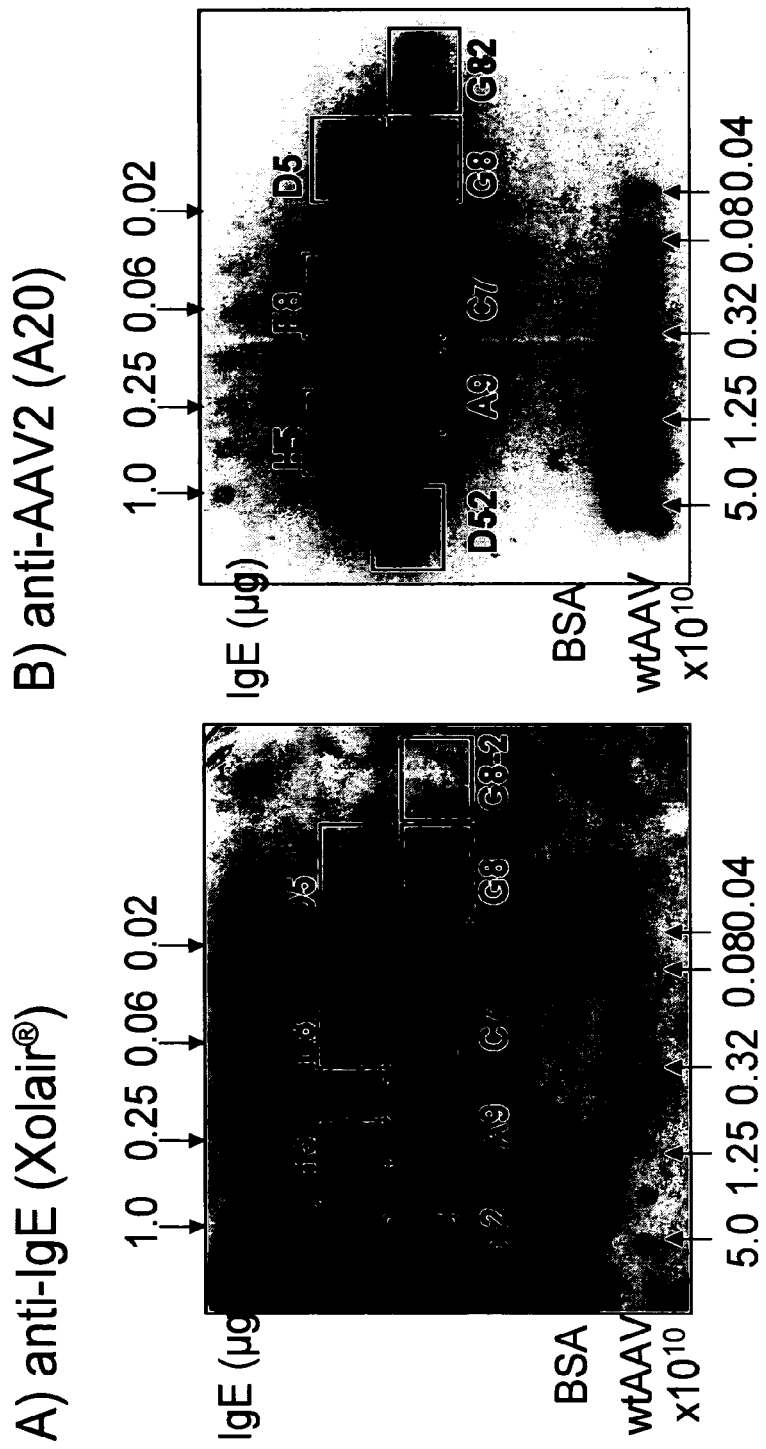

FIG. 7: Interaction of AAV variants with anti-IgE antibody $5.0 \times 10^{10}$ (left dot) and $1.0 \times 10^{10}$ (right dot) of the AAV variants (H5, D5, E8, A9, C7, G8) isolated by the screening of the AAV library with the anti-IgE antibody (Xolair®) were spotted onto a nitrocellulose membrane (shown in boxes). Only $1.0 \times 10^{10}$ capsids of the variant C7 were dotted. As negative control wtAAV was spotted ranging from $5.0 \times 10^{10}$ to $3.9 \times 10^8$ capsids per dot (lower lane). Likewise, serial dilutions of BSA (1.0 µg-0.03 µg) were spotted on the membrane as a negative control. As a positive control different dilutions of human IgE protein were spotted (1.0 µg-0.02 µg) (upper lane).

(A) The membrane was incubated with the anti-IgE antibody used for the screening of the AAV library and binding of the anti-IgE antibody to the spotted AAVLPs was detected with an anti-human IgG HRP conjugate.

(B) To demonstrate that equal amounts of AAV variants were spotted on the membrane, the membrane was stripped and spotted AAV capsids were detected using A20 mAb. Binding of the A20 mAb to the spotted AAVLPs was detected with an anti-mouse IgG (γ) HRP conjugate.

Figure 8:
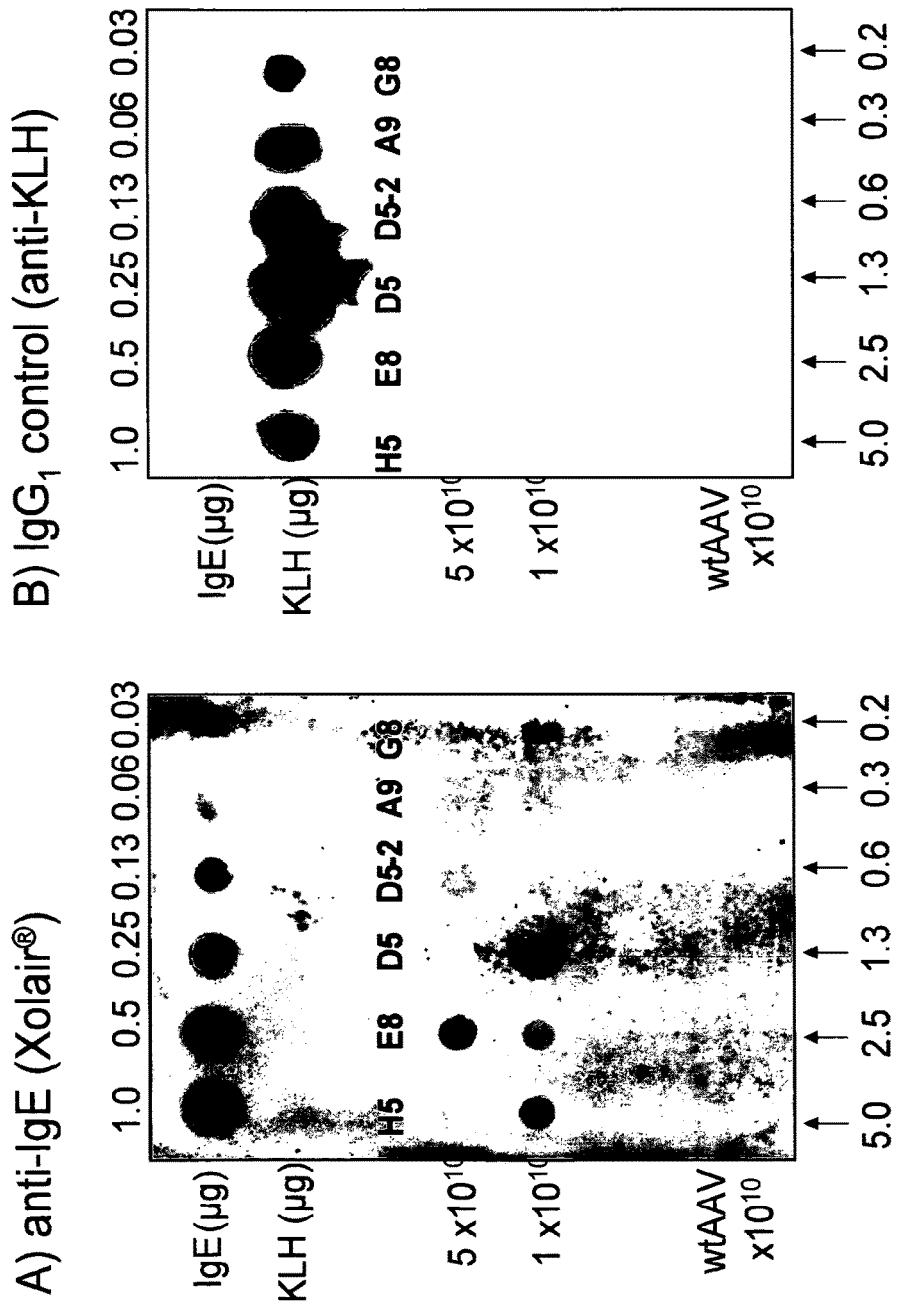

FIG. 8: Interaction of AAV variants with anti-IgE antibody vs. control antibody $5 \times 10^{10}$ and $1 \times 10^{10}$ particles of the AAV variants H5, E8, D5, A9, G8 (H5 only $1 \times 10^{10}$) were dotted onto a nitrocellulose membrane. As negative control wtAAV was spotted ranging from $5.0 \times 10^{10}$ to $1.6 \times 10^9$ capsids per dot (lower lane). As a positive control different dilutions of human IgE or KLH protein (1.0 µg-0.03 µg) were dotted (upper lanes). The membrane was incubated with (A) the anti-IgE antibody used for the screening of the AAV library or (B) the control antibody (anti-KLH). Binding of the antibodies to the AAV variants was detected using the respective secondary HRP-labeled antibodies.

Figure 9:
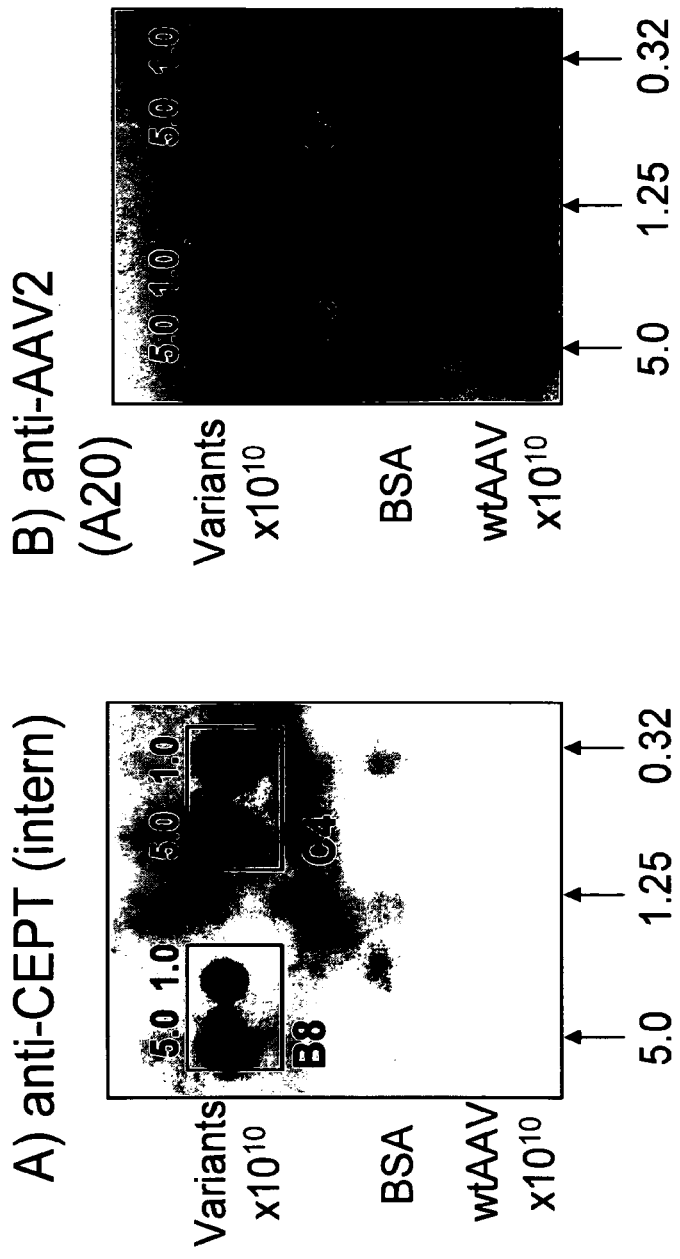

FIG. 9: Interaction of AAV variants with anti-CETP mAb $5.0 \times 10^{10}$ and $1.0 \times 10^{10}$ capsids of the AAV variants B8 and C4 isolated by the screening of the AAV library with the anti-CETP antibody were spotted onto a nitrocellulose membrane. As negative control wtAAV was spotted ranging from $5.0 \times 10^{10}$ to $3.2 \times 10^9$ capsids per dot (lower lane). Likewise, serial dilutions of BSA (1.0 µg-0.03 µg) were spotted on the membrane as a negative control.

(A) The membrane was incubated with the anti-CETP antibody used for the screening of the AAV library and binding of the anti-CETP antibody to the spotted AAV variants was detected with an anti-mouse IgG HRP conjugate.

(B) To demonstrate that equal amounts of AAV variants were spotted on the membrane, the membrane was stripped and spotted AAV capsids were detected using A20 mAb. Binding of the A20 mAb to the spotted AAVLPs was detected with an anti-mouse IgG (γ) HRP conjugate.

Figure 10:
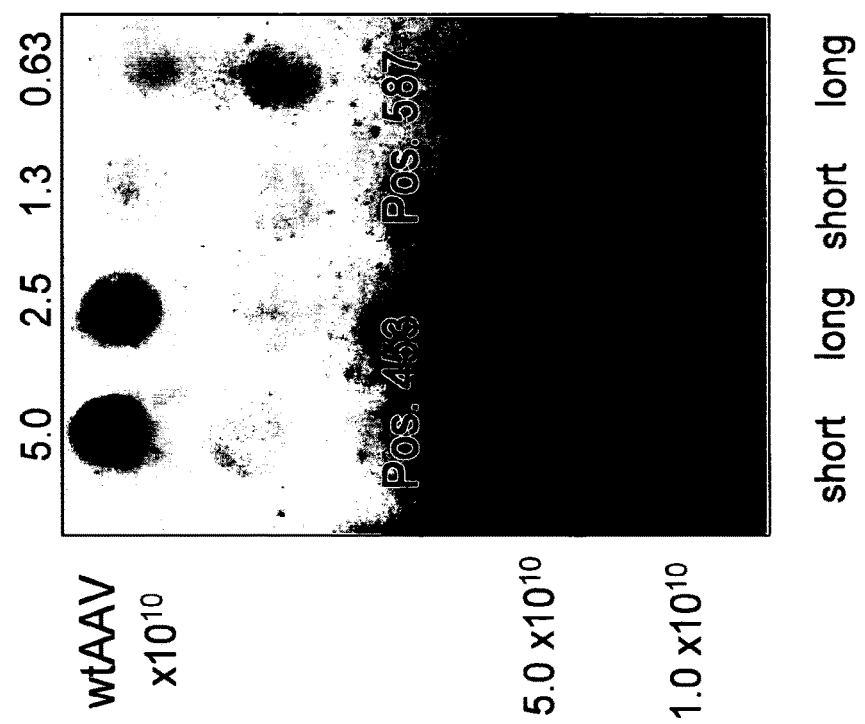

FIG. 10: Interaction of an anti-CETP antibody with the respective CETP epitope inserted into the AAV2 capsid at position 587

$5.0\times10^{10}$ capsids of the variants AAV-CETP-587-short and AAV-CETP-587-long and $5.0\times10^{10}$ and $1.0\times10^{10}$ capsids of the variants AAV-CETP-453-short and AAV-CETP-453-long were spotted onto a nitrocellulose membrane. As negative control wtAAV was spotted ranging from $5.0\times10^{10}$ to $6.3\times10^{9}$ capsids per dot. The membrane was incubated with a polyclonal anti-CETP antibody directed against the CETP epitope inserted into the AAV capsid. Binding of the anti-CETP antibody to the spotted AAV variants was detected with an anti-rabbit IgG HRP conjugate.

FIG. 11: Interaction of an anti-CETP antibody with the respective CETP epitope (CETP-intern) Inserted into the AAV1 capsid after $S_{588}$ or $D_{590}$.

Serial dilutions of 1:2 ranging from $5.0\times10^{11}$ to $3.1\times10^{10}$ capsids of the variants AAV1-CETP-588, rAAV1-GFP-CETP-588 and rAAV1-GFP-CETP-590 carrying the rabbit CETP-intern epitope were spotted onto a nitrocellulose membrane. As controls wild-type AAV1 ranging from $1.25\times10^{11}$ to $7.8\times10^{9}$ capsids per dot and AAV2 with CETP insertions (CETP-intern) in 453 and 587 (AAV2-CETin-2×) ranging from $5.0\times10^{11}$ to $3.1\times10^{10}$ capsids per dot were spotted.

(A) Membrane was incubated with an anti AAV1 intact particle antibody (Progen). Binding of the anti-AAV1 antibody to the spotted AAV variants was detected with an anti-mouse IgG HRP conjugate. (B) Membrane was incubated with a polyclonal anti-CETP antibody directed against the CETP epitope (CETP-intern) inserted into the AAV capsid. Binding of the anti-CETP antibody to the spotted AAV variants was detected with an anti-rabbit IgG HRP conjugate.

The HRP was detected by chemiluminescence using the ECL system (Pierce).

FIG. 12: ELISA for determination of binding efficiency of AAV1 to serum of AAV2 vaccinated rabbits.

Capsids were coated in equal amounts in serial dilutions from $1.0\times10^{9}$ to $1.56\times10^{7}$ capsids per well for 1 h at 37° C. Wells were incubated with sera from rabbits vaccinated with AAV2 (1:400 in 1% milk powder in PBS containing 0.05% Tween-20) for 1 h at 37° C. OD was measured at 450 nm.

FIG. 13: ELISA for determination of binding efficiency of AAV1 to serum of AAV2 vaccinated rabbits.

Equal amounts of capsids ($1\times10^{9}$) of rAAV2-GFP, rAAV1-GFP, rAAV1-GFP-CETP-588 and rAAV1-GFP-CETP-590 were coated onto Maxisorp 96 well plates (Nunc) and incubated with serial dilutions of sera from rabbits vaccinated with AAV2 (1:100-1:6400). OD was measured at 450 nm.

FIG. 14: Interaction of an anti-IgE antibody (Bsw17) with the respective IgE epitope inserted into the AAV2 capsid at position 587

$2.5\times10^{10}$ capsids of the AAV variant AAV-Kricek displaying an IgE epitope inserted at position 587 at the surface were dotted onto a nitrocellulose membrane. As negative control serial dilutions of wtAAV ($5.0\times10^{10}$ to $1.6\times10^{9}$) or of the AAV variant D5 ($5.0\times10^{10}$ to $0.5\times10^{10}$) were dotted. As a positive control human IgE was dotted ranging from 1.0 μg to 0.03 μg. The membrane was incubated with the anti-IgE mAb Bsw17 and binding of Bsw17 to the spotted AAV variants was detected with an anti-mouse IgG HRP conjugate FIG. 15: FcεRIα expression of transfected 293 cells 293 cell clones were stably transfected with the α- and γ-chain of human FcεRI. The γ-chain is expressed under the control of an EF1α or CMV promoter. Cell surface expression of FcεRIα was analyzed by flow-cytometry using a PE-labeled anti-FcεRIα mAb.

FIG. 16: IgE binding of transfected 293 cells

The 293 cell clone D11 stably expressing the α- and γ-chain of human FcεRI was used for evaluation of IgE binding and the effect of anti-IgE antibodies (XOLAIR® or Bsw17) thereon. Cells were incubated with increasing concentrations of human biotin-labeled IgE in the absence or presence of a constant concentration of anti-IgE antibodies or a control antibody (mouse $IgG_1$). IgE binding was detected by flow-cytometry using PE-labeled streptavidin.

FIG. 17: Histamine release of transfected RBL2H3 cells

Rat RBL2H3 cells were stably transfected with the α-chain of human FcεRI. The stably transfected cell clone E5 was used for evaluation of histamine release induced by sensitization of the cells with human IgE and subsequent cross-linking of receptor-bound human IgE using a anaphylactic anti-human IgE antibody (Le27). Cells were sensitized with increasing concentrations of human IgE and stimulated with the anaphylactic anti-IgE antibody Le27 (▲). Histamine release was measured using a commercially available histamine ELISA. In controls cells were sensitized with increasing concentrations of human IgE without subsequent stimulation with Le27 (■).

FIG. 18: Effect of anti-IgE mAb on histamine release

Rat RBL2H3 cells stably transfected with the α-chain of human FcεRI were sensitized with human IgE in the absence or presence of increasing concentrations of anti-human IgE mAb XOLAIR®. Histamine release was induced by cross-linking of receptor-bound IgE using the anaphylactic anti-IgE mAb Le27. Histamine release was measured using a commercially available histamine ELISA.

FIG. 19: Detection of a β-amyloid epitope displayed by AAV2 at I-587 or I-453/I-587 by β-amyloid-specific antibody Serial dilutions ($2\times10^{11}$-$2\times10^{8}$ capsids) of purified AAV particles displaying a β-amyloid epitope at I-587, I-453 and I-587, a CETP epitope at I-587 (as negative control) and 1 μg to 1 ng of the β-amyloid peptide (aa 1-42, Biosource, as positive control) were dotted on a membrane. The β-amyloid epitope was detected using an anti-β-amyloid mAb 6E10 (Chemicon) and as secondary antibody a peroxidase-labeled anti-mouse IgG antibody (CALTAG). Signals were detected by chemiluminescence.

FIG. 20: Induction of auto-antibodies by AAV-based vaccines vs. peptide based vaccines Rabbits (n=2) were immunized with the AAV-based CETP vaccines AAV-TP11, AAV-TP12, AAV-TP13, or AAV-TP18 s.c. in the presence of an adjuvant. AAV-based CETP vaccines were compared with the corresponding peptide vaccines containing the same epitope coupled to LPH (Limulus polyphemus hemocyanine). The titer of CETP auto-antibodies in the immune sera was measured after the $2^{nd}$ (gray) and $3^{rd}$ (black) boost immunization.

FIG. 21: Induction of epitope specific anti-peptide antibodies by AAV-based vaccines vs. peptide based vaccines Rabbits (n=2) were immunized with the AAV-based CETP vaccines AAV-TP11. AAV-TP12, AAV-TP13, or AAV-TP18 s.c. in the presence of an adjuvant. AAV-based CETP vaccines were compared with the corresponding peptide vaccines containing the same epitope coupled to LPH. The titer of antibodies directed against the epitope (linear peptide) in the immune sera was measured after the $2^{nd}$ (gray) and $3^{rd}$ (black) boost immunization.

Figure 22:
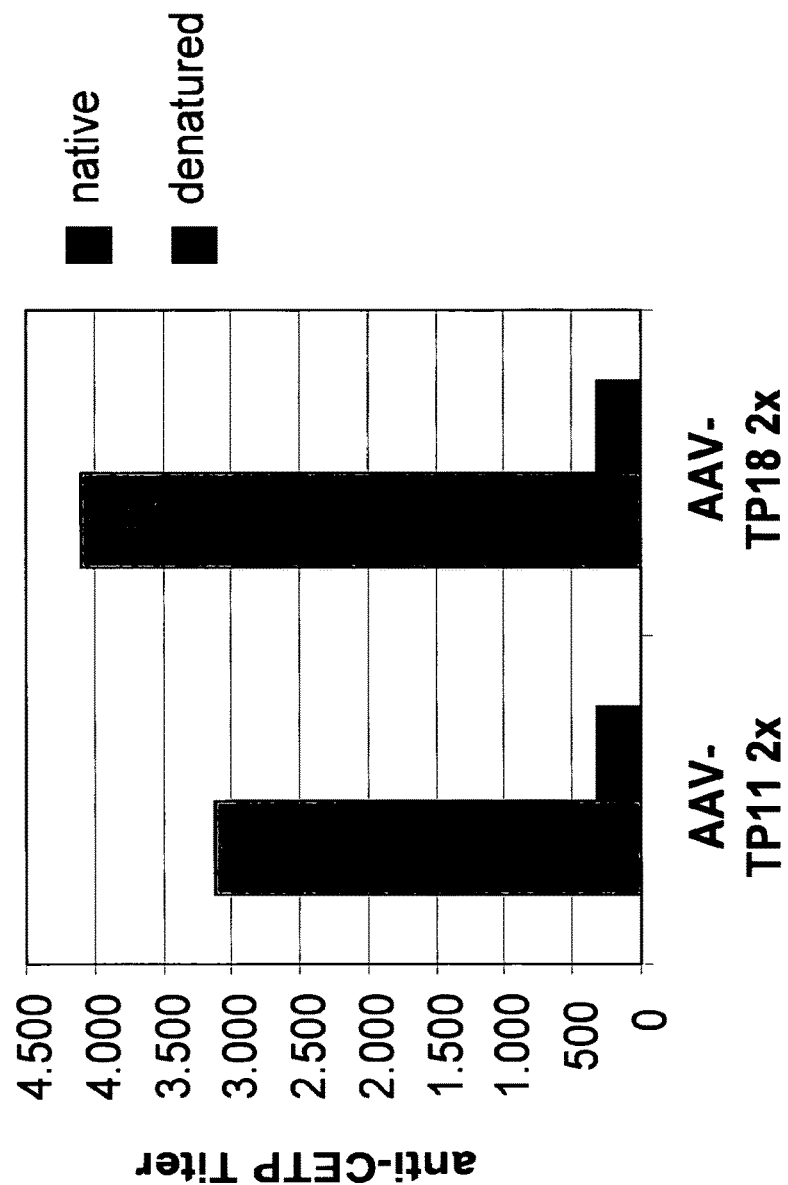

FIG. 22: Induction of auto-antibodies by native and heat-denatured AAV-based vaccines Rabbits (n=4) were immunized with native (gray) or heat-denatured (black) AAV-based CETP vaccines AAV-TP11 2× or AAV-TP18 2× s.c. in the presence of an adjuvant. The titer of CETP auto-antibodies in the immune sera was measured after the $1^{st}$ boost immunization.

Figure 23:
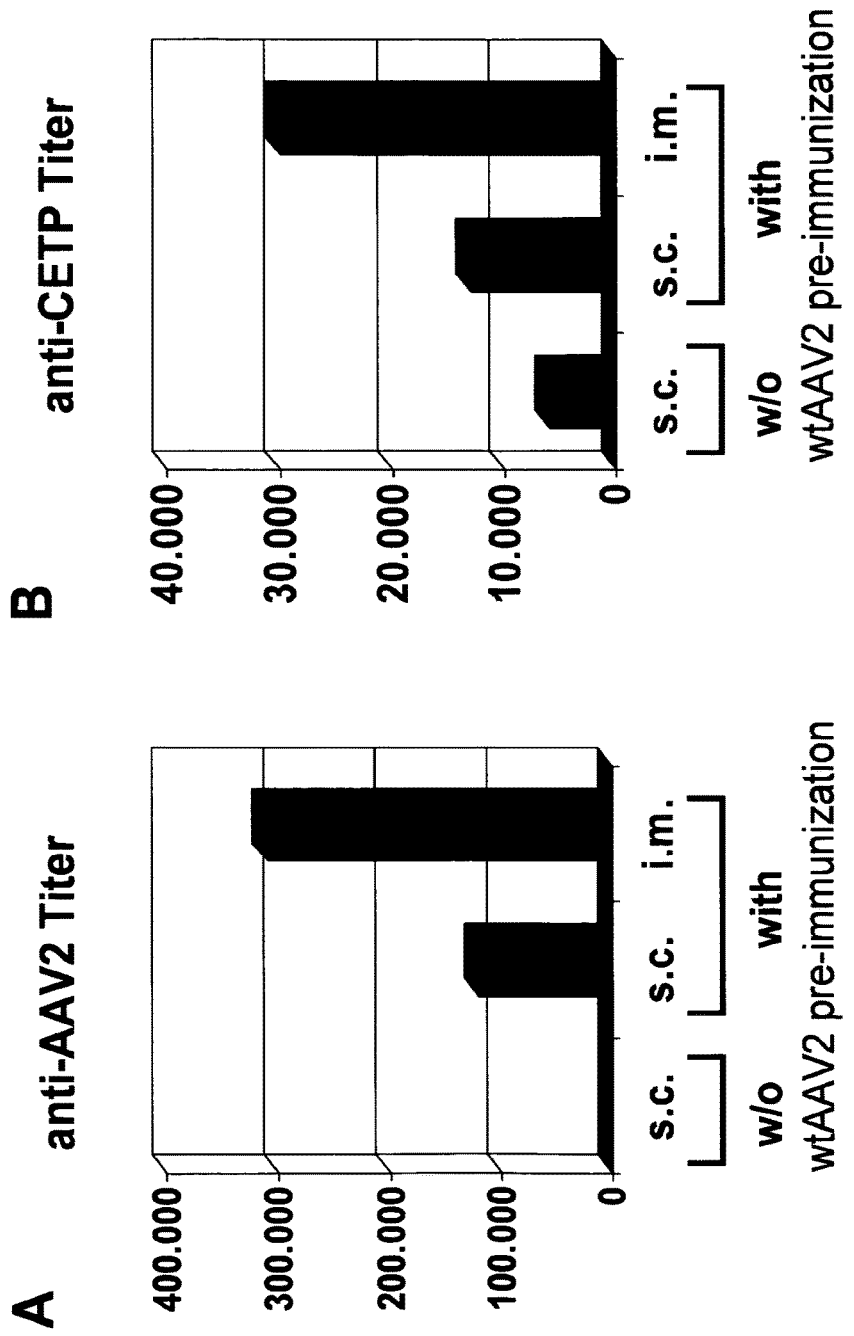

FIG. 23: Evaluation of the impact of anti-AAV2 antibodies on immunization with AAV2-based vaccines (A) To evaluate the impact of anti-AAV2 antibodies on the immunization success of AAV2-based vaccines, rabbits (n=3) were pre-immunized by two applications of 4.5 µg wtAAV2 (s.c. or i.m.). Serum was analyzed two weeks after $2^{nd}$ application for the level of anti-AAV2 antibodies. A control group (n=2) was not pre-immunized with wtAAV2.

(B) Following pre-immunization with wtAAV2 rabbits were vaccinated with the AAV2-based vaccine AAV-TP18 (7.2 µg per application). The vaccine was administered s.c. or i.m. in the presence of an adjuvant. Sera were analyzed two weeks after the $1^{st}$ boost vaccination for the level of CETP auto-antibodies. Results were compared to vaccination (s.c.) of animals without wtAAV2 pre-immunization.

Figure 24:
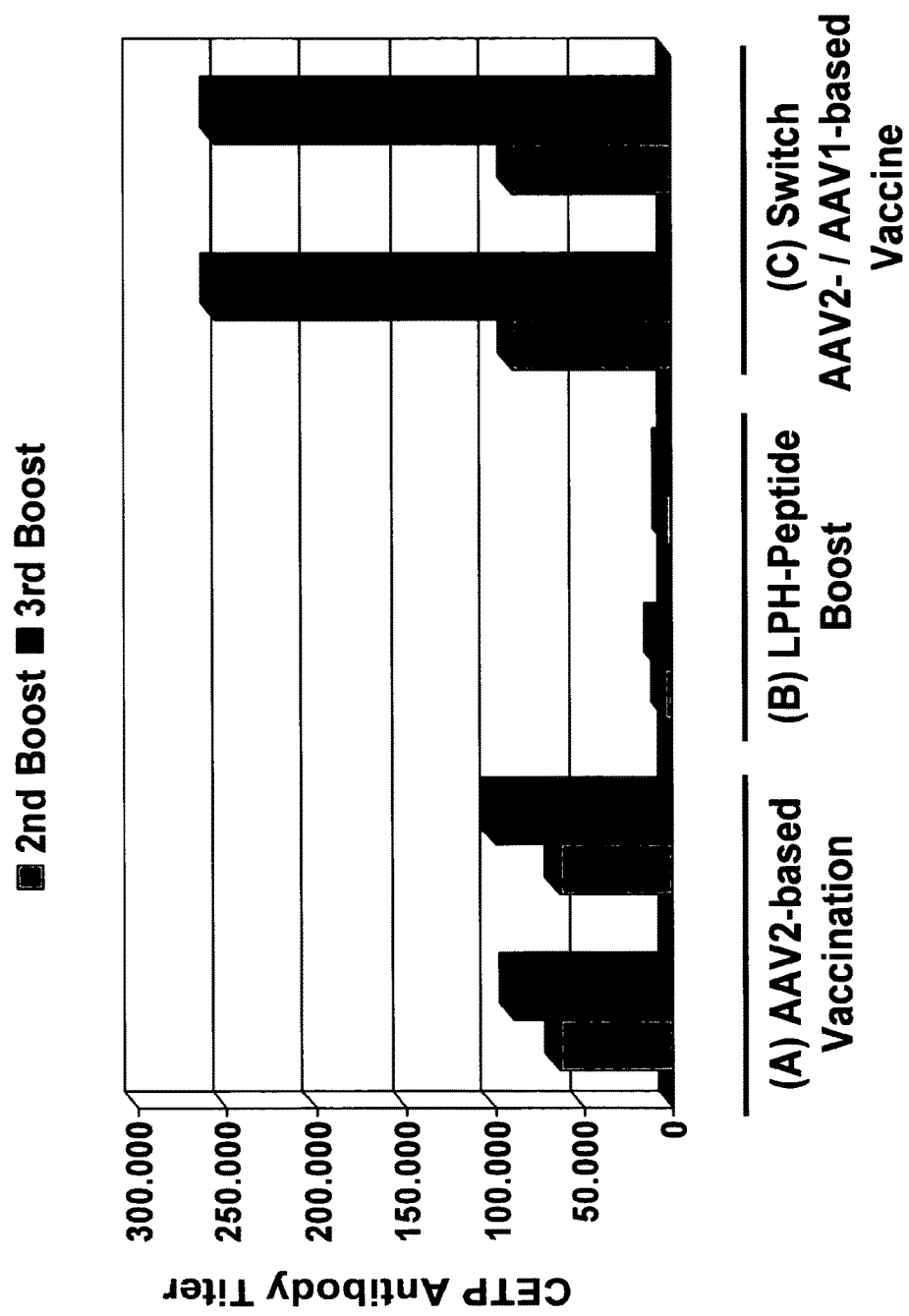

FIG. 24: Evaluation of different prime/boost regimens for AAV-based vaccines

Three different prime/boost regimens were evaluated. Group A received one prime and three boost applications of AAV2-CETin-2× (AAV2-based vaccination). Group B received one prime and one boost immunization with AAV2-CETin-2× followed by two boost immunizations with the LPH-coupled CETP-intern peptide (LPH-peptide boost). Group C received one prime and one boost immunization with AAV2-CETin-2× followed by two boost immunizations with AAV1-CETin (switch AAV2-/AAV1-based vaccine). Immune sera were analyzed for anti-CETP-reactivity (CETP auto-antibody titer) two weeks after the $2^{nd}$ (gray) and $3^{rd}$ boost (black) immunization.

Figure 25:
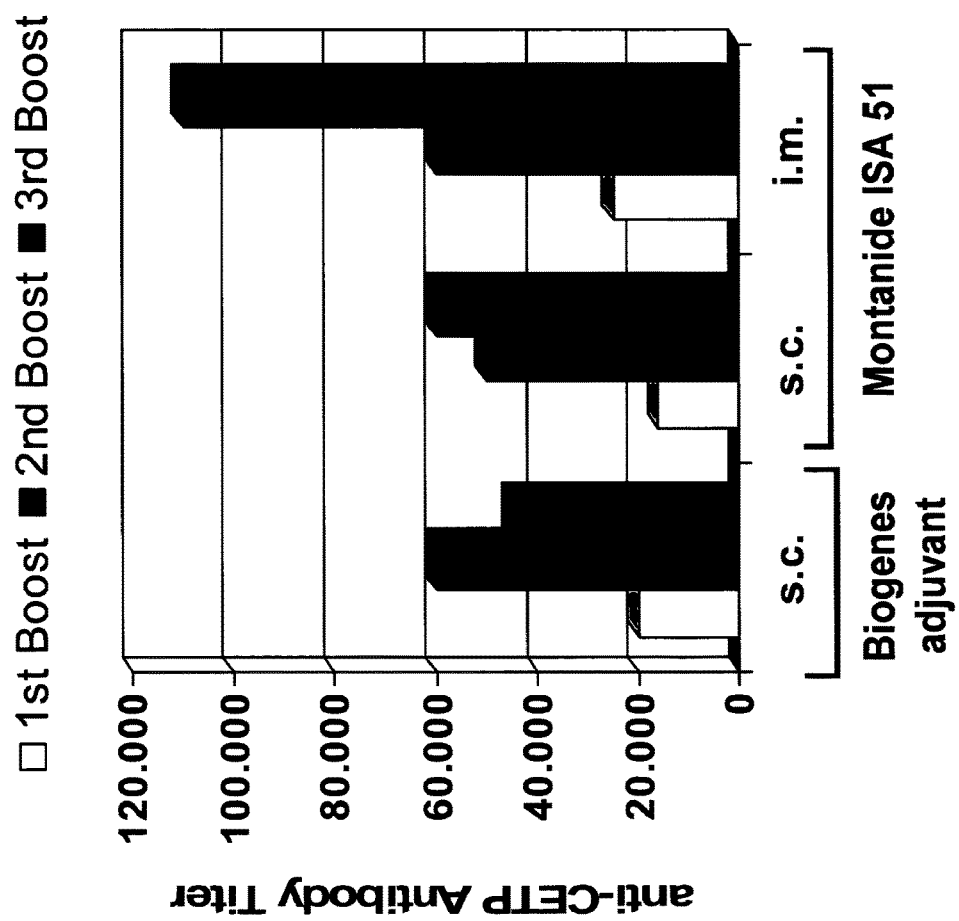

FIG. 25: Evaluation of the impact of Montanide ISA 51 on immunization with AAV2-based vaccines Rabbits (n=2) were immunized with the CETP vaccine AAV-TP18 i.m. or s.c. in the presence of the adjuvant Montanide ISA 51. A control group was immunized with the same vaccine s.c. in the presence of an adjuvant provided by Biogenes. Immune sera were analyzed for anti-CETP-reactivity (CETP auto-antibody titer) two weeks after the $1^{st}$ (white), $2^{nd}$ (gray) and $3^{rd}$ boost (black) immunization.

Figure 26:
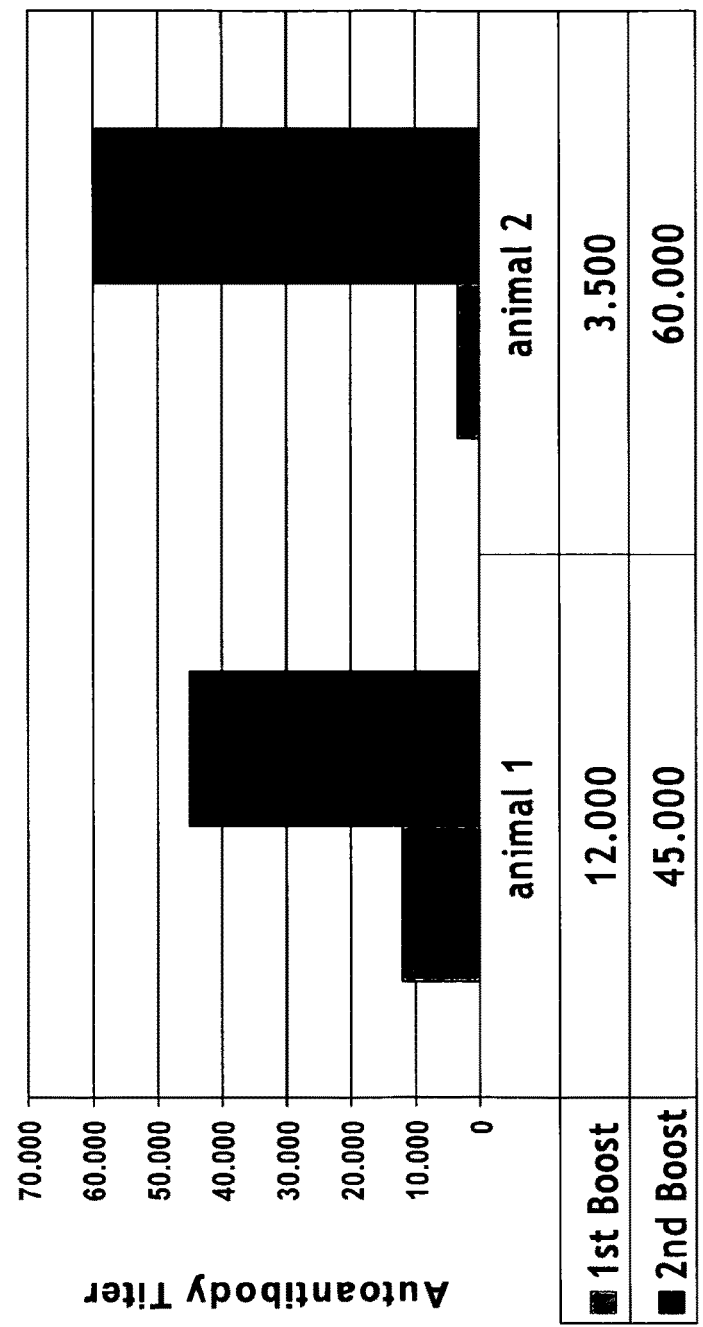

FIG. 26: Vaccination against CETP using AAV1 backbone

Rabbits (n=2) were immunized with AAV1 particles carrying rabbit CETP-intern epitope at position I-588. The particles (11.7 µg per vaccination) were administered i.m. at each prime or boost immunization in the presence of an adjuvant provided by Biogenes. Immune sera were analyzed for anti-CETP-reactivity two weeks after the $1^{st}$ (gray) and $2^{nd}$ boost (black) immunization.

Figure 27:
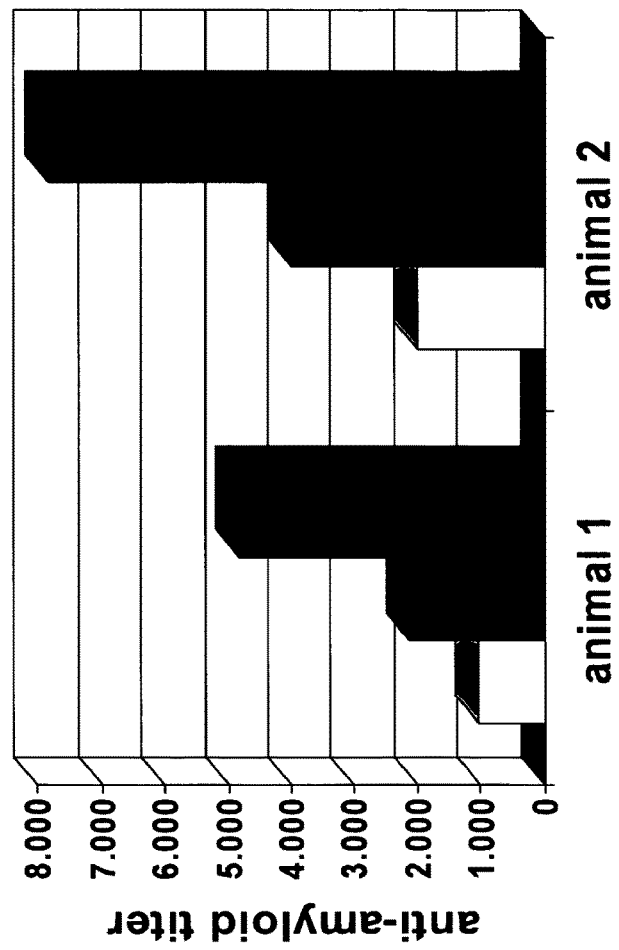

FIG. 27: Vaccination against human β-amyloid

Rabbits (n=2) were immunized with AAV2 particles carrying a human β-amyloid epitope (aa 1-9; DAEFRHDSG, SEQ ID NO: 158) at position I-587. The particles (1 µg per application) were administered s.c. at each prime or boost immunization in the presence of an adjuvant provided by Biogenes. Immune sera were analyzed for anti-β-amyloid (Aβ 1-42) reactivity two weeks after the $1^{st}$ (white), $2^{nd}$ (gray) and $3^{rd}$ (black) boost immunization.

Figure 28:
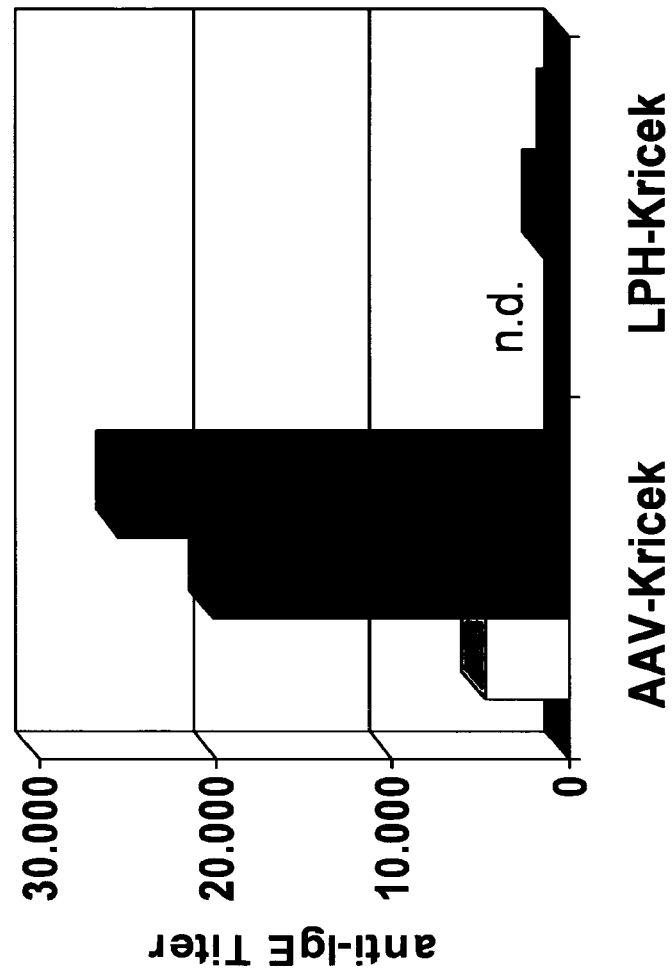

FIG. 28: Vaccination against human IgE

Rabbits (n=2) were immunized with AAV2 particles carrying a human IgE epitope ("Kricek") at position I-587. In a control group rabbits were immunized with the same IgE epitope coupled to LPH (LPH-Kricek). Immune sera were analyzed for anti-IgE reactivity two weeks after the $1^{st}$ (white), $2^{nd}$ (gray) and $3^{rd}$ (black) boost immunization. n. d.: not determined.

Figure 29:
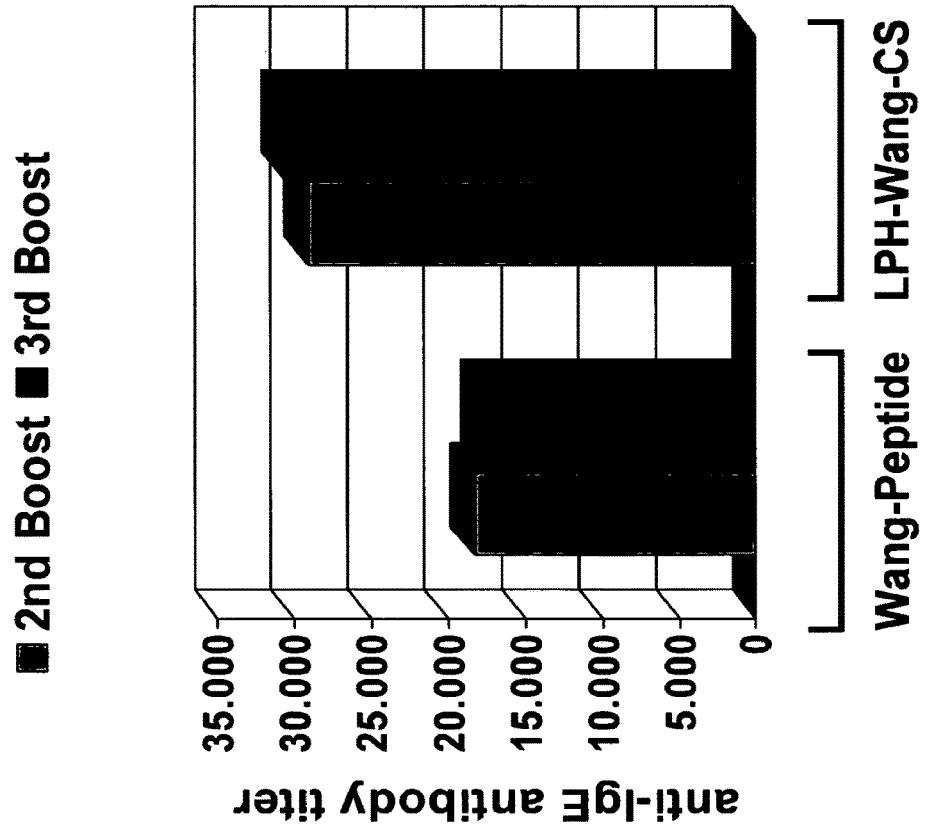

FIG. 29: Vaccination of rabbits with IgE derived peptides

Rabbits (n=2) were immunized with a human IgE derived epitope (GETYQSRVTHPHLPRALMRSTTK, SEQ ID NO: 236) coupled to a synthetic T-helper epitope (Wang-peptide). Another group of rabbits were immunized with a shortened variant of the epitope "Wang-CS" coupled to LPH as carrier protein (LPH-Wang-CS). Immune sera were analyzed for anti-IgE reactivity two weeks after the $2^{nd}$ (gray) and $3^{rd}$ (black) boost immunization.

Figure 30:
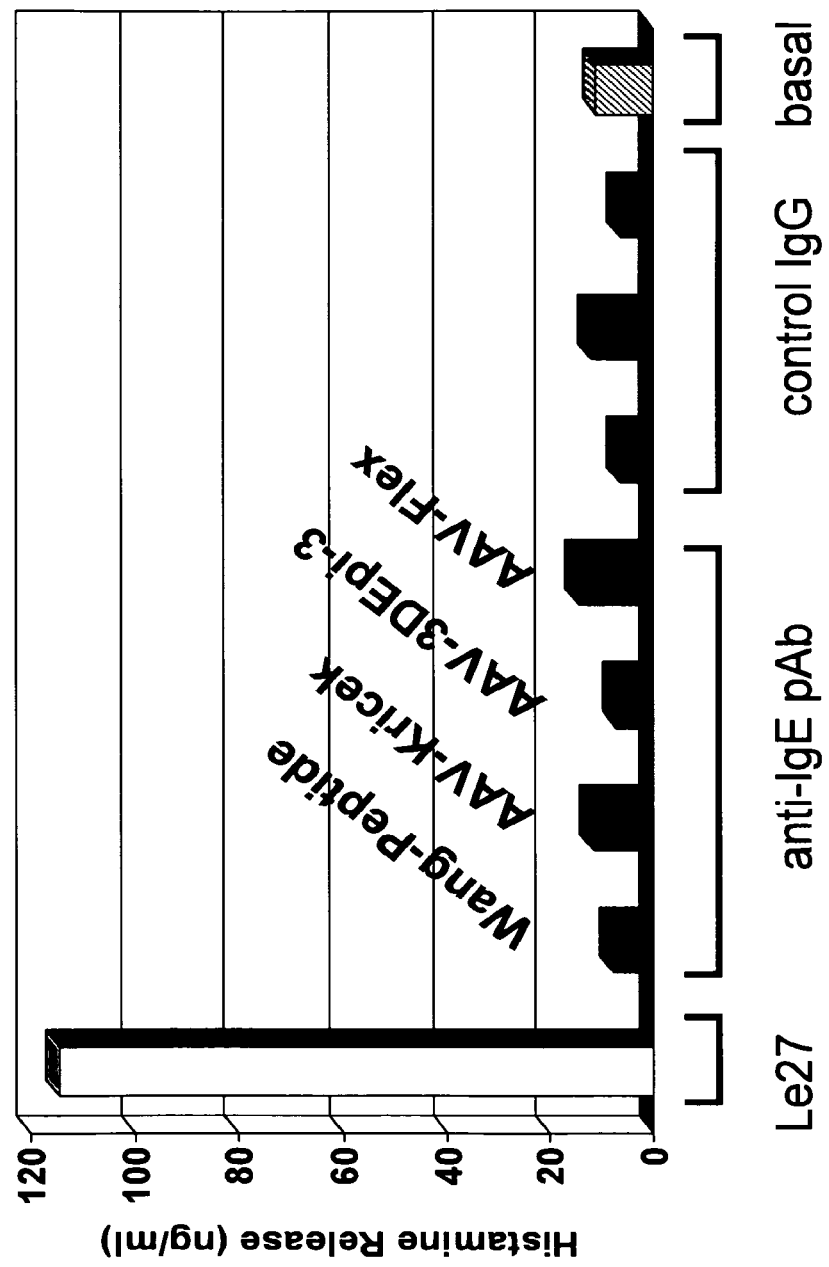

FIG. 30: Evaluation of the anaphylactic properties of the anti-IgE antibodies

The effect of the anti-IgE antibodies (derived from immunization of rabbits with Wang-peptide, AAV-Kricek, AAV-3DEpi3, or AAV-Flex) on IgE mediated degranulation of basophils was investigated using RBL2H3 cells overexpressing the alpha-chain of human FcεRI. Cells were sensitized by incubation with 250 ng/ml human IgE and subsequently stimulated with polyclonal anti-IgE antibodies (total IgG fraction of immunized rabbits) at a concentration of 3 mg/ml total IgG. The anaphylactic monoclonal anti-IgE antibody Le27 (15 ng/ml) was used as positive control. Rabbit total IgG derived from unrelated immunizations (i.e. vaccinations against CETP or β-amyloid) was used as negative control. Histamine release was measured using a commercially available histamine ELISA (Neogen).

Figure 31:
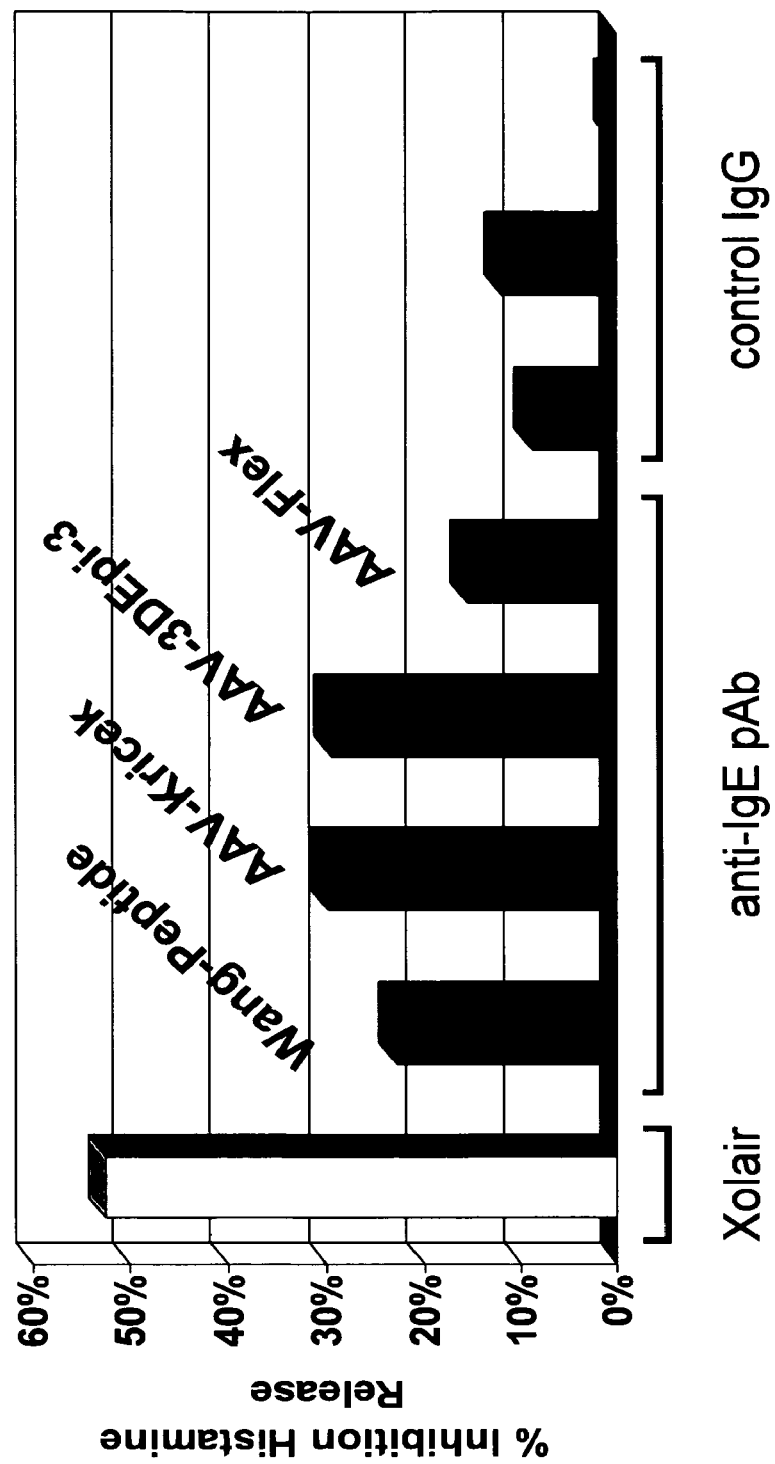

FIG. 31: Evaluation of the IgE neutralizing properties of the anti-IgE antibodies To evaluate whether the polyclonal anti-IgE antibodies induced by vaccination of rabbits are able to neutralize IgE, the effect of the anti-IgE antibodies on IgE mediated degranulation of basophils was investigated. Human IgE (250 ng/ml) was pre-incubated with 3 mg/ml polyclonal anti-IgE antibodies (total IgG fraction of rabbits immunized with Wang-peptide, AAV-Kricek, AAV-3DEpi3 or AAV-Flex). As a positive control IgE (250 ng/ml) was pre-incubated with Xolair (1 µg/ml). Rabbit total IgG derived from unrelated immunizations (i.e. vaccinations against CETP or β-amyloid) was used as negative control. Rat basophilic RBL2H3 cells overexpressing the alpha-chain of human FcεRI were sensitized by incubation with the human IgE/anti-IgE complexes. The anaphylactic monoclonal anti-IgE antibody Le27 was used for cross-linking of receptor bound IgE. IgE-mediated histamine release was measured using a commercially available histamine ELISA.

Figure 32:
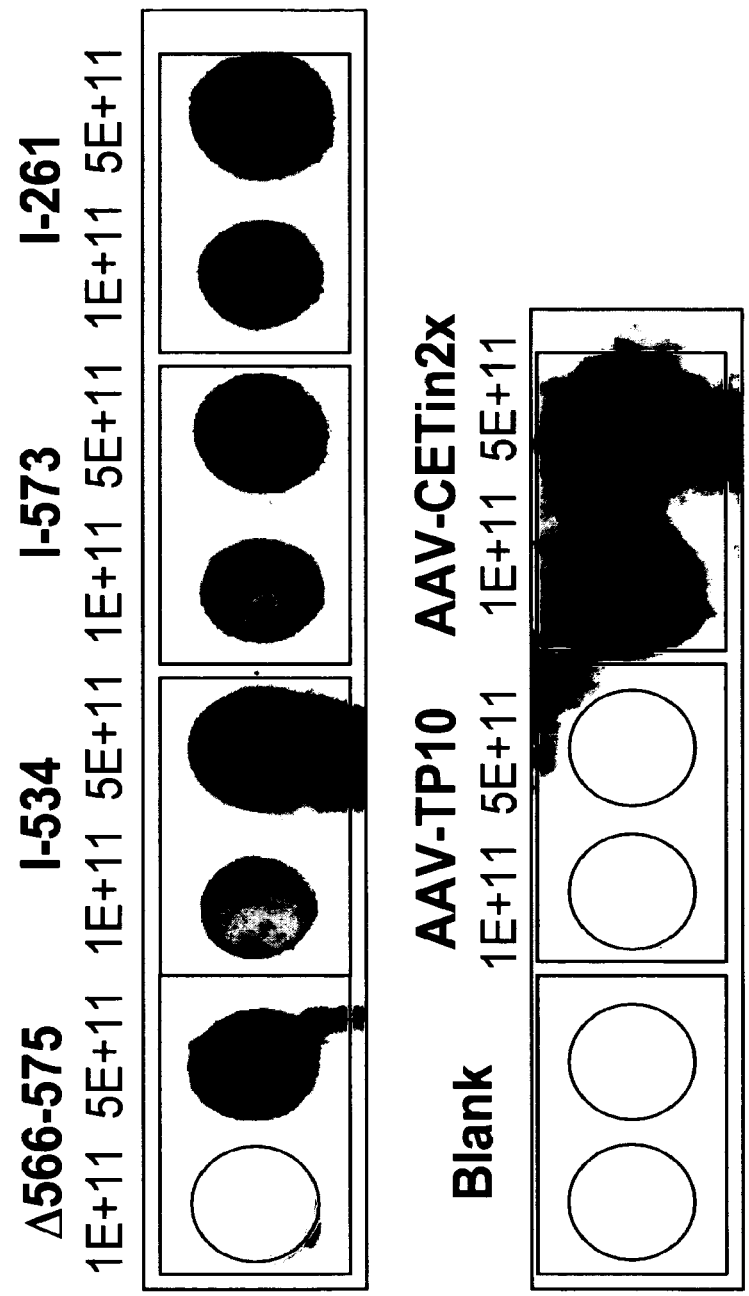

FIG. 32: Interaction of an anti-CETP antibody with the respective CETP epitope Inserted Into the AAV2 capsid at different Insertion sites $1.0 \times 10^{11}$ and $5.0 \times 10^{11}$ capsids of different AAV variants carrying the CETP epitope "CETP-intern" at the indicated insertion sites were dotted on a membrane (upper panel). As negative control AAV particles with the CETP epitope TP10 at position I-587 were spotted (AAV-TP10). As a positive control AAV2 variants with the CETP-intern epitope integrated at position I-453 and I-587 (AAV2-CETin-2×) were spotted (lower panel). The membrane was incubated with a polyclonal anti-CETP antibody directed against the CETP-intern epitope. Binding of the anti-CETP antibody to the spotted AAV variants was detected with an anti-rabbit IgG HRP (horse radish peroxidase) conjugate.

EXAMPLES

The following examples exemplify the invention for AAV, especially for AAV2. Due to the general similarities within the structures of the adeno-associated viruses and other parvoviruses the invention can be easily transferred to other parvoviruses.

1. Generation of an AAV Library

The cloning of the AAV library and the production of AAV capsid-modified viral particles is described by Perabo et al. (Perabo et al., 2003). The AAV library consists of approximately $4 \times 10^6$ capsid-modified viral particles carrying random insertions of 7 amino acids at position I-587 of the AAV capsid protein. The choice of a 7-mer was empirical and was dictated by the need to insert a sequence long enough to generate an acceptable amount of diversity, but without impairing the stability of the capsid. Since typical B-cell epitopes are in general composed of 5 or 6 amino acids in length (US 2004/0228798), the peptide sequences of the library are sufficient to define B-cell epitopes that are capable to induce specific B-cell responses directed against the inserted peptide sequence when the AAV capsid variant is used as vaccine.

2. Coupling of Pheno- and Genotype of the AAV Library

The AAV library contains a pool of AAV capsid mutants which differ from each other by the random insertion of seven amino acids at position I-587 in the VP3 region of all 60 capsid proteins. When producing the AAV library, a pool of plasmids coding for the mutant capsid proteins, the viral replication proteins Rep, and harboring the inverted terminal repeats (ITRs), is introduced into 293 cells by transfection (Perabo et al., 2003).

In general, transfection of high DNA concentrations of a given plasmid pool results in the introduction of several copies per cell. Therefore, each single 293 cell takes up several different AAV plasmids all replicating in the cell and expressing AAV capsid proteins with different inserted 7mer sequences. Therefore, many transfected cells will build up a mosaic capsid composed of capsid proteins with different 7mer insertions. Since these capsids encapsulate one AAV genome being randomly chosen, many of the AAV particles will contain a vector genome which is not related to any of its 60 capsid proteins of which its capsid is composed, meaning that the geno- and phenotypes of these mosaic viruses are uncoupled. As the anti-idiotype AAV library screening approach described below is in general based on the AAV phenotype (the capsid variant of the individual AAV particles) and because the sequence information for the selected AAV variant is preferably deduced from the respective AAV genome, the coupling of geno- and phenotype is highly preferred. Therefore, a coupling step may be introduced which results in a pool of viral mutants each consisting of a viral capsid displaying only one kind of peptide insertion and containing only the respective viral genome.

To achieve replication of only one AAV mutant per cell, coupling through cell transduction with low virus concentrations was established aiming to introduce one viral genome per cell. Two different methods to transduce HeLa cells with single or low numbers of AAV particles were established: A) unspecific uptake, and B) virus infection of HeLa cells with a limited number of AAV particles.

2.1. Coupling of Geno- and Phenotype by Unspecific Uptake

The coupling of the geno- and phenotype of the AAV library was performed by unspecific AAV capsid uptake and subsequent AAV amplification by infected HeLa cells.

2.1.1. Binding of AAV to Immobilized A20 Antibody

One cell culture plate (Ø15 cm, TPP) was coated with 10 ml AAV2 capsid-specific A20 antibody (supernatant of respective hybridoma) for 2 h at room temperature. The A20 antibody binds to intact AAV capsids (Grimm et al., 1999, Wistuba et al., 1997) independently from the sequence inserted in position I-587. The A20-coated plates were washed three times with 20 ml D-PBS containing 1% Tween-20 to remove unbound A20 antibody. After washing the coated plates were incubated with 20 ml blocking buffer (5% milk powder in D-PBS containing 1% Tween-20) for 2 h at room temperature to avoid unspecific binding of the AAV particles to the plates.

The plates were then incubated with the AAV library at genomic particles per cell (GPC) of 10, 100 and 1000 in a total volume of 10 ml blocking buffer for 2 h at room temperature. The genomic titer of the AAV population had been determined by quantitative real-time PCR as described below. After incubation of the A20-coated plates with the AAV library, unbound virus was removed by 20 washes with 10 ml D-PBS/1% Tween-20 followed by four washes with 10 ml D-PBS.

2.1.2. Uptake and Amplification of AAV by HeLa Cells $4.0 \times 10^6$ HeLa cells per Ø15 cm culture plate were seeded onto the AAV particles captured by the A20 antibody. Simultaneously, HeLa cells were infected with Adenovirus Type-2 (AdV2) at a MOI of 5 to induce replication of AAV particles. Infection and cultivation of the HeLa cells was performed in a total volume of 10 ml DMEM containing 10% (v/v) fetal calf serum (FCS) and 1% (v/v) Penicillin/Streptomycin for 24 h at 37° C. and 5% $CO_2$ in a humidified atmosphere. After 24 h of cultivation another 10 ml of DMEM containing 10% (v/v) FCS and 1% Penicillin/Streptomycin was added to the plate to a total volume of 20 ml. Cells were cultured for an additional 24 h at 37° C. and 5% $CO_2$ in a humidified atmosphere. After 24 h of cultivation, HeLa cells were harvested using a cell scraper and collected by centrifugation (3000 g, 10 min, 4° C.). Cells were washed with 5 ml D-PBS. After centrifugation (3000 g, 10 min, 4° C.) the cell pellet was resuspended in 500 µl lysis buffer (150 mM NaCl, 50 mM Tris, pH 8.5). Cells were lyzed by three thaw/freeze cycles using liquid nitrogen and a thermoblock tempered at 37° C. The cell lysate was treated with 50 U/ml benzonase (Merck) for 30 min at 37° C. After benzonase treatment the cell lysate was cleared by centrifugation (3700 g, 4° C., 20 min).

2.1.3. Evaluation of AAV Genomic Titers by Light Cycler PCR

For determination of genomic titers 50 µl of virus containing benzonase-treated cell lysate was used for isolation of DNA. For inactivation of AdV the lysate was incubated at 60° C. for 30 min. The lysate was diluted four-fold with PBS and total DNA was purified using the DNeasy Tissue Kit including a Proteinase K treatment (Qiagen). DNA was eluted in 200 µl Tris-HCl, pH 7.5. 2.0 µl DNA were applied to the Light Cycler PCR Master Mix using the Light Cycler FastStart DNA Master SYBR Green I Kit (Roche). Primers 4066-Back 5'-ATG TCC GTC CGT GTG TGG-3' and (SEQ ID NO: 86)

3201-For 5'-GGT ACG ACG ACG ATT GCC-3' (SEQ ID NO: 87)

were used for PCR amplification. Titers were determined by computer evaluation using the program provided with the Roche Light Cycler 2.0 and compared to a standard.

2.1.4. PCR Amplification and Subcloning of the AAV Library Insertion Site

To analyze the coupling of the geno- and phenotype of the AAV library after the unspecific up-take and amplification of AAV by the HeLa cells, the AAV library DNA containing the insertion site was amplified by PCR, subcloned into pRC-Kotin (described below) and analyzed by sequencing. Therefore, total DNA was purified from a 50 µl aliquot of the transduced HeLa cell lysate as described above. The cell lysate was diluted fourfold in PBS and total DNA was prepared using the DNeasy Tissue Kit according to the instructions of the manufacturer. Total DNA was eluted in 50 µl H$_2$O. The fragment of the AAV genome containing the library insertion site was amplified by PCR using 5.0 µl of the total DNA prepared from the cell lysate as template and 20 pmol of the primers BsiWI back 5'-TAC CAG CTC CCG TAC GTC CTC GGC-3' (SEQ ID NO: 88)

and

SnaBI forward 5'-CGC CAT GCT ACT TAT CTA CG-3' (SEQ ID NO: 89)

in a total volume of 50 µl. PCR was performed using the High Fidelity Platinum Pfx Polymerase Kit (Invitrogen). After an initial heat denaturation of the DNA template at 95° C. for 3 min. DNA was amplified by 35 PCR cycles (45 sec at 95° C. denaturation, 40 sec at 56° C. annealing, 2 min at 68° C. extension). Amplification was terminated after a final extension step at 68° C. for 10 min. An aliquot of the PCR reaction was analyzed on a 1% TBE agarose gel. The PCR product was purified using the PCR Purification Kit (Qiagen). The PCR product was cloned into the BsiWI/SnaBI site of the vector pRC-Kotin. The pRC plasmid was previously described (Girod et al. 1999). In pRC-Kotin the ITRs have been removed and an additional SnaBI restriction site was introduced downstream of the Cap ORF. Electro-competent *E. coli* XL-1 Blue MRF were transformed with the vectors by electroporation. The plasmids of 100 single independent clones of the cloning reaction were prepared and the insertion site of the library was sequenced using the primer 4066-back 5'-ATG TCC GTC CGT GTG TGG-3'. SEQ ID NO: 86

2.1.5. Statistical Analysis of the AAV Library Sequences after Unspecific Uptake by HeLa Cells The nucleotide sequences obtained from sequencing of at least 100 plasmids of single clones were translated into protein sequences and the 7mer peptide sequence inserted at position I-587 of AAV2 cap was analyzed. The state of geno- and phenotype coupling of the AAV2 library is reflected by the amount of stop codons detected within the 7mer peptide sequence inserted at position I-587. Since sequences encoding stop codons in-frame with the capsid protein can only be assembled in intact AAV capsids if more than one capsid encoding plasmid was transfected into one HeLa cell. Regarding the codon-usage, 14.6 stop codons in one hundred 7mer peptide sequences are statistically expected (due to the NNB design of the library), and 8.6 out of a hundred occurred in the original non-coupled AAV library, whereas 9.0 stop codons were found in average in the respective AAV DNA library.

Considering the number of stop codons as an indicator for the coupling state of the library, the number of stop codons should be markedly decreased after pheno-/genotype coupling of the library. In addition, the biodiversity of the library should be maintained. An indicator for the biodiversity is the absence of duplicate sequences.

Regarding single sequences about 40% of sequences occurred more than once after AAV uptake at GPC 10, which is to be regarded as a reduced biodiversity. In the uptake experiments utilizing GPC 100 and 1000 there were no duplicate sequences pointing to a better ratio between genomic particles and cells and a better diversity. The number of stop codons was lower as in the original library, which points to a well coupled library (Table 8). The number of stop codons calculated per 100 sequences increased as expected, when higher GPC were used, since in case of GPC 1000 it was very likely that more than one viral mutant was able to be taken up by one cell. Taken together the uptake with GPC of 100 is appropriate in terms of the coupling of pheno- and genotype and the maintenance of an adequate diversity of the AAV library.

TABLE 8

Frequency of stop codons after coupling by uptake (GPC 10, 100 and 1000): At least 100 sequences were analyzed and the number of stop codons was calculated per 100 sequences.

| | viral pool | uptake | | |
|---|---|---|---|---|
| | uncoupled | GPC 10 | GPC 100 | GPC 1000 |
| stop codons. per 100 seq. | 8.6 | 1.4 | 2.0 | 4.6 |

2.2. Coupling of Geno- and Phenotype by Infection

Coupling of an AAV library by infection without loss of biodiversity will work, if each mosaic virion from a non-coupled AAV library contains at least one cell binding motif which renders the AAV particle infectious. Alternatively, if e.g. only each 10th particle is still infectious (due to low abundance of corresponding binding and intracellular trafficking motifs), a 10 fold excess of particles has to be processed to ensure that each sequence from the library is taken up by a cell at least once as the likelihood is proportionally augmented that each genome is packaged at least into one infectious particle. As for the uptake experiment different GPCs were tested to determine the optimal coupling efficiency retaining full biodiversity of the AAV library.

2×10$^6$ HeLa cells were seeded in 15 ml medium (DMEM containing 10% (v/v) FCS and 1% Penicillin/Streptomycin) in Ø15 cm cell culture plates (TPP) and cultivated for 24 h at 37° C., 5% CO$_2$ in a humidified atmosphere. After 24 h medium was changed and the cells were infected with AAV genomic particles per cell (GPC) of 10, 100 and 1000 and incubated for 48 h in the presence of adenovirus (MOI 5) to allow replication and packaging of AAV. HeLa cells were harvested using a cell scraper and collected by centrifugation (3000 g, 10 min, 4° C.). Cells were washed with 5 ml D-PBS. After centrifugation (3000 g, 10 min, 4° C.) the cell pellet was resuspended in 500 µl lysis buffer (150 mM NaCl, 50 mM Tris, pH 8.5). Cells were lyzed by three thaw/freeze cycles using liquid nitrogen and a thermoblock tempered at 37° C. The cell lysate was cleared by centrifugation.

Total DNA was purified, viral DNA amplified by PCR and cloned into the AAV pRC-Kotin vector as described above. Plasmids were transformed into bacteria and single clones were picked and sequenced as described above.

2.2.1. Statistical Analysis of the AAV Library Sequences after Infection of HeLa Cells The nucleotide sequences obtained from sequencing of at least 100 plasmids of single clones were translated into protein sequences and the 7mer peptide sequence inserted at position I-587 of AAV2 VP was analyzed. As described above (2.1.5) the state of geno- and phenotype coupling of the AAV library is reflected by the amount of stop codons detected within the 7mer peptide sequence inserted at position I-587.

As observed for the coupling by unspecific uptake a comparatively high number of sequences occurred more than once when a GPC of 10 is used for infection of HeLa cells with the AAV library. The diversity of the library was higher when GPCs of 100 and 1000 were used for infection of HeLa cells with the AAV library, since no duplicate sequences were identified among at least 100 analyzed sequences. The number of stop codons, as an indicator for the state of geno- and phenotype coupling, was down to zero with GPCs of 100 and 1000 (Table 9) demonstrating the efficient coupling of pheno- and genotype of the library.

TABLE 9

Frequency of Stop codons in infection experiment with GPC 10, 100 and 1000: At least 100 sequences were analyzed and the number of stop codons was calculated per 100 sequences.

| | viral pool | infection | | |
|---|---|---|---|---|
| | uncoupled | GPC 10 | GPC 100 | GPC 1000 |
| stop codons. per 100 seq. | 8.6 | 1.2 | 0 | 0 |

2.3. Coupling of Geno- and Phenotype by Limited Dilution

In addition to the coupling methods described above (uptake or infection), the coupling of the geno- and phenotype of the AAV library can be performed by transfection of HeLa cells with a limited number of library plasmids. The amount of plasmids used for transfection is either calculated so that statistically only one single plasmid is taken up by each HeLa cell and finally entering the nucleus, or, the ideal number of AAV library genomes is determined with following model read-out system:

A self-replicating (e.g. B1/EBNA or SV40ori/large-T antigen) reporter gene plasmid (such as GFP) is transfected in increasing amounts together with a non-relevant carrier DNA such as pUC19, keeping the total DNA amount constant. The use of a self-replicating plasmid system ensures that each transfected cell produces enough GFP to be detected in a flow-cytometry assay. Fluorescence per cell and percent GFP positive cells define a crossing point, where increasing copy numbers of the reporter gene plasmid are no more proportional to an increase of GFP positive cells and where the fluorescence per cell is increasing indicating the uptake of more than one single reporter gene plasmid per cell. The amount of reporter gene plasmid respective library plasmid below the concentration at the crossing point has to be chosen to ensure the uptake of at maximum one library plasmid per cell.

Therefore, after infection with adenovirus each transfected cell produces only one defined type of AAV variant corresponding to the library plasmid that was taken up by the cell.

3. Evaluation of Unspecific-Uptake of AAV by HeLa Cells

Since the random peptide sequence of the AAV library is introduced at position 587 of the AAV capsid comprising the heparin binding domain of AAV, the AAV variants can be differentiated into variants that still bind to heparin due to reconstitution of the binding motif by the inserted random peptide sequence (Binder) and variants that do not bind to heparin (Nonbinder).

An AAV helper plasmid containing random peptides inserted into cap (helper plasmid library) was co-transfected with a double-stranded GFP vector plasmid to generate a GFP vector virion library. This library was coupled by infection. This coupled library was applied to a heparin affinity column to separate heparin binding from non-binding variants. For this, the library was applied to a heparin column (HiTrap, Amersham Bioscience). The flow-through contained the Nonbinders, whereas the Binders were bound to the column and then eluted from the column by 1M NaCl. Then both fractions were purified by Iodixanol step gradient centrifugation to concentrate the virions. Thereafter, genomic titers of both pools were determined by Light Cycler PCR. After the purification step genomic titers of $1 \times 10^7$ per µl (500 µl total) were obtained.

Infection and uptake experiments on HeLa cells with the Binder and the Nonbinder pools should reflect the different capabilities of the variants to enter the cells. Binders and Nonbinders were expected to show clear differences regarding their infectivity due to the different heparin-binding properties and the ability to interact with HSPG. In contrast, Binders and Nonbinders were expected to show no major differences regarding their transduction efficacy in uptake experiments, since uptake was assumed to be independent form HSPG and a heparin binding motif.

To analyze this, $5.0 \times 10^4$ HeLa cells/well were seeded into a 24-well cell culture plate in a volume of 0.5 ml medium (DMEM with 10% (v/v) FCS and 1% (v/v) Penicillin/Streptomycin). After cultivation of the cells for 1 d at 37° C. in a humidified atmosphere containing 5.0% $CO_2$, cells were infected with $1 \times 10^8$ genomic particles per well (GPC $1 \times 10^3$) of the Binder/GFP, Nonbinder/GFP pool or rAAV/GFP (recombinant wtAAV encoding GFP as a control). After 48 h of cultivation at 37° C. in a humidified atmosphere containing 5.0% $CO_2$ GFP expression levels of the cells were determined by flow cytometry (FIG. 3). For the uptake experiments, 24-well plates were coated with 100 µl/well A20 antibody (hybridoma supernatant recognizing the intact AAV capsid) for 1 h at room temperature. Unbound A20 was removed by 10 washes using D-PBS/1% Tween-20. Wells were blocked by incubation with 0.5 ml/well blocking buffer (10% milk powder in D-PBS/1% Tween-20) for 2 h at room temperature. A20-coated wells were incubated with rAAV/GFP, the Binder library or the Nonbinder library with $1 \times 10^8$ genomic particles per well (GPC $1 \times 10^3$). After incubation for 1 h at room temperature, unbound AAV particles were removed by 10 washes using D-PBS/1% Tween-20 followed by 4 washes with D-PBS. Then $1.0 \times 10^5$ HeLa cells/well were seeded on top of the bound AAV particles in a volume of 0.5 ml medium (DMEM with 10% FCS and 1% Penicillin/Streptomycin) and incubated for 48 h at 37° C. in a humidified atmosphere containing 5.0% $CO_2$. Transduction efficiency (GFP expression of the cells) was determined by flow cytometry (FIG. 3).

As expected, the Binder pool and rAAV/GFP showed comparable transduction efficacies in the infection experiments, whereas the infectivity of the Nonbinder pool was strongly reduced. The residual 20% transduction efficiency observed for the Nonbinder pool in the infection experiments is most probably mediated by HSPG independent pathways such as makro- or pinocytosis or alternative receptors.

In contrast to the infection experiments, the transduction efficacy of the Binder and Nonbinder pool was found to be comparable in the uptake experiments.

These data demonstrate that in contrast to infection the uptake of AAV variants by HeLa cells is independent from the heparin binding domain and independent from the peptide sequence inserted at position 587 of the AAV capsid.

4. Production and Purification of AAV Variants 4.1. AdV Helper Plasmid

An AdV helper plasmid encoding AdV E2, E4 and VAI-VAII was used for AAV manufacturing in 293 or 293T cells. The helper plasmid pUCAdvE2/E4-VAI-VAII was constructed by subcloning of the BamHI restriction fragment encoding the adenovirus E2 and E4-ORF6 from pAdEasy-1 into the site BamHI site of pUC19. The resulting plasmid is referred to as pUCAdVE2/E4. The VAI-VAII fragment from pAdvantage was amplified by PCR using the primers XbaI-VAI-780-3' 5'-TCT AGA GGG CAC TCT CCC GTG GTC TGG TGG-3' (SEQ ID NO: 90)

and

XbaI-VAII-1200-5' 5'-TCT AGA GCA AAA AAG GGG CTC GTC CCT GTT TCC-3', (SEQ ID NO: 91)

cloned into pTOPO and then subcloned into the XbaI site of pUCAdvE2/E4. The resulting plasmid pUCAdVE2/E4-VAI-VAII (in short pUCAdV) was evaluated in co-transfection experiments for production of AAV as described below. AAV particle formation was analyzed using the A20 ELISA.

4.2. Production of AAV Variants by Co-Transfection of HEK 293 T-Cells

For production of AAV particles HEK 293-T cells were co-transfected with the vector plasmid pRC-Kotin containing the subcloned library insertion sequence, pGFP and the helper plasmid pUCAdV (described above). The plasmid pGFP contains a GFP (green fluorescent protein) cDNA under the control of a CMV promoter. This GFP cassette is flanked with AAV derived ITRs. Therefore, co-transfection of 293-T cells with these three plasmids will result in the production of AAV particles displaying the library 7mer sequence at the surface and containing the GFP cassette with ITRs as viral genome.

AAV variants obtained by the direct cloning approach (described below) were produced as described above with the following modification. For co-transfection of the vector plasmid pUCAV2 containing the epitope/mimotope (in I-453 or I-587) and pUCAdV a molar ratio of the plasmids of 1:1 was chosen. For Calcium phosphate transfection of one culture plate with 293-T cells using the Calcium phosphate transfection protocol as described above, 12.0 µg pUCAV2 (containing the epitope/mimotope in I-453 or I-587) and 24.0 µg pUCAdV were used. Transfection was performed as described above.

For co-transfection $7.5 \times 10^6$ 293-T cells were seeded into each Ø15 cm cell culture plate in a total volume of 17.5 ml medium (DMEM containing 10% FCS, 5 mM L-Gln and ABAM) 24 h before transfection and cultivated at 37° C., 5% $CO_2$ in a humidified atmosphere. For co-transfection of pRC-Kotin, pGFP and pUCAdV a molar ratio of the plasmids of 1:1:1 was chosen. For Calcium phosphate transfection of one culture plate with 293-T cells using the Calcium phosphate transfection protocol as disclosed in US 2004/0053410, 9.0 µg pRC-Kotin, 9.0 µg pGFP and 18.0 µg pUCAdV were mixed in 875 µl 270 mM $CaCl_2$. In brief, 875 µl 2×BBS (50 mM BES (pH 6.95), 280 mM NaCl and 1.5 mM $Na_2HPO_4$) was added to the mixture and the resulting solution was carefully mixed by pipetting. The solution was incubated for 20 min at room temperature and then added drop-wise to the cell culture plate. Cells were incubated at 35° C., 3% $CO_2$ in a humidified atmosphere for 18 h. After 18 h at 35° C. and 3% $CO_2$ cells were cultivated for an additional 3 d at 37° C., 5% $CO_2$ in a humidified atmosphere.

293-T cells were harvested with a cell lifter, transferred into 50 ml plastic tubes (Falcon) and centrifuged at 3000 g at 4° C. for 10 min. The cell pellet was resuspended in 1.0 ml lysis buffer (150 mM NaCl, 50 mM Tris, pH 8.5) and objected to three rounds of freeze and thaw cycles. The lysate was treated with 100 U/ml benzonase (Merck) at 37° C. for 30 min. The cell lysate was cleared by two centrifugation steps (3700 g, 4° C., 20 min) and the AAV-containing supernatant was used for further purification.

The AAV capsid titer of the lysate was determined using a commercially available ELISA (AAV Titration ELISA, Progen).

4.3. Purification of AAV Particles by Density Gradient Centrifugation Using Iodixanol AAV particles were purified by iodixanol gradient centrifugation. The virus-containing cell lysate was cleared by centrifugation (3700 g, 4° C., 20 min) and the cleared lysate was transferred to Qickseal ultracentrifugation tubes (26×77 mm, Beckman). Iodixanol solutions (Sigma) of different concentrations were layered beneath the virus containing lysate. By this an Iodixanol gradient was created composed of 6.0 ml 60% on the bottom, 5.0 ml 40%, 6.0 ml 25% and 9.0 ml 15% Iodixanol with the virus solution on top. The gradient was spun in an ultracentrifuge at 416.000 g for 1 h at 18° C. The 40% phase containing the AAV particles was then extracted with a cannula by puncturing the tube underneath the 40% phase and allowing the solution to drip into a collecting tube until the 25% phase was reached. The AAV capsid titer of the 40% phase was determined using a commercially available ELISA (AAV Titration ELISA, Progen).

5. Selection of AAV Particles with Specific Affinity for a Target Antibody from the Coupled Viral Library 5.1. Anti-Idiotype Selection Using an Anti-KLH Antibody To proof the concept of selection of anti-idiotype AAV variants, an anti-KLH (Keyhole Limpet Hemocyanin) mouse monoclonal antibody (R&D Systems) was used as selection antibody. The mouse anti-KLH monoclonal antibody ($IgG_1$ isotype) was obtained from a mouse immunized with purified KLH as antigen. In another approach unspecific binding of AAV particles to the cell culture plate in the absence of an immobilized selection antibody was analyzed (negative control). In the experiments described in this example, an AAV library was used, whose geno- and phenotype was coupled by infection at GPC1000 as described above (2.2)

5.1.1. Binding of AAV to Immobilized Anti-KLH Antibody Vs. Binding of AAV to Uncoated Cell Culture Plate A cell culture plate (Ø10 cm, TPP) was coated with 5 ml anti-KLH monoclonal IgG, antibody at a concentration of 10 µg/ml in coating buffer (0.8 ml 0.2M $NaHCO_3$, 1.7 ml 0.2M $Na_2CO_3$ ad 10 ml $H_2O$) for 18 h-24 h at 4° C. In another approach (negative control) plates were treated with coating buffer in the absence of an antibody. All plates were washed three times with 10 ml D-PBS containing 1% Tween-20. After washing the plates were incubated with 10 ml blocking buffer (5% milk powder in D-PBS containing 1% Tween-20) for 2 h at room temperature to avoid unspecific binding of the AAV particles to the plate. The plate was then incubated with $1 \times 10^8$ genome-containing AAV library particles in a total volume of 5 ml blocking buffer for 2 h at room temperature. The genomic titer of the AAV population was determined by quantitative real-time PCR as described above. After incubation of the anti-KLH mAb-coated plate or uncoated plate (negative control) with the AAV library, unbound virus was removed by 20 washes with 10 ml D-PBS/1% Tween-20 followed by four washes with 10 ml D-PBS.

5.1.2. Uptake and Amplification of AAV by HeLa Cells $1.0 \times 10^6$ HeLa cells per plate were seeded onto the AAV particles captured by the anti-KLH mAb or adsorbed by the plate in an unspecific way in the control approach (negative control). Simultaneously, HeLa cells were infected with Adenovirus Type-2 (AdV2) at a MOI of 5 to induce replication of AAV particles. Infection and cultivation of the HeLa cells was performed in a total volume of 10 ml DMEM containing 10% (v/v) fetal calf serum (FCS) and 1% (v/v) Penicillin/Streptomycin for 48 h at 37° C. and 5% $CO_2$ in a humidified atmosphere. After 48 h of cultivation, HeLa cells were harvested using a cell scraper and collected by centrifugation (3000 g, 10 min, 4° C.). Cells were washed with 5 ml D-PBS. After centrifugation (3000 g, 10 min, 4° C.) the cell pellet was resuspended in 250 µl lysis buffer (150 mM NaCl, 50 mM Tris, pH 8.5). Cells were lyzed by three freeze/thaw cycles using liquid nitrogen and a thermoblock tempered at 37° C.

5.1.3. PCR Amplification and Subcloning of the AAV Library Insertion Site

Total DNA was purified from a 50 µl aliquot of the transduced HeLa cell lysate. The cell lysate was diluted fourfold in PBS and total DNA was prepared using the DNeasy Tissue Kit according to the instructions of the manufacturer. Total DNA was eluted in 50 µl H$_2$O. The fragment of the AAV genome containing the library insertion site was amplified by PCR using 5 µl of the total DNA prepared from the cell lysate as template and 20 µmol of the primers BsiWI back 5'-TAC CAG CTC CCG TAC GTC CTC GGC-3' (SEQ ID NO: 92)

and

SnaBI forward 5'-CGC CAT GCT ACT TAT CTA CG-3' (SEQ ID NO: 93)

in a total volume of 50 µl. PCR was performed using the High Fidelity Platinum Pfx Polymerase Kit (Invitrogen). After initial heat denaturation of the DNA template at 95° C. for 3 min, DNA was amplified by 35 PCR cycles (45 sec at 95° C. denaturation, 40 sec at 56° C. annealing, 2 min at 68° C. extension). Amplification was terminated after a final extension step at 68° C. for 10 min. An aliquot of the PCR reaction was analyzed on a 1% TBE agarose gel. The PCR product was purified using the PCR Purification Kit (Qiagen). The PCR product was cloned into the BsiWI/SnaBI site of the vector pRC-Kotin. Electro-competent E. coli XL-1 Blue MRF were transformed with the vectors by electroporation. The plasmids of 100 single clones were prepared and the insertion site of the library was sequenced using the primer 4066 back 5'-ATG TCC GTC CGT GTG TGG-3'. (SEQ ID NO: 86)

The obtained nucleotide sequences were translated into protein sequences and the 7mer peptide sequence inserted at position I-587 of AAV2 VP was analyzed. The results are summarized in Table 10. AAV particles containing the same peptide sequence at the library insertion site as AAV particles obtained by screening of the library using the uncoated culture plates (negative control) were considered as non-specifically bound particles and were excluded from further analysis.

TABLE 10

AAV Variants identified in the Library Screening approach

| AAV variant | selection antibody | sequence | frequency | | | |
|---|---|---|---|---|---|---|
| | | | round I | round II | round III | round IV |
| H3 | anti-KLH | ARAGLPG SEQ ID NO: 94 | 20.9 | 0.0 | N/A | N/A |
| B6 | anti-KLH | LRPDARP SEQ ID NO: 95 | 15.4 | 50.0 | N/A | N/A |
| A6 | anti-KLH | PRTDSPR SEQ ID NO: 96 | 26.4 | 45.0 | N/A | N/A |
| F10 | anti-KLH | PTLTPPR SEQ ID NO: 97 | 19.8 | 0.0 | N/A | N/A |
| D9 | anti-KLH | STLAPPA SEQ ID NO: 98 | 2.2 | 0.0 | N/A | N/A |
| C4 | anti-CETP | SRPPNPA SEQ ID NO: 99 | 73.2 | 22.2 | 33.3 | N/A |
| B8 | anti-CETP | MGSPSTR SEQ ID NO: 100 | 0.0 | 33.3 | 33.3 | N/A |
| E2 | anti-CETP | RDHPGIR SEQ ID NO: 101 | 0.0 | 0.0 | 29.8 | N/A |
| B6 | anti-CETP | VGSPSTR SEQ ID NO: 102 | 0.0 | 0.0 | 3.5 | N/A |
| A2 | anti-CETP | LPTARSP SEQ ID NO: 103 | 2.8 | 0.0 | 0.0 | N/A |
| C7 | anti-IgE | VYSPTGK SEQ ID NO: 104 | 0.0 | 8.1 | 84.0 | 97.4 |
| D5 | anti-IgE | SDAPLPR SEQ ID NO: 105 | 65.2 | 86.0 | 0.0 | 0.0 |
| H5 | anti-IgE | ETQLRAT SEQ ID NO: 106 | 0.0 | 72.7 | 17.1 | 0.0 |
| E8 | anti-IgE | GLGTQPR SEQ ID NO: 107 | 0.0 | 0.0 | 22.9 | 61.5 |

TABLE 10-continued

AAV Variants identified in the Library Screening approach

| AAV variant | selection antibody | sequence | frequency | | | |
|---|---|---|---|---|---|---|
| | | | round I | round II | round III | round IV |
| G8 | anti-IgE | DKTGSKP SEQ ID NO: 108 | 23.8 | 0.0 | 0.0 | 0.0 |
| A9 | anti-IgE | TSASRAP SEQ ID NO: 109 | 0.0 | 0.0 | 12.0 | 0.0 |
| E11 | anti-IgE | ACAPTGV SEQ ID NO: 110 | 0.0 | 0.0 | 5.7 | 0.0 |

5.1.4. Second Round of Anti-KLH mAb Screening

The number of genomic particles (genomic AAV titer) contained in the HeLa cell lysate was determined by quantitative real-time PCR (see 2.1.3). For the second round of selection, cell culture plates were coated with anti-KLH mAb or were left uncoated (negative control) as described above. Blocking and washing of the plates was performed as describe above. Plates were incubated with the volume of HeLa cell lysate (containing the AAV pool of the first selection round) corresponding to GPC of 100 in a total volume of 5 ml blocking buffer. After incubation of the plates with the AAV pool obtained from the first round of selection for 2 h at room temperature, unbound virus was removed by 20 washes with 10 ml D-PBS/1% Tween-20 followed by four washes with 10 ml D-PBS. Uptake and amplification of the anti-KLH mAb bound AAV or non-specifically bound AAV (negative control) by HeLa cells was performed as described above. Preparation of total DNA, PCR amplification and subcloning of the AAV library insertion site was performed as described above. The results are summarized in Table 10. AAV particles containing the same peptide sequence at the library insertion site as AAV particles obtained by screening of the library using the uncoated culture plates were considered as non-specifically bound particles and were excluded from further analysis.

5.1.5. Characterization of AAV Particles Obtained by Anti-KLH Screening of the AAV Library AAV particles of the library screening approach were produced and purified as described above. AAV capsid titers were analyzed using the AAV titration ELISA.

Dot Blot Analysis

The AAV capsid variants (H3, B6, F10, A6, D09) isolated by the screening of the AAV library with the anti-KLH mAb were analyzed by dot blot experiments (FIG. 4). $5.0 \times 10^{10}$ and $1.0 \times 10^{10}$ AAV particles were spotted onto a nitrocellulose membrane using a vacuum device. As negative control wtAAV was spotted ranging from $1.0 \times 10^{10}$ to $1.6 \times 10^{8}$ capsids per dot. Likewise serial dilutions of BSA (1.0 µg-0.03 µg) were spotted on the membrane as a negative control. As a positive control different dilutions of KLH protein were spotted (1.0 µg-0.02 µg).

After blocking of the membrane with blocking buffer (5% milk powder in PBS containing 0.05% Tween-20), the membrane was incubated with the anti-KLH antibody (0.5 µg/ml in 1% milk powder in PBS containing 0.05% Tween-20) used for the screening of the AAV library at 4° C. for 18 h-24 h. After washing of the membrane with PBS/0.05% Tween-20, binding of the anti-KLH antibody to the spotted AAV variants was detected with an anti-mouse IgG (γ) HRP conjugate (CALTAG). The membrane was incubated with the anti-mouse IgG (γ) HRP conjugate for 1 h at room temperature. After washing, signals were detected by chemiluminescence using the ECL system (Amersham Bioscience) (FIG. 4A).

To demonstrate that equal amounts of AAV variants were spotted on the membrane, the AAV capsids were detected using the AAV Capsid-specific mAb A20 (Progen). After stripping of the membrane with stripping buffer (0.1 M glycine, pH 2.5), binding of AAV variants to the membrane was demonstrated using A20 mAb at 5.0 µg/ml in 1% milk powder in PBS containing 0.05% Tween-20. The membrane was incubated with the A20 antibody (Progen) (hybridoma supernatant 1:10 diluted in 1% milk powder in PBS containing 0.05% Tween-20) for 2 h at room temperature. After washing of the membrane with PBS/0.05% Tween-20, binding of the A20 mAb to the spotted AAV variants was detected with an anti-mouse IgG (γ) HRP conjugate (CALTAG). The membrane was incubated with the anti-mouse IgG (γ) HRP conjugate for 1 h at room temperature. After washing, signals were detected by chemiluminescence using the ECL system (Amersham Bioscience) (FIG. 4B).

The result demonstrates that there is a specific detection of AAV capsid variants H3, B6, A6 and B9 by the anti-KLH antibody, which was used for screening of the AAV library. There is no cross-reaction with wtAAV. The weak detection of B6 by the A20 antibody might be due to the immobilization of a lower amount of capsids or due to a poor detection of the B6 variant by the A20 antibody caused by structural modifications of the AAV capsid variant. The weak detection of KLH by A20 in the upper row of panel B is due to incomplete stripping of the membrane shown on the left.

To analyze whether the anti-KLH antibody recognized a structural motif or a linear motif of the AAV variants, $1 \times 10^{10}$ native or heat-inactivated (10 min at 95° C.) capsids were spotted onto a nitrocellulose membrane (FIG. 5). As negative control wtAAV was spotted ranging from $5.0 \times 10^{10}$ to $1.6 \times 10^{9}$ capsids per dot. As a positive control different dilutions of KLH protein were spotted (1.0 µg-0.03 µg). After blocking, the membrane was incubated with the anti-KLH antibody used for the screening of the AAV library as described above. Binding of the anti-KLH antibody to the spotted AAVLP variants was detected with an anti-mouse IgG HRP conjugate (FIG. 5).

These data demonstrate that native but not heat-denatured H3 and B6 variants are recognized by the anti-KLH antibody, indicating that the antibody recognizes a structural rather than a linear epitope within the AAV capsid. A6 and D9 are not recognized by the antibody most probably due to the low number of spotted capsids ($1 \times 10^{10}$).

ELISA Experiments

To confirm the results of the dot blot experiments, the detection of the AAV variants by the KLH antibody was also analyzed in an ELISA format (FIG. 6). $5 \times 10^{10}$ AAV particles (H3, F10, B6, A6, D9) were coated onto a Maxisorp microtiter plate (Nunc). As negative control wtAAV was coated ranging from $5.0 \times 10^{10}$ to $7.8 \times 10^{8}$ capsids per well. After blocking, the wells were incubated with the anti-KLH antibody used for screening of the AAV library. Binding of the anti-KLH antibody to the immobilized AAV variants was detected with an anti-mouse IgG HRP conjugate using TMB as substrate. The absorbance was read at 450 nm.

These data demonstrate that variants B6 and A6 are detected in the KLH-specific ELISA, although the sensitivity of the ELISA seems to be lower than the sensitivity of the dot blot. This might be due to the binding of lower amounts of AAV particles to the plate or due to structural changes of the capsids caused by the adsorption to the plastic surface of the plate.

5.2. Anti-Idiotype Selection Using an Anti-IgE Antibody

To proof the concept of selection for an anti-idiotype AAV vaccine, an anti-IgE antibody was used for screening of the AAV capsid library. In this experiment, a AAV library was used, whose geno- and phenotype was coupled by infection at GPC 1000 or unspecific uptake at GPC 100 as described above (2.1 and 2.2).

5.2.1. Binding of AAV to Immobilized Anti-IgE Antibody

A cell culture plate (Ø15 cm, TPP) was coated with 10.0 ml anti-IgE antibody (XOLAIR®) at a concentration of 10 μg/ml in coating buffer (0.8 ml 0.2M NaHCO$_3$, 1.7 ml 0.2M Na$_2$CO$_3$ ad 10 ml H$_2$O) for 18 h-24 h at 4° C. The anti-IgE antibody coated plate was washed three times with 20 ml D-PBS containing 1% Tween-20 to remove unbound antibody. After washing the coated plate was incubated with 20 ml blocking buffer (5% milk powder in D-PBS containing 1% Tween-20) for 2 h at room temperature to avoid unspecific binding of the AAV particles to the plate. The plate was then incubated with $4 \times 10^{8}$ genome-containing AAV library particles in a total volume of 10 ml blocking buffer for 2 h at room temperature. The genomic titer of the AAV population was determined by quantitative real-time PCR as described above. After incubation of the anti-IgE antibody coated plate with the AAV library, unbound virus was removed by 20 washes with 20 ml D-PBS/1% Tween-20 followed by four washes with 20 ml D-PBS.

5.2.2. Uptake and Amplification of AAV by HeLa Cells $4.0 \times 10^{6}$ HeLa cells per plate were seeded onto the AAV particles captured by the anti-IgE mAb. Simultaneously, HeLa cells were infected with Adenovirus Type-2 (AdV2) at an MOI of 5 to induce replication of AAV particles. Infection and cultivation of the HeLa cells was performed in a total volume of 20 ml DMEM containing 10% (v/v) fetal calf serum (FCS) and 1% (v/v) Penicillin/Streptomycin for 24 h at 37° C. and 5% CO$_2$ in a humidified atmosphere. After 48 h of cultivation, HeLa cells were harvested using a cell scraper and collected by centrifugation (3000 g, 10 min, 4° C.). Cells were washed with 5 ml D-PBS. After centrifugation (3000 g, 10 min, 4° C.) the cell pellet was resuspended in 500 μl lysis buffer (150 mM NaCl, 50 mM Tris, pH 8.5). Cells were lyzed by three freeze/thaw cycles using liquid nitrogen and a thermoblock tempered at 37° C.

5.2.3. PCR Amplification and Subcloning of the AAV Library Insertion Site

Total DNA was purified from a 50 μl aliquot of the transduced HeLa cell lysate. The cell lysate was diluted fourfold in PBS and total DNA was prepared using the DNeasy Tissue Kit (Qiagen) according to the instructions of the manufacturer. Total DNA was eluted in 50 μl H$_2$O. The fragment of the AAV genome containing the library insertion site was amplified by PCR using 5 μl of the total DNA prepared from the cell lysate as template and 20 pmol of the primers BsiWI back 5'-TAC CAG CTC CCG TAC GTC CTC GGC-3' (SEQ ID NO: 92)

and

SnaBI forward 5'-CGC CAT GCT ACT TAT CTA CG-3' (SEQ ID NO: 89)

in a total volume of 50 μl. PCR was performed using the High Fidelity Platinum Pfx Polymerase Kit (Invitrogen). After initial heat denaturation of the DNA template at 95° C. for 3 min, DNA was amplified by 35 PCR cycles (45 sec at 95° C. denaturation, 40 sec at 56° C. annealing, 2 min at 68° C. extension). Amplification was terminated after a final extension step at 68° C. for 10 min. An aliquot of the PCR reaction was analyzed on a 1% TBE agarose gel. The PCR product was purified using the PCR Purification Kit (Qiagen). The PCR product was cloned into the BsiWI/SnaBI site of the vector pRC-Kotin. Electro-competent E. coli XL-1 Blue MRF were transformed with the vectors by electroporation. The plasmids of 100 single clones of the cloning reaction were prepared and the insertion site of the library was sequenced using the primer 4066 back 5'-ATG TCC GTC CGT GTG TGG-3'. (SEQ ID NO: 86)

The obtained nucleotide sequences were translated into protein sequences and the 7mer peptide sequences inserted at position I-587 of AAV2 VP was analyzed. The results are summarized in Table 10. AAV particles containing the same peptide sequence at the library insertion site as AAV particles obtained by screening of the library using an uncoated culture plate (see 5.1) were considered as non-specifically bound particles and were excluded from further analysis.

5.2.4. Second, Third and Fourth Round of Anti-IgE Antibody Screening

The number of genomic particles (genomic AAV titer) contained in the HeLa cell lysate was determined by quantitative real-time PCR (see 2.1.3). For the second, third and fourth round of selection, cell culture plates were coated with anti-IgE antibody (XOLAIR®) as described above. Blocking and washing of the coated plates was performed as describe above. Anti-IgE antibody coated plates were incubated with the volume of HeLa cell lysate (containing the AAV pool of the first, second or third selection round, respectively) corresponding to GPC 100 in a total volume of 10 ml blocking buffer. After incubation of the anti-IgE antibody coated plates with the AAV pool obtained from preceding round of selection for 2 h at room temperature, unbound virus was removed by 20 washes with 20 ml D-PBS/1% Tween-20 followed by four washes with 20 ml D-PBS. Uptake and amplification of the anti-IgE mAb bound AAV by HeLa cells was performed as described above. Preparation of total DNA, PCR amplification and subcloning of the AAV library insertion site was performed as described above. The results of the 2nd, 3rd and 4th selection round are summarized in Table 10. AAV particles containing the same peptide sequence at the library insertion site as AAV particles obtained by screening of the library using an uncoated culture plate (see 4.1) were considered as non-specifically bound particles and were excluded from further analysis.

5.2.5. Characterization of AAV Particles Obtained by Anti-IgE Antibody Screening of the AAV Library AAV particles of the library screening approach were produced and purified as described above. AAV capsid titers were analyzed using the AAV Titration ELISA.

Dot Blot Analysis

The AAV capsid variants (H5, D5, E8, A9, C7, G8) isolated by the screening of the AAV library with the anti-IgE antibody (XOLAIR®) were analyzed by dot blot experiments (FIG. 7). $5.0 \times 10^{10}$ and $1.0 \times 10^{10}$ capsids of the AAV variants were spotted onto a nitrocellulose membrane using a vacuum device except for C7 where $1 \times 10^{10}$ capsids only were spotted. As negative control wtAAV was spotted ranging from $5.0 \times 10^{10}$ to $3.9 \times 10^8$ capsids per dot. Likewise, serial dilutions of BSA (1.0 µg-0.03 µg) were spotted on the membrane as a negative control. As a positive control different dilutions of human IgE protein were spotted (1.0 µg-0.02 µg). After blocking of the membrane with blocking buffer (5% milk powder in PBS containing 0.1% Tween-20), the membrane was incubated with the XOLAIR® antibody (0.15 µg/ml in 1% milk powder in PBS containing 0.05% Tween-20) used for the screening of the AAV library at 4° C. for 18 h-24 h. After washing of the membrane with PBS/0.05% Tween-20, binding of the anti-IgE antibody to the spotted AAV variants was detected with an anti-human IgG HRP conjugate (FIG. 7A)).

To demonstrate that equal amounts of AAV variants were spotted on the membrane, the membrane was stripped as described above and spotted AAV capsids were detected using A20 (FIG. 7B). For this, the membrane was incubated with the A20 antibody (Progen) (hybridoma supernatant 1:10 diluted in 1% milk powder in PBS containing 0.05% Tween-20) for 2 h at room temperature. After washing of the membrane with PBS/0.05% Tween-20, binding of the A20 mAb to the spotted AAV variants was detected with an anti-mouse IgG (γ) HRP conjugate (CALTAG). The result demonstrates that there is a specific detection of AAV variants H5, D5 and E8 by the anti-IgE antibody (XOLAIR®) used for screening of the AAV capsid library.

To demonstrate the specificity of the binding of anti-IgE antibody to the AAV variants, the experiments were repeated and a control mAb (anti-KLH) was included into the experiments (FIG. 8). $5 \times 10^{10}$ and $1 \times 10^{10}$ particles of the AAV variants (H5 only $1 \times 10^{10}$) were dotted onto a nitrocellulose membrane. As negative control wtAAV was spotted ranging from $5.0 \times 10^{10}$ to $1.6 \times 10^9$ capsids per dot. As a positive control different dilutions of human IgE or KLH protein (1.0 µg-0.03 µg) were dotted. After blocking of the membrane with blocking buffer (5% milk powder in PBS containing 0.1% Tween-20), the membrane was incubated with the XOLAIR® antibody (0.15 µg/ml in 1% milk powder in PBS containing 0.05% Tween-20) used for the screening of the AAV library (FIG. 8A) or the control anti-KLH mAb (0.5 µg/ml in 1% milk powder in PBS containing 0.05% Tween-20) (FIG. 8B) at 4° C. for 18 h-24 h. After washing of the membrane with PBS/0.05% Tween-20, binding of the anti-IgE antibody or anti-KLH mAb to the spotted AAV variants was detected with a secondary HRP conjugated antibody. Please note that the signal for D5 ($5 \times 10^{10}$ particles) was so strong that the substrate was exhausted at the time of exposure.

These data demonstrate that variants H5, E8 and D5 specifically bind to the anti-IgE antibody, whereas there is no binding to the control anti-KLH antibody. In contrast variant G8 seems to bind to immunoglobulins in an unspecific way.

5.3. Anti-Idiotype Selection Using an Anti-CETP Antibody

To proof the concept of selection for an anti-idiotype AAV vaccine, an anti-CETP antibody was used for screening of the AAV capsid library. In this experiment, a AAV library was used, whose geno- and phenotype was coupled by infection at GPC 1000 described above (2.2).

5.3.1. Binding of AAV to Immobilized Anti-CETP Antibody

A cell culture plate (Ø10 cm, TPP) was coated with 5.0 ml anti-CETP antibody (clone ATM192, Acris-Antibodies) at a concentration of 10 µg/ml in coating buffer (0.8 ml 0.2M NaHCO$_3$, 1.7 ml 0.2M Na$_2$CO$_3$ ad 10 ml H$_2$O) for 18 h-24 h at 4° C. The anti-CETP antibody-coated plate was washed three times with 10 ml D-PBS containing 1% Tween-20 to remove unbound antibody. After washing the coated plate was incubated with 10 ml blocking buffer (5% milk powder in D-PBS containing 1% Tween-20) for 2 h at room temperature to avoid unspecific binding of the AAV particles to the plate. The plate was then incubated with $1 \times 10^8$ genome-containing AAV library particles in a total volume of 5 ml blocking buffer for 2 h at room temperature. The genomic titer of the AAV population was determined by quantitative real-time PCR as described above. After incubation of the anti-CETP antibody-coated plate with the AAV library, unbound virus was removed by 20 washes with 10 ml D-PBS/1% Tween-20 followed by four washes with 10 ml D-PBS.

5.3.2. Uptake and Amplification of AAV by HeLa Cells $1.0 \times 10^6$ HeLa cells per plate were seeded onto the AAV particles captured by the anti-CETP mAb. Simultaneously, HeLa cells were infected with AdV2 at an MOI of 5 to induce replication of AAV particles. Infection and cultivation of the HeLa cells was performed in a total volume of 10 ml DMEM containing 10% (v/v) fetal calf serum (FCS) and 1% (v/v) Penicillin/Streptomycin for 48 h at 37° C. and 5% CO$_2$ in a humidified atmosphere. After 48 h of cultivation, HeLa cells were harvested using a cell scraper and collected by centrifugation (3000 g, 10 min, 4° C.). Cells were washed with 5 ml D-PBS. After centrifugation (3000 g, 10 min, 4° C.) the cell pellet was resuspended in 250 µl lysis buffer (150 mM NaCl, 50 mM Tris, pH 8.5). Cells were lyzed by three freeze/thaw cycles using liquid nitrogen and a thermoblock tempered at 37° C.

5.3.3. PCR Amplification and Subcloning of the AAV Library Insertion Site

Total DNA was purified from a 50 µl aliquot of the transduced HeLa cell lysate.

The cell lysate was diluted fourfold in PBS and total DNA was prepared using the DNeasy Tissue Kit according to the instructions of the manufacturer. Total DNA was eluted in 50 µl H$_2$O. The fragment of the AAV genome containing the library insertion site was amplified by PCR using 5 µl of the total DNA prepared from the cell lysate as template and 20 pmol of the primers BsiWI back 5'-TAC CAG CTC CCG TAC GTC CTC GGC-3' (SEQ ID NO: 88)

and

SnaBI forward 5'-CGC CAT GCT ACT TAT CTA CG-3' (SEQ ID NO: 89)

in a total volume of 50 µl. PCR was performed using the High Fidelity Platinum Pfx Polymerase Kit (Invitrogen). After initial heat denaturation of the DNA template at 95° C. for 3 min, DNA was amplified by 35 PCR cycles (45 sec at 95° C. denaturation, 40 sec at 56° C. annealing, 2 min at 68° C. extension). Amplification was terminated after a final extension step at 68° C. for 10 min. An aliquot of the PCR reaction was analyzed on a 1% TBE agarose gel. The PCR product was purified using the PCR Purification Kit (Qiagen). The PCR product was cloned into the BsiWI/SnaBI site of the vector pRC-Kotin. Electro-competent *E. coli* XL-1 Blue MRF were transformed with the vectors by electroporation. The plasmids of 100 single clones of the cloning reaction were prepared and the insertion site of the library was sequenced using the primer 4066 back 5'-ATG TCC GTC CGT GTG TGG-3'. (SEQ ID NO: 86)

The obtained nucleotide sequences were translated into protein sequences and the 7mer peptide sequence inserted at position I-587 of AAV2 VP was analyzed. The results are summarized in Table 10. AAV particles containing the same peptide sequence at the library insertion site as AAV particles obtained by screening of the library using an uncoated culture plate (see 4.1) were considered as non-specifically bound particles and were excluded from further analysis 5.3.4. Second and Third Round of Anti-CETP Antibody Screening The number of genomic particles (genomic AAV titer) contained in the HeLa cell lysate was determined by quantitative real-time PCR (see 2.1.3). For the second and third round of selection, cell culture plates were coated with anti-CETP antibody as described above. Blocking and washing of the coated plates was performed as described above. Anti-CETP antibody-coated plates were incubated with the volume of HeLa cell lysate (containing the AAV pool of the first and second selection round, respectively) corresponding to GPC 100 in a total volume of 5 ml blocking buffer. After incubation of the anti-CETP antibody coated plates with the AAV pool obtained from the first and second round of selection for 2 h at room temperature, unbound virus was removed by 20 washes with 10 ml D-PBS/1% Tween-20 followed by four washes with 10 ml D-PBS. Uptake and amplification of the anti-CETP mAb-bound AAV by HeLa cells was performed as described above. Preparation of total DNA, PCR amplification and subcloning of the AAV library insertion site was performed as described above. AAV particles containing the same peptide sequence at the library insertion site as AAV particles obtained by screening of the library using an uncoated culture plate (see 4.1) were considered as non-specifically bound particles and were excluded from further analysis.

5.3.5. Characterization of AAV Particles Obtained by Anti-CETP Antibody Screening of the AAV Library AAV particles of the library screening approach were produced and purified as described above. AAV capsid titers were analyzed using the AAV Titration ELISA.

Dot Blot Analysis

The AAV capsid variants B8 and C4 isolated by the screening of the AAV library with the anti-CETP antibody were analyzed by dot blot experiments (FIG. 9). $5.0 \times 10^{10}$ and $1.0 \times 10^{10}$ AAV variants were spotted onto a nitrocellulose membrane using a vacuum device. As negative control wtAAV was spotted ranging from $5.0 \times 10^{10}$ to $3.2 \times 10^{9}$ capsids per dot. Likewise, serial dilutions of BSA (1.0 µg-0.03 µg) were spotted on the membrane as a negative control. After blocking of the membrane with blocking buffer (5% milk powder in PBS containing 0.1% Tween-20), the membrane was incubated with the anti-CETP antibody (5 µg/ml in 1% milk powder in PBS containing 0.05% Tween-20) used for the screening of the AAV library at 4° C. for 18 h-24 h. After washing of the membrane with PBS/0.05% Tween-20, binding of the anti-CETP antibody to the spotted AAV variants was detected with an anti-mouse IgG HRP conjugate. The membrane was incubated with an anti-mouse IgG HRP conjugate for 1 h at room temperature. After washing, signals were detected by chemiluminescence using the ECL system (Amersham Bioscience) (FIG. 9A).

To demonstrate that equal amounts of AAV variants were spotted on the membrane, the membrane was stripped as described above and spotted AAV capsids were detected using A20 (FIG. 9B). For this, the membrane was incubated with the A20 antibody (Progen) (1:10 diluted in 1% milk powder in PBS containing 0.05% Tween-20) for 2 h at room temperature. After washing of the membrane with PBS/0.05% Tween-20, binding of the A20 mAb to the spotted AAV variants was detected with an anti-mouse IgG (γ) HRP conjugate (CALTAG). The membrane was incubated with the anti-mouse IgG (γ) HRP conjugate for h at room temperature. After washing, signals were detected by chemiluminescence using the ECL system (Amersham Bioscience) (FIG. 9B). The result demonstrates that there is a specific detection of AAV variants B8 and C4 by the anti-CETP antibody used for screening of the AAV capsid library.

5.4. Optimizing the Presentation of the Selection Antibody

The presentation of the antibody used for selection can be improved by pre-coating of the cell culture plates or other supports (like sepharose beads) with a species and isotype-specific F(ab)₂ fragment that binds to the constant $F_r$ region of the selection antibody. This allows an orientated presentation of the selection antibody with the constant region bound to the immobilized F(ab)₂ fragment and leaves the idiotype portion of the antibody accessible for AAV variants. Therefore, a lower number of false-positive AAV variants that bind to other regions of the selection antibody (e.g. $F_c$ portion) will be isolated in the screening approach. Likewise other molecules, including protein A or protein G, that bind to the constant region of immunoglobulins can be used to orient the selection antibody.

In addition, the surface density of immobilized selection antibodies can be increased by the use of other supports (like sepharose beads) instead of plastic cell culture plates.

5.5. PCR-Based Amplification of the Genome of AAV Particles Captured by a Selection Antibody As an alternative to cellular uptake and amplification of AAV particles following infection of HeLa cells by AdV (as described above), the genome of AAV particles bound to a target antibody after the first or a subsequent selection round can be amplified by a PCR-based approach. AAV particles captured by the selection antibody are lyzed by a suitable buffer and DNA is isolated by a suitable method. For example, the AAV genome can be isolated using the DNeasy Blood & Tissue Kit (Qiagen) according to the protocol "Purification of Total DNA from Animal Blood or Cells" provided by the manufacturer. The fragment of the cap-gene containing the library insertion site with the respective inserted sequence can be amplified by PCR using the isolated DNA and suitable primers. The fragment can be subcloned into a suitable vector and analyzed by sequencing. For example, the DNA fragment of the cap gene containing the library insertion site can be amplified by Platinum Pfx DNA polymerase (Invitrogen) using a $PCR_x$ enhancer solution (Invitrogen), Pfx amplification buffer (Invitrogen) and the primers BsiWI-back: 5'-TAC CAG CTC CCG TAC GTC CTC GGC-3' (SEQ ID NO: 88)

and

SnaBI-forward: 5'-CGC CAT GCT ACT TAT CTA CG-3' (SEQ ID NO: 89)

according to the following PCR program: Initial denaturation at 95° C., 3 min; 35 amplification cycles: 95° C. for 45 s, 56° C. for 40 s, 68° C. for 2 min; and a final Elongation at 68° C., 10 min.

Following restriction with BsiWI and SnaBI, the PCR product can be cloned into the BsiwI/SnaBI linearized vector pUCAV2 (pUCAV2 is described in detail in U.S. Pat. No. 6,846,665). Clones can be analyzed by sequencing using the primer 4066back 5'-ATG TCC GTC CGT GTG TGG-3' (SEQ ID NO: 86)

6. Generation of Modified AAV Variants by Insertion of Epi- or Mimotope Sequences at Position I-587 or I-453 of the AAV Capsid by Genetic Manipulation The Approach Described Below is Used for the Insertion of Epi- or Mimotopes into the AAV capsid at position I-587 using a defined cloning strategy. This strategy includes the generation of a NotI and AscI restriction site within the cap gene by site-directed mutagenesis that allows the insertion of DNA fragments encoding epi- or mimotope at position I-587 of AAV cap flanked by a short or long alanine adaptor sequence.

6.1. Creation of Singular NotI and AscI Restriction Sites in Vector pCI-VP2

The vector pCI-VP2 was created by PCR amplification of the AAV2 VP2 gene mutating the minor ACG start codon into an ATG and cloning of the respective PCR product into the polylinker sequence of pCI (Promega). The NotI site at a nucleotide 18 of pCI-VP2 (nucleotide 1099 of pCI) was destroyed by site directed mutagenesis using the primers mutashe-3: 5'-GAG TCG ACC CGG GCA GCC GCT TCG AGC-3' (SEQ ID NO: 111)

and mutashe-4 5'-GCT CGA AGC GGC TGC CCG GGT CGA CTC-3' (SEQ ID NO: 112)

together with the QuickChange II Site-Directed Mutagenesis Kit (Stratagene) according to the instructions of the manufacturer. The resulting vector was referred to as pCI-VP2-ΔNotI 8. To introduce a NotI and AscI restriction site that allows the cloning of epitope or mimotope sequences at position I-587 of the AAV capsid, the vector pCI-VP2-ΔNotI8 was modified by site directed mutagenesis using the primers pCI-VP2-ΔNot-I587-for 5'-CC AAC CTC CAG AGA GGC AAC GCG GCC GCA AGG CGC GCC AAG CAG CTA CCG CAG-3' (SEQ ID NO: 113)

and pCI-VP2-ΔNot-I587-rev 5'-CTG CGG TAG CTG CTT GGC GCG CC TT GCG GCC GCG TTG CCT CTC TGG AGG TTG G-3'. (SEQ ID NO: 114)

Site specific mutagenesis was performed using the QuikChange II Site-Directed Mutagenesis Kit (Stratagene) according to the instructions of the manufacturer. The resulting vector is referred to as pCIVP2-I587-Not-AscI.

6.2. Cloning of Epitope or Mimotope Sequences into pCIVP2-I1587-NotI-AscI

For cloning of epi- or mimotope sequences into pCIVP2-I587-NotI-AscI sense and anti-sense oligonucleotides were designed that encode the respective epi- or mimotope sequences with a short or long alanine adaptor sequence and contain a 5'-site extension. The 5'-site extension of the oligonucleotides was designed so that annealing of the sense and anti-sense oligonucleotides results in a dsDNA with 5'-site and 3'-site overhangs compatible with overhangs generated by NotI and AscI restriction of the plasmid pCIVP2-I587-NotI-AscI. The sequences of the oligonucleotides and the respective epi- or mimotope sequences including the alanine adaptors are summarized in Table 11. Each of the inserted epi- or mimotope sequences is flanked by a short or long alanine adaptor according to the following scheme ($X_n$ represents the mimotope or epitope sequence):

short Ala adaptor: $(Ala)_3$-$X_n$-$(Ala)_2$
long Ala adaptor: $(Ala)_5$-$X_n$-$(Ala)_5$

TABLE 11

| Oligonucleotides used for cloning of epi- or mimotope sequences ||||||
|---|---|---|---|---|---|
| Name/ Peptide Seq. | Type | sense Oligonucleotide | anti-sense Oligonucleotide | Alanine Adaptor |
| Kricek VNLTWSRASG (SEQ ID NO: 85) | Epitope | 5' GGCCGCAGTGAACC TGACCTGGAGCAGAGCC TCCGGCGCGCG 3' SEQ ID NO: 115 | 5' CGCGCCGCGCCGGAG GCTCTGCTCCAGGTCAGG TTCACTGC 3' SEQ ID NO: 116 | short |
| | | 5' GGCCGCAGCGGCGG TGAACCTGACCTGGAGC AGAGCCTCCGGCGCGGC GGCGGCGG 3' SEQ ID NO: 117 | 5' CGCGCCGCCGCCGCC GCGCCGGAGGCTCTGCTC CAGGTCAGGTTCACCGCC GCTGC 3' SEQ ID NO: 118 | long |
| Rudolf EFCINHRGYWVCGD (SEQ ID NO: 84) | Mimotope | 5' GGCCGCAGAATTCT GCATAAACCACAGGGGA TACTGGGTGTGCGGAGA CGCGG 3' SEQ ID NO: 119 | 5' CGCGCCGCGTCTCCG CACACCCAGTATCCCCTG TGGTTTATGCAGAATTCT GC 3' SEQ ID NO: 120 | short |
| | | 5' GGCCGCAGCGGCGG AATTCTGCATAAACCAC AGGGGATACTGGGTGTG CGGAGACGCGGCGGCGG CGG 3' SEQ ID NO: 121 | 5' CGCGCCGCCGCCGCC GCGTCTCCGCACACCCAG TATCCCCTGTGGTTTATG CAGAATTCCGCCGCTGC 3' SEQ ID NO: 122 | long |

TABLE 11-continued

Oligonucleotides used for cloning of epi- or mimotope sequences

| Name/<br>Peptide Seq. | Type | sense<br>Oligonucleotide | anti-sense<br>Oligonucleotide | Alanine<br>Adaptor |
|---|---|---|---|---|
| CETP-intern<br>CDAGSVRTNAPD<br>SEQ ID NO: 123 | Epitope | 5' GGCCGCATGCGACG<br>CTGGCAGTGTGCGCACC<br>AATGCACCAGACGCGG<br>3'<br>SEQ ID NO: 124 | 5' CGCGCCGCGTCTGGT<br>GCATTGGTGCGCACACTG<br>CCAGCGTCGCATGC 3'<br>SEQ ID NO: 125 | short |
|  |  | 5' GGCCGCAGCGGCGT<br>GCGACGCTGGCAGTGTG<br>CGCACCAATGCACCAGA<br>CGCGGCGGCGGCGG 3'<br>SEQ ID NO: 126 | 5' CGCGCCGCCGCCGCC<br>GCGTCTGGTGCATTGGTG<br>CGCACACTGCCAGCGTCG<br>CACGCCGCTGC 3'<br>SEQ ID NO: 127 | long |

To anneal the oligonucleotides 50.0 μg of the sense oligonucleotide and 50.0 μg of the anti-sense oligonucleotide were mixed in a total volume of 200 μl 1×PCR-Buffer (Qiagen) and incubated for 3 min at 95° C. in a thermomixer. After 3 min at 95° C. the thermomixer was switched off and the tubes were left in the incubator for an additional 2 h to allow annealing of the oligonucleotides during the cooling down of the incubator. To clone the annealed oligonucleotides into pCIVP2-I587-NotI-AscI the vector was linearized by restriction with NotI and AscI and the cloning reaction was performed using the Rapid DNA Ligation Kit (Roche). Briefly, the annealed oligonucleotides were diluted 10-fold in 1×DNA Dilution Buffer and incubated for 5 min at 50° C. 100 ng of these annealed oligonucleotides and 50 ng of the linearized vector pCIVP2-I587-NotI-AscI were used in the ligation reaction, which was performed according to the instructions of the manufacturer of the Rapid DNA Ligation Kit (Roche). E. coli XL1 blue were transformed with an aliquot of the ligation reaction and plated on LB-Amp agar plates. Plasmids were prepared according to standard procedures and were analyzed by sequencing.

6.3. Subcloning of Epitope or Mimotope Sequences Form pCIVP2 into pUCAV2

For production of recombinant AAV particles carrying a mimo- or epitope insertion at position I-587 the BsiWI/XmaI fragment of pCI-VP2-587-NotI-AscI encoding a VP2 fragment containing the epitope or mimotope at position I-587 was sub-cloned into pUCAV2, which was modified as described below.

Cloning of vector pUCAV2 is described in detail in U.S. Pat. No. 6,846,665. Basically, this vector contains the complete AAV genome (BgI II fragment) derived from pAV2 (Laughlin et al., 1983) cloned into BamHI of pUC19.

pUCAV2 is used for production of the modified AAV particles. Since there are three XmaI sites in pUCAV2 it is not possible to use the XmaI site of pUCAV2 for subcloning of the BsiWI/XmaI fragment of pCI-VP2-587-NotI-AscI. Therefore, a new AgeI site was introduced into pUCAV2 that is compatible with XmaI and is not present in pUCAV2. To introduce the AgeI site pUCAV2 was linearized by SnaBI (position nt 2873 of pUCAV2), dephosphorylated and subsequently blunt-end ligated with a short ds oligonucleotide adaptor containing an internal AgeI site. The ds oligonucleotide adaptor was generated by annealing of a sense 5'-GTA GCC CTG GAA ACT AGA ACC GGT GCC TGC GCC-3' (SEQ ID NO: 128)

and anti-sense 5'-GGC GCA GGC ACC GGT TCT AGT TTC CAG GGC TAC 3' (SEQ ID NO: 129)

oligonucleotide containing an AgeI restriction site as described above. The annealed oligonucleotides were ligated with the SnaBI linearized, dephosphorylated pUCAV2 using the Rapid DNA Ligation Kit (Roche) as described above. The resulting vector is referred to as pUCAV2-AgeI. pUCAV2-AgeI was linearized with BsiWI and AgeI and ligated with the BsiWI/XmaI fragment of pCI-VP2-587-NotI-AscI encoding the VP2 fragment containing the respective epitope or mimotope at position I-587.

6.4. Production of AAV Variants by Co-Transfection of HEK 293 T-Cells

For production of AAV variants HEK 293-T cells were co-transfected with the vector plasmid pUCAV2 containing the subcloned mimo- or epiotope sequence, and the helper plasmid pUCAdV as described above (3.2). AAV variants were purified by Iodixanol gradient centrifugation as described above (3.3).

6.4.1. Insertion of a CETP Epitope into the AAV2 Capsid at Position I-587

An epitope (CDAGSVRTNAPD, SEQ ID NO: 123) of rabbit CETP (cholesteryl ester transfer protein) was introduced at position I-587 of AAV2 by the cloning approach described above. The epitope is flanked by a short or long alanine adaptor. For production of AAV variants HEK 293-T cells were co-transfected with the vector plasmid pUCAV2 containing the subcloned CETP epitope sequence at position I-587, and the helper plasmid pUCAdV as described above (4.2). AAV variants were purified by Iodixanol gradient centrifugation as described above (4.3).

The AAV capsid variants AAV-CETP-587-short and AAV-CETP-587-long were analyzed by dot blot experiments (FIG. 10). $5 \times 10^{10}$ purified AAV particles were spotted onto a nitrocellulose membrane using a vacuum device. Likewise, $5 \times 10^{10}$ or $1 \times 10^{10}$ purified AAV particles displaying the same epitope of rabbit CETP flanked by a short or long Ala adaptor sequence at position I-453 of AAV2 (see 6.4.3) were spotted onto the same membrane. As negative control wtAAV was spotted ranging from $5.0 \times 10^{10}$ to $6.3 \times 10^{9}$ capsids per dot. After blocking of the membrane with blocking buffer (5% milk powder in PBS containing 0.05% Tween-20), the membrane was incubated with a polyclonal anti-CETP serum generated by immunizing rabbits with the CETP epitope coupled to KLH. After washing of the membrane with PBS/0.05% Tween-20, binding of the anti-CETP antibodies to the spotted AAV variants was detected with an anti-rabbit IgG HRP conjugate (CALTAG). After washing, signals were detected by chemiluminescence using the ECL system (Amersham Bioscience).

The result demonstrate that there is a specific detection of the CETP epitope inserted into the AAV capsid at position I-587 and I-453 (for methods see 6.4.3) by the respective CETP antibody demonstrating that the epitope is displayed on the surface of the AAV particle.

6.4.2. Insertion of an IgE Epitope into the AAV2 Capsid at Position I-587

An epitope of IgE (VNLTWSRASG, SEQ ID NO: 85), that is recognized by the monoclonal anti-IgE antibody Bsw17 (Kricek et al., 1999)), was introduced at position I-587 of AAV2 by the cloning approach described above. The epitope is flanked by a long alanine adaptor in the AAV capsid. For production of the respective AAV variant (AAV-Kricek) HEK 293-T cells were co-transfected with the vector plasmid pUCAV2 containing the subcloned IgE epitope sequence at position I-587, and the helper plasmid pUCAdV as described above (3.2). AAV variants (AAV-Kricek) were purified by Iodixanol gradient centrifugation as described above (3.3).

The AAV capsid variant AAV-Kricek was analyzed by a dot blot experiment (FIG. 14). $2.5\times10^{10}$ AAV-Kricek particles were dotted onto a nitrocellulose membrane using a vacuum device. As negative control serial dilutions of wtAAV ($5.0\times10^{10}$ to $1.6\times10^{9}$) or the AAV variant D5 (see 4.2.5.1) were dotted. As a positive control human IgE was dotted ranging from 1.0 μg to 0.03 μg. After blocking of the membrane with blocking buffer (5% milk powder in PBS containing 0.05% Tween-20), the membrane was incubated with the anti-IgE mAb Bsw17. After washing of the membrane with PBS/0.05% Tween-20, binding of Bsw17 to the spotted AAV variants was detected with an anti-mouse IgG HRP conjugate (CALTAG). After washing, signals were detected by chemiluminescence using the ECL system (Amersham Bioscience).

The result shows that there is a specific detection of the AAV-Kricek particles by the Bsw17 mAb demonstrating that the antibody recognizes the IgE derived epitope (VNLTWSRASG, SEQ ID NO: 85) integrated in the AAV capsid at position I-587.

destroyed as described above (6.1). The resulting vector was referred to as pCI-VP2-ΔNot18. To introduce a NotI and AscI restriction site that allows the cloning of epitope or mimotope sequences at position I-453 of the AAV capsid, the vector pCI-VP2-ΔNot18 was modified by site directed mutagenesis using the primers mutashe-5 5'-CA AAC ACT CCA AGT GGA GGG CGC GCC GCT ACC ACC ACG CAG TC-3' (SEQ ID NO: 130)

and mutashe-6 5'-GA CTG CGT GGT GGT AGC GGC GCG CCC TCC ACT TGG AGT GTT TG-3' (SEQ ID NO: 131)

to introduce the AscI site first as well as the primers mutashe-7 5'-CA AAC ACT CCA AGT GGA GCG GCC GCA GGG CGC GCC GCT AC-3' (SEQ ID NO: 132)

and mutashe-8 5'-GT AGC GGC GCG CCC TGC GGC CGC TCC ACT TGG AGT GTT TG-3' (SEQ ID NO: 133)

to introduce the NotI site subsequently.

Site specific mutagenesis was performed using the QuickChange II Site-Directed Mutagenesis Kit (Stratagene) according to the instructions of the manufacturer. The resulting vector is referred to as pCIVP2-1453-NotI-AscI.

Cloning of CETP Epitope into pCIVP2-1453-NotI-AscI

For cloning of the CETP epitope (CDAGSVRTNAPD, SEQ ID NO: 123) into pCIVP2-1453-NotI-AscI forward and reverse oligonucleotides were designed that encode the respective epitope sequence flanked by a short $(Ala)_3$-CDAGSVRTNAPD-R-$(Ala)_2$ (SEQ ID NO: 134)

or long $(Ala)_5$-CDAGSVRTNAPD-$(Ala)_2$-R-$(Ala)_2$ (SEQ ID NO: 135)

alanine adaptor sequence and contain 5'-site extensions (Table 12). The 5'-site extension of the oligonucleotides was designed so that annealing of the forward and reverse oligonucleotides results in a dsDNA with 5'-site and 3'-site overhangs compatible with overhangs generated by NotI and AscI restriction of the plasmid pCIVP2-1453-NotI-AscI.

TABLE 12

Oligonucleotides used for cloning of CETP epitope sequence at position I-453

| Name/ Peptide Seq. | Type | Forward Oligonucleotide | Reverse Oligonucleotide | Alanine Adaptor |
|---|---|---|---|---|
| CETP-intern CDAGSVRTNAPD SEQ ID NO: 123 | Epitope | 5'-ggccgcatgcgacgctgg cagtgtgcgcaccaatgcacc agac-3' SEQ ID NO: 136 | 5'-cgcggtctggtgcattggt gcgcacactgccagcgtcgc a tgc-3' SEQ ID NO: 137 | short |
| | | 5'-ggccgcagccgcatgcga cgctggcagtgtgcgcaccaat gcaccagacgcggca-3' SEQ ID NO: 138 | 5'-cgcgtgccgcgtctggtgc attggtgcgcacactgccagc gtcgcatgcggctgc-3' SEQ ID NO: 139 | long |

6.4.3. Insertion of a CETP Epitope into the AAV2 Capsid at Position I-453

The approach described below is used for the insertion of a CETP epitope (CDAGSVRTNAPD, SEQ ID NO: 123) into the AAV capsid at position I-453.

Creation of Singular NotI and AscI Restriction Sites in Vector pCI-VP2

The vector pCI-VP2 was created by PCR amplification of the AAV2 VP2 gene mutating the minor ACG start codon into an ATG and cloning of the respective PCR product into the polylinker sequence of pCI (Promega). The NotI site at nucleotide 18 of pCI-VP2 (nucleotide 1099 of pCI) was To anneal the oligonucleotides 50.0 μg of the forward oligonucleotide and 50.0 μg of the reverse oligonucleotide were mixed in a total volume of 200 μl 1×PCR-Buffer (Qiagen) and incubated for 3 min at 95° C. in a thermomixer. After 3 min at 95° C. the thermomixer was switched off and the tubes were left in the incubator for an additional 2 h to allow annealing of the oligonucleotides during the cooling down of the incubator. To clone the annealed oligonucleotides into pCIVP2-1453-NotI-AscI the vector was linearized by restriction with NotI and AscI and the cloning reaction was performed using the Rapid DNA Ligation Kit (Roche). Briefly, the annealed oligonucleotides were diluted 10-fold in 1×DNA Dilution Buffer and incubated for 5 min at 50° C. 100 ng of these annealed oligonucleotides and 50 ng of the linearized vector pCIVP2-1453-NotI-AscI were used in the ligation reaction, which was performed according to the instructions of the manufacturer of the Rapid DNA Ligation Kit (Roche). *E. coli* XL1 blue were transformed with an aliquot of the ligation reaction and plated on LB-Amp agar plates. Plasmids were prepared according to standard procedures and were analyzed by sequencing.
Subcloning of the CETP Epitope from pCIVP2 into pUCAV2 at Position I-453

For production of recombinant AAV particles carrying the CETP epitope at position I-453 the BsiWI/XmaI fragment of pCI-VP2-453-NotI-AscI encoding a VP2 fragment containing the epitope at position I-453 was sub-cloned into pUCAV2, which was modified as described above (6.3). pUCAV2-AgeI was linearized with BsiWI and AgeI and ligated with the BsiWI/XmaI fragment of pCI-VP2-453-NotI-AscI encoding the VP2 fragment containing the CETP epitope at position I-453.

Production of AAV Variants by Co-Transfection of HEK 293 T-Cells

For production of AAV variants HEK 293-T cells were co-transfected with the vector plasmid pUCAV2 containing the subcloned CETP epitope sequence at position I-453, and the helper plasmid pUCAdV as described above (4.2). AAV variants were purified by Iodixanol gradient centrifugation as described above (4.3).

The AAV capsid variants AAV-CETP-453-short and AAV-CETP-453-long were analyzed by dot blot experiments as described above (6.4.1, FIG. 10).

6.4.4. Generation of Further AAV Variants

Insertion of CETP Epitopes into the AAV2 Capsid at Position I-587

The following rabbit CETP derived were cloned into position I-587 of the AAV2 capsid using annealed oligonucleotides as described above and were used for production of AAV particles. Each of the inserted epitope sequences is flanked by one of the following alanine/glycine adaptors according to the following scheme ($X_n$ represents the epitope sequence):

Type I adaptor: Ala-$(Gly)_3$-$X_n$-$(Gly)_4$-Ala

Type II adaptor: Ala-$(Gly)_4$-$X_n$-$(Gly)_4$-Ala

Type III adaptor: Ala-$(Gly)_4$-$X_n$-Ala-$(Gly)_3$-Ala

TABLE 13

CETP derived epitopes.

| Name/ Peptide Seq. | Type | sense Oligonucleotide | anti-sense Oligonucleotide | Adaptor |
|---|---|---|---|---|
| CETP TP10 AKAVSNLTESRS ESLQS SEQ ID NO: 237 | Epitope | 5'GGCCGGCGGAGGTGCCAA GGCCGTGAGCAACCTACCGA GAGCAGAAGCGAGAGCCTGC AGAGCGGGGGTGGCGGTG 3' SEQ ID NO: 245 | 5'CGCGCACCGCCACC CCCGCTCTGCAGGCTC TCGCTTCTGCTCTCGG TCAGGTTGCTCACGGC CTTGGCACCTCCGCC 3' SEQ ID NO: 246 | Type I |
| CETP TP11 SLTGDEFKKVLET SEQ ID NO: 238 | Epitope | 5'GGCCGGCGGAGGTAGCCT GACCGGCGACGAATTCAAGA AGGTGCTGGAGACCGGGGGT GGCGGTG 3' SEQ ID NO: 247 | 5'CGCGCACCGCCACC CCCGGTCTCCAGCACC TTCTTGAATTCGTCGC CGGTCAGGCTACCTCC GCC 3' SEQ ID NO: 248 | Type I |
| CETP TP12 REAVAYRFEED SEQ ID NO: 239 | Epitope | 5'GGCCGGCGGAGGTAGAGA GGCCGTGGCCTACAGATTCG AAGAGGACGGGGGTGGCGGT G 3' SEQ ID NO: 249 | 5'CGCGCACCGCCACC CCCGTCCTCTTCGAAT CTGTAGGCCACGGCCT CTCTACCTCCGCC 3' SEQ ID NO: 250 | Type I |
| CETP TP13 INPEIITLDG SEQ ID NO: 240 | Epitope | 5'GGCCGGCGGAGGTATCAA CCCCGAGATCATCACCCTGG ACGGCGGGGGTGGCGGTG 3' SEQ ID NO: 251 | 5'CGCGCACCGCCACC CCCGCCGTCCAGGGTG ATGATCTCGGGGTTGA TACCTCCGCC 3' SEQ ID NO: 252 | Type I |
| CETP TP18 DISVTGAPVITAT YL SEQ ID NO: 241 | Epitope | 5'GGCCGGCGGAGGTGACAT GCGTGACCGGTGCACCCG TGATCACCGCCACCTACCTG GGGGGTGGCGGTG 3' SEQ ID NO: 253 | 5'CGCGCACCGCCACC CCCCAGGTAGGTGGCG GTGATCACGGGTGCAC CGGTCACGCTGATGTC ACCTCCGCC 3' SEQ ID NO: 254 | Type I |
| CETP TP20 DISVTGAPVITA SEQ ID NO: 242 | Epitope | 5'GGCCGGCGGAGGTGACAT CAGCGTGACCGGTGCACCCG TGATCACCGCCGGGGGTGGC GGTG 3' SEQ ID NO: 255 | 5'CGCGCACCGCCACC CCCGGCGGTGATCACG GGTGCACCGGTCACGC TGATGTCACCTCCGCC 3' SEQ ID NO: 256 | Type I |

TABLE 13-continued CETP derived epitopes.

| Name/Peptide Seq. | Type | sense Oligonucleotide | anti-sense Oligonucleotide | Adaptor |
|---|---|---|---|---|
| Ritsch-1 DQSVDFEIDSA SEQ ID NO: 243 | Epitope | 5'GGCCGGCGGAGGTGACCA GAGCGTGGACTTCGAGATCG ACAGCGCCGGGGGTGGCGGT G 3' SEQ ID NO: 257 | 5'CGCGCACCGCCACC CCCGGCGCTGTCGATC TCGAAGTCCACGCTCT GGTCACCTCCGCC 3' SEQ ID NO: 258 | Type I |
| Ritsch-3 KNVSEAFPLRA SEQ ID NO: 244 | Epitope | 5'GGCCGGCGGAGGTAAGAA CGTGAGCGAGGCCTTCCCTC TGAGAGCCGGGGGTGGCGGT G 3' SEQ ID NO: 259 | 5'CGCGCACCGCCACC CCCGGCTCTCAGAGGG AAGGCCTCGCTCACGT TCTTACCTCCGCC 3' SEQ ID NO: 260 | Type I |

The following sequences, which are human homologues to the corresponding rabbit CETP sequences can be integrated into the AAV2 capsid at position I-587 according to the methods described above:

TABLE 14

CETP derived epitopes at position I-587

| Epitope | Rabbit Sequence | Human Sequence |
|---|---|---|
| CETP intern | CDAGSVRTNAPD SEQ ID NO: 123 | CDSGRVRTDAPD SEQ ID NO: 223 |
| CETP C-Term | FPKHLLVDFLQSLS SEQ ID NO: 261 | FPEHLLVDFLQSLS SEQ ID NO: 224 |
| TP10 | AKAVSNLTESRSESLQS SEQ ID NO: 237 | PKTVSNLTESSSESVQS SEQ ID NO: 214 |
| TP11 | SLTGDEFKKVLET SEQ ID NO: 238 | SLMGDEFKAVLET SEQ ID NO: 215 |
| TP12 | REAVAYRFEED SEQ ID NO: 239 | QHSVAYTFEED SEQ ID NO: 216 |
| TP13 | INPEIITLDG SEQ ID NO: 240 | INPEIITRDG SEQ ID NO: 217 |
| TP18 | DISVTGAPVITATYL SEQ ID NO: 241 | DISLTGDPVITASYL SEQ ID NO: 218 |

TABLE 14-continued

CETP derived epitopes at position I-587

| Epitope | Rabbit Sequence | Human Sequence |
|---|---|---|
| TP20 | DISVTGAPVITA SEQ ID NO: 242 | DISLTGDPVITA SEQ ID NO: 219 |
| Ritsch-1 | DQSVDFEIDSA SEQ ID NO: 243 | DQSIDFEIDSA SEQ ID NO: 220 |
| Ritsch-2 | KNVSEAFPLRAFPPGLLGDS SEQ ID NO: 262 | KNVSEDLPLPTFSPTLLGDS SEQ ID NO: 221 |
| Ritsch-3 | KNVSEAFPLRA SEQ ID NO: 244 | KNVSEDLPLPT SEQ ID NO: 222 |

Insertion of CETP Epitopes into the AAV2 Capsid at Position I-453

The following rabbit CETP derived epitopes were cloned into position I-453 of the AAV2 capsid using annealed oligonucleotides as described above. Each of the inserted epitope sequences in the AAV2 backbone at I-453 is flanked by the following alanine/glycine adaptors according to the following scheme ($X_n$ represents the epitope sequence):

Type I Ala/Gly adaptor:
$(Ala)_2$-$(Gly)_3$-$X_n$-$(Gly)_4$-Arg-$(Ala)_2$

Type II Ala/Gly adaptor:
$(Ala)_3$-$(Gly)_3$-$X_n$-$(Gly)_4$-Arg-$(Ala)_2$

TABLE 15 rabbit CETP derived epitopes at position I-453

| Name/ Peptide Seq. | Type | sense Oligonucleotide | anti-sense Oligonucleotide | Adaptor |
|---|---|---|---|---|
| CETP TP10 AKAVSNLTESRS ESLQS SEQ ID NO: 237 | Epitope | 5'GGCCGGCGGTGGAGCCA AGGCCGTGAGCAACCTGAC CGAGAGCAGAAGCGAGAGC CTGCAGAGCGGTGGCGGTG GA 3' SEQ ID NO: 263 | 5'CGCGTCCACCGCCACCG CTCTGCAGGCTCTCGCTTC TGCTCTCGGTCAGGTTGCT CACGGCCTTGGCTCCACCG CC 3' SEQ ID NO: 264 | Type I Ala/Gly |
| CETP TP11 SLTGDEFKKVLET SEQ ID NO: 238 | Epitope | 5'GGCCGGCGGTGGAAGCC TGACCGGCGACGAATTCAA GAAGGTGCTGGAGACCGGT GGCGGTGGA 3' SEQ ID NO: 265 | 5'CGCGTCCACCGCCACCG GTCTCCAGCACCTTCTTGA ATTCGTCGCCGGTCAGGCT TCCACCGCC 3' SEQ ID NO: 266 | Type I Ala/Gly |
| CETP TP12 REAVAYRFEED | Epitope | 5'GGCCGGCGGTGGAAGAG AGGCCGTGGCCTACAGATT | 5'CGCGTCCACCGCCACCG TCCTCTTCGAATCTGTAGG | Type I Ala/Gly |

TABLE 15-continued rabbit CETP derived epitopes at position I-453

| Name/ Peptide Seq. | Type | sense Oligonucleotide | anti-sense Oligonucleotide | Adaptor |
|---|---|---|---|---|
| SEQ ID NO: 239 | | CGAAGAGGACGGTGGCGGT GGA 3' SEQ ID NO: 267 | CCACGGCCTCTCTTCCACC GCC 3' SEQ ID NO: 268 | |
| CETP TP13 INPEIITLDG SEQ ID NO: 240 | Epitope | 5'GGCCGGCGGTGGAATCA ACCCCGAGATCATCACCCT GGACGGCGGTGGCGGTGGA 3' SEQ ID NO: 269 | 5'CGCGTCCACCGCCACCG CCGTCCAGGGTGATGATCT CGGGGTTGATTCCACCGCC 3' SEQ ID NO: 270 | Type I Ala/Gly |
| CETP TP18 DISVTGAPVITAT YL SEQ ID NO: 241 | Epitope | 5'GGCCGGCGGTGGAGACA TCAGCGTGACCGGTGCACC CGTGATCACCGCCACCTAC CTGGGTGGCGGTGGA 3' SEQ ID NO: 271 | 5'CGCGTCCACCGCCACCC AGGTAGGTGGCGGTGATCA CGGGTGCACCGGTCACGCT GATGTCTCCACCGCC 3' SEQ ID NO: 272 | Type I Ala/Gly |
| CETP TP20 DISVTGAPVITA SEQ ID NO: 242 | Epitope | 5'GGCCGGCGGTGGAGACA TCAGCGTGACCGGTGCACC CGTGATCACCGCCGGTGGC GGTGGA 3' SEQ ID NO: 273 | 5'CGCGTCCACCGCCACCG GCGGTGATCACGGGTGCAC CGGTCACGCTGATGTCTCC ACCGCC 3' SEQ ID NO: 274 | Type I Ala/Gly |
| Ritsch-1 DQSVDFEIDSA SEQ ID NO: 243 | Epitope | 5'GGCCGGCGGTGGAGACC AGAGCGTGGACTTCGAGAT CGACAGCGCCGGTGGCGGT GGA 3' SEQ ID NO: 275 | 5'CGCGTCCACCGCCACCG GCGTGTCGATCTCGAAGT CCACGCTCTGGTCTCCACC GCC 3' SEQ ID NO: 276 | Type I Ala/Gly |

The following sequences, which are human homologues to the corresponding rabbit CETP sequences can be integrated into the AAV2 capsid at position I-453 according to the methods described above:

TABLE 16

CETP derived epitopes at position I-453

| Epitope | Rabbit Sequence | Human Sequence |
|---|---|---|
| CETP intern | CDAGSVRTNAPD SEQ ID NO: 123 | CDSGRVRTDAPD SEQ ID NO: 223 |
| CETP C-Term | FPKHLLVDFLQSLS SEQ ID NO: 261 | FPEHLLVDFLQSLS SEQ ID NO: 224 |
| TP10 | AKAVSNLTESRSESLQS SEQ ID NO: 237 | PKTVSNLTESSSESVQS SEQ ID NO: 214 |
| TP11 | SLTGDEFKKVLET SEQ ID NO: 238 | SLMGDEFKAVLET SEQ ID NO: 215 |
| TP12 | REAVAYRFEED SEQ ID NO: 239 | QHSVAYTFEED SEQ ID NO: 216 |
| TP13 | INPEIITLDG SEQ ID NO: 240 | INPEIITRDG SEQ ID NO: 217 |
| TP18 | DISVTGAPVITATYL SEQ ID NO: 241 | DISLTGDPVITASYL SEQ ID NO: 218 |
| TP20 | DISVTGAPVITA SEQ ID NO: 242 | DISLTGDPVITA SEQ ID NO: 219 |
| Ritsch-1 | DQSVDFEIDSA SEQ ID NO: 243 | DQSIDFEIDSA SEQ ID NO: 220 |
| Ritsch-2 | KNVSEAFPLRAFPPGLLGDS SEQ ID NO: 262 | KNVSEDLPLPTFSPTLL GDS SEQ ID NO: 221 |
| Ritsch-3 | KNVSEAFPLRA SEQ ID NO: 244 | KNVSEDLPLPT SEQ ID NO: 222 |

Insertion of CETP Epitopes into the AAV2 Capsid at Position I-453 and I-587

Using the cloning strategy described in 9, the following AAV2 capsid variants carrying rabbit CETP epitopes at position I-453 and I-587 were produced:

TABLE 17

CETP double insertion mutants

| Name | Epitope at I-453 | Epitope at I-587 |
|---|---|---|
| AAV-TP10-2x | AKAVSNLTESRSESLQS SEQ ID NO: 237 | AKAVSNLTESRSESLQS SEQ ID NO: 237 |
| AAV-TP11-2x | SLTGDEFKKVLET SEQ ID NO: 238 | SLTGDEFKKVLET SEQ ID NO: 238 |
| AAV-TP12/13 | REAVAYRFEED SEQ ID NO: 239 | INPEIITLDG SEQ ID NO: 240 |
| AAV-TP12-2x | REAVAYRFEED SEQ ID NO: 239 | REAVAYRFEED SEQ ID NO: 239 |
| AAV-TP13-2x | INPEIITLDG SEQ ID NO: 240 | INPEIITLDG SEQ ID NO: 240 |
| AAV-TP18-2x | DISVTGAPVITATYL SEQ ID NO: 241 | DISVTGAPVITATYL SEQ ID NO: 241 |
| AAV-TP20-2x | DISVTGAPVITA SEQ ID NO: 242 | DISVTGAPVITA SEQ ID NO: 242 |

TABLE 17-continued

CETP double insertion mutants

| Name | Epitope at I-453 | Epitope at I-587 |
|---|---|---|
| AAV-Ritsch1-2x | DQSVDFEIDSA SEQ ID NO: 243 | DQSVDFEIDSA SEQ ID NO: 243 |
| AAV2-CETin-2x | CDAGSVRTNAPD SEQ ID NO: 123 | CDAGSVRTNAPD SEQ ID NO: 123 |

Insertion of Human IgE Epitopes into the AAV2 Capsid at Position I-587

The following human IgE derived epitopes were cloned into position I-587 of the AAV2 capsid using annealed oligonucleotides as described above and were used for production of AAV particles. Each of the inserted epitope sequences is flanked by one of the following alanine/glycine adaptors according to this section 6.4.4 for I-587 above.

TABLE 18 human IgE derived epitopes in I-587

| Name/ Peptide Seq. | Type | sense Oligonucleotide | anti-sense Oligonucleotide | Adaptor |
|---|---|---|---|---|
| 3DEpi3 | Epitope | 5' GGCCGGCGGAGGTGGTG ACAGCAACCCTAGAGGCGT GAGCGCCTACCTGAGCAGA GGGGGTGCGGTG 3' SEQ ID NO: 277 | 5' CGCGCACCGCCACCCCC TCTGCTCAGGTAGGCGCTC ACGCCTCTAGGGTTGCTGT CACCACCTCCGCC 3' SEQ ID NO: 278 | Type II |
| Wang-CS | Epitope | 5' GGCCGGCGGAGGTACCC ACCCCCACCTGCCCAGAGC CCTGATGAGAAGCGGGGGT GGCGGTG 3' SEQ ID NO: 279 | 5' CGCGCACCGCCACCCCC GCTTCTCATCAGGGCTCTG GGCAGGTGGGGGTGGGTAC CTCCGCC 3' SEQ ID NO: 280 | Type I |
| Flex | Epitope | 5' GGCCGGCGGAGGTGAGG ACGGCCAGGTGATGGACGT GGACCTGAGCGGGGGTGGC GGTG 3' SEQ ID NO: 281 | 5' CGCGCACCGCCACCCCC GCTCAGGTCCACGTCCATC ACCTGGCCGTCCTCACCTC CGCC3' SEQ ID NO: 282 | Type I |
| Bind2 | Epitope | 5' GGCCGGCGGAGGTGAGA AGCAGAGAAACGGCACCCT GACCGGTGGTGGCGGTG 3' SEQ ID NO: 283 | 5' CGCGCACCGCCACCACC GGTCAGGGTGCCGTTTCTC TGCTTCTCACCTCCGCC 3' SEQ ID NO: 284 | Type I |
| C21 | Epitope | 5' GGCCGGCGGAGGTGGTC TGCCCAGAGCCCTGATGAG AAGCGCCGGTGGCGGTG 3' SEQ ID NO: 285 | 5' CGCGCACCGCCACCGGC GCTTCTCATCAGGGCTCTG GGCAGACCACCTCCGCC 3' SEQ ID NO: 286 | Type III |

Insertion of Cytokine Epitopes into the AAV2 Capsid at Position I-587

The following murine cytokine derived epitopes were cloned into position I-587 of the AAV2 capsid using annealed oligonucleotides as described above and were used for production of AAV particles. Each of the inserted epitope sequences is flanked by one of the following alanine/glycine adaptors according to this section 6.4.4 for I-587 above.

TABLE 19 murine cytokine derived epitopes in I-587

| Name/ Peptide Seq. | Type | sense Oligonucleotide | anti-sense Oligonucleotide | Adaptor |
|---|---|---|---|---|
| mTNFα-V1 SSQNSSDKPV AHVVANHQVE SEQ ID NO: 287 | Epitope | 5' GGCCGGCGGAGGTAGCA GCCAGAACAGCAGCGACAA GCCCGTGGCCCACGTGGTG GCTAACCACCAGGTGGAGG GGGGTGGCGGTG 3' SEQ ID NO: 294 | 5' CGCGCACCGCCACCCCC CTCCACCTGGTGGTTAGCC ACCACGTGGGCCACGGGCT TGTCGCTGCTGTTCTGGCT GCTACCTCCGCC 3' SEQ ID NO: 295 | Type I |
| mTNFα-V2 SQNSSDKPVA HVVANH | Epitope | 5' GGCCGGCGGAGGTAGCC AGAACAGCAGCGACAAGCC CGTGGCCCACGTGGTGGCT | 5' CGCGCACCGCCACCCCC GTGGTTAGCCACCACGTGG GCCACGGGCTTGTCGCTGC | Type I |

TABLE 19-continued

| murine cytokine derived epitopes in I-587 | | | | |
|---|---|---|---|---|
| Name/ Peptide Seq. | Type | sense Oligonucleotide | anti-sense Oligonucleotide | Adaptor |
| SEQ ID NO: 288 | | AACCACGGGGGTGGCGGTG 3' SEQ ID NO: 296 | TGTTCTGGCTACCTCCGCC 3' SEQ ID NO: 297 | |
| mTNFα-V3 SSQNSSDKP SEQ ID NO: 289 | Epitope | 5' GGCCGGCGGAGGTAGCA GCCAGAACAGCAGCGACAA GCCCGGGGGTGGCGGTG 3' SEQ ID NO: 298 | 5' CGCGCACCGCCACCCCC GGGCTTGTCGCTGCTGTTC TGGCTGCTACCTCCGCC 3' SEQ ID NO: 299 | Type I |
| mIL-17-V1 NAEGKLDHHM NSVL SEQ ID NO: 290 | Epitope | 5' GGCCGGCGGAGGTAACG CCGAGGGCAAGCTTGACCA CCACATGAACAGCGTGCTG GGGGGTGGCGGTG 3' SEQ ID NO: 300 | 5' CGCGCACCGCCACCCCC CAGCACGCTGTTCATGTGG TGGTCAAGCTTGCCCTCGG CGTTACCTCCGCC 3' SEQ ID NO: 301 | Type I |
| mIL-17-V2 EGKLDHHMNSV SEQ ID NO: 291 | Epitope | 5' GGCCGGCGGAGGTGAGG GCAAGCTTGACCACCACAT GAACAGCGTGGGGGGTGGC GGTG 3' SEQ ID NO: 302 | 5' CGCGCACCGCCACCCCC CACGCTGTTCATGTGGTGG TCAAGCTTGCCCTCACCTC CGCC 3' SEQ ID NO: 303 | Type I |
| mIL-6-V1 KSLEEFLKVTL RSTRQ SEQ ID NO: 292 | Epitope | 5' GGCCGGCGGAGGTAAGA GCCTGGAGGAATTCCTGAA GGTGACCCTGAGAAGCACC AGACAGGGGGGTGGCGGTG 3' SEQ ID NO: 304 | 5' CGCGCACCGCCACCCCC CTGTCTGGTGCTTCTCAGG GTCACCTTCAGGAATTCCT CCAGGCTCTTACCTCCGCC 3' SEQ ID NO: 305 | Type I |
| mIL-6-V2 LEEFLKVTLRS SEQ ID NO: 293 | Epitope | 5' GGCCGGCGGAGGTCTGG AGGAATTCCTGAAGGTGAC CCTGAGAAGCGGGGGTGGC GGTG 3' SEQ ID NO: 306 | 5' CGCGCACCGCCACCCCC GCTTCTCAGGGTCACCTTC AGGAATTCCTCCAGACCTC CGCC 3' SEQ ID NO: 307 | Type I |

The following sequences, which are human homologues to the corresponding murine cytokine sequence can be integrated into the AAV2 capsid at position I-587 according to the methods described above:

TABLE 20

| cytokine derived epitopes | | |
|---|---|---|
| Cytokine | murine epitope | human epitope |
| TNF-α V1 | SSQNSSDKPVAHVVANHQVE SEQ ID NO: 287 | SSRTPSDKPVAHVVANPQAE SEQ ID NO: 226 |
| TNF-α V2 | SQNSSDKPVAHVVANH SEQ ID NO: 288 | SRTPSDKPVAHVVANP SEQ ID NO: 227 |
| TNF-α V3 | SSQNSSDKP SEQ ID NO: 289 | SSRTPSDKP SEQ ID NO: 228 |
| IL-17 V1 | NAEGKLDHHMNSVL SEQ ID NO: 290 | NADGNVDYHMNSVP SEQ ID NO: 229 |

TABLE 20-continued

| cytokine derived epitopes | | |
|---|---|---|
| Cytokine | murine epitope | human epitope |
| IL-17 V2 | EGKLDHHMNSV SEQ ID NO: 291 | DGNVDYHMNSV SEQ ID NO: 230 |
| IL-6 V1 | KSLEEFLKVTLRSTRQ SEQ ID NO: 292 | RSFKEFLQSSLRALRQ SEQ ID NO: 231 |
| IL-6 V2 | LEEFLKVTLRS SEQ ID NO: 293 | FKEFLQSSLRA SEQ ID NO: 232 |

Insertion of Cytokine Epitopes into the AAV2 Capsid at Position I-453

The following murine cytokine derived epitopes were cloned into position I-453 of the AAV2 capsid using annealed oligonucleotides as described above. Each of the inserted epitope sequences in the AAV2 backbone at I-453 is flanked by the alanine/glycine adaptors according this section 6.4.4 for I-453 above.

TABLE 21

| murine cytokine derived epitopes in I-453 | | | | |
|---|---|---|---|---|
| Name/ Peptide Seq. | Type | sense Oligonucleotide | anti-sense Oligonucleotide | Adaptor |
| mTNFα-V1 SSQNSSDKPVA | Epitope | 5' GGCCGCCGGTGGAGGCA GCAGCCAGAACAGCAGCGA | 5' CGCGCCCTCCACCGCCC TCCACCTGGTGGTTAGCCA | Type II Ala/Gly |

TABLE 21-continued murine cytokine derived epitopes in I-453

| Name/<br>Peptide Seq. | Type | sense<br>Oligonucleotide | anti-sense<br>Oligonucleotide | Adaptor |
|---|---|---|---|---|
| HVVANHQVE<br>SEQ ID NO: 287 | | CAAGCCCGTGGCCCACGTG<br>GTGGCTAACCACCAGGTGG<br>AGGGCGGTGGAGGG 3'<br>SEQ ID NO: 308 | CCACGTGGGCCACGGGCTT<br>GTCGCTGCTGTTCTGGCTG<br>CTGCCTCCACCGGC 3'<br>SEQ ID NO: 309 | |
| mIL-17-V1<br>NAEGKLDHHMN<br>SVL<br>SEQ ID NO: 290 | Epitope | 5' GGCCGCCGGTGGAGGCA<br>ACGCCGAGGGCAAGCTTGA<br>CCACCACATGAACAGCGTG<br>CTGGGCGGTGGAGGG 3'<br>SEQ ID NO: 310 | 5' CGCGCCCTCCACCGCCC<br>AGCACGCTGTTCATGTGGT<br>GGTCAAGCTTGCCCTCGGC<br>GTTGCCTCCACCGGC 3'<br>SEQ ID NO: 311 | Type II<br>Ala/Gly |
| mIL-6-V2<br>LEEFLKVTLRS<br>SEQ ID NO: 293 | Epitope | 5' GGCCGCCGGTGGAGGCC<br>TGGAGGAATTCCTGAAGGT<br>GACCCTGAGAAGCGGCGGT<br>GGAGGG 3'<br>SEQ ID NO: 312 | 5' CGCGCCCTCCACCGCCG<br>CTTCTCAGGGTCACCTTCA<br>GGAATTCCTCCAGGCCTCC<br>ACCGGC 3'<br>SEQ ID NO: 313 | Type II<br>Ala/Gly |

The following sequences, which are homologues to the corresponding murine cytokine sequences, can be integrated into the AAV2 capsid at position I-453 according to the methods described above:

TABLE 22 human cytokine derived epitopes in I-453

| Cytokine | murine epitope | human epitope |
|---|---|---|
| TNF-α V1 | SSQNSSDKPVAHVVANHQVE<br>SEQ ID NO: 287 | SSRTPSDKPVAHVVANPQAE<br>SEQ ID NO: 226 |
| TNF-α V2 | SQNSSDKPVAHVVANH<br>SEQ ID NO: 288 | SRTPSDKPVAHVVANP<br>SEQ ID NO: 227 |
| TNF-α V3 | SSQNSSDKP<br>SEQ ID NO: 289 | SSRTPSDKP<br>SEQ ID NO: 228 |
| IL-17 V1 | NAEGKLDHHMNSVL<br>SEQ ID NO: 290 | NADGNVDYHMNSVP<br>SEQ ID NO: 229 |
| IL-17 V2 | EGKLDHHMNSV<br>SEQ ID NO: 291 | DGNVDYHMNSV<br>SEQ ID NO: 230 |
| IL-6 V1 | KSLEEFLKVTLRSTRQ<br>SEQ ID NO: 292 | RSFKEFLQSSLRALRQ<br>SEQ ID NO: 231 |
| IL-6 V2 | LEEFLKVTLRS<br>SEQ ID NO: 293 | FKEFLQSSLRA<br>SEQ ID NO: 232 |

Insertion of Cytokine Epitopes into the AAV2 Capsid at Position I-453 and I-587

Using the cloning strategy described in 9, the following AAV variants carrying different cytokine epitopes at position I-453 and I-587 can be generated (bivalent vaccines):

TABLE 23 double insertion variants
for cytokine derived epitopes

| combination | Epitope at I-453 | Epitope at I-587 |
|---|---|---|
| TNFα/IL-17 | mTNFα-V1<br>SSQNSSDKPVAHVVANHQVE<br>SEQ ID NO: 287 | mIL-17-V1<br>NAEGKLDHHMNSVL<br>SEQ ID NO: 290 |

TABLE 23-continued double insertion variants
for cytokine derived epitopes

| combination | Epitope at I-453 | Epitope at I-587 |
|---|---|---|
| TNF-α/IL-6 | mTNFα-V1<br>SSQNSSDKPVAHVVANHQVE<br>SEQ ID NO: 287 | mIL-6-V2<br>LEEFLKVTLRS<br>SEQ ID NO: 293 |
| IL-17/TNF-α | mIL-17-V1<br>NAEGKLDHHMNSVL<br>SEQ ID NO: 290 | mTNFα-V1<br>SSQNSSDKPVAHVVANHQVE<br>SEQ ID NO: 287 |
| IL-6/TNF-α | mIL-6-V2<br>LEEFLKVTLRS<br>SEQ ID NO: 293 | mTNFα-V1<br>SSQNSSDKPVAHVVANHQVE<br>SEQ ID NO: 287 |
| IL-17/IL-6 | mIL-17-V1<br>NAEGKLDHHMNSVL<br>SEQ ID NO: 290 | mIL-6-V2<br>LEEFLKVTLRS<br>SEQ ID NO: 293 |
| IL-6/IL-17 | mIL-6-V2<br>LEEFLKVTLRS<br>SEQ ID NO: 293 | mIL-17-V1<br>NAEGKLDHHMNSVL<br>SEQ ID NO: 290 |

7. Generation of an Chimeric AAV2 Rep/AAV1 Cap Vector

The approach described below is used for the generation of expression plasmids for the production of AAV1 capsids. This strategy includes the generation of a NotI and AscI restriction site within the cap gene by site-directed mutagenesis that allows the insertion of DNA fragments encoding an epi- or mimotope C-terminally of amino acids $S_{588}$ or $D_{590}$ of AAV1 Cap flanked by a glycine adaptor sequence.

7.1. Substitution of AAV2 Cap by AAV1 Cap within pUC"Rep/Fs/cap"

Cloning of vector pUCrep/fs/cap is described in detail in US 2004/0087026 (section 0124 and previous sections, there referred to as pUC"rep/fs/cap"Δ37). The complete AAV1 cap ORF, as published by Xiao et al. (Xiao et al., 1999), was amplified by PCR using Expand High FidelityPlus PCR System (Roche; #03300242001). Using specificy modified primers restriction sites were inserted into the cap fragment. SwaI was inserted N-terminally from the VP-1 ATG and NdeI was inserted C-terminally from the polyA site using the primers:

AAV1 Swa for:
(SEQ ID NO: 140)
5'-GAT TTA AAT CAG GTA TGG CGT CCG ATG-3'

AAV1 Nde back:
(SEQ ID NO: 141)
5'-ACC GAT AAC ATA TGA AGG ACA GGA G-3'

The original sequence of AAV1's N-terminus (Seq. GP-No. 9632548) therefore was modified to read:

(SEQ ID NO: 142)
2201 5'-......caataaatga tttaaat cag gtatggctgc cgatggttat cttccagatt.....3'

Start ATG of VP-1 in bold, SwaI restriction site boxed.
The original sequence AAV1's C-terminus therefore was modified to read:

(SEQ ID NO: 143)
4441 5'-..ttaatcaata aaccggttga ttcgtttcag ttgaactttg gtctcctgtc ctt catatg t tatcggttac..3'

PolyA-Signal in bold, 3'-end of mRNA underlined, NdeI restriction site boxed.

The PCR fragment was purified and digested with the restriction enzymes SwaI and NdeI (New England Biolabs) according to the instructions of the manufacturer. The same digestion was performed with pUC"rep/fs/cap". Since SwaI is not a single cutting enzyme in pUC"rep/fs/cap" a partial digestion of NdeI-linearized pUC"rep/fs/cap" was performed with SwaI. The PCR fragment and the desired backbone fragment pUC"rep/fs/cap" of 5077 bp (SwaI cut in pUCrep/fs/cap at bp 7311) were excised and purified using a Qiagen Gelextraction Kit (Qiagen #28104). PCR fragment and backbone were ligated using the Rapid DNA Ligation Kit (Roche #11 635 379 001) according to manufacturer's protocol. The resulting vector is referred to as pUCrep/fs/cap_AAV1.

7.2. Substitution of AAV2 Cap by AAV1 Cap within pUCAV_AgeI

Cloning of vector pUCAV2_AgeI is described in detail in 6.3. The complete AAV1 cap ORF, as published by Xiao et al. (Xiao et al., 1999), was amplified by PCR using standard procedures using Expand High FidelityPlus PCR System (Roche; #03300242001). Using specifically modified primers restriction sites were inserted into the cap fragment. SwaI was inserted N-terminally from the VP-1 ATG and SnaBI was inserted C-terminally from the polyA site using the primers:

AAV1 Swa for:
(SEQ ID NO: 140)
5'-GAT TTA AAT CAG GTA TGG CGT CCG ATG-3'

AAV1 SnaBI back:
(SEQ ID NO: 144)
5'-CGA TAA GAT ACG TAG GAC AGG AGA C-3'

The original sequence of AAV1's N-terminus was therefore modified to read as described in 7.1.

The original sequence AAV1's C-terminus therefore was modified to read:

(SEQ ID NO: 145)
4441 5'-.ttaatcaata aaccggttga ttcgtttcag ttgaactttg gtctcctgtc ct acgtat ct tatcggttac.-3'

PolyA-Signal in bold, 3'-end of mRNA underlined, SnaBI restriction site boxed.

The PCR fragment was purified and digested with the restriction enzymes SwaI and SnaBI (New England Biolabs) according to the instructions of the manufacturer. The same digestion was performed with pUAV2_AgeI. Complete digests were analyzed in an agarose gel, and PCR fragment and the desired backbone fragment of pUCAV2_AgeI were purified utilizing a Qiagen Gelextraction Kit (Qiagen #28104). PCR fragment and backbone were ligated using the Rapid DNA Ligation Kit (Roche #11 635 379 001) according to manufactures protocol. The resulting vector is referred to as pUAV1_AgeI.

7.3. Creation of Singular NotI and AscI Restriction Sites at Amino Acid Position $S_{588}$ or $D_{590}$ within AAV1 Cap To introduce NotI and AscI restriction sites that allow the cloning of epitope or mimotope sequences C-terminally of amino acid $S_{588}$ or $D_{590}$ of the AAV1 capsid, the vector pUCrep/fs/cap_AAV1 was modified by site directed mutagenesis using the primers:

```
AAV1 590 NotI AscI for:
                                          (SEQ ID NO: 146)
5'-ttc cag agc agc agc aca gac gcg gcc gca aag gcg cgc cct gcg acc gga gat gtg cat-3'

AAV1 590 NotI AscI reverse:
                                          (SEQ ID NO: 147)
5'-atg cac atc tcc ggt cgc agg gcg cgc ctt tgc ggc
```

-continued
```
cgc gtc tgt gct gct gct ctg gaa-3'

AAV1 588 NotI AscI for:
                                    (SEQ ID NO: 148)
5'-gtc aat ttc cag agc agc agc gcg gcc gca agg cgc gcc aca gac cct gcg acc gga gat-3'

AAV1 588 NotI AscI reverse:
                                    (SEQ ID NO: 149)
5'-atc tcc ggt cgc agg gtc tgt ggc gcg cct tgc ggc cgc gct gct gct gaa att gac-3'
```

Underlined are the sequences of the inserted NotI or AscI restriction sites.

Site directed mutagenesis was performed using the QuikChange II Site-Directed Mutagenesis Kit (Stratagene) according to the manufacturer's instructions. The resulting vectors are referred to as pUCrep/fs/cap_AAV1_I588 and pUCrep/fs/cap_AAV1_I590, respectively.

7.4. Cloning of AAV1 Variants 7.4.1. Cloning of Rabbit CETP-Intern Epitope Sequence into pUCrep/fs/cap_AAV1_I588 or pUCrep/Fs/cap_AAV1_I590

For cloning of the rabbit CETP-intern sequence (CDAGS-VRTNAPD, SEQ ID NO: 123) into pUCrep/fs/cap_AAV1_I588 and pUCrep/fs/cap_AAV1_I590, respectively, forward and reverse oligonucleotides were designed that encode the respective CETPint sequence with an adaptor sequence of three glycin residues at each side and containing a 5'-site extension. The 5'-site extension of the oligonucleotides was designed so that annealing of the forward and reverse oligonucleotides results in a dsDNA with 5'-site and 3'-site overhangs compatible with overhangs generated by NotI and AscI restriction of the plasmid pUCrep/fs/cap_AAV1_I588 and pUCrep/fs/cap_AAV1_I590, respectively.

Oligonucleotides

```
CE_int_I590 AAV1 for:
                                    (SEQ ID NO: 150)
5'-G gcc gca ggc ggt gga tgc gac gct ggc agt gtg cgc acc aat gca cca gac ggc ggt gga gcgg-3'

CE_int_I590 AAV1 rev:
                                    (SEQ ID NO: 151)
5'-Cg cgc cgc tcc acc gcc gtc tgg tgc att ggt gcg cac act gcc agc gtc gca tcc acc gcc tgc-3'

CE_int_I588 AAV1 for:
                                    (SEQ ID NO: 152)
5'-G gcc gca ggc ggt gga tgc gac gct ggc agt gtg cgc acc aat gca cca gac ggc ggt gga gcg-3'

CE_int_I588 AAV1 rev:
                                    (SEQ ID NO: 153)
5'-C gcg cgc tcc acc gcc gtc tgg tgc att ggt gcg cac act gcc agc gtc gca tcc acc gcc tgc-3'
```

Underlined are G-linkers, bold is the inserted CETP sequence.

For protocol for cloning the oligonucleotides into the vector see example 6.4.3 part 'Cloning of CETP epitope . . . '.

7.4.2. Cloning of IgE Epitopes (Kricek and 3DEpi3) into pUCrep/fs/cap_AAV1_I588

The strategy for cloning the Kricek sequence VNLTWS-RASG (SEQ ID NO: 85) and the 3DEpi3 sequence into pUCrep/fs/cap_AAV1_I-588, respectively, was the same as described for the CETP insertion in 7.4. Regarding the adaptor sequence five glycin residues were incorporated up and downstream from the 3DEpi3 insertion. An alanin linker was designed for the Kricek insertion resulting in 5 alanins up and downstream of the Kricek insertion within the AAV1 sequence. Since the general design for the insertion of oligonucleotides for the 453 insertion in AAV2 is compatible with the 588 insertion in AAV1, oligonuclotides generated originally for AAV2 insertion could be used for AAV1 588 insertion.

Oligonucleotides:

Kricek long AAV1 for (SEQ ID NO: 314)

5'-G GCC GCA GCC GCA GTG AAC CTG ACC TGG AGC AGA GCC TCC GGC GCG GCA GCT GCA GCT-3'

Kricek long AAV1 rev (SEQ ID NO: 315)

5'-C GCG AGC TGC AGC TGC CGC GCC GGA GGC TCT GCT CCA GGT CAG GTT CAC TGC GGC TGC-3'

Underlined are A-linkers, bold is the inserted Kricek sequence.

3DEpi3 453 uni:

(SEQ ID NO: 316)

5'-GGCC GGC GGT GGA GGC GGT GAC AGC AAC CCT AGA GGC GTG AGC GCC TAC CTG AGC AGA GGA GGC GGT GGA GGG-3'

3DEpi3 453 rev:

(SEQ ID NO: 317)

5'-CGCG CCC TCC ACC GCC TCC TCT GCT CAG GTA GGC GCT CAC GCC TCT AGG GTT GCT GTC ACC GCC TCC ACC GCC-3'

Underlined are G-linkers, bold is the inserted 3DEpi3 sequence.

For protocol for cloning the oligonucleotides into the vector see example 6.4.3 part 'Cloning of CETP epitope . . . '.

7.4.3. Subcloning of Rabbit CETP-Intern Epitope from pUCrep/fs/cap_AAV1_I588 or pUCrep/fs/cap_AAV1_I590 into pUCAV1_AgeI pUCAV1-AgeI was linearized with BsiWI and AgeI and ligated with the BsiWI/AgeI fragment of pUCrep/fs/cap_AAV1_I588 or pUCrep/fs/cap_AAV1_I590 encoding the VP-2 fragment containing the rabbit CETP-intern epitope after the respective amino acid $S_{588}$ or $D_{590}$ according to standard procedures.

7.4.4. Subcloning of Kricek and 3DEpi3 from pUCrep/fs/cap_AAV1_I588 into pUCAV1_AgeI pUCAV1-AgeI was linearized with BsiWI and AgeI and ligated with the BsiWI/AgeI fragment of pUCrep/fs/cap_AAV1_I588 encoding the VP-2 fragment containing the Kricek and the 3DEpi3 epitope, respectively, according to standard procedures.

7.4.5. Subcloning of NotI and AscI Restriction Sites at Amino Acid Position $S_{588}$ from pUCrep/fs/cap_AAV1_I588 into pUCAV1_AgeI To allow direct cloning of polypeptides into pUCAV1 AgeI the NotI/AscI insertion site was cloned into pUCAV1 AgeI. Therefore, pUCAV1-AgeI was linearized with BsiWI and AgeI and ligated with the BsiWI/AgeI fragment of pUCrep/fs/cap_AAV1_I588 encoding the VP-2 fragment containing NotI/AscI insertion respectively according to standard procedures.

The resulting vector is named pUCAV1-AgeI-I588.

7.4.6. Cloning of Rabbit CETP Sequence TP18 into pUCAV1-AgeI-I588

The strategy for cloning the TP18 sequence DISVT-GAPVITATYL (SEQ ID NO: 241) into pUCAV1-AgeI-I588 respectively was the same as described for the CETP insertion in 7.4. Regarding the adaptor sequence three glycin residues were incorporated up and and 4 glycin residues downstream from the TP18 insertion. Since the general design for the insertion of oligonucleotides for the 453 insertion in AAV2 is compatible with the 588 insertion in AAV1, oligonuclotides generated originally for AAV2 insertion could be used for AAV1 588 insertion.

Oligonucleotides:

TP18-453 uni
(SEQ ID NO: 318)
5'-GGCC <u>GGC GGT GGA</u> GAC ATC AGC GTG ACC GGT GCA CCC GTG ATC ACC GCC ACC TAC CTG <u>GGT GGC GGT GGA</u>-3'

TP18-453 rev
(SEQ ID NO: 319)
5'-CGCG <u>TCC ACC GCC ACC</u> CAG GTA GGT GGC GGT GAT CAC GGG TGC ACC GGT CAC GCT GAT GTC <u>TCC ACC GCC</u>-3'

Underlined are G-linkers, bold is the inserted TP18 sequence.

For protocol for cloning the oligonucleotides into the vector see example 6.4.3 part 'Cloning of CETP epitope . . . '.

7.5. Production of AAV1 Variants by Co-Transfection of HEK 293-T-Cells

For production of AAV particles HEK 293-T cells were co-transfected with the vector plasmid pUCAV1 or pUCrep/fs/cap_AAV1 with or without the subcloned epitope (after amino acids $S_{588}$ or $D_{590}$) and the helper plasmid pUCAdV. For the production of pUCrep/fs/cap_AAV1 derived capsids (with or without the subcloned epitope) pGFP was additionally transfected since pUCrep/fs/cap_AAV1 does not encode for the AAV ITRs which function as a packaging signal. pGFP encodes GFP flanked by the AAV2 ITRs. Thus GFP is packaged as a transgene.

Resulting viral particles carrying the rabbit CETP epitope CETP-intern were named: AAV1-CETP-588 and AAV1-CETP-590 which were derived from pucAV1 derivates and rAAV1-GFP-CETP-588, rAAV1-GFP-CETP-590 which were derived from pUCrep/fs/cap_AAV1 derivates.

Production and purification of viral particles were performed as described above (see example 4).

Surprisingly yields for AAV1-particles were about 3-6 times higher compared to AAV2-particles, making AAV1 mutated structural proteins an especially preferred embodiment of this invention in all its aspects.

Figure 11:
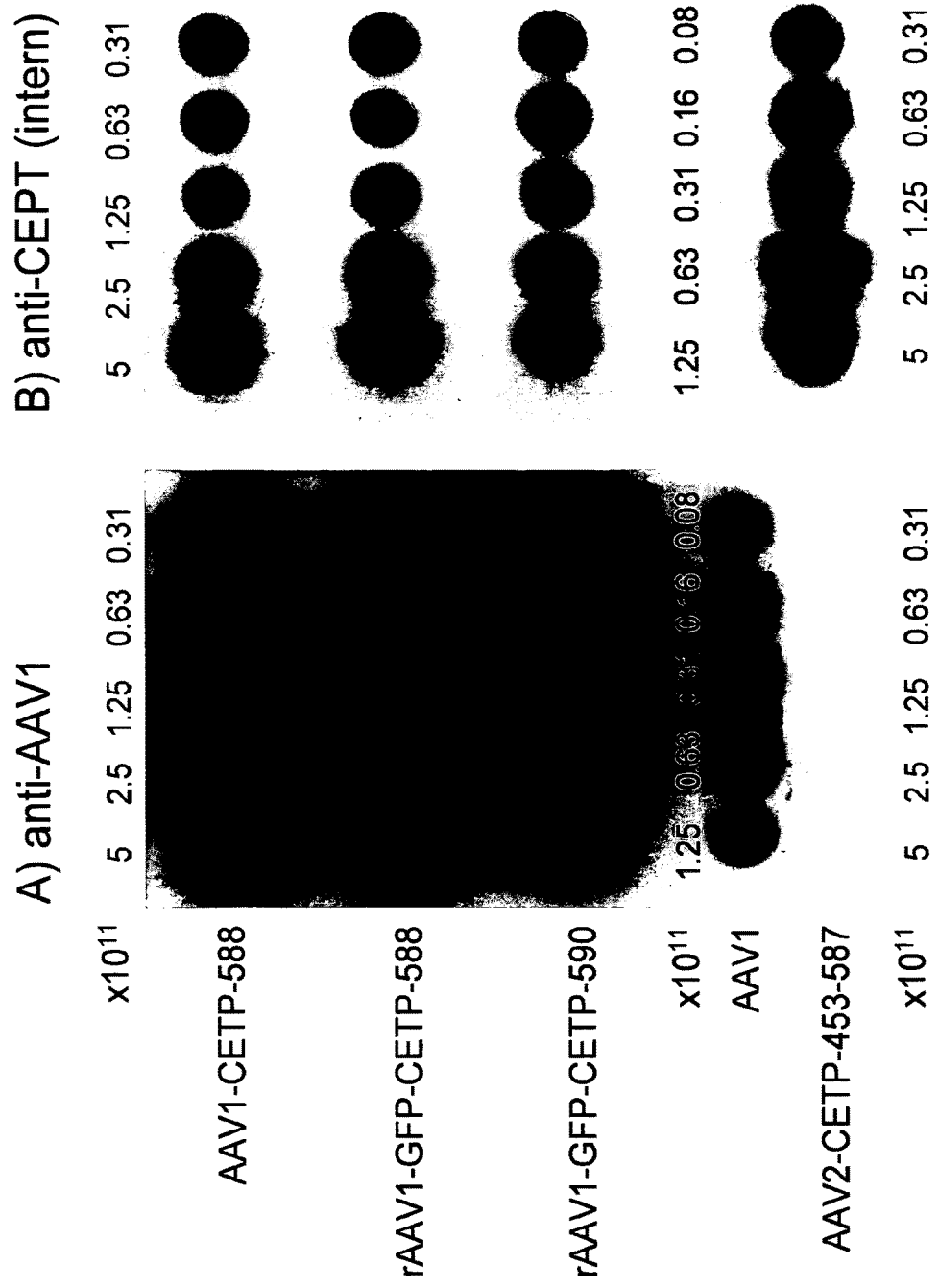

7.6. Evaluation of AAV1 Particles Carrying the Rabbit CETP-Intern Epitope after Amino Acids $S_{588}$ or $D_{590}$ The AAV1 capsid variants carrying the CETP-intern epitope at position 588 or 590 were analyzed by dot blot analysis (FIG. 11). $5.0 \times 10^{11}$ to $3.1 \times 10^{10}$ AAV capsids were spotted onto a nitrocellulose membrane using a vacuum device. As controls AAV2-CETPin 2× (AAV2 particles carrying the CETP-intern epitope at position I-453 and I-587) and wtAAV1 particles were spotted. After blocking of the membrane with blocking buffer (5% milk powder in PBS containing 0.05% Tween-20) for 1 h at room temperature, the membrane was incubated with the anti-CETP polyclonal rabbit serum (1:2,500 in 1% milk powder in PBS containing 0.05% Tween-20) for 1 h at room temperature. The serum was derived from rabbits vaccinated with the CETP-intern peptide coupled to LPH. After washing the membrane with PBS/0.05% Tween-20, binding of the anti-CETP serum to the spotted AAV variants was detected with an anti-mouse IgG HRP conjugate. The membrane was incubated with an anti-rabbit IgG HRP conjugate (1:2,500 in 1% milk powder in PBS containing 0.05% Tween-20) for 1 h at room temperature. After washing, signals were detected by chemiluminescence using the ECL system (Pierce) (FIG. 11B).

To demonstrate that equal amounts of AAV variants were spotted on the membrane, and to exclude cross reactions of the antibodies, an additional membrane was spotted as described above and spotted AAV capsids were detected using an anti-AAV1 antibody recognizing intact AAV1 particle (Progen) (FIG. 11B). For this, the membrane was incubated with the anti-antibody (Progen) (1:500 diluted in 1% milk powder in PBS containing 0.05% Tween-20) for 1 h at room temperature. After washing of the membrane with PBS/0.05% Tween-20, binding of the AAV1 mAb to the spotted AAV variants was detected with an anti-mouse IgG (γ) HRP conjugate (CALTAG). The membrane was incubated with the anti-mouse IgG (γ) HRP conjugate for 1 h at room temperature. After washing, signals were detected by chemiluminescence using the ECL system (Pierce) (FIG. 11A).

The results demonstrate that AAV1 CETP variants are specifically detected by the anti-CETP serum indicating that the CETP epitope inserted at both positions (after amino acids $S_{588}$ and $D_{590}$) is displayed on the surface of the capsid.

7.7. Analysis of Cross-Reactivity of AAV1 Capsids with Serum of AAV2 Vaccinated Rabbits Wild-type AAV2 and AAV1 capsids were coated onto Maxisorp 96 well plates (Nunc). Capsids were coated in equal amounts in serial dilutions from $1.0 \times 10^9$ to $1.56 \times 10^7$ capsids per well for 1 h at 37° C. After blocking with blocking buffer (5% milk powder in PBS containing 0.05% Tween-20) for 1 h at 37° C., wells were incubated with sera from rabbits vaccinated with AAV2 (1:400 in 1% milk powder in PBS containing 0.05% Tween-20) for 1 h at 37° C. After washing the wells with PBS/0.05% Tween-20, binding of the polyclonal rabbit serum to the coated AAV variants were detected with an anti-rabbit IgG HRP conjugate (DAKO). Wells were incubated with the anti-rabbit IgG HRP conjugate for 1 h at room temperature. After washing, substrate (TMB) was added to the wells. The reaction was stopped after 15 min by adding 0.2 M $H_2SO_4$. OD at 450 nm was measured in an ELISA reader.

Figure 12:
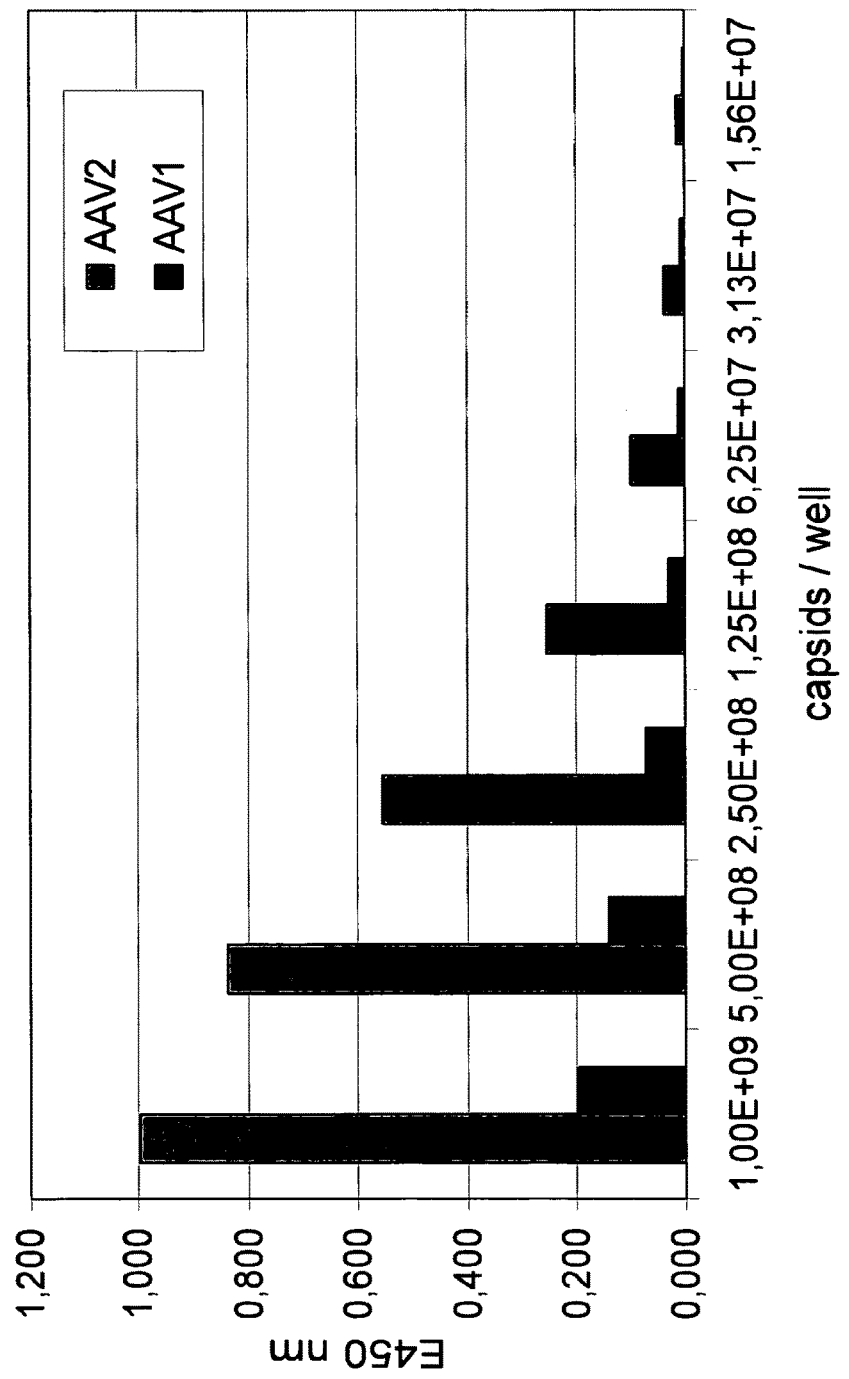

The result demonstrates that serum from AAV2 vaccinated rabbits binds less efficiently to AAV1 (up to factor 8 regarding the OD values) compared to AAV2 (FIG. 12) confirming that AAV1 and AAV2 are different serotypes with little cross-reactivity of anti-capsid antibodies. Therefore, it can be concluded that the cross-reactive antibodies in AAV2 sero-positive humans have only limited neutralizing activity on AAV1 vaccines applied to humans. As (neutralizing) antibodies against the viral backbone can limit both vaccination and gene transfer efficacy, this indicates that AAV1 is a preferable serotype for treatment of AAV2 sero-positive humans, both regarding vaccination and gene transfer.

Figure 13:
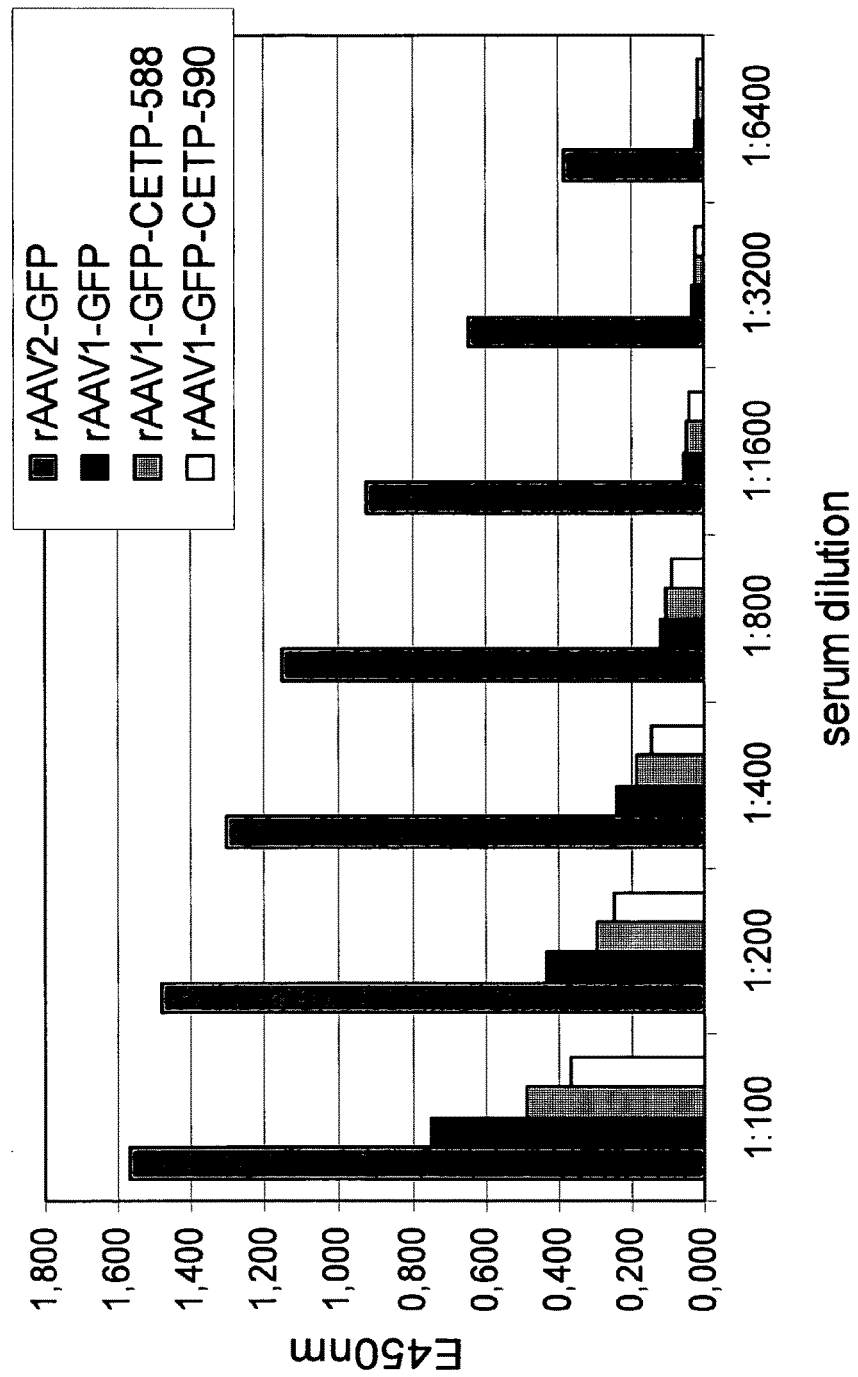

These results were confirmed in a similar experiment, where same amounts of capsids ($1\times10^9$) of rAAV2-GFP, rAAV1-GFP, rAAV1-GFP-CETP-588 and rAAV1-GFP-CETP-590 were coated onto Maxisorp 96 well plates (Nunc) and incubated with serial dilutions of sera from rabbits vaccinated with AAV2 (1:100-1:6400). The binding assay was performed as described above (FIG. 13).

This experiment further confirms the results above and shows additionally that the CETP insertion does not interfere with this result.

8. Tools to Study Anti-IgE Antibodies
8.1. Generation of 293 Cells Overexpressing the α- and γ-Chain of Human FcεRI The cDNA of the α-chain of human FcERI (FcεRIα) (including the stop-codon) cloned into pENTR™ 221 was obtained from Invitrogen and was sub-cloned into the expression vector pEF5/FRT/V5-Dest (Invitrogen) using the Gateway Cloning System (Invitrogen) according to the instructions of the manufacturer. The resulting expression vector is referred to as pEF5-FcεRIα. The FcεRIα cDNA Is expressed under the control of the eukaryotic μF1α promoter in this vector.

Flp-In™ 293 cells (Invitrogen) were transfected with the vector pEF5-FcεRIα using Lipofectamine™ 2000. $4\times10^5$ cells were seeded into one well of a 6-well cell culture plate in a total volume of 2.0 ml DMEM supplemented with 10% FCS, 5 mM glutamine, NEAA (1×) (non-essential amino acids) and 100 μg/ml zeocin. After 24 h of cultivation, medium was replaced with serum-free DMEM and cells were transfected with a mixture of 10 μl lipofectamine, 2 μg vector pEF5-FcεRIα and 2 μg vector pOG44 (Invitrogen) in a total volume of 100 μl MEM according to the instructions of the manufacturer.

The vector pOG44 encodes a recombinase (Flp recombinase) that mediates the integration of a vector containing the gene of interest (FcεRIα) and a FRT site into the genome of the Flp-In™ 293 cells via Flp Recombination Target (FRT) sites. After 6 h FCS was added to the cells to a final concentration of 5%. 48 h after transfection cells were split in a 1:10 ratio and cultivated in DMEM, 10% FCS, 5 mM glutamine, NEAA (1×) and 100 μg/ml hygromycin B to select transfected cells. Single stably transfected cell clones were isolated by sub-culturing of picked cell clusters in DMEM, 10% FCS, 5 mM glutamine, NEAA (1×) and 100 μg/ml hygromycin B.

Integration of the FcεRIα cDNA into the genome of the cells was analyzed by PCR. Genomic DNA of the transfected cells was isolated using the DNeasy Tissue DNA Isolation Kit (Qiagen). PCR was performed using the primers FcεRIα-uni 5'-TGT GTG TAG CCT TAC TGT TCT TCG C-3' (SEQ ID NO: 154)
and
FcεRIα-rev 5'-CTTCTCACGCGGAGCTTTTATTAC-3' (SEQ ID NO: 155)

and a Taq Polymerase Mastermix (Qiagen). Since the primers are located at exon-intron boundaries of the human FcεRIα gene, only the cDNA of FcεRIα integrated into the genome of the cells is amplified by PCR.

Although the cDNA of FcεRIα was stably integrated into the genome of the transfected cells, no significant cell surface expression of FcεRIα could be detected by flow cytometry using a PE-labeled FcεRIα specific mAb (eBioscience) at a final concentration of 2.5 μg/ml in PBS supplemented with 0.5% BSA.

Since co-expression of the γ-chain of FcεRI is known to increase cell surface expression of FcεRIα (Kuster et al., 1990), a single 293 cell clone stably transfected with the α-chain (clone A3) was transfected with the cDNA of FcεRIγ. The cDNA of FcεRIγ (including stop-codon) cloned into the vector pENTR™ 221 was obtained from Invitrogen and was sub-cloned into the expression vectors pEF-DEST51 (Invitrogen) and pcDNA6.2-V5-DEST (Invitrogen). The cDNA is expressed under the control of the eukaryotic μF1α promoter or the CMV promoter in pEF-DEST51 or pcDNA6.2-V5-DEST, respectively. The 293 cell clone A3 was transfected with the vectors pEF-FcεRIγ or pcDNA6.2-FcεRIγ, respectively, using Lipofectamine™2000 and 4 μg of the vector as described above. Transfected cells expressing the α- and γ-chain of FcεRI were selected by cultivation of the cells in DMEM with 10% FCS, 5 mM glutamine, NEAA (1×), 100 μg/ml hygromycin B and 5 μg/ml blasticidin (selection medium). Single stably transfected cell clones were isolated by sub-culturing of picked cell clusters of the transfected cell pool in the selection medium.

Figure 15:
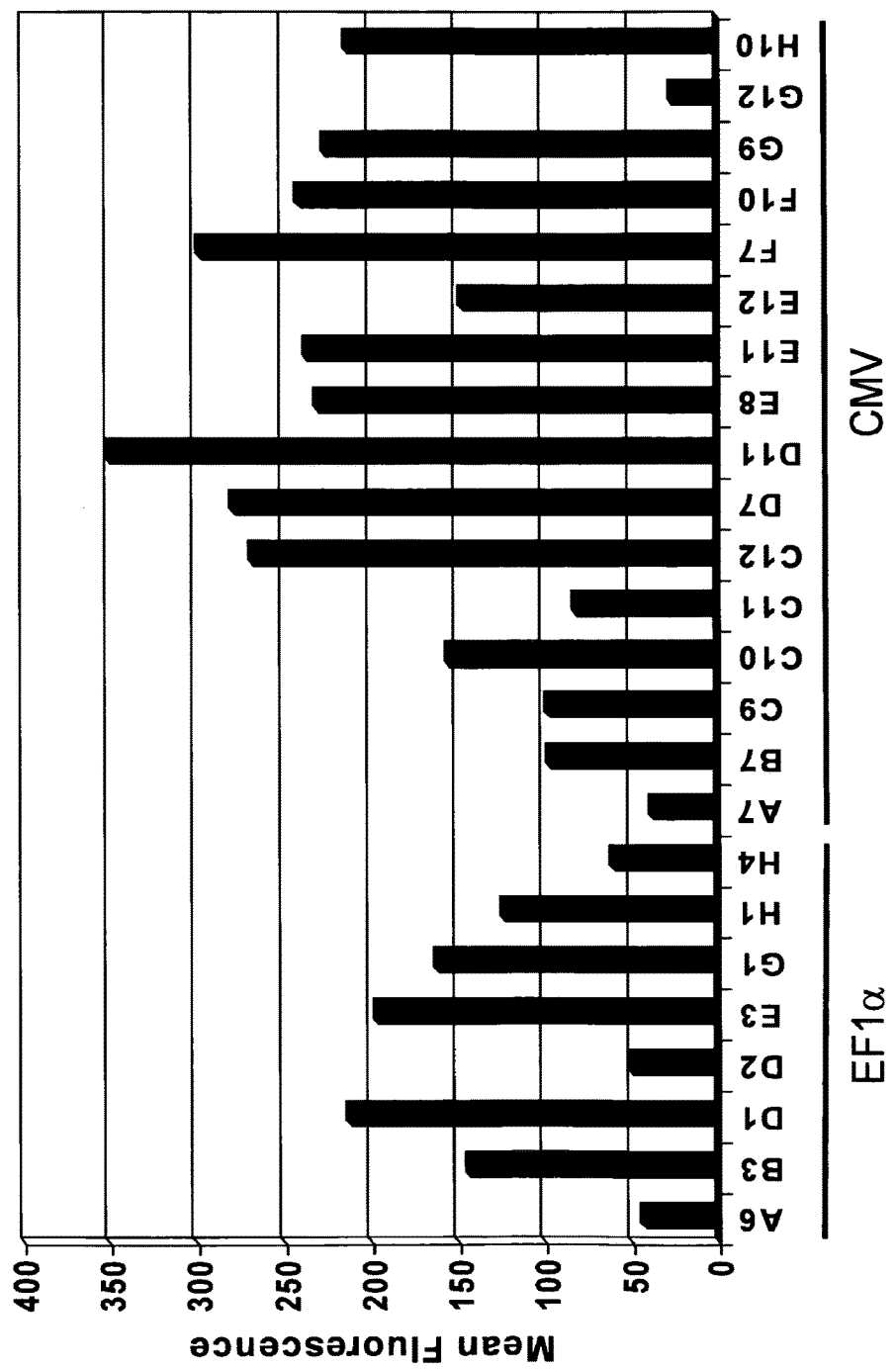

FcεRIα cell surface expression of the cell clones was monitored by flow-cytometry using a PE-labeled anti-human FcεRIα mAb (eBioscience) at a final concentration of 2.5 μg/ml in PBS supplemented with 0.1% BSA (FIG. 15). IgE binding of the cells was analyzed by incubation of $1.0\times10^5$-$5.0\times10^5$ cells with biotin-labeled human IgE (Dianova) at a concentration of 20 μg/ml in a total volume of 100 μl PBS, 0.5% BSA (incubation buffer) for 30 min at room temperature (RT). After washing of the cells with incubation buffer, IgE binding was detected by flow-cytometry using PE-labeled streptavidin (CALTAG) at 15 μg/ml (in 20 μl incubation buffer). Cells were stained with the PE-labeled streptavidin for 30 min on ice (data not shown).

The results demonstrate that co-expression of the γ-chain increases the cell surface expression of the FcεRIα-chain. The increased cell surface expression is associated with an increased binding of human IgE by the transfected cells demonstrating that the cell surface exposed α-chain is functionally active. The individual cell clones differed with respect to the cell surface expression of FcεRIα and the clone showing the highest expression and IgE binding was selected for subsequent assays.

Figure 16:
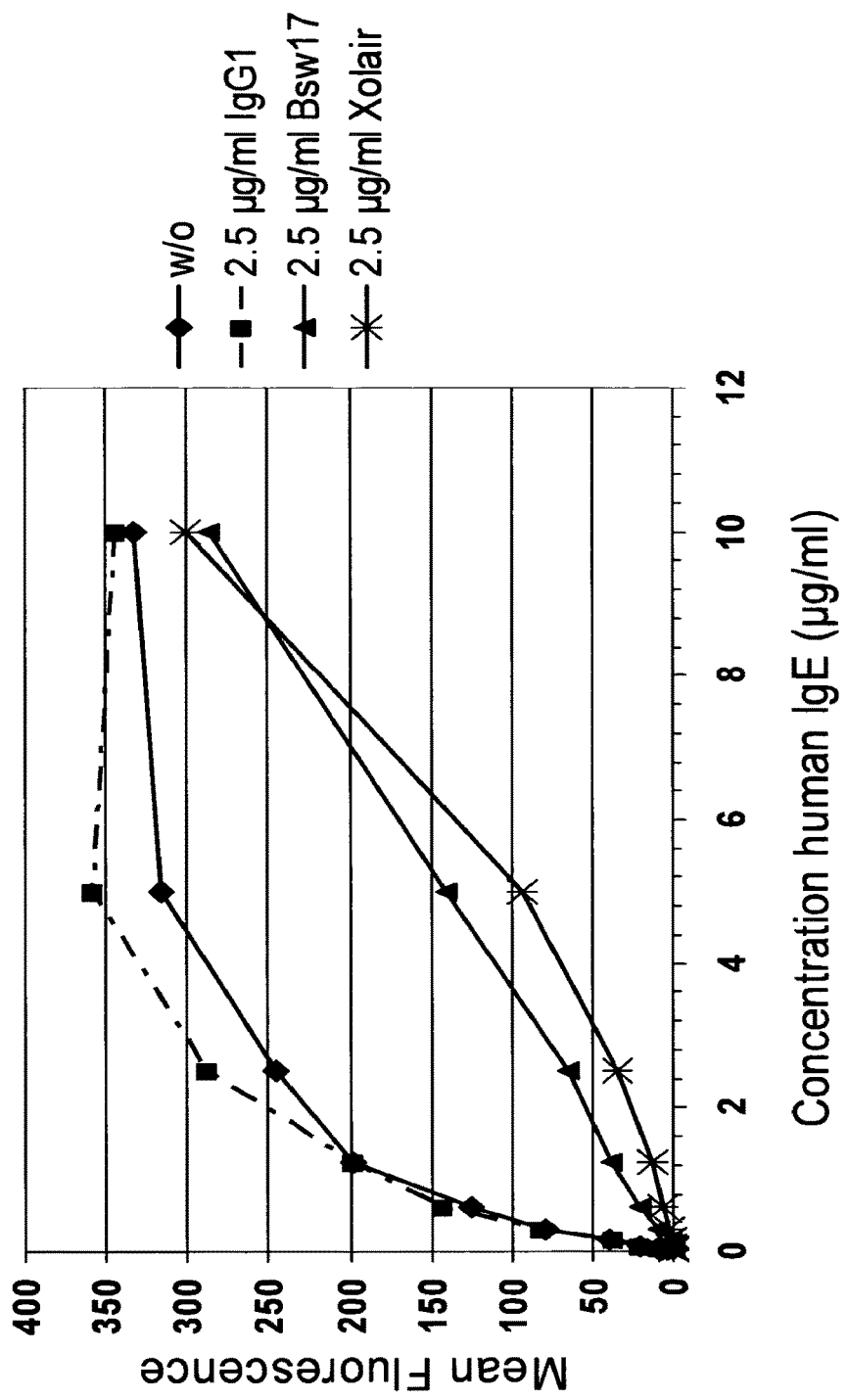

To evaluate the effect of anti-IgE antibodies on binding of human IgE to FcεRIα, the cell clone D11 co-expressing the α-chain (under control of EF1α promoter) and the γ-chain (under control of a CMV promoter) was used for IgE binding assays (FIG. 16). Increasing concentrations of biotin-labeled human IgE (78 ng/ml to 10 μg/ml) were pre-incubated with a constant concentration (2.5 μg/ml) of anti-IgE antibodies Bsw17 (kindly provided by Prof. Stadler, Bern) or XOLAIR® in a total volume of 100 μl incubation buffer for 1.5 h at RT. As a negative control IgE was pre-incubated with mouse IgG$_1$ under the same conditions. A T175 cell culture flask with 80-90% confluent cells (clone D11) was harvested using Cell Dissociation Buffer (Gibco) and cells were resuspended in 15 ml DMEM medium. 200 μl of this cell suspension was added to each well of a 96-well tissue culture plate. The plate was centrifuged and the cells were washed with incubation buffer and resuspended in 100 μl of the IgE/anti-IgE mixture. Cells were incubated for 30 min a RT. After washing of the cells with incubation buffer, cells were stained with the PE-labeled streptavidin (15 μg/ml) for 30 min on ice. IgE binding was detected by flow-cytometry (FIG. 16).

These data demonstrate that the transfected 293 cells expressing the α- and γ-chain of human FcεRI provide a tool to monitor the binding of human IgE to FcεRIα and the effect of anti-IgE antibodies thereon.

8.2. Generation of RBL2H3 Cells Overexpreessing the α-of Human FcεRI

The α-chain of human FcεRI (FcεRIα) (including the stop-codon) cloned into pENTR™ 221 was obtained from Invitrogen and was sub-cloned into the expression vectors pEF-DEST51 (Invitrogen) and pcDNA6.2-V5-DEST (Invitrogen) using the Gateway Cloning System (Invitrogen). Rat basophile RBL2H3 cells (80-90% confluent) were transfected with the resulting vectors pEF-FcεRIα or pcDNA6.2-FcεRIα, respectively, using Lipofectamine™ 2000 and 4 µg of the vector as described above. Transfected cells expressing the α-chain of FcεRI were selected by cultivation of the cells in RPMI with 10% FCS, 5 mM glutamine, 1×NEAA supplemented with 15 µg/ml blasticidin (selection medium). Single stably transfected cell clones were isolated by subculturing of picked cell clusters of the transfected cell pool in the selection medium. FcεRIα cell surface expression of the cell clones was monitored by flow-cytometry using a PE-labeled anti-human FcεRIα mAb (eBioscience) at a final concentration of 2.5 µg/ml in PBS supplemented with 0.5% BSA (data not shown).

Figure 17:
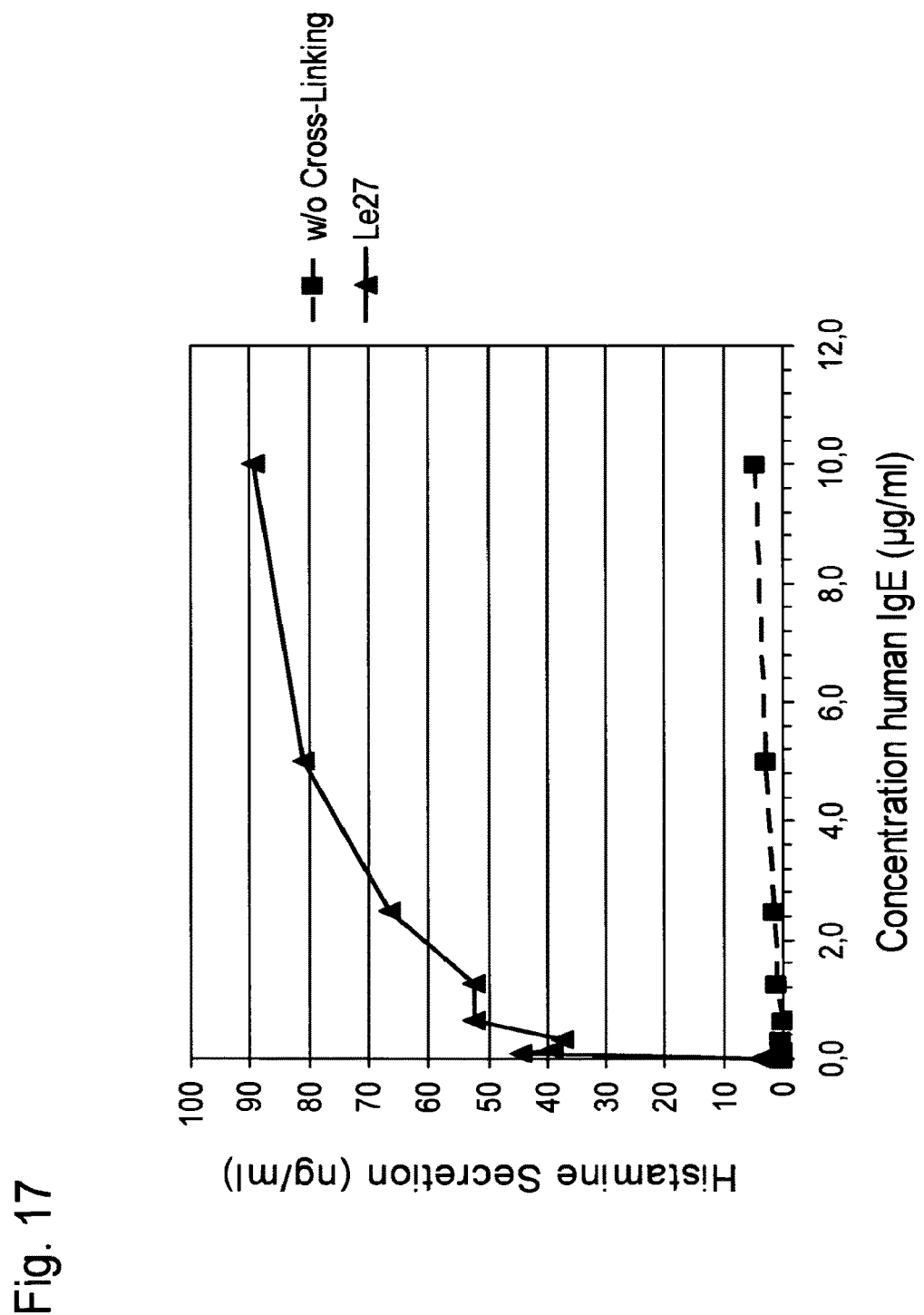

The cell clone E5 (stably expressing the α-chain under control of an EF1α promoter) was used for evaluation of human IgE-mediated histamine release. 1.0 30×10$^4$ cells were seeded into a well of 96-well tissue culture plate and cultivated in a total volume of 200 µl RPMI/10% FCS/5 mM glutamine/1×NEAA in a humidified atmosphere at 37° C. and 5.0% $CO_2$. Cells were sensitized by cultivation in the presence of human IgE (Dianova) at increasing concentrations (0.08-10.0 µg/ml) in complete RPMI medium for 2 h or 48 h in a total volume of 250 µl. Cells were washed with Tyrode's Salt Solution (Sigma) supplemented with 0.1% BSA and histamine release was induced by cross-linking of receptor-bound human IgE by the anti-human IgE antibody Le27 (100 nM) (kindly provided by Prof. Stadler, Bern; (Grassi et al., 1986)) in a total volume of 100 µl Tyrode's Salt Solution/0.1% BSA for 1 h. Histamine content of the medium was measured using a commercially available histamine ELISA (Neogen) (FIG. 17).

Figure 18:
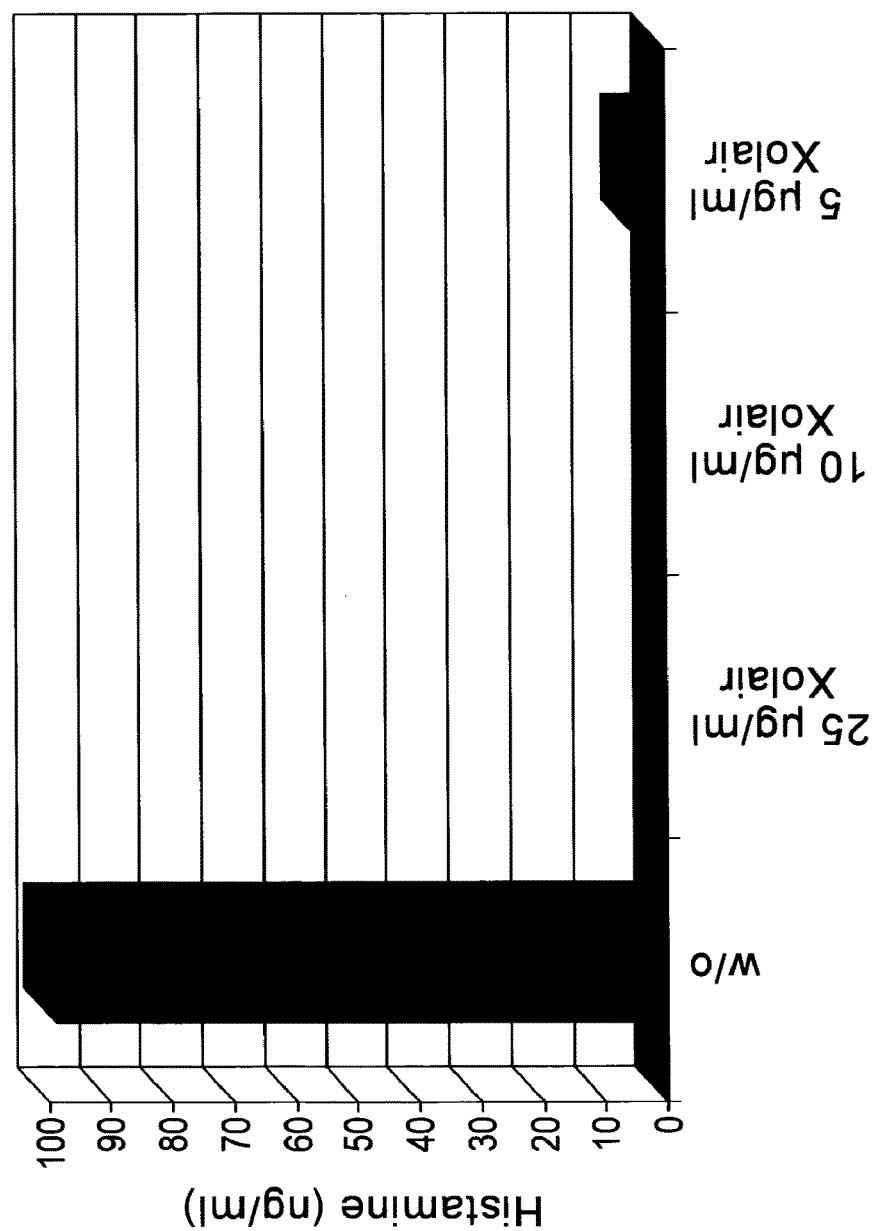

To evaluate the effect of anti-IgE antibodies on the human IgE-dependent histamine release of the stably transfected RBL2H3 cells, cells (clone E5) were sensitized with 2.0 µg/ml human IgE, which was pre-incubated with XOLAIR® mAb (5.0-25.0 µg/ml) for 2 h at room temperature. For sensitization, cells were cultivated with the IgE/XOLAIR® mAb mixture for 2 h as described above in a total volume of 100 µl RPMI medium. Histamine release was induced by the anti-IgE mAb Le27 as described above and the histamine content of the medium was measured by ELISA (Neogen) (FIG. 18).

These data demonstrate that the transfected RBL2H3 cells expressing the α-chain of human FcεRI can be sensitized with human IgE and can be induced to release histamine in the presence of a human IgE cross-linking agent. The cells provide a tool to study the human IgE-induced degranulation of basophiles and the effect of anti-IgE antibodies thereon.

8.3. In Vitro Binding Assays Using Recombinant FcεRIα

The α-chain of human FcεRI can be expressed as a recombinant protein in prokaryotic or eukaryotic cells. After purification the recombinant FcεRIα can be immobilized in a suitable matrix (e.g. plastic plate, beads). Purification and immobilization can also be performed using a suitable tag fused to the recombinant FcεRIα at the N- or C-terminus (e.g. His-tag, FLAG-tag, S-Tag, GST-tag). The immobilized FcεRIα will be incubated with labeled human IgE. The label can be a, for example, fluorescent dye, biotin, peroxidase or alkaline phosphatase. Binding of IgE will be detected using this label and the appropriate detection system (fluorescence measurement, labeled streptavidin, peroxidase substrate, alkaline phosphatase substrate). To evaluate the effect of anti-IgE antibodies on the interaction of IgE with recombinant FcεRIαx, IgE will be preincubated with the anti-IgE antibodies and subsequently used in the binding assay described above.

9. Double Insertion of a β-Amyloid Epitope at Position I-453 and I-587 of the AAV Capsid The cloning approach described below is used for the double insertion of an epi- or mimotope sequence into the AAV capsid at position I-453 and I-587 using a defined cloning strategy 9.1. Insertion of an FseI Restriction Site into pCIVP2

An FseI restriction site was inserted into the vectors pCIVP2-I587-NotI-AscI and pCIVP2-I453-NotI-AscI located between I-453 and I-587 by site-directed mutagenesis using the QuikChange II Site-Directed Mutagenesis Kit (Stratagene) and the oligonucleotides

```
mutashe-9
                                    (SEQ ID NO: 156)
5'-GGT GAA TCC GGG GCC GGC CAT GGC AAG C-3'
and mutashe-10
                                    (SEQ ID NO: 157)
5'-GCT TGC CAT GGC CGG CCC CGG ATT CAC C-3'.
```

9.2. Cloning of a β-Amyloid Epitope at Position I-587 of pUCAV2

The β-amyloid epitope DAEFRHDSG (SEQ ID NO: 158) (aa 1-9 of human β-amyloid) was cloned into the NotI/AscI restriction site of the vector pCIVP2-I587-NotI-AscI (modified as described in 9.1) using the sense and anti-sense oligonucleotides

```
β-amyloid-for
                                    (SEQ ID NO: 159)
5'-GGC CGC AGG CGG AGG GGG AGG CGA CGC CGA GTT CAG ACA CGA CAG CGG CGG CGG AGG GGG AGG CGC GG-3'
and β-amyloid-rev
                                    (SEQ ID NO: 160)
5'-CGC GCC GCG CCT CCC CCT CCG CCG CCG CTG TCG

TGT CTG AAC TCG GCG TCG CCT CCC CCT CCG CCT GC-3'
```

The oligonucleotides encode the β-amyloid epitope with a glycine adaptor sequence:

$$\text{(SEQ ID NO: 161)}$$
$$(A)_3\text{-}(G)_5\text{-DAEFRHDSG-}(G)_5\text{-}(A)_2$$

Cloning was performed as described above (6.2).

The BsiWI/XmaI fragment of pCI-VP-2-587-NotI-AscI encoding a VP-2 fragment containing the β-amyloid epitope at position I-587 was sub-cloned into pUCAV2-AgeI as described above (6.3). The resulting vector was referred to as pUCAV2-amyloid-587.

9.3. Cloning of a β-Amyloid Epitope at Position I-453 of pCIVP2

The β-amyloid epitope (DAEFRHDSG, SEQ ID NO: 158) was cloned into the NotI/AscI restriction site at the insertion site I-453 of the vector pCIVP2-I453-NotI-AscI (modified as described in 9.1) using the sense and anti-sense oligonucleotides

```
Amyloid 453for
                                    (SEQ ID NO: 162)
5'-G GCC GGC GGA GGC GGT GGG GAC GCC GAA TTC

AGA CAC GAC AGC GGC GGA GGC GGT GGA GGG-3'

Amyloid 453rev
                                    (SEQ ID NO: 163)
5'-C GCG CCC TCC ACC GCC TCC GCC GCT GTC GTG

TCT GAA TTC GGC GTC CCC ACC GCC TCC GCC-3'
```

The oligonucleotides encode the 1-amyloid epitope with a glycine adaptor sequence:

```
                                    (SEQ ID NO: 164)
(A)₂-(G)₅-DAEFRHDSG-(G)₅-R-(A)₂
```

Cloning was performed as described above (6.2).

9.4. Cloning of a β-Amyloid Epitope at Position I-453 and I-587 of pUCAV2

For production of recombinant AAV particles carrying the 1-amyloid epitope at position I-587 and I-453, the vector pUCAV2-amyloid-587 was cut with BsiWI/FseI and ligated with the 0.6 kb BsiWI/FseI fragment of pCI-VP2-453-NotI-AscI. The BsiWI/FseI fragment of pCI-VP2-453-NotI-AscI encodes the VP-2 fragment containing the β-amyloid epitope at position I-453. The resulting vector was referred to as pUCAV2-amyloid-453-587.

9.5. Production, Purification and Evaluation of AAV Particles Carrying a β-Amyloid Epitope at I-453 and I-587

For production of recombinant AAV particles carrying the β-amyloid epitope at position I-587 and I-453, 293 cells were transfected with the vector pUCAV2-amyloid-453-587 and the helper plasmid pUCAdV as described above (4.2 and 4.3). The corresponding AAV particles were referred to as AAV-amyloid-453-587.

Figure 19:
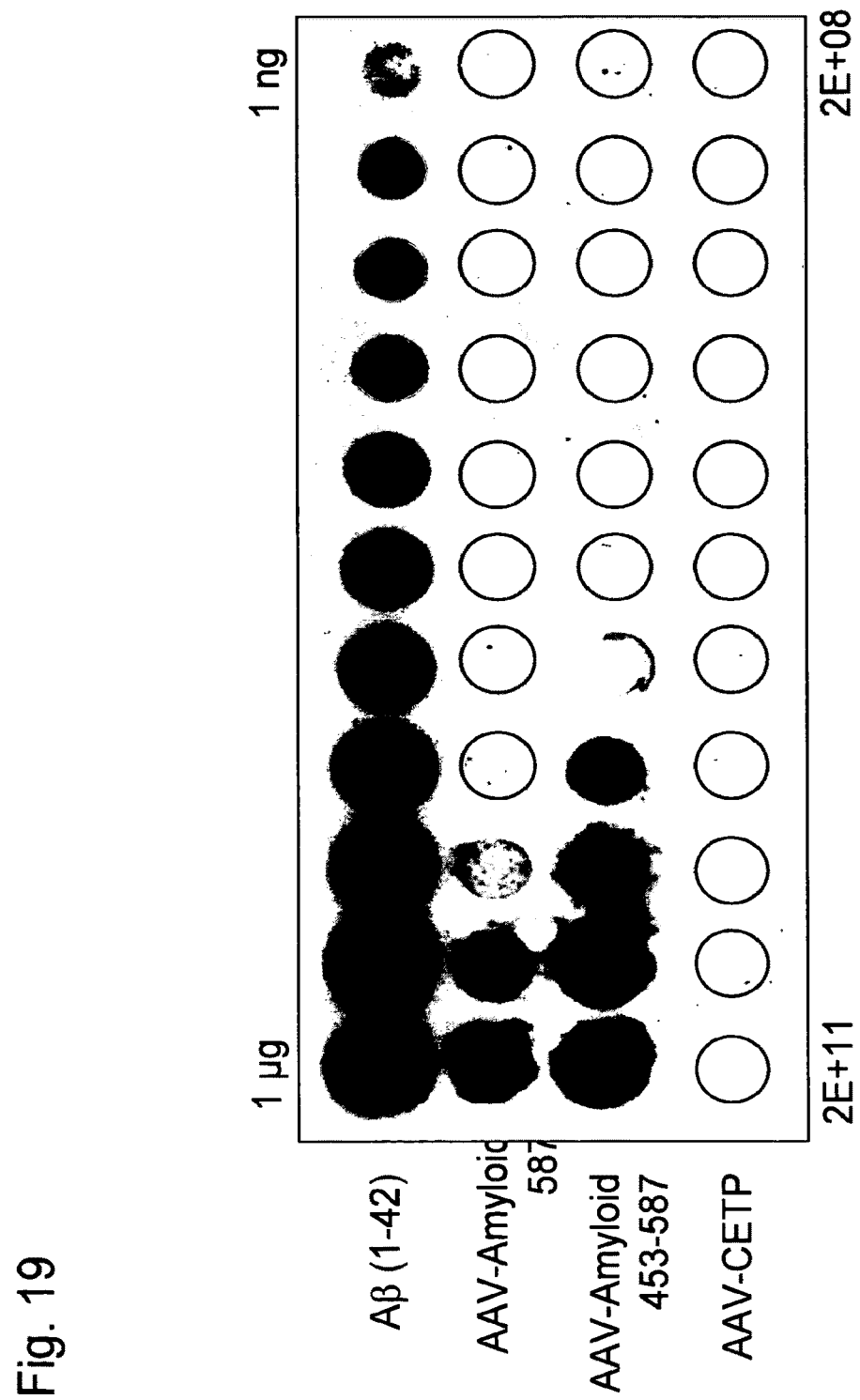

For production of recombinant AAV particles carrying the β-amyloid epitope at position I-587, 293 cells were transfected with the vector pUCAV2-amyloid-587 and the helper plasmid pUCAdV as described above. The corresponding AAV particles were referred to as AAV-amyloid-587. All AAV particles were purified as described above To evaluate the expression of the 3-amyloid epitope at the surface of the AAV capsid, serial dilutions of purified AAV particles AAV-amyloid-453-587 and AAV-amyloid-587 were dotted on a membrane (FIG. 19). As a negative control AAV particles carrying a CETP epitope at position I-587 were dotted. As a positive control a β-amyloid peptide (aa 1-42) (Biosource) was dotted. After blocking of the membrane with blocking buffer (5% milk powder in PBS containing 0.05% Tween-20), the β-amyloid epitope was detected using an anti-β-amyloid mAb 6E10 (Chemicon) (FIG. 19). The anti-β-amyloid mAb was used at a concentration of 1.0 µg/ml in PBS/1% milk powder/0.05% Tween-20. Binding of the anti-β-amyloid mAb was detected using a peroxidase labeled anti-mouse IgG antibody (CALTAG). After washing, signals were detected by chemiluminescence using the SuperSignal West Pico Chemiluminescent Substrate (Pierce).

These data demonstrate that the double insertion of the epitope into the insertion sites I-453 and I-587 results in higher epitope density at the capsid surface than the singular insertion of the epitope at position I-587.

10. Immunization of Rabbits with AAV-Based Vaccines 10.1. Production and Purification of AAV2-Based Vaccines for Immunization Experiments For production of AAV particles HEK 293-T cells were co-transfected with the vector plasmid pUCAV2 containing the subcloned epitope (in I-453 and/or I-587) and the helper plasmid pUCAdV as described above. For large scale production 30-60 Ø15 cm cell culture plates with 7.5×10⁶ 293-T cells were seeded and cultivated at 37° C., 5% $CO_2$ in a humidified atmosphere. Co-transfection of the cells with the vector plasmid pUCAV2 containing the epitope (in I-453 or I-587) and pUCAdV was performed as described above. 72 h after transfection 293-T cells and medium were harvested and centrifuged at 3000 g at 4° C. for 15 min. The cell pellet was resuspended in 15-30 ml lysis buffer (50 mM HEPES, 200 mM NaCl, 2.5 mM $MgCl_2$; pH 6.8) and objected to three rounds of freeze and thaw cycles. The cleared cell culture supernatant was concentrated by TFF (tangential flow filtration) using the SARTOFLOW Slice 200 Benchtop Cross-flow system using a SARTOCON® Slice 200 cassette (Hdyrosart membrane). The TFF concentrate of the cell culture supernatant (about 35 ml) was pooled with the cleared crude lysate and subsequently treated with 1667 U/ml benzonase (Merck) at 37° C. for 2 h-4 h. After benzonase treatment the pool of crude lysate and TFF concentrate was centrifuged at 3600 g for 5 min at 4° C. The AAV-containing supernatant was separated through a size exclusion chromatography (SEC) column. SEC was performed using a XK50/20 column packed with SUPERDEX 200® resin beads and SEC running buffer (50 mM HEPES, 400 mM NaCl, 2.5 mM $MgCl_2$; pH 6.8). SEC fractions were analyzed by AAV2 ELISA. AAV-containing fractions were pooled and objected to iodixanol gradient centrifugation. Iodixanol solutions of different concentrations were layered beneath the pool of virus containing SEC fraction in QUICKSEAL® centrifugation tubes (25×89 mm; Beckman). By this an Iodixanol gradient was created composed of 4.0 ml 60% on the bottom, 5.0 ml 40%, 4.0 ml 25% and 5.5 ml 15% Iodixanol with the virus solution on top. The gradient was centrifuged using a fixed angel rotor (Ti 70.1 rotor, Beckman) at 65000 rpm for 1 h at 18° C. The 40% phase containing the AAV particles was then extracted with a cannula by puncturing the tube underneath the 40% phase and allowing the solution to drip into collecting tubes. Fractions of about 0.5 ml were collected until the 25% phase was reached. The AAV capsid titer of the fractions was determined using a commercially available ELISA (AAV Titration ELISA, Progen). Purity of the AAV-containing fractions was determined by SDS-PAGE and subsequent colloidal Coomassie staining. Fractions with high purity of AAV particles were pooled and the capsid titer of the final pool was determined by AAV2 titration ELISA.

10.2. Breaking of Self-Tolerance by AAV-Based Vaccines

A panel of AAV-based vaccines carrying epitopes derived from rabbit CETP was generated as described above. AAV-based CETP vaccines were compared with the corresponding peptide vaccines containing the same epitope coupled to LPH (Limulus polyphemus hemocyanine) as a carrier protein. The peptides were chemically synthesized with a C- or N-terminal Cystein residue that was used for coupling of the peptides to LPH. Synthesis and coupling of the peptides was performed by Biogenes (Berlin, Germany).

The vaccines decribed in Table 24 were used for immunization of rabbits:

TABLE 24

Vaccines used for immunization of rabbits

| Name of vaccine | Vaccine carrier | Insertion Site | Epitope | Dose (µg) |
|---|---|---|---|---|
| AAV-TP11 | AAV2 | I-587 | SLTGDEFKKVLET SEQ ID NO: 238 | 10.9 |
| AAV-TP12 | AAV2 | I-587 | REAVAYRFEED SEQ ID NO: 239 | 14.1 |
| AAV-TP13 | AAV2 | I-587 | INPEIITLDG SEQ ID NO: 240 | 13.3 |
| AAV-TP18 | AAV2 | I-587 | DISVTGAPVITATYL SEQ ID NO: 241 | 7.2 |
| LPH-TP11 | LPH | N/A | CSLTGDEFKKVLET SEQ ID NO: 320 | see text |
| LPH-TP12 | LPH | N/A | CREAVAYRFEED SEQ ID NO: 321 | see text |
| LPH-TP13 | LPH | N/A | CINPEIITLDG SEQ ID NO: 322 | see text |
| LPH-TP18 | LPH | N/A | CDISVTGAPVITATYL SEQ ID NO: 323 | see text |

For each vaccination approach two rabbits were immunized s.c. with the vaccines shown in the table above four times (one prime and three boost immunizations). The first boost immunization was performed 2 weeks after an initial prime immunization. Rabbits were boosted another two times with the vaccines at intervals of 3 weeks. Serum of the immunized animals was prepared two weeks after each boost immunization.

The purified AAV-based vaccines were mixed an equal volume of formulation buffer (PBS with 1% sorbitol, 0.2% Tween-20, 25% propylenglycol, 200 mM NaCl and 2.5 mM $MgCl_2$) for stabilization of the particles and stored at $-80°$ C. until administration. If necessary, the volume of the AAV-based vaccines was adjusted to 0.3 ml with formulation buffer directly before application. The vaccines were administered s.c. in the presence of 0.7 ml adjuvant (total volume 1 ml). The adjuvant was provided by Biogenes and contained amongst others 0.01% lipopolysaccharide derived from Phormidium, 95% paraffin oil, 2.4% Tween-40 and 0.1% cholesterol.

The LPH-coupled peptides (in 0.3 ml TBS) were administered s.c. In the presence of 0.7 ml of the adjuvant provided by Biogenes. 1 mg of the LPH-peptide conjugate was administered for the prime immunization. 0.5 mg of the conjugate was used for the $1^{st}$ boost immunization and 0.25 mg of the conjugate were used for the $2^{rd}$ and $3^{rd}$ boost immunization.

Induction of anti-CETP auto-antibodies in the vaccinated animals was determined by ELISA using recombinant rabbit CETP as antigen. For production of rabbit CETP, the CETP cDNA was amplified by RT-PCR using the primers
rCETP-uni 5'-GGG GAA TTC ATG TCC CAA AGG CGC CTC CTA CG-3' (SEQ ID NO: 324) and
rCETP-rev 5'-GGG GGA TCC CTA GCT CAG GCT CTG GAG GAA ATC C-3' (SEQ ID NO: 325)
and rabbit liver PolyA$^+$ RNA (Clontech) as template. The CETP cDNA was cloned into the EcoRI/BamHI site of the vector p3x FLAG-CMV-8 (SIGMA). The resulting vector encodes the mature CETP sequence with a C-terminal FLAG®-tag and an N-terminal preprotrypsin leader sequence for secretion of the recombinant protein. For expression of recombinant rabbit CETP 293T cells were transfected with the vector by calcium phosphate transfection as described above. CETP was purified from the cell culture supernatant by affinity chromatography using anti-FLAG® M2 agarose beads (SIGMA). Purity of the recombinant rabbit CETP was analyzed by SDS-PAGE and subsequent colloidal coomassie staining. CETP activity was determined using a commercially available CETP activity assay (Roar).

For titration of rabbit CETP auto-antibodies in the immune sera, a 96-well Maxisorp plate (Nunc) was coated with purified recombinant rabbit CETP (100 ng/well) for 1 h at 37° C. After coating wells were washed with wash buffer (PBS/0.1% Tween-20) and subsequently incubated with blocking buffer (5% skim milk in wash buffer) for 1 h at 37° C. After blocking of the wells, immobilized CETP was incubated with serial dilutions of the immune sera in dilution buffer (wash buffer with 1% skim milk and 1% BSA) for 1 h at 37° C. Rabbit pre-immune sera or rabbit sera of unrelated vaccinations served as negative controls. After washing binding of rabbit IgG to the immobilized CETP was detected using a HRP-labelled anti-rabbit IgG antibody (H+L) (DAKO; 1:2500 in dilution buffer). Signals (OD) were detected using TMB (KemEnTec) as substrate.

CETP auto-antibody titers were determined by end point dilution. The titer of the immune serum corresponds to the intersection point of the titration curve of the immune sera with the limit of detection of the assay.

The limit of detection (LOD) of the assay was calculated as follows:

$$\frac{\text{Mean OD (unspecific sera)} + 3.3 \times \text{standard deviation}}{\text{OD (unspecific sera)}}$$

In addition to the CETP auto-antibody titers, the anti-peptide titers of the immune sera were analyzed. The free peptides (corresponding to the epitopes integrated in the AAV capsid or coupled to LPH) were covalently immobilized in a 96-well plate (REACTI-BIND™ Amine-binding, Maleic Anhydride Activated Plates; Pierce). For immobilization of the peptide, the 96-well plate was incubated with 1 µg peptide per well in a total volume of 50 µl PBS for at least 1 h at 37° C. After coating of the peptides wells were blocked with 200 µl/well blocking buffer (PBS/5% skim milk/0.1% Tween-20) for 1 h at 37° C. After blocking of the wells, immobilized peptides were incubated with serial dilutions of the immune sera in dilution buffer (PBS with 1% skim milk, 1% BSA, 0.1% Tween-20) for 1 h at 37° C. Rabbit pre-immune sera or rabbit sera of unrelated vaccinations served as negative controls. After washing binding of rabbit IgG to the immobilized CETP was detected using a HRP-labelled anti-rabbit IgG antibody (DAKO; 1:2500 in dilution buffer). Signals (OD) were detected using TMB (KemEnTec) as substrate. Antibody titers were determined as described above.

Figure 20:
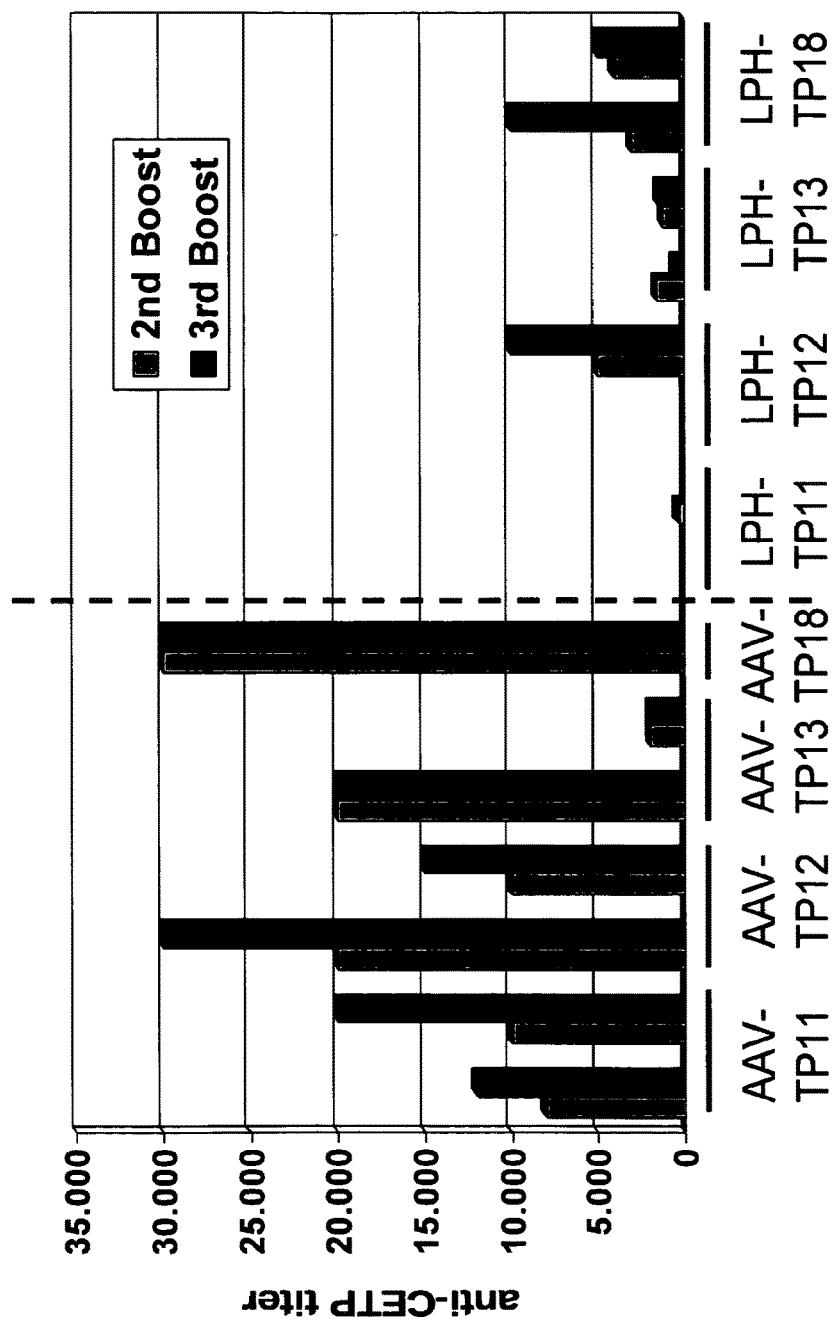
Figure 21:
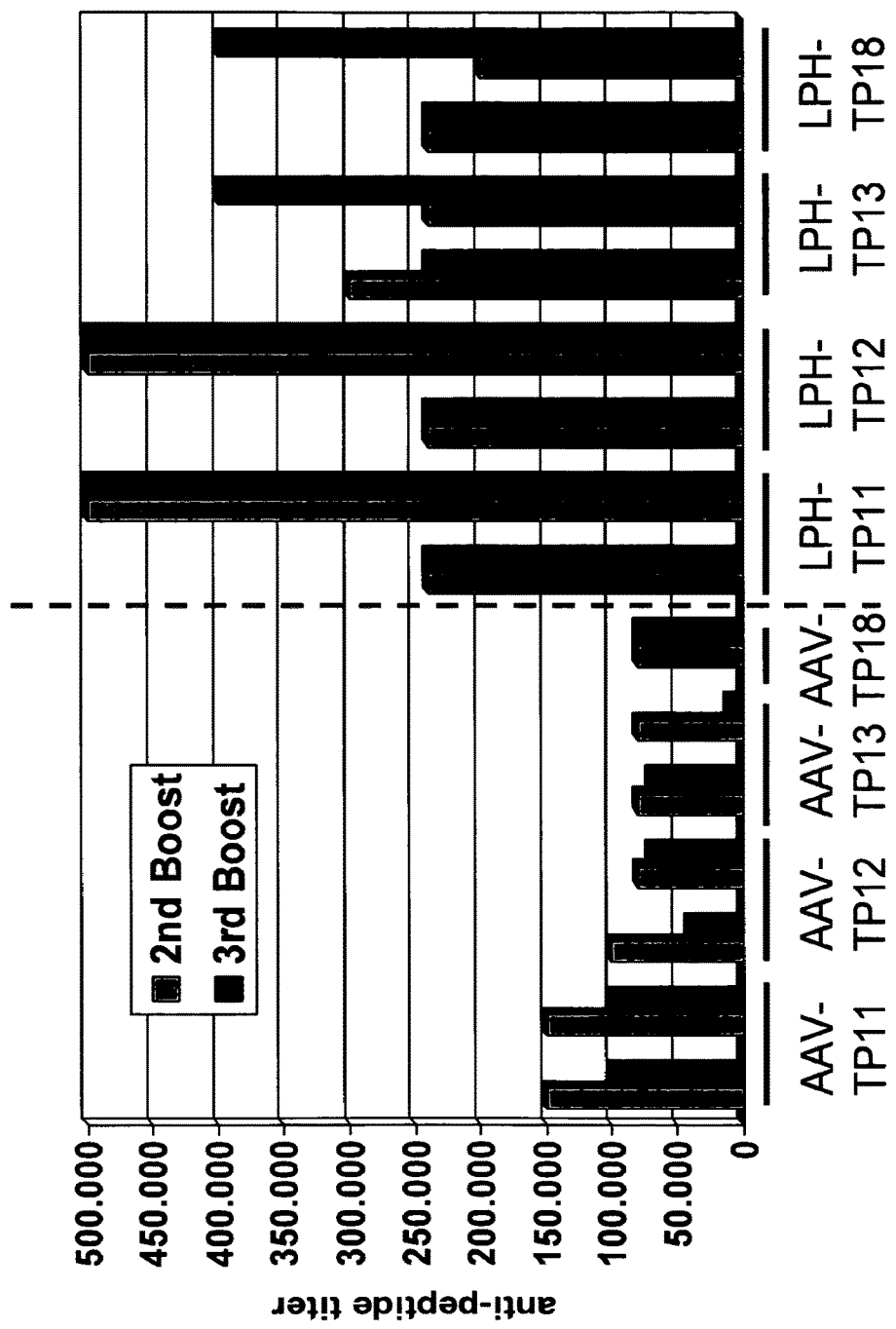

Except for one animal vaccinated with AAV-TP13 the data demonstrate that vaccination with AAV-based vaccines induces high titers of target-specific auto-antibodies that are not obtained using peptide-based vaccines. Accordingly, AAV-based vaccines are able to break self-tolerance and induce high levels of auto-antibodies (FIG. 20). The immunogenic properties of the peptide based vaccines are reflected by the high titers of peptide specific antibodies induced by the peptide vaccines (FIG. 21). However, these antibodies show only weak reaction with native rabbit CETP (FIG. 20) suggesting that peptide based vaccines—although immunogenic—have only a limited potential to break self-tolerance and induce low levels of auto-antibodies.

10.3. The AAV Capsid Structure is Essential for Breaking of Self-Tolerance and Induction of Auto-Antibodies To demonstrate that the capsid structure and the structured, repetitive presentation of epitopes within the AAV-capsid are essential for breaking of self-tolerance of the immune system and induction of auto-antibodies, rabbits were immunized with heat-denatured AAV-TP11-2× or AAV-TP18-2× particles. Results were compared with vaccinations using the corresponding native particles. The AAV-variant AAV-TP11-2× carries the rabbit CETP TP11 epitope (SLTGDEFKKVLET. SEQ ID NO: 238) at positions I-453 and I-587. The AAV-variant AAV-TP18-2× carries the rabbit CETP TP18 epitope (DISVTGAPVITATYL, SEQ ID NO: 241) at positions I-453 and I-587. For heat denaturation the particles were mixed with an equal volume of formulation buffer (PBS with 1% sorbitol, 0.2% Tween-20, 25% propylenglycol, 200 mM NaCl and 2.5 mM $MgCl_2$) and incubated at 90° C. for 15 min. Destruction of the particle conformation was analyzed by AAV2 titration ELISA recognizing a conformational epitope within the native capsid. Protein concentration of the heat-denatured particles was determined by Micro BCA assay (Pierce) and analyzed by Western blotting using a polyclonal anti-AAV2 antibody generated by immunization of rabbits with purified VP3 protein of AAV2 (data not shown).

Rabbits were immunized with heat-denatured AAV-TP11-2× particles (5.7 µg per application) or AAV-TP18-2× particles (1.8 µg per application) s.c. in the presence of an adjuvant provided by Biogenes as described above. 2 weeks after an initial prime immunization rabbits were boosted with the heat-denatured particles. Serum of the animals was analyzed 2 weeks after the boost immunization for levels of CETP auto-antibodies as described above. In a control group rabbits were vaccinated with native AAV-TP11-2× or AAV-TP18-2× particles using the same regimen as for the heat-denatured particles.

Analysis of the CETP auto-antibody titer in the sera of the immunized animals demonstrates that destruction of the native capsid conformation results in a strongly impaired induction of CETP antibodies compared with the native vaccine (FIG. 22) showing that the native capsid structure and the structured presentation of the epitopes within the capsid is essential for breaking of self-tolerance.

10.4. Evaluation of the Impact of Anti-AAV2 Antibodies on Immunization with AAV2-Based Vaccines The immunization experiments demonstrated that AAV-based vaccines induce high titers of anti-AAV capsid antibodies in addition to the target specific antibodies (data not shown). However, most humans are AAV2 positive meaning that these people have anti-AAV2 antibody titers that potentially might affect vaccination results using AAV2-based particles. To evaluate the impact of anti-AAV2 antibodies on the immunization success of AAV2-based vaccines, rabbits were pre-immunized by two applications of wtAAV2 (4.5 µg per application), before immunization (prime and two boost immunizations) with an AAV2-based CETP vaccine (AAV-TP18) was started. wtAAV2 particles were administered s.c. or i.m. in the presence of an adjuvant provided by Biogenes as described above. 2 weeks after an initial prime immunization with wtAAV2, rabbits were boosted once again with wtAAV2. Serum was analyzed two weeks after the prime and $1^{st}$ boost immunization for the level of anti-AAV2 antibodies. The anti-AAV2 antibody titer was determined by ELISA using immobilized wtAAV2 particles as described below. The data demonstrate that high levels of anti-wtAAV2 antibodies are detectable after two applications of wtAAV2 for both s.c. and i.m. administration (FIG. 23A).

3 weeks after boost immunization with wtAAV2, rabbits received the first prime immunization with the AAV2-based vaccine AAV-TP18 (7.2 µg per application). The vaccine was administered s.c. or i.m. in the presence of adjuvant provided by Biogenes as described above. Rabbits were boosted with the vaccines 2 weeks after the prime vaccination. Sera were analyzed 2 weeks after the boost vaccination for the level of CETP auto-antibodies (FIG. 23B). CETP auto-antibody titers were determined as described above. Results were compared to vaccination (s.c.) of animals not pre-immunized with wtAAV2.

The data demonstrate that wtAAV2 pre-immunization results in high titers of anti-AAV2 capsid antibodies. However, these high anti-AAV2 capsid antibodies do not impair the immunization success of an AAV2-based vaccine, in this case regarding the induction of anti-CETP auto-antibodies. Accordingly, it is concluded that AAV2 sero-positive humans are equally eligible for vaccitation with AAV2-particles as sero-negative humans and that sero-conversion of a vaccinated human during a vaccination protocol does not impair vaccination success.

Determination of Anti-wtAAV2 Antibody Titers:

The anti-AAV2 antibody titer was determined by ELISA using immobilized wtAAV2 particles. Briefly, 5×10 wtAAV2 particles were immobilized in each well of a 96-well Maxisorp plate (Nunc) in a total volume of 50 µl PBS per well. The plate was incubated at 37° C. for 1 h. After blocking of the wells with PBS, 5% skim milk, 0.1% Tween-20, immobilized wtAAV2 particles were incubated with serial dilutions of the immune sera in dilution buffer (PBS with 1% skim milk, 1% BSA, 0.1% Tween-20) for 1 h at 37° C. Rabbit pre-immune sera or rabbit sera of unrelated vaccinations served as negative controls. After washing, binding of rabbit IgG to the immobilized AAV2 was detected using a HRP-labelled anti-rabbit IgG antibody and TMB as substrate. Antibody titers were determined as described above.

10.5. Prime/Boost Regimen for AAV-Based Vaccines 16.4 µg AAV2 particles carrying the CETP-intern epitope (CDAGSVRTNAPD, SEQ ID NO: 123) at position I-453 and I-587 (AAV2-CETin-2×) were administered i.m. at each prime or boost immunization together with the adjuvant provided by Biogenes as described above.

Three different regimens were evaluated. Group A received one prime and three boost applications of AAV2-CETin-2× (AAV2-based vaccination). Group B received one prime and one boost immunization with AAV2-CETin-2× followed by two boost immunizations with the LPH-coupled CETP-intern peptide (LPH-peptide boost). Group C received one prime and one boost immunization with AAV2-CETIn-2× followed by two boost immunizations with AAV1-CETin (AAV1 particle carrying the CETP-intern epitope at position I-588; 11.7 µg/application). In each group the first boost immunization was performed two weeks after the prime immunization. The $2^{nd}$ and $3^{rd}$ boost immunization was performed three weeks after the preceding boost vaccination.

Immune sere were analyzed for anti-CETP-reactivity (CETP auto-antibody titer) two weeks after the 1st, 2nd and 3rd boost immunization as described above (FIG. 24).

These data demonstrate that high levels of CETP auto-antibodies are detectable in animals vaccinated with AAV2-CETin-2× only (group A). There is no increase of CETP auto-antibodies observed in the group of animals boosted with LPH-coupled CETP peptide (group B). Furthermore, data demonstrate that switching of the serotype of the AAV-backbone (group C) has the potential to increase the immune response to a self-antigen compared to boost vaccinations with an individual AAV serotype.

10.6. Evaluation of the Impact of Different Adjuvants on Immunization with AAV2-Based Vaccines Since the adjuvant provided by Biogenes may not be suitable for application in humans, alternative adjuvants were evaluated. In a first approach Montanide ISA 51 VG sterile (Seppic) was tested. Rabbits were immunized with the CETP vaccine AAV-TP18 (7.2 µg per application) i.m. or s.c. The volume of the purified vaccine was adjusted to 0.5 ml with formulation buffer and mixed with an equal volume of Montanide ISA 51 VG sterile. A control group was immunized s.c. with AAV-TP18 using the adjuvant provided by Biogenes as described above. For each vaccination approach two rabbits were immunized four times (one prime and three boost immunizations). The first boost immunization was performed 2 weeks after an initial prime immunization. Rabbits were boosted another two times with the vaccines at intervals of 3 weeks. Immune sera were analyzed for anti-CETP-reactivity (CETP auto-antibody titer) two weeks after the 1st, 2nd and 3rd boost immunization as described above. Analysis of the CETP auto-antibody titers of animals vaccinated s.c. with AAV-TP18 in the presence of Montanide ISA 51, demonstrates that similar titers are induced as in the vaccination approach using the Biogenes adjuvant (FIG. 25). Comparison of s.c. and i.m. administration of the AAV-TP18 vaccine in the presence of Montanide ISA 51 shows, that higher auto-antibody titers are generated by i.m. vaccination. These data demonstrate that AAV-base vaccines are able to induce auto-antibodies in the presence of a clinically applicable adjuvant like Montanide ISA 51 VG sterile.

In addition, the combination of AAV-based vaccine with other adjuvants such as aluminum based adjuvant Alhydrogel 2% can be evaluated with respect to induction of auto-antibodies accordingly.

10.7. Vaccination of Rabbits with an AAV1-Based CETP Vaccine

In order to prove that results obtained with AAV2 based particles can easily be transferred to other AAV-serotypes or other parvoviruses the CETP-intern peptide (CDAGSVRT-NAPD, SEQ ID NO: 123) had been inserted into the AAV1 capsid as described in 7.4.1.

For the vaccination approach two rabbits were immunized i.m. with 11.7 µg each of the construct AAV1-CETP-588 (insertion of CETP-intern epitope at position 588) as described in 10.2. The first boost immunization was performed 2 weeks after an initial prime immunization. Rabbits were boosted another 2 times with the vaccines at intervals of 3 weeks. Serum of the immunized animals was prepared two weeks after each boost immunization. CETP auto-antibody titers were determined as described above.

Data obtained demonstrate that the AAV1-based CETP vaccine AAV1-CETP-588 induces high levels of CETP auto-antibodies (FIG. 26). The induction of CETP auto-antibody was at least comparable to AAV2-CETin-2× vaccination (see 10.5). From this experiment it can be concluded that the AAV2 backbone can be substituted by the AAV1 backbone.

10.8. Vaccination Against Human β-Amyloid

For vaccination against human β-amyloid 1.0 µg of AAV2 particles carrying the human β-amyloid (aa 1-9)-epitope (DAEFRHDSG, SEQ ID NO: 158) at position I-587 were administered s.c. at each prime or boost immunization in the presence of the adjuvant provided by Biogenes. Two rabbits were immunized four times (one prime and three boost immunizations). The first boost immunization was performed 2 weeks after an initial prime immunization. Rabbits were boosted another two times with the vaccine at intervals of 3 weeks. Immune sera were analyzed for anti-β-amyloid reactivity two weeks after the $1^{st}$, $2^{nd}$ and $3^{rd}$ boost immunization as described below.

Resulting data demonstrate that immunization of rabbits with the AAV2-based β-amyloid vaccine efficiently induces antibodies against β-amyloid (FIG. 27).

Determination of Anti-β-Amyloid Antibody Titers:

The anti-β-amyloid antibody titer was determined by ELISA using immobilized Aβ(1-42) (Biosource) as antigen. Briefly, 250 ng Aβ(1-42) peptide was immobilized in each well of a 96-well Maxisorp plate (Nunc) in a total volume of 50 µl PBS per well. The plate was incubated at 37° C. for 1 h. After blocking of the wells with PBS/5% skim milk/0.1% Tween-20, immobilized Aβ(1-42) was incubated with serial dilutions of the immune sera in dilution buffer (PBS with 1% skim milk, 0.1% Tween-20) for 1 h at 37° C. Rabbit pre-immune sera or rabbit sera of unrelated vaccinations served as negative controls. After washing binding of rabbit IgG to immobilized Aβ(1-42) was detected using a HRP-labelled anti-rabbit IgG antibody and TMB as substrate. Antibody titers were determined as described above.

10.9. Immunization Against Human IgE Using AAV-Based Vaccines

A panel of AAV-based vaccines carrying epitopes derived from human IgE was generated as described above. AAV-based IgE vaccines were compared to the corresponding peptide vaccines containing the same epitope coupled to LPH as carrier protein. The peptides were chemically synthesized with a C- or N-terminal cystein residue that was used for coupling of the peptides to LPH. Synthesis and coupling of the peptides was performed by Biogenes (Berlin, Germany).

The following vaccines were used for immunization of rabbits:

TABLE 25

AAV- and LPH-based vaccines used for immunization against human IgE

| Name of vaccine | Vaccine carrier | Insertion Site | Epitope | Dose (µg) | Appl. |
|---|---|---|---|---|---|
| AAV-Kricek | AAV2 | I-587 | VNLTWSRASG (SEQ ID NO: 85) | 3.1 | s.c. |
| AAV-3DEpi3 | AAV2 | I-587 | 3DEpi3 | 4.4 | s.c. |
| AAV-Flex | AAV2 | I-587 | Flex | 16.3 | i.m. |

TABLE 25-continued

AAV- and LPH-based vaccines used for immunization against human IgE

| Name of vaccine | Vaccine carrier | Insertion Site | Epitope | Dose (µg) | Appl. |
|---|---|---|---|---|---|
| AAV-Bind2 | AAV2 | I-587 | Bind2 | 5.1 | i.m. |
| LPH-Kricek | LPH | N/A | VNLTWSRASGC SEQ ID NO: 326 | see text | i.m. |
| LPH-3DEpi3 | LPH | N/A | CDSNPRGVSAYLSR SEQ ID NO: 327 | see text | i.m. |
| LPH-Flex | LPH | N/A | CEDGQVMDVDLS SEQ ID NO: 328 | see text | i.m. |
| LPH-Bind2 | LPH | N/A | CEKQRNGTLT SEQ ID NO: 329 | see text | i.m. |

For each vaccination approach two rabbits were immunized with the vaccines shown in the table above four times (one prime and three boost immunizations). The first boost immunization was performed 2 weeks after an initial prime immunization. Rabbits were boosted another two times with the vaccines at intervals of 3 weeks.

The purified AAV-based vaccines were mixed with an equal volume of formulation buffer (PBS with 1% sorbitol, 0.2% Tween-20, 25% propylenglycol, 200 mM NaCl and 2.5 mM $MgCl_2$) for stabilization of the particles and stored at −80° C. until administration. If necessary, the volume of the vaccine was adjusted to 0.3 ml-0.5 ml with formulation buffer directly before application. The AAV-based vaccines were administered s.c. or i.m. together with the Biogenes adjuvant (total volume 1 ml).

The LPH-coupled peptides (in 0.3 ml TBS) were administered i.m. in the presence of 0.7 ml of the adjuvant provided by Biogenes. 1 mg of the LPH-peptide conjugate was administered for the prime immunization. 0.5 mg of the conjugate was used for the $1^{st}$ boost immunization and 0.25 mg of the conjugate were used for the $2^{nd}$ and $3^{rd}$ boost immunization.

Induction of anti-human IgE antibodies in the vaccinated animals was determined by ELISA using human IgE (Diatec, Oslo, Norway) as antigen. A 96-well Maxisorp plate (Nunc) was coated with human IgE (1 µg/well) for 1 h at 37° C. After coating wells were washed with wash buffer (PBS/0.1% Tween-20) and subsequently incubated with blocking buffer (5% skim milk in wash buffer) for 1 h at 37° C. After blocking of the wells, immobilized human IgE was incubated with serial dilutions of the immune sera in dilution buffer (wash buffer with 1% skim milk and 1% BSA) for 1 h at 37° C. Rabbit pre-immune sera or rabbit sera of unrelated vaccinations served as negative controls. After washing binding of rabbit IgG to the immobilized IgE was detected using a HRP-labelled anti-rabbit IgG antibody (DAKO; 1:2500 in dilution buffer). Signals (OD) were detected using TMB (KemEnTec) as substrate.

In addition to the IgE titers, the anti-peptide titers of the immune sera were analyzed. The free peptides (corresponding to the epitopes integrated in the AAV capsid or coupled to LPH) were covalently immobilized in a 96-well plate (REACTI-BIND™ Amine-binding, Maleic Anhydride Activated Plates; PIERCE) as described above. After blocking of the wells, immobilized peptides were incubated with serial dilutions of the immune sera in dilution buffer (PBS with 1% skim milk, 1% BSA, 0.1% Tween-20) for 1 h at 37° C. Rabbit pre-immune sera or rabbit sera of unrelated vaccinations served as negative controls. After washing binding of rabbit IgG to the immobilized CETP was detected using a HRP-labelled anti-rabbit IgG antibody (DAKO; 1:2500 in dilution buffer). Signals (OD) were detected using TMB (KemEnTec) as substrate. Antibody titers were determined as described above The anti-IgE titers of the immune sera are summarized in Table 26 below:

TABLE 26

Mean anti-IgE titer of immunizations with AAV- vs. LPH-based IgE vaccines

| Vaccine | anti-IgE Titer $1^{st}$ Boost | anti-IgE Titer $2^{nd}$ Boost | anti-IgE Titer $3^{rd}$ Boost |
|---|---|---|---|
| AAV-Kricek | 4750 | 20150 | 25460 |
| AAV-Kricek* | n.d. | 7950 | 27000 |
| AAV-3DEpi3* | 5000 | 18200 | 30140 |
| AAV-Bind2 | 575 | 3075 | 7750 |
| AAV-Flex | 17200 | 40300 | 38100 |
| LPH-Kricek | n.d. | 1300 | 400 |
| LPH-3DEpi3 | 705 | 1400 | 1600 |
| LPH-Flex | 15000 | 14000 | 23250 |
| LPH-Bind2 | 0 | 0 | 0 |

*AAV-based vaccines were used for the prime and $1^{st}$ boost immunization; $2^{nd}$ and $3^{rd}$ boost immunization were performed with the corresponding LPH-coupled peptide Interestingly, vaccination of rabbits with LPH-Kricek, LPH-3DEpi3 or LPH-Bind2 failed to induce significant levels of antibodies against human IgE. The immunogenic properties of the peptide based vaccines are reflected by the high titers of peptide specific antibodies induced by the peptide vaccines (data not shown). However, these antibodies show no or only weak reaction with native human IgE. Only LPH-Flex induced reasonably high titers of antibodies specific for native human IgE. This is in clear contrast to the results obtained with the corresponding AAV-based vaccines like AAV-Kricek (FIG. 28) which generate considerably higher human IgE specific antibody titers compared to the corresponding LPH-fusion constructs. This indicates that the fixed conformation of the corresponding IgE epitopes in the AAV2 capsid resembles the structure of the sequence within the IgE molecule in a better way than the LPH-coupled peptides. It should be noted that the generation of anti-human IgE antibodies in this animal model with rabbits does not overcome tolerance of the immune system to self-antigens.

For evaluation of the safety and efficacy of the AAV-based anti-human IgE vaccines in non-human primate models (e.g. cynomolgus monkeys) it is critical that the human and non-human primate IgE epitope is identical in both species. The cynomolgus IgE sequence (Fc region) was sequenced at the German Primate Centre (Göttingen, Germany). The sequence of cynomolgus IgE is shown below. Sequence alignment of human and cynomolgus IgE (data not shown) revealed that the Kricek and 3DEpi3 epitope are identical in both species. Therefore, cynomologus is a suitable animal model for safety and efficacy testing of vaccines carrying the Kricek or 3DEpi3 epitope. From sequencing data it is not fully clear whether at position 86 there is an M(bold) or T. This may be due to a sequencening error or a polymorphism. The human sequence has an M at this position.

Sequence of Cynomolgus IgE (Fc Region):

```
                                             (SEQ ID NO: 233)
001 SVFTASIQSP FVFPLIPCCK HIASNATSVT LGCLATGYFP EPVMVTWDAG

051 SLNRSTMTLP ATTFTPSGHY ATISLLTVSG AWAKEMFTCH VVHTPSSADK

101 EVNKTFGVCS RNFTPPTVKI LQSSCDDDGH FPPTIQLLCL ISGYTPGAIN

151 VTWLENGQVM KVNSPTPPAT QEGELASTQS EFTLAQKHWL SDRTYTCQVT

201 YQGTTYNDST KKCADSNPRG VSAYLSRPSP FDLFISKSPT ITCLVVDLAP

251 SKETVNLTWS RASGKPVPHI PATEKKQQRN GTLTVTSILP VVTQDWIEGE

301 TYQCRVTHPH LPRALVRSMT KTSGPRAAPE VYVFATPEKL ESRDKRTLAC

351 LIQNFMPEDI SVQWLHSDVQ LPDARHSVTQ PRKTKGSGFF VFSRLEVTKA

401 EWEQKDEFIC RAVHEAASPS WIVQQAVSVN PGK*
```

10.10. Vaccination of Rabbits with an IgE Epitope Fused to a Synthetic T-Helper Epitope According to published data ((Wang, 2003 #65); WO 99/67293), the IgE derived peptide CGETYQSRVTHPHLPRALMRSTTKC (SEQ ID NO: 234) is able to induce high titers of neutralizing anti-IgE antibodies in mice if a disulfide bond is formed between the terminal cystein terminal residues (shown in bold printed letters) and the cyclic peptide is linked to a synthetic T-helper epitope according to the following scheme:

```
                                    (SEQ ID NO: 235)
TAKSKKFPSYTATYQFGGKKKIITITRIITIITTIDGGC*GETYQSRVT

HPHLPRALMRSTTKC*
*linked by a disulfide bond
```

To evaluate this IgE peptide vaccine in our immunization experiments, the vaccine ("Wang peptide") was synthesized (Activotec) and used for immunization of rabbits (Biogenes). 100 μg of the peptide vaccine (in 0.2 ml PBS) was administered i.m. in the presence of the adjuvant provided by Biogenes.

In addition to the complete IgE derived sequence described by Wang et al. a shortened sequence of this peptide containing a putative B-cell epitope called "Wang-CS" was synthesized, coupled to LPH (via an additional N-terminal cystein residue) and used for i.m. vaccination of rabbits in the presence of the adjuvant provided by Biogenes. The LPH-coupled peptide Wang-CS (in 0.3 ml TBS) were administered i.m. in the presence of 0.7 ml of the adjuvant provided by Biogenes. 1 mg of the LPH-peptide conjugate was administered for the prime immunization. 0.5 mg of the conjugate was used for the $1^{st}$ boost immunization and 0.25 mg of the conjugate were used for the $2^{nd}$ and $3^{rd}$ boost immunization.

Rabbits were immunized with the different peptide vaccines four times (one prime and three boost immunizations). The first boost immunization was performed 2 weeks after an initial prime immunization. Rabbits were boosted another two times with the vaccines at intervals of 3 weeks. Immune sera were analyzed for anti-human IgE reactivity two weeks after the 1st, 2nd and 3rd boost immunization as described above.

These data demonstrate that vaccination of rabbits with the short LPH-coupled peptide "Wang-CS" results in anti-IgE titers that are in the range of the titers obtained with the vaccine "Wang peptide" described above (FIG. 29).

Since published data demonstrate that the Wang-peptide induces neutralizing anti-IgE antibodies in vaccinated animals (WO 99/67293), the functional properties of these polyclonal antibodies was evaluated in a cellular histamine release assay (see below).

The "Wang-CS" sequence was inserted into the AAV2 capsid at position I-587 as described above and will be used for vaccination experiments. A major advantage of the AAV-based vaccines carrying the epitope "Wang-CS" or the full-length sequences GETYQSRVTHPHLPRALMRSTTK (SEQ ID NO: 236) or "Wang" GETYQCRVTHPHLPRALMRSTTK (SEQ ID NO: 212) is their high potential of breaking self-tolerance and induction of high levels of anti-human IgE auto-antibodies.

11. Characterization of Anti-Human IgE Antibodies in Cellular Assays 11.1. Purification of Total IgG from Serum of Vaccinated Rabbits Total IgG of the immune sera was prepared using a commercially available kit (*Proteus*) based on the interaction of rabbit IgG with protein A. Purification was performed according to the protocol provided by the manufacturer. Protein concentration of total IgG was analyzed by MICRO BCA™ protein assay (PIERCE); purity of the prepared total IgG was analyzed by SDS-PAGE and colloidal Coomassie staining (data not shown).

11.2. Evaluation of the Anaphylactic Properties of the Anti-IgE Antibodies

To evaluate whether the polyclonal anti-IgE antibodies induced by vaccination of rabbits are anaphylactic, the effect of the anti-IgE antibodies on IgE mediated degranulation of basophils was investigated (Takagi et al., 2003). Rat basophilic RBL2H3 cells ($1\times10^3$ cells) overexpressing the alpha-chain of human FcεRI were sensitized by incubation with 250 ng/ml human IgE (Dianova) for 2 h in a total volume of 200 µl RPMI medium (supplemented with 10% FCS and NEAA) in a 96-well plate. Cells were washed with medium and resuspended in 100 µl Tyrode's salt solution (Sigma) supplemented with 0.1% BSA. Polyclonal anti-IgE antibodies (total IgG fraction of immunized rabbits) were added to the sensitized cells at a maximum concentration of 3 mg/ml total IgG. Different concentrations of the anaphylactic monoclonal anti-IgE antibody Le27 were used as positive control. Rabbit total IgG derived from unrelated immunizations (i.e. vaccinations against CETP or β-amyloid) was used as negative control. Cells were incubated for 1 h and histamine release was measured using a commercially available histamine ELISA (Neogen).

Resulting data demonstrate that none of the evaluated polyclonal anti-human IgE antibodies induced by vaccination of rabbits with AAV-based IgE vaccines (AAV-Kricek, AAV-3DEpi3 or AAV-Flex) induces the degranulation of IgE sensitized basophils demonstrating that these anti-IgE antibodies have no detectable anaphylactic properties (FIG. 30).

11.3. Evaluation of the IgE Neutralizing Properties of the Anti-IgE Antibodies

To evaluate whether the polyclonal anti-IgE antibodies induced by vaccination of rabbits are able to neutralize IgE, the effect of the anti-IgE antibodies on IgE mediated degranulation of basophils was investigated. Human IgE (250 ng/ml; Dianova) was pre-incubated with the polyclonal anti-IgE antibodies (3 mg/ml total IgG fraction) for 2 h at RT. As a positive control human IgE was pre-incubated with XOLAIR® (1 µg/ml). Rat basophilic RBL2H3 cells (1E+05 cells) overexpressing the alpha-chain of human FcεRI were sensitized by incubation with the human IgE/anti-IgE complexes for 2 h in a total volume of 100 µl RPMI medium (supplemented with 10% FCS and NEAA) in a 96-well plate. Cells were washed once with medium and once with Tyrode's salt solution and were subsequently resuspended in 100 µl Tyrode's salt solution (Sigma) supplemented with 0.1% BSA. The anaphylactic monoclonal anti-IgE antibody Le27 (100 nM) was used for cross-linking of receptor bound IgE. Cells were incubated for 1 h with Le27 and histamine release was measured using a commercially available histamine ELISA (Neogen).

Data obtained demonstrate that the polyclonal anti-IgE antibodies induced by vaccination of rabbits with AAV-Kricek or AAV-3DEpi3 reduce the IgE mediated histamine release by about 30% (FIG. 31) The polyclonal anti-IgE antibodies induced by vaccination of rabbits with the "Wang-peptide" (see above) inhibit the histamine release by about 20%. No significant effect was observed for polyclonal antibodies obtained from immunization of rabbits with AAV-Flex or unrelated vaccinations (i.e. vaccinations against CETP or β-amyloid).

12. Evaluation of Additional Epi- or Mimotope Insertion Sites within the AAV2-Backbone Two different strategies were followed for introduction of integration sites within the AAV2 capsid
a) Insertion of foreign epitopes at a defined insertion site (e.g. I-328)
b) Insertion by deletion of amino acid residues of AAV2 capsid and substitution by a given epi- or mimotope sequences (e.g. Δ324-332)

TABLE 27

Insertion sites within the AAV2 capsid

| Integration Site | AAV2 sequence at integration site |
|---|---|
| I-261 | YKQIS$_{261}$ SQSGA<br>SEQ ID NO: 24 |
| I-328 | TQNDG$_{328}$ TTTIA<br>SEQ ID NO: 330 |
| Δ324-332 | KEVTQNDGTTTIANN<br>SEQ ID NO: 331 |
| Δ374-380 | MVPQYGYLTLNNGS<br>SEQ ID NO: 332 |
| Δ566-575 | EEEIRTTNPVATEQYGS<br>SEQ ID NO: 333 |
| I-534 | EEKFF$_{534}$ PQSGV<br>SEQ ID NO: 31 |
| I-573 | NPVAT$_{573}$ EQYGS<br>SEQ ID NO: 32 |
| I-709 | NKSVN$_{709}$ VDFTV<br>SEQ ID NO: 334 |
| Δ708-714 | SNYNKSVNVDFTVDTNG<br>SEQ ID NO: 335 |

Insertion sites are marked with reference to the preceding amino acid;
Deleted/substituted sequences are depicted in bold letters.

For insertion of epi- or mimotope sequences into sites as listed in Table 27 two restriction sites (MroI/AscI) were inserted into the vector pCR-Kotin-C11 at the positions shown in the table above. The vector pCR-Kotin-C11 contains the complete AAV2 genome without ITRs and contains the following substitutions of amino acids within the cap gene: R459K, Y500F, G512D, N551D, A664T ((Endell, 2006 #711), page 45).

Insertion sites were introduced by site directed mutagenesis using the QICKCHANGE® II Site directed Mutagenesis kit (STRATEGENE) together with the primers listed in Table 28.

TABLE 28

Primers used for site directed mutagenesis of AAV2 Cap

| Insertion Site | Mutagenesis primer 1 (universe) | Mutagenesis primer 2 (reverse) |
|---|---|---|
| I-261 | 5'-c tac aaa caa att tcc GGC GCG CCA GGA TCC GGA agc caa tca gga gcc-3'<br>SEQ ID NO: 336 | 5'-ggc tcc tga ttg gct TCC GGA TCC TGG CGC GCC gga aat ttg ttt gta g<br>SEQ ID NO: 337 |

TABLE 28-continued

Primers used for site directed mutagenesis of AAV2 Cap

| Insertion Site | Mutagenesis primer 1 (universe) | Mutagenesis primer 2 (reverse) |
|---|---|---|
| I-328 | 5'-gtc acg cag aat gac ggt GGC GCG CCA GGA TCC GGA acg acg acg att gcc-3'<br>SEQ ID NO: 338 | 5'-ggc aat cgt cgt cgt TCC GGA TCC TGG CGC GCC acc gtc att ctg cgt gac<br>SEQ ID NO: 339 |
| I-534 | 5'-c gat gaa gaa aag ttt ttt GGC GCG CCA GGA TCC GGA cct cag agc ggg gtt ctc-3'<br>SEQ ID NO: 340 | 5'-gag aac ccc gct ctg agg TCC GGA TCC TGG CGC GCC aaa aaa ctt ttc ttc atc g-3'<br>SEQ ID NO: 341 |
| I-573 | 5'-cc aat ccc gtg gct acg GGC GCG CCA GGA TCC GGA gag cag tat ggt tct gta tc-3'<br>SEQ ID NO: 342 | 5'-ga tac aga acc ata ctg ctc TCC GGA TCC TGG CGC GCC cgt agc cac ggg att gg-3'<br>SEQ ID NO: 343 |
| I-709 | 5'-ctac aac aag tct gtt aat GGC GCG CCA GGA TCC GGA gtg gac ttt act gtg g-3'<br>SEQ ID NO: 344 | 5'-c cac agt aaa gtc cac TCC GGA TCC TGG CGC GCC att aac aga ctt gtt gta g-3'<br>SEQ ID NO: 345 |
| Δ374-380 | 5'-gac gtc ttc atg gtg cca GGC GCG CCA GGA TCC GGA aac aac ggg agt cag gc-3'<br>SEQ ID NO: 346 | 5'-gc ctg act ccc gtt gtt TCC GGA TCC TGG CGC GCC tgg cac cat gaa gac gtc-3'<br>SEQ ID NO: 347 |
| Δ324-332 | 5'-c att caa gtc aaa gag gtc GGC GCG CCA GGA TCC GGA gcc aat aac ctt acc agc-3'<br>SEQ ID NO: 348 | 5'-gct ggt aag gtt att ggc TCC GGA TCC TGG CGC GCC gac ctc ttt gac ttg aat g-3'<br>SEQ ID NO: 349 |
| Δ566-575 | 5'-ca gac gaa gag gaa atc GGC GCG CCA GGA TCC GGA tat ggt tct gta tct acc-3'<br>SEQ ID NO: 350 | 5'-ggt aga tac aga acc ata TCC GGA TCC TGG CGC GCC gat ttc ctc ttc gtc tg-3'<br>SEQ ID NO: 351 |
| Δ708-714 | 5'-cc aac tac aac aag tct GGC GCG CCA GGA TCC GGA gac act aat ggc gtg tat tc-3'<br>SEQ ID NO: 352 | 5'-ga ata cac gcc att agt gtc TCC GGA TCC TGG CGC GCC aga ctt gtt gta gtt gg-3'<br>SEQ ID NO: 353 |

Introduction of the AscI/MroI restriction site also resulted in the insertion of a new BamHI restriction site located between the AscI/MroI site. Deletion of a given sequence was also performed by site directed mutagenesis using the primers shown in Table 28. Deletion of the sequences using these primers results in the insertion of a MroI and AscI restriction site at the corresponding positions.

The EcoNI/SnaBI restriction fragments of pRC-Kotin C11 containing the new insertion sites were sub-cloned into the vector pUCAV2 for production of AAV-particles.

To evaluate whether an epi- or mimotope can be integrated at the newly created insertion sites a CETP epitope (CETP-intern) was inserted at the corresponding positions. The CETP epitope was cloned into the new AscI/MroI restriction site of pUCAV2 using annealed oligonucleotides CETin-AscI-uni and CETin-MroI-rev:

CETin-AscI-uni (SEQ ID NO: 354)

5'-CGCG GGC GGA tgc gac gcc ggc agt gtg cgc acc aat gca cca gac GGT GGC G-3'

CETin-MroI-rev (SEQ ID NO: 355)

5'-CCGG C GCC ACC gtc tgg tgc att ggt gcg cac act gcc ggc gtc gca TCC GCC-3'

Annealing of the universe and reverse oligonucleotide results in a dsDNA fragment with 5' and 3' site overhangs (shown in upper case letters) complementary to MroI and AscI restricted pUCAV2. The annealed oligonucleotides encode the CETP-intern epitope sequence (encoded by the oligonucleotide sequence shown in lower case letters) flanked by alanine/glycine residues. The annealed were cloned into the AscI/MroI restriction site of the modified pUCAV2 as described above. The epitope (shown in bold printed letters) is flanked by an alanine/glycine linker within the AAV capsid according to the following scheme:

```
                                              (SEQ ID NO: 356)
GAGG CDAGSVRTNAPD GGAG
```

The AAV variants were produced in small-scale as described above and the capsid titer of the cell lysate was measured using a commercially available AAV2 ELISA (Progen) based on the A20 mAb recognizing a conformational epitope within the AAV2 capsid (A20 ELISA). To quantify AAV2 variants with a modified capsid conformation that are not recognized by the AAV2 ELISA (A20 negative particles), capsids were produced in large-scale, purified by iodixanol gradient centrifugation as described above and quantified using an ELISA based on the mAb B1 (Progen). B1 mAb recognizes a linear epitope sequence at the C-terminus of the capsid proteins that is not modified by the insertion of the epitope. For quantification of AAV variants, the purified particles found in the 40% phase of the iodixanol gradient were denatured by heat-treatment, immobilized on a MaxiSorp 96-well plate (Nunc) and detected by the B1 mAb followed by a HRP-conjugated anti-mouse IgG antibody. In parallel, a standard curve was generated by immobilizing a dilution series of heat-denatured wtAAV2 capsids with a known capsid titer. The standard curve was used for quantification of the AAV variants.

The data of the B1 and A20 based ELISAs demonstrate that insertion of the CETP epitope at positions I-534 or I-573 as well as I-261 results in formation of particles that are recognized by B1 but not by A20 ELISA (Table 29). Particles with the CETP epitope at position I-328 can hardly be detected within the 40% phase of the iodixanol gradient by A20 or B1 ELISA. The difference between the capsid titers of the variant Δ566-575 in the 40% iodixanol phase measured by A20 or B1 ELISA is likely due to the deletion of a known minor A20 epitope (Wobus, 2000 #67) that results in a lower affinity of this variant to A20 mAb in the A20-based titration ELISA (Table 29).

No particle formation was observed for the variants with the CETP epitope integrated at position Δ324-332, Δ374-380, Δ708-714 or I-709.

TABLE 29

Capsid titers (capsids/ml) of AAV2-variants carrying the CETP-intern epitope

| Insertion Site | A20 ELISA | B1 ELISA |
|---|---|---|
| I-328 | $5.2 \times 10^{10}$ | BDL |
| I-261 | BDL | $1.1 \times 10^{13}$ |
| I-573 | BDL | $1.1 \times 10^{13}$ |
| I-534 | BDL | $2.6 \times 10^{13}$ |
| Δ566-575 | $1.5 \times 10^{12}$ | $1.4 \times 10^{13}$ |

BDL: below detection limit of the ELISA

To evaluate whether the CETP epitope is located at the capsid surface of the new variants, the purified particles (40% iodixanol phase) were dotted onto a membrane (5.0× $10^{11}$ or 1.0×$10^{11}$ particles per dot). As a positive control AAV2 particles carrying the CETP-intern epitope at position I-453 and I-587 (AAV2-CETin-2×) were dotted. As a negative control, an AAV2 variant carrying an unrelated CETP epitope (TP10) was dotted. The blot was incubated with a polyclonal Immune serum directed against the CETP-intern epitope that was generated by immunization of rabbits with the LPH-coupled CETP-intern peptide. Binding of the CETP antibody to the AAV-variants was detected using an HRP-conjugated anti-rabbit IgG antibody (FIG. 32).

The data demonstrate that for the new capsid variants Δ566-575 (I-570), I-534, I-573, I-261 and I-328 the CETP epitope is recognized by the antibody proving that the epitope is located at the surface of the capsids. There is no unspecific cross-reaction of the CETP antibody with the AAV-capsid, since the AAV variant AAV-TP10 is not recognized by the antibody. Accordingly I-261, I-573, I-534 and insertion by substitution Δ566-575 are further preferred insertion sites regarding all aspects of the present invention.

Corresponding insertion sites of different AAV serotypes or different parvoviruses can be taken from FIG. 1 as depicted for I-453 and I-587.

LITERATURE (HEREBY INCORPORATED BY REFERENCE)

Arnold, G. S., Sasser, A. K., Stachler, M. D. and Bartlett, J. S. (2006) Mol Ther, 14, 97-106.
Asokan, A. and Samulski, R. J. (2006) Nat Biotechnol, 24, 158-60.
Asquith, D. L. and I. B. McInnes (2007) 19(3): 246-51.
Bachmann, M. F., Rohrer, U. H., Kundig, T. M., Burki, K., Hengartner, H. and Zinkemagel, R. M. (1993) Science, 262, 1448-51.
Bousquet, J., Cabrera, P., Berkman, N., Buhl, R., Holgate, S., Wenzel, S., Fox, H.,
Hedgecock, S., Blogg, M. and Cioppa, G. D. (2005) Allergy, 60, 302-8.
Brown, C. S., Welling-Wester, S., Feijlbrief, M., Van Lent, J. W. and Spaan, W. J. (1994) Virology, 198, 477-88.
Casal, J. I. (1999) Biotechnology and Applied Biochemistry, 29, 141-150.
Chackerian, B., Lowy, D. R. et al. (1999). Proc Natl Acad Sci USA 96(5): 2373-8.
Chackerian, B., Lowy, D. R. and Schiller, J. T. (2001) J Clin Invest, 108, 415-23.
Chatterjee, M. B., Foon, K. A. and Kohler, H. (1994) Cancer Immunology Immunotherapy, 38, 75-82.

Cook, J. P., Henry, A. J., McDonnell, J. M., Owens, R. J., Sutton, B. J and Gould, H. J. (1997) Biochemistry, 36, 15579-88.

Corpet, F. (1988) Nucleic Acids Res, 16, 10881-90.

Dean, D. A., Strong, D. D. and Zimmer. W. E. (2005) Gene Ther, 12, 881-90.

Gamsjaeger, R., C. K. Liew, et al. (2007). Trends Biochem Sci 32(2): 63-70.

Garman, S. C., Wurzburg, B. A., Tarchevskaya, S. S., Kinet, J. P. and Jardetzky, T. S. (2000) Nature, 406, 259-66.

Girod, A., Ried, M., Wobus, C., Lahm, H., Leike, K., Kleinschmidt, J., Deleage, G. and Hallek, M. (1999) Nat Med, 5, 1438.

Grassi, J., Didierlaurent, A. and Stadler, B. M. (1986) J Allergy Clin Immunol, 77, 808-22.

Grifman, M., Trepel, M., Speece, P., Gilbert. L. B., Arap, W., Pasqualini, R. and Weitzman, M. D. (2001) Mol Ther, 3, 964-75.

Grimm, D., Kern, A., Pawlita, M., Ferrari, F., Samulski, R. and Kleinschmidt, J. (1999) Gene Ther, 6, 1322-30.

Helm. B., Kebo, D., Vercelli, D., Glovsky, M. M., Gould, H., Ishizaka, K., Geha, R. and Ishizaka, T. (1989) Proc Natl Acad Sci USA, 86, 9465-9.

Helm, B., Marsh, P., Vercelli, D., Padlan, E., Gould, H. and Geha, R. (1988) Nature, 331, 180-3.

Huttner, N. A., Girod, A., Perabo, L., Edbauer, D., Kleinschmidt, J. A., Buning, H. and Hallek, M. (2003) Gene Ther, 10, 2139-47.

Jefferis, R. (1993) Immunol Today, 14, 119-21.

Jerne, N. K. (1974) Ann Immunol (Paris), 125C, 373-89.

Jerne, N. K., Roland, J. and Cazenave, P. A. (1982) Embo J, 1, 243-7.

Klenerman, P., Tolfvenstam, T., Price, D. A., Nixon, D. F., Broliden, K. and Oxenius, A. (2002) Pathol Biol (Paris), 50, 317-25.

Kricek. F., Ruf, C., Rudolf, M. P., Effenberger, F., Mayer, P. and Stadler, B. M. (1999) Int Arch Allergy Immunol, 118, 222-3.

Kuster, H., Thompson, H. and Kinet, J. P. (1990) J Biol Chem, 265, 6448-52.

Laity, J. H., B. M. Lee, et al. (2001). Curr Opin Struct Biol 11(1): 39-46.

Laughlin, C. A., Tratschin, J. D., Coon, H. and Carter, B. J. (1983) Gene, 23, 65-73.

Levy, D. A. and Chen, J. (1970) N Engl J Med, 283, 541-2.

Li, Q., Cao. C., Chackerian, B., Schiller, J., Gordon, M., Ugen, K. E. and Morgan, D. (2004) BMC Neurosci, 5, 21.

Lieber, A. (2003) Nat Biotechnol, 21, 1011-3.

Lux, K., Goerlitz, N., Schlemminger, S., Perabo. L., Goldnau, D., Endell, J., Leike, K., Kofler, D. M., Finke, S., Hallek, M. and Buning, H. (2005) J Virol, 79, 11776-87.

Maheshri, N., Koerber, J. T., Kaspar, B. K. and Schaffer, D. V. (2006) Nat Biotechnol, 24, 198-204.

Moskalenko, M., Chen, L., van Roey, M., Donahue, B. A., Snyder, R. O., McArthur, J. G. and Patel, S. D. (2000) J Virol, 74, 1761-6.

Muller, O. J., Kaul, F., Weitzman, M. D., Pasqualini, R., Arap, W., Kleinschmidt, J. A. and Trepel, M. (2003) Nat Biotechnol, 21, 1040-6.

Muzyczka, N. (1992) Curr Top Microbiol Immunol, 158, 97-129.

Nicklin, S. A., Buening, H., Dishart, K. L., de Aiwis, M., Girod, A., Hacker, U., Thrasher, A.

J., All, R. R., Hallek, M. and Baker, A. H. (2001) Mol Ther, 4, 174-81.

Nygren, P. A. and Skerra, A. (2004) J Immunol Methods, 290, 3-28.

Parker, K. C., M. A. Bednarek, et al. (1994). J Immunol 152(1): 163-75.

Perabo, L., Buning, H., Kofier, D. M., Ried, M. U., Girod, A., Wendtner, C M., Enssle, J. and Hallek, M. (2003) Mol Ther, 8, 151-7.

Presta, L., Shields, R., O'Connell, L., Lahr, S., Porter, J., Gorman, C. and Jardieu, P. (1994) J Biol Chem, 269, 26368-73.

Ried, M. U., Girod, A., Leike, K., Buning, H. and Hallek, M. (2002) J Virol, 76, 4559-66.

Riemer, A. B., Untersmayr, E., Knittelfelder, R., Duschl, A., Pehamberger, H., Zielinski, C. C., Scheiner, O. and Jensen-Jarolim, E. (2007) Cancer Res, 67, 3406-11.

Rittershaus, C. W., Miller, D. P., Thomas, L. J., Picard, M. D., Honan, C. M., Emmett, C. D., Pettey, C. L., Adari, H., Hammond, R. A., Beattie, D. T., Callow, A. D., Marsh, H. C. and Ryan, U. S. (2000) Arterioscler Thromb Vasc Biol, 20, 2106-12.

Rudolf, M. P., Vogel, M., Kricek, F., Ruf, C., Zurcher, A. W., Reuschel, R., Auer, M., Miescher. S. and Stadler, B. M. (1998) J Immunol, 160, 3315-21.

Rudolf, M. P., Zuercher, A. W., Nechansky, A., Ruf, C., Vogel, M., Miescher, S. M., Stadler, B. M. and Kricek, F. (2000) J Immunol, 165, 813-9.

Shi, W., Arnold. G. S. and Bartlett, J. S. (2001) Hum Gene Ther. 12, 1697-711.

Shi, W. and Bartlett. J. S. (2003) Mol Ther, 7, 515-25.

Smolen, J. S. and Steiner, G. (2003) Nat Rev Drug Discov, 2, 473-88.

Stachler. M. D. and Bartlett, J. S. (2006) Gene Ther, 13, 926-31.

Stadler, B. M., Zurcher, A. W., Miescher, S., Kricek, F. and Vogel, M. (1999) Int Arch Allergy Immunol, 118, 119-21.

Szomolanyi-Tsuda, E., Brien, J. D., Dorgan, J. E., Garcea, R. L., Woodland. R. T. and Welsh, R. M. (2001) Virology, 280, 160-8.

Szomolanyi-Tsuda, E., Brien. J. D., Dorgan, J. E., Welsh, R. M. and Garcea, R. L. (2000) J Immunol, 164, 5877-82.

Szomolanyi-Tsuda, E., Le, Q. P., Garcea, R. L. and Welsh, R. M. (1998) J Virol, 72, 6665-70.

Szomolanyi-Tsuda, E. and Welsh, R. M. (1998) Curr Opin Immunol, 10, 431-5.

Takagi, K., R. Nakamura, et al. (2003). Biol Pharm Bull 26(2): 252-5.

Uversky V. N., Fernández A. and Fink A. L. (2006) chapter 1, 1-20 in: Protein Reviews Volume 4, editor: M. Zouhair Atassi: Protein Misfolding, Aggregation, and Conformational Disease, Part A: Protein Aggregation and Conformational Disease; Springer.

Varela, F. J. and Coutinho, A. (1991) Immunol Today, 12, 159-66.

Vogel, M., Miescher, S., Kuhn, S., Zurcher, A. W., Stadler, M. B., Ruf, C., Effenberger, F., Kricek, F. and Stadler, B. M. (2000) J Mol Biol, 298, 729-35.

Vogel, M., Tschopp, C., Bobrzynski, T., Fux, M., Stadler, M. B., Miescher, S. M. and Stadler, B. M. (2004) J Mol Blol, 341, 477-89.

Wang, C. Y., Walfield, A. M., Fang, X., Hammerberg, B., Ye, J., Li, M. L., Shen, F., Shen, M., Alexander. V. and MacGlashan, D. W. (2003) Vaccine, 21, 1580-90.

Warrington, K. H., Jr., Gorbatyuk, O. S., Harrison, J. K., Opie, S. R., Zolotukhin, S. and Muzyczka, N. (2004) J Virol, 78, 6595-609.

Waterkamp, D. A., Muller, O. J., Ying, Y., Trepel, M. and Kleinschmidt, J. A. (2006) J Gene Med, 8, 1307-19.

White, S. J., Nicklin, S. A., Buning, H., Brosnan, M. J., Leike, K., Papadakis, E. D., Hallek, M. and Baker, A. H. (2004) Circulation, 109, 513-9.

Wistuba, A., Kern, A., Weger, S., Grimm, D. and Kleinschmidt, J. A. (1997) J Virol, 71, 1341-52.

Work, L. M., Buning, H., Hunt, E., Nicklin, S. A., Denby, L., Britton, N., Leike, K., Odenthal, M., Drebber, U., Hallek, M. and Baker, A. H. (2006) Mol Ther, 13, 683-93.

Work, L. M., Nicklin, S. A., Brain, N. J., Dishart, K. L., Von Seggem, D. J., Hallek, M., Buning, H. and Baker, A. H. (2004) Mol Ther, 9, 198-208.

Wu. P., Xiao, W., Conlon. T., Hughes. J., Agbandje-McKenna, M., Ferkol, T., Flotte. T. and Muzyczka, N. (2000) J Virol, 74, 8635-47.

Xiao, W., Chirmule, N., Berta, S. C., McCullough, B., Gao, G. and Wilson, J. M. (1999) J Virol, 73, 3994-4003.

Zinkemagel, R. M. (2002) Immunological Reviews, 185, 103-125.

The invention claimed is:

1. A method for identifying a parvovirus mutated structural protein capable of specifically binding to a binder for an antigen, wherein the binder comprises a therapeutic antibody, a therapeutic single chain antibody, or an antibody fragment of a therapeutic antibody, the method comprising the steps of:
   a) providing a library of parvovirus virions expressing at least one mutated parvovirus structural protein,
   b) providing a binder for an antigen,
   c) selecting at least one parvovirus virion specifically binding to the binder, and
   d) identifying
      i) the parvovirus mutated structural protein or a mutated part thereof, or
      ii) the gene or a mutated part thereof encoding the parvovirus mutated structural protein of the parvovirus virion selected in step c).

2. The method of claim 1 wherein the at least one parvovirus virion selected in step c) is amplified by viral replication and subsequent packaging in a production cell under suitable conditions, and wherein at least steps b) to c) are repeated 1, 2, 3, 4, 5, 6, 7, 8, 9, or 10 times.

3. The method of claim 1, wherein the selecting step is performed using a binder immobilized on a carrier.

4. The method of claim 1, wherein the selecting step is performed using the binder in suspension.

5. The method of claim 1, wherein said selecting at least one parvovirus virion further comprises selecting for non-binding to a second binder.

6. The method of claim 1, wherein said method further comprises the steps of
   e) randomizing the gene encoding the parvovirus mutated structural protein by inserting a randomly or partially randomly generated sequence into the coding region of the parvoviral structural gene, f) packaging the randomized genes into a further library of parvoviruses, and g) repeating the steps a)-d).

7. The method of claim 1, wherein the parvovirus mutated structural protein further comprises at least one random mutation compared to the respective parvovirus wild-type structural protein.

8. The method of claim 7, wherein the parvovirus is selected from the group consisting of adeno-associated virus (AAV), bovine AAV (b-AAV), canine AAV (CAAV), canine parvovirus (CPV), mouse parvovirus, minute virus of mice (MVM), B19, H1, avian AAV (AAAV), feline panleukopenia virus (FPV), and goose parvovirus (GPV).

9. The method of claim 8, wherein the AAV is AAV-1, AAV-2, AAV-3b, AAV-4, AAV-5, AAV-6, AAV-7, AAV-8, AAV-9, AAV-10, AAV-11 or AAV-12.

10. The method of claim 1, wherein the library has a multiplicity of parvoviral mutants of greater than $10^5$.

11. The method of claim 1, wherein the parvovirus mutant structural protein comprises at least one insertion of 4-30 amino acids.

12. The method of claim 11, wherein said insertion is of 5-20 amino acids.

13. The method of claim 12, wherein said insertion is 5-15 amino acids.

14. The method of claim 11, wherein the insertion comprises two cysteines capable of forming a disulfide bond to form a loop consisting of the inserted amino acids.

15. The method of claim 11, wherein a) the insertion is inserted into one or more positions selected from the group consisting of the positions before and/or after amino acids I-1, I-34, I-138, I-139, I-161, I-261, I-266, I-381, I-447, I-448, I-453, I-459, I-471, I-534, I-570, I-573, I-584, I-587, I-588, I-591, I-657, I-664, I-713, and I-716; or b) the insertion is inserted into two positions selected from the group consisting of the positions before and/or after amino acids I-261, I-453, I-534, I-570, I-573, and I-587.

16. The method of claim 15, wherein the insertion is inserted at the positions before and/or after amino acids I-261, I-453, I-534, I-570, I-573, or I-587.

17. The method of claim 15, wherein said two positions are I-261 in combination with I-587 or I-261 in combination with I-453.

18. The method of claim 1, wherein the parvovirus mutated structural protein comprises at least one further mutation selected from the group consisting of a point mutation, an internal or terminal deletion, a second insertion, and a substitution.

19. The method of claim 18, wherein said further mutation is a second insertion and said second insertion is internal or a N- or C-terminal fusion, and has a length of 4 to 40, 5 to 30, or 7 to 20 amino acids.

20. The method of claim 19, wherein the second insertion is a tag useful for binding to a ligand.

21. The method of claim 1, wherein said parvovirus mutated structural protein comprises at least one B-cell epitope heterologous to the parvovirus, wherein the B-cell epitope is located on the surface of the virus.

22. The method of claim 21, wherein said B-cell epitope is a tolerogen-derived epitope.

23. The method of claim 1, wherein the therapeutic antibody is a monoclonal antibody or a fragment thereof.

24. The method of claim 1, wherein the binder consists of a therapeutic antibody, a therapeutic single chain antibody, or an antibody fragment of a therapeutic antibody.

* * * * *

SEQUENCE LISTING

<160> NUMBER OF SEQ ID NOS: 358

<210> SEQ ID NO 1
<211> LENGTH: 10
<212> TYPE: PRT
<213> ORGANISM: Artificial Sequence
<220> FEATURE:
<223> OTHER INFORMATION: Synthetic Construct

<400> SEQUENCE: 1

Phe Gln Ser Ser Ser Thr Asp Pro Ala Thr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Construct

<400> SEQUENCE: 2

Leu Gln Arg Gly Asn Arg Gln Ala Ala Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Leu Gln Ser Ser Asn Thr Ala Pro Thr Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Construct

<400> SEQUENCE: 4

Leu Gln Ser Ser Ser Thr Asp Pro Ala Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

Leu Gln Ala Ala Asn Thr Ala Ala Gln Thr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic Construct

<400> SEQUENCE: 6

Leu Gln Gln Gln Asn Thr Ala Pro Gln Ile
1               5                   10

```
<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Leu Gln Gln Ala Asn Thr Gly Pro Ile Val
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Asn Gln Asn Ala Thr Thr Ala Pro Ile Thr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic Construct

<400> SEQUENCE: 9

Asn Gln Ser Ser Thr Thr Ala Pro Ala Thr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic Construct

<400> SEQUENCE: 10

Gln Asn Gln Ser Gly Ser Ala Gln Asn Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic Construct

<400> SEQUENCE: 11

Asn Thr Pro Ser Gly Thr Thr Thr Gln Ser
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct

<400> SEQUENCE: 12

Gly Thr Thr Ser Gly Thr Thr Asn Gln Ser
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

Gln Asn Gln Ser Gly Ser Ala Gln Asn Lys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

Ser Asn Pro Gly Gly Thr Ala Gly Asn Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

<400> SEQUENCE: 15

Gln Thr Thr Gly Gly Thr Ala Asn Thr Gln
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

Gln Ser Thr Gly Gly Thr Gln Gly Thr Gln
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Ser Gly Glu Thr Leu Asn Gln Gly Asn Ala
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Construct

<400> SEQUENCE: 18

Phe Val Ser Thr Asn Asn Thr Gly Gly Val
1               5                   10
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic Construct

<400> SEQUENCE: 19

Met Ala Ala Asp Gly Tyr
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Pro Pro Pro Lys Pro Ala Glu Arg His Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Glu Pro Val Lys Thr Ala Pro Gly Lys Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic Construct

<400> SEQUENCE: 22

Pro Val Lys Thr Ala Pro Gly Lys Lys Arg
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic Construct

<400> SEQUENCE: 23

Ser Gly Thr Gly Lys Ala Gly Gln Gln Pro
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Construct

<400> SEQUENCE: 24

Tyr Lys Gln Ile Ser Ser Gln Ser Gly Ala
1               5                   10

<210> SEQ ID NO 25
```

```
<211> LENGTH: 10
<212> TYPE: PRT
<213> ORGANISM: Artificial Sequence
<220> FEATURE:
<223> OTHER INFORMATION: Synthetic Construct

<400> SEQUENCE: 25

Ser Gln Ser Gly Ala Ser Asn Asp Asn His
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic Construct

<400> SEQUENCE: 26

Tyr Leu Thr Leu Asn Asn Gly Ser Gln Ala
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic Construct

<400> SEQUENCE: 27

Tyr Tyr Leu Ser Arg Thr Asn Thr Pro Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic Construct

<400> SEQUENCE: 28

Tyr Leu Ser Arg Thr Asn Thr Pro Ser Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Construct

<400> SEQUENCE: 29

Thr Thr Gln Ser Arg Leu Gln Phe Ser Gln
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Ala Ser Asp Ile Arg Asp Gln Ser Arg Asn
1               5                   10

<210> SEQ ID NO 31
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 31

Glu Glu Lys Phe Phe Pro Gln Ser Gly Val
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

Asn Pro Val Ala Thr Glu Gln Tyr Gly Ser
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Ser Thr Asn Leu Gln Arg Gly Asn Arg Gln
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Synthetic Construct

<400> SEQUENCE: 34

Gln Arg Gly Asn Arg Gln Ala Ala Thr Ala
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthetic Construct

<400> SEQUENCE: 35

Asn Arg Gln Ala Ala Thr Ala Asp Val Asn
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthetic Construct

<400> SEQUENCE: 36

Val Pro Ala Asn Pro Ser Thr Thr Phe Ser
1               5                   10

<210> SEQ ID NO 37
<211> LENGTH: 10
<212> TYPE: PRT
```

```
<213> ORGANISM: Artificial Sequence
<220> FEATURE:
<223> OTHER INFORMATION: Synthetic Construct

<400> SEQUENCE: 37

Thr Phe Ser Ala Ala Lys Phe Ala Ser Phe
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Asn Val Asp Phe Thr Val Asp Thr Asn Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Construct

<400> SEQUENCE: 39

Phe Thr Val Asp Thr Asn Gly Val Tyr Ser
1               5                   10

<210> SEQ ID NO 40
<211> LENGTH: 7
<212> TYPE: PRT
<213> ORGANISM: Artificial Sequence
<220> FEATURE:
<223> OTHER INFORMATION: Synthetic Construct

<400> SEQUENCE: 40

Thr Ala Pro Gly Lys Lys Arg
1               5

<210> SEQ ID NO 41
<211> LENGTH: 10
<212> TYPE: PRT
<213> ORGANISM: Artificial Sequence
<220> FEATURE:
<223> OTHER INFORMATION: Synthetic Construct

<400> SEQUENCE: 41

Ser Ser Ser Thr Asp Pro Ala Thr Gly Asp
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Asn Asn Leu Gln Ser Ser Asn Thr Ala Pro
1               5                   10

<210> SEQ ID NO 43
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 43

Gly Gly Asp Gln Ser Asn Ser Asn Leu Pro
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Thr Asn Asn Gln Ser Ser Thr Thr Ala Pro
1               5                   10

<210> SEQ ID NO 45
<211> LENGTH: 14
<212> TYPE: PRT
<213> ORGANISM: Artificial Sequence
<220> FEATURE:
<223> OTHER INFORMATION: Synthetic Construct

<400> SEQUENCE: 45

Gln Ala Gly Thr Phe Ala Leu Arg Gly Asp Asn Pro Gln Gly
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic Construct

<400> SEQUENCE: 46

Ser Ile Gly Tyr Pro Leu Pro
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic Construct

<400> SEQUENCE: 47

Cys Asp Cys Arg Gly Asp Cys Phe Cys
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Construct

<400> SEQUENCE: 48

Arg Gly Asp Ala Val Gly Val
1               5

<210> SEQ ID NO 49
<211> LENGTH: 7
<212> TYPE: PRT
<213> ORGANISM: Artificial Sequence
<220> FEATURE:
```

```
<223> OTHER INFORMATION: Synthetic Construct

<400> SEQUENCE: 49

Arg Gly Asp Thr Pro Thr Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic Construct

<400> SEQUENCE: 50

Gly Glu Asn Gln Ala Arg Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Arg Ser Asn Ala Val Val Pro
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct

<400> SEQUENCE: 52

Asn Ser Ser Arg Asp Leu Gly
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic Construct

<400> SEQUENCE: 53

Asn Asp Val Arg Ala Val Ser
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Glu Tyr His His Tyr Asn Lys
1               5

<210> SEQ ID NO 55
<211> LENGTH: 16
<212> TYPE: PRT
<213> ORGANISM: Artificial Sequence
<220> FEATURE:
<223> OTHER INFORMATION: Synthetic Construct
```

```
<400> SEQUENCE: 55

Met Thr Pro Phe Pro Thr Ser Asn Glu Ala Asn Leu Gly Gly Gly Ser
1               5                   10                  15

<210> SEQ ID NO 56
<211> LENGTH: 7
<212> TYPE: PRT
<213> ORGANISM: Artificial Sequence
<220> FEATURE:
<223> OTHER INFORMATION: Synthetic Construct

<400> SEQUENCE: 56

Gln Pro Glu His Ser Ser Thr
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Construct

<400> SEQUENCE: 57

Val Asn Thr Ala Asn Ser Thr
1               5

<210> SEQ ID NO 58
<211> LENGTH: 7
<212> TYPE: PRT
<213> ORGANISM: Artificial Sequence
<220> FEATURE:
<223> OTHER INFORMATION: Synthetic Construct

<400> SEQUENCE: 58

Asn Asp Val Arg Ser Ala Asn
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Asn Asp Val Arg Ala Val Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Construct

<400> SEQUENCE: 60

Val Thr Ala Gly Arg Ala Pro
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 61

Ala Pro Val Thr Arg Pro Ala
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic Construct

<400> SEQUENCE: 62

Asp Leu Ser Asn Leu Thr Arg
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Construct

<400> SEQUENCE: 63

Gly Gln His Pro Arg Pro Gly
1               5

<210> SEQ ID NO 64
<211> LENGTH: 8
<212> TYPE: PRT
<213> ORGANISM: Artificial Sequence
<220> FEATURE:
<223> OTHER INFORMATION: Synthetic Construct

<400> SEQUENCE: 64

Gln Arg Gly Asn Arg Gln Ala Ala
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

<400> SEQUENCE: 65

Ala Ser Ile Gly Tyr Pro Leu Pro Ala
1               5

<210> SEQ ID NO 66
<211> LENGTH: 12
<212> TYPE: PRT
<213> ORGANISM: Artificial Sequence
<220> FEATURE:
<223> OTHER INFORMATION: Synthetic Construct

<400> SEQUENCE: 66

Ala Thr Gly Cys Asp Cys Arg Gly Asp Cys Phe Cys
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Synthetic Construct

<400> SEQUENCE: 67
```

```
Ala Ala Ala Arg Gly Asp Ala Val Gly Val Ala Ala
1               5                   10
```

<210> SEQ ID NO 68
<211> LENGTH: 12
<212> TYPE: PRT
<213> ORGANISM: Artificial Sequence
<220> FEATURE:
<223> OTHER INFORMATION: Synthetic Construct

<400> SEQUENCE: 68

```
Ala Ala Ala Arg Gly Asp Thr Pro Thr Ser Ala Ala
1               5                   10
```

<210> SEQ ID NO 69
<211> LENGTH: 12
<212> TYPE: PRT
<213> ORGANISM: Artificial Sequence
<220> FEATURE:
<223> OTHER INFORMATION: Synthetic Construct

<400> SEQUENCE: 69

```
Ala Ala Ala Gly Glu Asn Gln Ala Arg Ser Ala Ala
1               5                   10
```

<210> SEQ ID NO 70
<211> LENGTH: 12
<212> TYPE: PRT
<213> ORGANISM: Artificial Sequence
<220> FEATURE:
<223> OTHER INFORMATION: Synthetic Construct

<400> SEQUENCE: 70

```
Ala Ala Ala Arg Ser Asn Ala Val Val Pro Ala Ala
1               5                   10
```

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

```
Gly Asn Ser Ser Arg Asp Leu Gly Ala
1               5
```

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct

<400> SEQUENCE: 72

```
Gly Asn Asp Val Arg Ala Val Ser Ala
1               5
```

<210> SEQ ID NO 73
<211> LENGTH: 10
<212> TYPE: PRT
<213> ORGANISM: Artificial Sequence
<220> FEATURE:
<223> OTHER INFORMATION: Synthetic Construct

<400> SEQUENCE: 73

```
Ala Ser Glu Tyr His His Tyr Asn Lys Ala
1               5                   10
```

<210> SEQ ID NO 74
<211> LENGTH: 19
<212> TYPE: PRT
<213> ORGANISM: Artificial Sequence
<220> FEATURE:
<223> OTHER INFORMATION: Synthetic Construct

<400> SEQUENCE: 74

```
Ala Ser Met Thr Pro Phe Pro Thr Ser Asn Glu Ala Asn Leu Gly Gly
1               5                   10                  15

Gly Ser Ala
```

<210> SEQ ID NO 75
<211> LENGTH: 10
<212> TYPE: PRT
<213> ORGANISM: Artificial Sequence
<220> FEATURE:
<223> OTHER INFORMATION: Synthetic Construct

<400> SEQUENCE: 75

```
Ala Ser Gln Pro Glu His Ser Ser Thr Ala
1               5                   10
```

<210> SEQ ID NO 76
<211> LENGTH: 10
<212> TYPE: PRT
<213> ORGANISM: Artificial Sequence
<220> FEATURE:
<223> OTHER INFORMATION: Synthetic Construct

<400> SEQUENCE: 76

```
Ala Ser Val Asn Thr Ala Asn Ser Thr Ala
1               5                   10
```

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77

```
Gly Asn Asp Val Arg Ser Ala Asn Ala
1               5
```

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

```
Gly Asn Asp Val Arg Ala Val Ser Ala
1               5
```

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Gly Val Thr Ala Gly Arg Ala Pro Ala
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Construct

<400> SEQUENCE: 80

Gly Ala Pro Val Thr Arg Pro Ala Ala
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Construct

<400> SEQUENCE: 81

Gly Asp Leu Ser Asn Leu Thr Arg Ala
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Construct

<400> SEQUENCE: 82

Gly Gly Gln His Pro Arg Pro Gly Ala
1               5

<210> SEQ ID NO 83
<211> LENGTH: 14
<212> TYPE: PRT
<213> ORGANISM: Artificial Sequence
<220> FEATURE:
<223> OTHER INFORMATION: Synthetic Construct

<400> SEQUENCE: 83

Glu Phe Cys Ile Asn His Arg Gly Tyr Trp Val Cys Gly Asp
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic Construct

<400> SEQUENCE: 84

Val Asn Leu Thr Trp Ser Arg Ala Ser Gly
1               5                   10

<210> SEQ ID NO 85
<211> LENGTH: 18
<212> TYPE: DNA
<213> ORGANISM: Artificial Sequence
<220> FEATURE:
<223> OTHER INFORMATION: Synthetic Construct

<400> SEQUENCE: 85
atgtccgtcc gtgtgtgg                                             18

<210> SEQ ID NO 86
<211> LENGTH: 18
<212> TYPE: DNA
<213> ORGANISM: Artificial Sequence
<220> FEATURE:
<223> OTHER INFORMATION: Synthetic Construct

<400> SEQUENCE: 86
ggtacgacga cgattgcc                                             18

<210> SEQ ID NO 87
<211> LENGTH: 24
<212> TYPE: DNA
<213> ORGANISM: Artificial Sequence
<220> FEATURE:
<223> OTHER INFORMATION: Synthetic Construct

<400> SEQUENCE: 87
taccagctcc cgtacgtcct cggc                                      24

<210> SEQ ID NO 88
<211> LENGTH: 20
<212> TYPE: DNA
<213> ORGANISM: Artificial Sequence
<220> FEATURE:
<223> OTHER INFORMATION: Synthetic Construct

<400> SEQUENCE: 88
cgccatgcta cttatctacg                                           20

<210> SEQ ID NO 89
<211> LENGTH: 30
<212> TYPE: DNA
<213> ORGANISM: Artificial Sequence
<220> FEATURE:
<223> OTHER INFORMATION: Synthetic Construct

<400> SEQUENCE: 89
tctagagggc actcttccgt ggtctggtgg                                30

<210> SEQ ID NO 90
<211> LENGTH: 33
<212> TYPE: DNA
<213> ORGANISM: Artificial Sequence
<220> FEATURE:
<223> OTHER INFORMATION: Synthetic Construct

<400> SEQUENCE: 90
tctagagcaa aaagggggct cgtccctgtt tcc                            33

<210> SEQ ID NO 91
<211> LENGTH: 24
<212> TYPE: DNA
<213> ORGANISM: Artificial Sequence
<220> FEATURE:
<223> OTHER INFORMATION: Synthetic Construct

<400> SEQUENCE: 91
taccagctcc cgtacgtcct cggc                                      24

<210> SEQ ID NO 92
<211> LENGTH: 20
<212> TYPE: DNA
<213> ORGANISM: Artificial Sequence

```
<220> FEATURE:
<223> OTHER INFORMATION: Synthetic Construct

<400> SEQUENCE: 92
cgccatgcta cttatctacg                                               20

<210> SEQ ID NO 93
<211> LENGTH: 7
<212> TYPE: PRT
<213> ORGANISM: Artificial Sequence
<220> FEATURE:
<223> OTHER INFORMATION: Synthetic Construct

<400> SEQUENCE: 93

Ala Arg Ala Gly Leu Pro Gly
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic Construct

<400> SEQUENCE: 94

Leu Arg Pro Asp Ala Arg Pro
1               5

<210> SEQ ID NO 95
<211> LENGTH: 7
<212> TYPE: PRT
<213> ORGANISM: Artificial Sequence
<220> FEATURE:
<223> OTHER INFORMATION: Synthetic Construct

<400> SEQUENCE: 95

Pro Arg Thr Asp Ser Pro Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct

<400> SEQUENCE: 96

Pro Thr Leu Thr Pro Pro Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic Construct

<400> SEQUENCE: 97

Ser Thr Leu Ala Pro Pro Ala
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 98

Ser Arg Pro Pro Asn Pro Ala
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Construct

<400> SEQUENCE: 99

Met Gly Ser Pro Ser Thr Arg
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

Arg Asp His Pro Gly Ile Arg
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101

Val Gly Ser Pro Ser Thr Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic Construct

<400> SEQUENCE: 102

Leu Pro Thr Ala Arg Ser Pro
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic Construct

<400> SEQUENCE: 103

Val Tyr Ser Pro Thr Gly Lys
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 104

Ser Asp Ala Pro Leu Pro Arg
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic Construct

<400> SEQUENCE: 105

Glu Thr Gln Leu Arg Ala Thr
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Construct

<400> SEQUENCE: 106

Gly Leu Gly Thr Gln Pro Arg
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic Construct

<400> SEQUENCE: 107

Asp Lys Thr Gly Ser Lys Pro
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Construct

<400> SEQUENCE: 108

Thr Ser Ala Ser Arg Ala Pro
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic Construct

<400> SEQUENCE: 109

Ala Cys Ala Pro Thr Gly Val
1               5

<210> SEQ ID NO 110
<211> LENGTH: 27
<212> TYPE: DNA
<213> ORGANISM: Artificial Sequence
<220> FEATURE:
<223> OTHER INFORMATION: Synthetic Construct

<400> SEQUENCE: 110
```
gagtcgaccc gggcagccgc ttcgagc                                              27

<210> SEQ ID NO 111
<211> LENGTH: 27
<212> TYPE: DNA
<213> ORGANISM: Artificial Sequence
<220> FEATURE:
<223> OTHER INFORMATION: Synthetic Construct

<400> SEQUENCE: 111
gctcgaagcg gctgcccggg tcgactc                                              27

<210> SEQ ID NO 112
<211> LENGTH: 53
<212> TYPE: DNA
<213> ORGANISM: Artificial Sequence
<220> FEATURE:
<223> OTHER INFORMATION: Synthetic Construct

<400> SEQUENCE: 112
ccaacctcca gagaggcaac gcggccgcaa ggcgcgccaa gcagctaccg cag                 53

<210> SEQ ID NO 113
<211> LENGTH: 53
<212> TYPE: DNA
<213> ORGANISM: Artificial Sequence
<220> FEATURE:
<223> OTHER INFORMATION: Synthetic Construct

<400> SEQUENCE: 113
ctgcggtagc tgcttggcgc gccttgcggc cgcgttgcct ctctggaggt tgg                 53

<210> SEQ ID NO 114
<211> LENGTH: 41
<212> TYPE: DNA
<213> ORGANISM: Artificial Sequence
<220> FEATURE:
<223> OTHER INFORMATION: Synthetic Construct

<400> SEQUENCE: 114
ggccgcagtg aacctgacct ggagcagagc ctccggcgcg g                              41

<210> SEQ ID NO 115
<211> LENGTH: 41
<212> TYPE: DNA
<213> ORGANISM: Artificial Sequence
<220> FEATURE:
<223> OTHER INFORMATION: Synthetic Construct

<400> SEQUENCE: 115
cgcgccgcgc cggaggctct gctccaggtc aggttcactg c                              41

<210> SEQ ID NO 116
<211> LENGTH: 56
<212> TYPE: DNA
<213> ORGANISM: Artificial Sequence
<220> FEATURE:
<223> OTHER INFORMATION: Synthetic Construct

<400> SEQUENCE: 116
ggccgcagcg gcggtgaacc tgacctggag cagagcctcc ggcgcggcgg cggcgg             56

<210> SEQ ID NO 117
<211> LENGTH: 56
<212> TYPE: DNA

```
<213> ORGANISM: Artificial Sequence
<220> FEATURE:
<223> OTHER INFORMATION: Synthetic Construct

<400> SEQUENCE: 117
cgcgccgccg ccgccgcgcc ggaggctctg ctccaggtca ggttcaccgc cgctgc        56

<210> SEQ ID NO 118
<211> LENGTH: 53
<212> TYPE: DNA
<213> ORGANISM: Artificial Sequence
<220> FEATURE:
<223> OTHER INFORMATION: Synthetic Construct

<400> SEQUENCE: 118
ggccgcagaa ttctgcataa accacagggg atactgggtg tgcggagacg cgg           53

<210> SEQ ID NO 119
<211> LENGTH: 53
<212> TYPE: DNA
<213> ORGANISM: Artificial Sequence
<220> FEATURE:
<223> OTHER INFORMATION: Synthetic Construct

<400> SEQUENCE: 119
cgcgccgcgt ctccgcacac ccagtatccc ctgtggttta tgcagaattc tgc           53

<210> SEQ ID NO 120
<211> LENGTH: 68
<212> TYPE: DNA
<213> ORGANISM: Artificial Sequence
<220> FEATURE:
<223> OTHER INFORMATION: Synthetic Construct

<400> SEQUENCE: 120
ggccgcagcg gcggaattct gcataaacca caggggatac tgggtgtgcg gagacgcggc    60
ggcggcgg                                                             68

<210> SEQ ID NO 121
<211> LENGTH: 68
<212> TYPE: DNA
<213> ORGANISM: Artificial Sequence
<220> FEATURE:
<223> OTHER INFORMATION: Synthetic Construct

<400> SEQUENCE: 121
cgcgccgccg ccgccgcgtc tccgcacacc cagtatcccc tgtggtttat gcagaattcc    60
gccgctgc                                                             68

<210> SEQ ID NO 122
<211> LENGTH: 12
<212> TYPE: PRT
<213> ORGANISM: Artificial Sequence
<220> FEATURE:
<223> OTHER INFORMATION: Synthetic Construct

<400> SEQUENCE: 122

Cys Asp Ala Gly Ser Val Arg Thr Asn Ala Pro Asp
1               5                   10

<210> SEQ ID NO 123
<211> LENGTH: 47
<212> TYPE: DNA
<213> ORGANISM: Artificial Sequence
<220> FEATURE:
```

<223> OTHER INFORMATION: Synthetic Construct

<400> SEQUENCE: 123
ggccgcatgc gacgctggca gtgtgcgcac caatgcacca gacgcgg         47

<210> SEQ ID NO 124
<211> LENGTH: 47
<212> TYPE: DNA
<213> ORGANISM: Artificial Sequence
<220> FEATURE:
<223> OTHER INFORMATION: Synthetic Construct

<400> SEQUENCE: 124
cgcgccgcgt ctggtgcatt ggtgcgcaca ctgccagcgt cgcatgc         47

<210> SEQ ID NO 125
<211> LENGTH: 62
<212> TYPE: DNA
<213> ORGANISM: Artificial Sequence
<220> FEATURE:
<223> OTHER INFORMATION: Synthetic Construct

<400> SEQUENCE: 125
ggccgcagcg gcgtgcgacg ctggcagtgt gcgcaccaat gcaccagacg cggcggcggc         60
gg         62

<210> SEQ ID NO 126
<211> LENGTH: 62
<212> TYPE: DNA
<213> ORGANISM: Artificial Sequence
<220> FEATURE:
<223> OTHER INFORMATION: Synthetic Construct

<400> SEQUENCE: 126
cgcgccgccg ccgccgcgtc tggtgcattg gtgcgcacac tgccagcgtc gcacgccgct         60
gc         62

<210> SEQ ID NO 127
<211> LENGTH: 33
<212> TYPE: DNA
<213> ORGANISM: Artificial Sequence
<220> FEATURE:
<223> OTHER INFORMATION: Synthetic Construct

<400> SEQUENCE: 127
gtagccctgg aaactagaac cggtgcctgc gcc         33

<210> SEQ ID NO 128
<211> LENGTH: 33
<212> TYPE: DNA
<213> ORGANISM: Artificial Sequence
<220> FEATURE:
<223> OTHER INFORMATION: Synthetic Construct

<400> SEQUENCE: 128
ggcgcaggca ccggttctag tttccagggc tac         33

<210> SEQ ID NO 129
<211> LENGTH: 43
<212> TYPE: DNA
<213> ORGANISM: Artificial Sequence
<220> FEATURE:
<223> OTHER INFORMATION: Synthetic Construct

<400> SEQUENCE: 129

```
caaacactcc aagtggaggg cgcgccgcta ccaccacgca gtc        43
```

<210> SEQ ID NO 130
<211> LENGTH: 43
<212> TYPE: DNA
<213> ORGANISM: Artificial Sequence
<220> FEATURE:
<223> OTHER INFORMATION: Synthetic Construct

<400> SEQUENCE: 130

```
gactgcgtgg tggtagcggc gcgccctcca cttggagtgt ttg        43
```

<210> SEQ ID NO 131
<211> LENGTH: 40
<212> TYPE: DNA
<213> ORGANISM: Artificial Sequence
<220> FEATURE:
<223> OTHER INFORMATION: Synthetic Construct

<400> SEQUENCE: 131

```
caaacactcc aagtggagcg gccgcagggc gcgccgctac            40
```

<210> SEQ ID NO 132
<211> LENGTH: 40
<212> TYPE: DNA
<213> ORGANISM: Artificial Sequence
<220> FEATURE:
<223> OTHER INFORMATION: Synthetic Construct

<400> SEQUENCE: 132

```
gtagcggcgc gccctgcggc cgctccactt ggagtgtttg            40
```

<210> SEQ ID NO 133
<211> LENGTH: 18
<212> TYPE: PRT
<213> ORGANISM: Artificial Sequence
<220> FEATURE:
<223> OTHER INFORMATION: Synthetic Construct

<400> SEQUENCE: 133

Ala Ala Ala Cys Asp Ala Gly Ser Val Arg Thr Asn Ala Pro Asp Arg
1               5                   10                  15

Ala Ala

<210> SEQ ID NO 134
<211> LENGTH: 22
<212> TYPE: PRT
<213> ORGANISM: Artificial Sequence
<220> FEATURE:
<223> OTHER INFORMATION: Synthetic Construct

<400> SEQUENCE: 134

Ala Ala Ala Ala Ala Cys Asp Ala Gly Ser Val Arg Thr Asn Ala Pro
1               5                   10                  15

Asp Ala Ala Arg Ala Ala
            20

<210> SEQ ID NO 135
<211> LENGTH: 43
<212> TYPE: DNA
<213> ORGANISM: Artificial Sequence
<220> FEATURE:
<223> OTHER INFORMATION: Synthetic Construct

<400> SEQUENCE: 135
ggccgcatgc gacgctggca gtgtgcgcac caatgcacca gac          43

<210> SEQ ID NO 136
<211> LENGTH: 43
<212> TYPE: DNA
<213> ORGANISM: Artificial Sequence
<220> FEATURE:
<223> OTHER INFORMATION: Synthetic Construct

<400> SEQUENCE: 136
cgcggtctgg tgcattggtg cgcacactgc cagcgtcgca tgc          43

<210> SEQ ID NO 137
<211> LENGTH: 55
<212> TYPE: DNA
<213> ORGANISM: Artificial Sequence
<220> FEATURE:
<223> OTHER INFORMATION: Synthetic Construct

<400> SEQUENCE: 137
ggccgcagcc gcatgcgacg ctggcagtgt gcgcaccaat gcaccagacg cggca     55

<210> SEQ ID NO 138
<211> LENGTH: 55
<212> TYPE: DNA
<213> ORGANISM: Artificial Sequence
<220> FEATURE:
<223> OTHER INFORMATION: Synthetic Construct

<400> SEQUENCE: 138
cgcgtgccgc gtctggtgca ttggtgcgca cactgccagc gtcgcatgcg gctgc     55

<210> SEQ ID NO 139
<211> LENGTH: 27
<212> TYPE: DNA
<213> ORGANISM: Artificial Sequence
<220> FEATURE:
<223> OTHER INFORMATION: Synthetic Construct

<400> SEQUENCE: 139
gatttaaatc aggtatggcg tccgatg                            27

<210> SEQ ID NO 140
<211> LENGTH: 25
<212> TYPE: DNA
<213> ORGANISM: Artificial Sequence
<220> FEATURE:
<223> OTHER INFORMATION: Synthetic Construct

<400> SEQUENCE: 140
accgataaca tatgaaggac aggag                              25

<210> SEQ ID NO 141
<211> LENGTH: 50
<212> TYPE: DNA
<213> ORGANISM: Artificial Sequence
<220> FEATURE:
<223> OTHER INFORMATION: Synthetic Construct

<400> SEQUENCE: 141
caataaatga tttaaatcag gtatggctgc cgatggttat cttccagatt    50

<210> SEQ ID NO 142
<211> LENGTH: 70
<212> TYPE: DNA

<213> ORGANISM: Artificial Sequence
<220> FEATURE:
<223> OTHER INFORMATION: Synthetic Construct

<400> SEQUENCE: 142
ttaatcaata aaccggttga ttcgtttcag ttgaactttg gtctcctgtc cttcatatgt    60
tatcggttac    70

<210> SEQ ID NO 143
<211> LENGTH: 25
<212> TYPE: DNA
<213> ORGANISM: Artificial Sequence
<220> FEATURE:
<223> OTHER INFORMATION: Synthetic Construct

<400> SEQUENCE: 143
cgataagata cgtaggacag gagac    25

<210> SEQ ID NO 144
<211> LENGTH: 70
<212> TYPE: DNA
<213> ORGANISM: Artificial Sequence
<220> FEATURE:
<223> OTHER INFORMATION: Synthetic Construct

<400> SEQUENCE: 144
ttaatcaata aaccggttga ttcgtttcag ttgaactttg gtctcctgtc ctacgtatct    60
tatcggttac    70

<210> SEQ ID NO 145
<211> LENGTH: 60
<212> TYPE: DNA
<213> ORGANISM: Artificial Sequence
<220> FEATURE:
<223> OTHER INFORMATION: Synthetic Construct

<400> SEQUENCE: 145
ttccagagca gcagcacaga cgcggccgca aaggcgcgcc ctgcgaccgg agatgtgcat    60

<210> SEQ ID NO 146
<211> LENGTH: 60
<212> TYPE: DNA
<213> ORGANISM: Artificial Sequence
<220> FEATURE:
<223> OTHER INFORMATION: Synthetic Construct

<400> SEQUENCE: 146
atgcacatct ccggtcgcag ggcgcgcctt tgcggccgcg tctgtgctgc tgctctggaa    60

<210> SEQ ID NO 147
<211> LENGTH: 60
<212> TYPE: DNA
<213> ORGANISM: Artificial Sequence
<220> FEATURE:
<223> OTHER INFORMATION: Synthetic Construct

<400> SEQUENCE: 147
gtcaatttcc agagcagcag cgcggccgca aggcgcgcca cagaccctgc gaccggagat    60

<210> SEQ ID NO 148
<211> LENGTH: 60
<212> TYPE: DNA
<213> ORGANISM: Artificial Sequence
<220> FEATURE:
<223> OTHER INFORMATION: Synthetic Construct

<400> SEQUENCE: 148
atctccggtc gcagggtctg tggcgcgcct tgcggccgcg ctgctgctct ggaaattgac    60

<210> SEQ ID NO 149
<211> LENGTH: 65
<212> TYPE: DNA
<213> ORGANISM: Artificial Sequence
<220> FEATURE:
<223> OTHER INFORMATION: Synthetic Construct

<400> SEQUENCE: 149
ggccgcaggc ggtggatgcg acgctggcag tgtgcgcacc aatgcaccag acggcggtgg    60
agcgg    65

<210> SEQ ID NO 150
<211> LENGTH: 65
<212> TYPE: DNA
<213> ORGANISM: Artificial Sequence
<220> FEATURE:
<223> OTHER INFORMATION: Synthetic Construct

<400> SEQUENCE: 150
cgcgccgctc caccgccgtc tggtgcattg gtgcgcacac tgccagcgtc gcatccaccg    60
cctgc    65

<210> SEQ ID NO 151
<211> LENGTH: 64
<212> TYPE: DNA
<213> ORGANISM: Artificial Sequence
<220> FEATURE:
<223> OTHER INFORMATION: Synthetic Construct

<400> SEQUENCE: 151
ggccgcaggc ggtggatgcg acgctggcag tgtgcgcacc aatgcaccag acggcggtgg    60
agcg    64

<210> SEQ ID NO 152
<211> LENGTH: 64
<212> TYPE: DNA
<213> ORGANISM: Artificial Sequence
<220> FEATURE:
<223> OTHER INFORMATION: Synthetic Construct

<400> SEQUENCE: 152
cgcgcgctcc accgccgtct ggtgcattgg tgcgcacact gccagcgtcg catccaccgc    60
ctgc    64

<210> SEQ ID NO 153
<211> LENGTH: 25
<212> TYPE: DNA
<213> ORGANISM: Artificial Sequence
<220> FEATURE:
<223> OTHER INFORMATION: Synthetic Construct

<400> SEQUENCE: 153
tgtgtgtagc cttactgttc ttcgc    25

<210> SEQ ID NO 154
<211> LENGTH: 24
<212> TYPE: DNA
<213> ORGANISM: Artificial Sequence
<220> FEATURE:

```
<223> OTHER INFORMATION: Synthetic Construct

<400> SEQUENCE: 154
cttctcacgc ggagctttta ttac                                          24

<210> SEQ ID NO 155
<211> LENGTH: 28
<212> TYPE: DNA
<213> ORGANISM: Artificial Sequence
<220> FEATURE:
<223> OTHER INFORMATION: Synthetic Construct

<400> SEQUENCE: 155
ggtgaatccg gggccggcca tggcaagc                                      28

<210> SEQ ID NO 156
<211> LENGTH: 28
<212> TYPE: DNA
<213> ORGANISM: Artificial Sequence
<220> FEATURE:
<223> OTHER INFORMATION: Synthetic Construct

<400> SEQUENCE: 156
gcttgccatg gccggccccg gattcacc                                      28

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct

<400> SEQUENCE: 157

Asp Ala Glu Phe Arg His Asp Ser Gly
1               5

<210> SEQ ID NO 158
<211> LENGTH: 68
<212> TYPE: DNA
<213> ORGANISM: Artificial Sequence
<220> FEATURE:
<223> OTHER INFORMATION: Synthetic Construct

<400> SEQUENCE: 158
ggccgcaggc ggaggggag gcgacgccga gttcagacac gacagcggcg gcggaggggg    60
aggcgcgg                                                            68

<210> SEQ ID NO 159
<211> LENGTH: 68
<212> TYPE: DNA
<213> ORGANISM: Artificial Sequence
<220> FEATURE:
<223> OTHER INFORMATION: Synthetic Construct

<400> SEQUENCE: 159
cgcgccgcgc ctccccctcc gccgccgctg tcgtgtctga actcggcgtc gcctcccct    60 ccgcctgc                                                            68

<210> SEQ ID NO 160
<211> LENGTH: 24
<212> TYPE: PRT
<213> ORGANISM: Artificial Sequence
<220> FEATURE:
<223> OTHER INFORMATION: Synthetic Construct
```

<400> SEQUENCE: 160

Ala Ala Ala Gly Gly Gly Gly Asp Ala Glu Phe Arg His Asp Ser
1               5                   10                  15

Gly Gly Gly Gly Gly Gly Ala Ala
            20

<210> SEQ ID NO 161
<211> LENGTH: 61
<212> TYPE: DNA
<213> ORGANISM: Artificial Sequence
<220> FEATURE:
<223> OTHER INFORMATION: Synthetic Construct

<400> SEQUENCE: 161
ggccggcgga ggcggtgggg acgccgaatt cagacacgac agcggcggag gcggtggagg    60
g                                                                    61

<210> SEQ ID NO 162
<211> LENGTH: 61
<212> TYPE: DNA
<213> ORGANISM: Artificial Sequence
<220> FEATURE:
<223> OTHER INFORMATION: Synthetic Construct

<400> SEQUENCE: 162
cgcgccctcc accgcctccg ccgctgtcgt gtctgaattc ggcgtcccca ccgcctccgc    60
c                                                                    61

<210> SEQ ID NO 163
<211> LENGTH: 23
<212> TYPE: PRT
<213> ORGANISM: Artificial Sequence
<220> FEATURE:
<223> OTHER INFORMATION: Synthetic Construct

<400> SEQUENCE: 163

Ala Ala Gly Gly Gly Gly Gly Asp Ala Glu Phe Arg His Asp Ser Gly
1               5                   10                  15

Gly Gly Gly Gly Gly Ala Ala
            20

<210> SEQ ID NO 164
<211> LENGTH: 22
<212> TYPE: PRT
<213> ORGANISM: Artificial Sequence
<220> FEATURE:
<223> OTHER INFORMATION: Synthetic Construct

<400> SEQUENCE: 164

Gln Arg Gly Asn Gln Ala Gly Thr Phe Ala Leu Arg Gly Asp Asn Pro
1               5                   10                  15

Gln Gly Arg Gln Ala Ala
            20

<210> SEQ ID NO 165
<211> LENGTH: 17
<212> TYPE: PRT
<213> ORGANISM: Artificial Sequence
<220> FEATURE:
<223> OTHER INFORMATION: Synthetic Construct

<400> SEQUENCE: 165

Gln Arg Gly Asn Ala Ser Ile Gly Tyr Pro Leu Pro Ala Arg Gln Ala

```
1               5                   10                  15

Ala

<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Gln Arg Gly Asn Asn Gly Arg Arg Gln Ala Ala
1               5                   10

<210> SEQ ID NO 167
<211> LENGTH: 19
<212> TYPE: PRT
<213> ORGANISM: Artificial Sequence
<220> FEATURE:
<223> OTHER INFORMATION: Synthetic Construct

<400> SEQUENCE: 167

Gln Arg Gly Asn Ala Thr Gly Cys Asp Cys Arg Gly Asp Cys Phe Cys
1               5                   10                  15

Gln Ala Ala

<210> SEQ ID NO 168
<211> LENGTH: 20
<212> TYPE: PRT
<213> ORGANISM: Artificial Sequence
<220> FEATURE:
<223> OTHER INFORMATION: Synthetic Construct

<400> SEQUENCE: 168

Gln Arg Gly Asn Ala Ala Ala Arg Gly Asp Ala Val Gly Val Ala Ala
1               5                   10                  15

Arg Gln Ala Ala
            20

<210> SEQ ID NO 169
<211> LENGTH: 20
<212> TYPE: PRT
<213> ORGANISM: Artificial Sequence
<220> FEATURE:
<223> OTHER INFORMATION: Synthetic Construct

<400> SEQUENCE: 169

Gln Arg Gly Asn Ala Ala Ala Arg Gly Asp Thr Pro Thr Ser Ala Ala
1               5                   10                  15

Arg Gln Ala Ala
            20

<210> SEQ ID NO 170
<211> LENGTH: 20
<212> TYPE: PRT
<213> ORGANISM: Artificial Sequence
<220> FEATURE:
<223> OTHER INFORMATION: Synthetic Construct

<400> SEQUENCE: 170

Gln Arg Gly Asn Ala Ala Ala Gly Glu Asn Gln Ala Arg Ser Ala Ala
1               5                   10                  15

Arg Gln Ala Ala
            20
```

<210> SEQ ID NO 171
<211> LENGTH: 20
<212> TYPE: PRT
<213> ORGANISM: Artificial Sequence
<220> FEATURE:
<223> OTHER INFORMATION: Synthetic Construct

<400> SEQUENCE: 171

Gln Arg Gly Asn Ala Ala Ala Arg Ser Asn Ala Val Val Pro Ala Ala
1               5                   10                  15

Arg Gln Ala Ala
            20

<210> SEQ ID NO 172
<211> LENGTH: 17
<212> TYPE: PRT
<213> ORGANISM: Artificial Sequence
<220> FEATURE:
<223> OTHER INFORMATION: Synthetic Construct

<400> SEQUENCE: 172

Gln Arg Gly Gln Arg Gly Asn Ser Ser Arg Asp Leu Gly Ala Gln Ala
1               5                   10                  15

Ala

<210> SEQ ID NO 173
<211> LENGTH: 17
<212> TYPE: PRT
<213> ORGANISM: Artificial Sequence
<220> FEATURE:
<223> OTHER INFORMATION: Synthetic Construct

<400> SEQUENCE: 173

Gln Arg Gly Gln Arg Gly Asn Asp Val Arg Ala Val Ser Ala Gln Ala
1               5                   10                  15

Ala

<210> SEQ ID NO 174
<211> LENGTH: 18
<212> TYPE: PRT
<213> ORGANISM: Artificial Sequence
<220> FEATURE:
<223> OTHER INFORMATION: Synthetic Construct

<400> SEQUENCE: 174

Gln Arg Gly Asn Ala Ser Glu Tyr His His Tyr Asn Lys Ala Arg Gln
1               5                   10                  15

Ala Ala

<210> SEQ ID NO 175
<211> LENGTH: 27
<212> TYPE: PRT
<213> ORGANISM: Artificial Sequence
<220> FEATURE:
<223> OTHER INFORMATION: Synthetic Construct

<400> SEQUENCE: 175

Gln Arg Gly Asn Ala Ser Met Thr Pro Phe Pro Thr Ser Asn Glu Ala
1               5                   10                  15

Asn Leu Gly Gly Gly Ser Ala Arg Gln Ala Ala
            20                  25

```
<210> SEQ ID NO 176
<211> LENGTH: 18
<212> TYPE: PRT
<213> ORGANISM: Artificial Sequence
<220> FEATURE:
<223> OTHER INFORMATION: Synthetic Construct

<400> SEQUENCE: 176

Gln Arg Gly Asn Ala Ser Gln Pro Glu His Ser Ser Thr Ala Arg Gln
1               5                   10                  15

Ala Ala

<210> SEQ ID NO 177
<211> LENGTH: 18
<212> TYPE: PRT
<213> ORGANISM: Artificial Sequence
<220> FEATURE:
<223> OTHER INFORMATION: Synthetic Construct

<400> SEQUENCE: 177

Gln Arg Gly Asn Ala Ser Val Asn Thr Ala Asn Ser Thr Ala Arg Gln
1               5                   10                  15

Ala Ala

<210> SEQ ID NO 178
<211> LENGTH: 17
<212> TYPE: PRT
<213> ORGANISM: Artificial Sequence
<220> FEATURE:
<223> OTHER INFORMATION: Synthetic Construct

<400> SEQUENCE: 178

Gln Arg Gly Gln Arg Gly Asn Asp Val Arg Ser Ala Asn Ala Gln Ala
1               5                   10                  15

Ala

<210> SEQ ID NO 179
<211> LENGTH: 17
<212> TYPE: PRT
<213> ORGANISM: Artificial Sequence
<220> FEATURE:
<223> OTHER INFORMATION: Synthetic Construct

<400> SEQUENCE: 179

Gln Arg Gly Gln Arg Gly Asn Asp Val Arg Ala Val Ser Ala Gln Ala
1               5                   10                  15

Ala

<210> SEQ ID NO 180
<211> LENGTH: 17
<212> TYPE: PRT
<213> ORGANISM: Artificial Sequence
<220> FEATURE:
<223> OTHER INFORMATION: Synthetic Construct

<400> SEQUENCE: 180

Gln Arg Gly Gln Arg Gly Val Thr Ala Gly Arg Ala Pro Ala Gln Ala
1               5                   10                  15

Ala

<210> SEQ ID NO 181
<211> LENGTH: 17
<212> TYPE: PRT
<213> ORGANISM: Artificial Sequence
```

```
<220> FEATURE:
<223> OTHER INFORMATION: Synthetic Construct

<400> SEQUENCE: 181

Gln Arg Gly Gln Arg Gly Ala Pro Val Thr Arg Pro Ala Ala Gln Ala
1               5                   10                  15

Ala

<210> SEQ ID NO 182
<211> LENGTH: 17
<212> TYPE: PRT
<213> ORGANISM: Artificial Sequence
<220> FEATURE:
<223> OTHER INFORMATION: Synthetic Construct

<400> SEQUENCE: 182

Gln Arg Gly Gln Arg Gly Asp Leu Ser Asn Leu Thr Arg Ala Gln Ala
1               5                   10                  15

Ala

<210> SEQ ID NO 183
<211> LENGTH: 17
<212> TYPE: PRT
<213> ORGANISM: Artificial Sequence
<220> FEATURE:
<223> OTHER INFORMATION: Synthetic Construct

<400> SEQUENCE: 183

Gln Arg Gly Gln Arg Gly Gly Gln His Pro Arg Pro Gly Ala Gln Ala
1               5                   10                  15

Ala

<210> SEQ ID NO 184
<211> LENGTH: 11
<212> TYPE: PRT
<213> ORGANISM: Artificial Sequence
<220> FEATURE:
<223> OTHER INFORMATION: Synthetic Construct

<400> SEQUENCE: 184

Lys Leu Lys Leu Leu Leu Leu Leu Lys Leu Lys
1               5                   10

<210> SEQ ID NO 185
<211> LENGTH: 736
<212> TYPE: PRT
<213> ORGANISM: adeno-associated virus 1

<400> SEQUENCE: 185

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95
```

-continued

```
Asp Ala Glu Phe Gln Glu Arg Leu Gln Glu Asp Thr Ser Phe Gly Gly
                100                 105                 110
Asn Leu Gly Arg Ala Val Phe Gln Ala Lys Lys Arg Val Leu Glu Pro
            115                 120                 125
Leu Gly Leu Val Glu Glu Gly Ala Lys Thr Ala Pro Gly Lys Lys Arg
        130                 135                 140
Pro Val Glu Gln Ser Pro Gln Glu Pro Asp Ser Ser Gly Ile Gly
145                 150                 155                 160
Lys Thr Gly Gln Gln Pro Ala Lys Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Thr Pro Ala Ala Val Gly Pro Thr Thr Met Ala Ser Gly Gly Gly
        195                 200                 205
Ala Pro Met Ala Asp Asn Asn Glu Gly Ala Asp Gly Val Gly Asn Ala
210                 215                 220
Ser Gly Asn Trp His Cys Asp Ser Thr Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Ala Ser Thr Gly Ala Ser Asn Asp Asn His
            260                 265                 270
Tyr Phe Gly Tyr Ser Thr Pro Trp Gly Tyr Phe Asp Phe Asn Arg Phe
        275                 280                 285
His Cys His Phe Ser Pro Arg Asp Trp Gln Arg Leu Ile Asn Asn Asn
        290                 295                 300
Trp Gly Phe Arg Pro Lys Arg Leu Asn Phe Lys Leu Phe Asn Ile Gln
305                 310                 315                 320
Val Lys Glu Val Thr Thr Asn Asp Gly Val Thr Thr Ile Ala Asn Asn
                325                 330                 335
Leu Thr Ser Thr Val Gln Val Phe Ser Asp Ser Glu Tyr Gln Leu Pro
            340                 345                 350
Tyr Val Leu Gly Ser Ala His Gln Gly Cys Leu Pro Pro Phe Pro Ala
        355                 360                 365
Asp Val Phe Met Ile Pro Gln Tyr Gly Tyr Leu Thr Leu Asn Asn Gly
        370                 375                 380
Ser Gln Ala Val Gly Arg Ser Ser Phe Tyr Cys Leu Glu Tyr Phe Pro
385                 390                 395                 400
Ser Gln Met Leu Arg Thr Gly Asn Asn Phe Thr Phe Ser Tyr Thr Phe
                405                 410                 415
Glu Glu Val Pro Phe His Ser Ser Tyr Ala His Ser Gln Ser Leu Asp
            420                 425                 430
Arg Leu Met Asn Pro Leu Ile Asp Gln Tyr Leu Tyr Tyr Leu Asn Arg
        435                 440                 445
Thr Gln Asn Gln Ser Gly Ser Ala Gln Asn Lys Asp Leu Leu Phe Ser
        450                 455                 460
Arg Gly Ser Pro Ala Gly Met Ser Val Gln Pro Lys Asn Trp Leu Pro
465                 470                 475                 480
Gly Pro Cys Tyr Arg Gln Gln Arg Val Ser Lys Thr Lys Thr Asp Asn
                485                 490                 495
Asn Asn Ser Asn Phe Thr Trp Thr Gly Ala Ser Lys Tyr Asn Leu Asn
            500                 505                 510
Gly Arg Glu Ser Ile Ile Asn Pro Gly Thr Ala Met Ala Ser His Lys
```

```
                515                 520                 525
Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Gln Ile Leu Ile Lys Asn Thr Pro Val Pro Ala
            645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 186
<211> LENGTH: 736
<212> TYPE: PRT
<213> ORGANISM: adeno-associated virus 2

<400> SEQUENCE: 186

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Phe Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160
```

```
Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
```

```
                    580                 585                 590
Thr Gly Asp Val His Val Met Gly Ala Leu Pro Gly Met Val Trp Gln
                595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 187
<211> LENGTH: 735
<212> TYPE: PRT
<213> ORGANISM: adeno-associated virus 2

<400> SEQUENCE: 187

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220
```

-continued

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Ser Gln Ser Gly Ala Ser Asn Asp Asn His Tyr
        260                 265                 270

Phe Gly Tyr Ser Thr Pro Trp Gly Tyr Phe Asp Phe Asn Arg Phe His
    275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn

```
                645                 650                 655
Pro Ser Thr Thr Phe Ser Ala Ala Lys Phe Ala Ser Phe Ile Thr Gln
                660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
        690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 188
<211> LENGTH: 736
<212> TYPE: PRT
<213> ORGANISM: adeno-associated virus 3

<400> SEQUENCE: 188

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285
```

```
Cys His Phe Ser Pro Arg Asp Trp Gln Arg Leu Ile Asn Asn Asn Trp
    290             295                 300
Gly Phe Arg Pro Lys Lys Leu Ser Phe Lys Leu Phe Asn Ile Gln Val
305             310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
                340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                    405                 410                 415
Asp Val Pro Phe His Ser Ser Tyr Ala His Ser Gln Ser Leu Asp Arg
                420                 425                 430
Leu Met Asn Pro Leu Ile Asp Gln Tyr Leu Tyr Tyr Leu Asn Arg Thr
            435                 440                 445
Gln Gly Thr Thr Ser Gly Thr Thr Asn Gln Ser Arg Leu Leu Phe Ser
450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
                500                 505                 510
Gly Arg Asp Ser Leu Val Asn Pro Gly Pro Ala Met Ala Ser His Lys
            515                 520                 525
Asp Asp Glu Glu Lys Phe Phe Pro Met His Gly Asn Leu Ile Phe Gly
530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                    565                 570                 575
Tyr Gly Thr Val Ala Asn Asn Leu Gln Ser Ser Asn Thr Ala Pro Thr
                580                 585                 590
Thr Arg Thr Val Asn Asp Gln Gly Ala Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly His Phe His Pro Ser Pro Leu Met Gly Gly Phe Gly Leu
625                 630                 635                 640
Lys His Pro Pro Pro Gln Ile Met Ile Lys Asn Thr Pro Val Pro Ala
                    645                 650                 655
Asn Pro Pro Thr Thr Phe Ser Pro Ala Lys Phe Ala Ser Phe Ile Thr
                660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Asn Lys Ser Val Asn Val Asp Phe Thr Val Asp Thr Asn Gly Val
```

```
                705                 710                 715                 720
Tyr Ser Glu Pro Arg Pro Ile Gly Thr Arg Tyr Leu Thr Arg Asn Leu
                    725                 730                 735

<210> SEQ ID NO 189
<211> LENGTH: 737
<212> TYPE: PRT
<213> ORGANISM: adeno-associated virus 7

<400> SEQUENCE: 189

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Ile Ala Asn
                325                 330                 335

Asn Leu Thr Ser Thr Ile Gln Val Phe Ser Asp Ser Glu Tyr Gln Leu
            340                 345                 350
```

```
Pro Tyr Val Leu Gly Ser Ala His Gln Gly Cys Leu Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
    530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 190
<211> LENGTH: 738
<212> TYPE: PRT
<213> ORGANISM: adeno-associated virus 8
```

<400> SEQUENCE: 190

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr

```
                    405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
        450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Asn Thr Ala
                580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 191
<211> LENGTH: 738
<212> TYPE: PRT
<213> ORGANISM: adeno-associated virus 10

<400> SEQUENCE: 191

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
```

-continued

Gly Tyr Lys Tyr Leu Gly Pro Phe Asn Gly Leu Asp Lys Gly Glu Pro
 35                  40                  45
                 50                  55                  60

Val Asn Ala Ala Asp Ala Ala Leu Glu His Asp Lys Ala Tyr Asp
 65                  70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Ala Ala Lys Thr Ala Pro Gly Lys Lys Arg
                130                 135                 140

Pro Val Glu Pro Ser Pro Gln Arg Ser Pro Asp Ser Thr Gly Ile
145                 150                 155                 160

Gly Lys Lys Gly Gln Gln Pro Ala Lys Lys Arg Leu Asn Phe Gly Gln
                165                 170                 175

Thr Gly Glu Ser Glu Ser Val Pro Asp Pro Gln Pro Ile Gly Glu Pro
                180                 185                 190

Pro Ala Gly Pro Ser Gly Leu Gly Ser Gly Thr Met Ala Ala Gly Gly
                195                 200                 205

Gly Ala Pro Met Ala Asp Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
                370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Ser Thr Gly Gly Thr Gln Gly Thr Gln Gln Leu Leu
450                 455                 460

Phe Ser Gln Ala Gly Pro Ala Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
            515                 520                 525

His Lys Asp Asp Glu Glu Arg Phe Phe Pro Ser Ser Gly Val Leu Met
        530                 535                 540

Phe Gly Lys Gln Gly Ala Gly Arg Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Ala Asn Thr Gly
            580                 585                 590

Pro Ile Val Gly Asn Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 192
<211> LENGTH: 734
<212> TYPE: PRT
<213> ORGANISM: adeno-associated virus 4

<400> SEQUENCE: 192

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
                20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
        50                  55                  60

Asn Ala Ala Asp Ala Ala Ala Leu Glu His Asp Lys Ala Tyr Asp Gln
65                  70                  75                  80

Gln Leu Lys Ala Gly Asp Asn Pro Tyr Leu Lys Tyr Asn His Ala Asp
                85                  90                  95

```
Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Gln Ala Gly Glu Thr Ala Pro Gly Lys Lys Arg Pro
    130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Ala Ala Val Glu Gly
        195                 200                 205        Gly

Gly Gln Gly Ala Asp Gly Val Gly Asn Ala Ser Gly Asp Trp His Cys
    210                 215                 220

Asp Ser Thr Trp Ser Glu Gly His Val Thr Thr Ser Thr Arg Thr
225                 230                 235                 240

Trp Val Leu Pro Thr Tyr Asn Asn His Leu Tyr Lys Arg Leu Gly Glu
            245                 250                 255

Ser Leu Gln Ser Asn Thr Tyr Asn Gly Phe Ser Thr Pro Trp Gly Tyr
        260                 265                 270

Phe Asp Phe Asn Arg Phe His Cys His Phe Ser Pro Arg Asp Trp Gln
    275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510
```

-continued

```
Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
            565                 570                 575

Asn Leu Pro Gly Gly Asp Gln Ser Ser Asn Leu Pro Thr Val Asp
                580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
            690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 193
<211> LENGTH: 733
<212> TYPE: PRT
<213> ORGANISM: adeno-associated virus 11

<400> SEQUENCE: 193

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160
```

-continued

```
Lys Gly Lys Gln Pro Ala Arg Lys Arg Leu Asn Phe Glu Glu Asp Thr
            165                 170                 175

Gly Ala Gly Asp Gly Pro Pro Glu Gly Ser Asp Thr Ser Ala Met Ser
        180                 185                 190

Ser Asp Ile Glu Met Arg Ala Ala Pro Gly Gly Asn Ala Val Asp Ala
    195                 200                 205

Gly Gln Gly Ser Asp Gly Val Gly Asn Ala Ser Gly Asp Trp His Cys
210                 215                 220

Asp Ser Thr Trp Ser Glu Gly Lys Val Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575
```

```
Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685

Ser Lys Arg Trp Asn Pro Glu Val Gln Phe Thr Ser Asn Tyr Gly Asn
    690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 194
<211> LENGTH: 736
<212> TYPE: PRT
<213> ORGANISM: bovine adeno-associated virus

<400> SEQUENCE: 194

Met Ser Phe Val Asp His Pro Pro Asp Trp Leu Glu Ser Ile Gly Asp
1               5                   10                  15

Gly Phe Arg Glu Phe Leu Gly Leu Glu Ala Gly Pro Pro Lys Pro Lys
            20                  25                  30

Ala Asn Gln Gln Lys Gln Asp Asn Ala Arg Gly Leu Val Leu Pro Gly
        35                  40                  45

Tyr Lys Tyr Leu Gly Pro Gly Asn Gly Leu Asp Lys Gly Asp Pro Val
    50                  55                  60

Asn Phe Ala Asp Glu Val Ala Arg Glu His Asp Leu Ser Tyr Gln Lys
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Ser Asp Thr Ser Phe Gly Gly Asn
            100                 105                 110

Leu Gly Lys Ala Val Phe Gln Ala Lys Lys Arg Ile Leu Glu Pro Leu
        115                 120                 125

Gly Leu Val Glu Thr Pro Asp Lys Thr Ala Pro Ala Lys Lys Arg
    130                 135                 140

Pro Leu Glu Gln Ser Pro Gln Glu Pro Asp Ser Ser Ser Gly Val Gly
145                 150                 155                 160

Lys Lys Gly Lys Gln Pro Ala Arg Lys Arg Leu Asn Phe Asp Asp Glu
                165                 170                 175

Pro Gly Ala Gly Asp Gly Pro Pro Glu Gly Pro Ser Ser Gly Ala
            180                 185                 190

Met Ser Thr Glu Thr Glu Met Arg Ala Ala Gly Asn Gly Gly
        195                 200                 205

Asp Ala Gly Gln Gly Ala Glu Gly Val Gly Asn Ala Ser Gly Asp Trp
    210                 215                 220
```

```
His Cys Asp Ser Thr Trp Ser Glu Ser His Val Thr Thr Ser Thr
225                 230                 235                 240

Arg Thr Trp Val Leu Pro Thr Tyr Asn Asn His Leu Tyr Leu Arg Leu
            245                 250                 255

Gly Ser Ser Asn Ala Ser Asp Thr Phe Asn Gly Phe Thr Pro Trp
        260                 265                 270

Gly Tyr Phe Asp Phe Asn Arg Phe His Cys His Phe Ser Pro Arg Asp
        275                 280                 285

Trp Gln Arg Leu Ile Asn Asn His Trp Gly Leu Arg Pro Lys Ser Met
        290                 295                 300

Gln Val Arg Ile Phe Asn Ile Gln Val Lys Glu Val Thr Thr Ser Asn
305                 310                 315                 320

Gly Glu Thr Thr Val Ser Asn Asn Leu Thr Ser Thr Val Gln Ile Phe
                325                 330                 335

Ala Asp Ser Thr Tyr Glu Leu Pro Tyr Val Met Asp Ala Gly Gln Glu
            340                 345                 350

Gly Ser Leu Pro Pro Phe Pro Asn Asp Val Phe Met Val Pro Gln Tyr
        355                 360                 365

Gly Tyr Cys Gly Leu Val Thr Gly Gly Ser Ser Gln Asn Gln Thr Asp
        370                 375                 380

Arg Asn Ala Phe Tyr Cys Leu Glu Tyr Phe Pro Ser Gln Met Leu Arg
385                 390                 395                 400

Thr Gly Asn Asn Phe Glu Met Val Tyr Lys Phe Glu Asn Val Pro Phe
                405                 410                 415

His Ser Met Tyr Ala His Ser Gln Ser Leu Asp Arg Leu Met Asn Pro
            420                 425                 430

Leu Leu Asp Gln Tyr Leu Trp Glu Leu Gln Ser Thr Thr Ser Gly Gly
        435                 440                 445

Thr Leu Asn Gln Gly Asn Ser Ala Thr Asn Phe Ala Lys Leu Thr Lys
450                 455                 460

Thr Asn Phe Ser Gly Tyr Arg Lys Asn Trp Leu Pro Gly Pro Met Met
465                 470                 475                 480

Lys Gln Gln Arg Phe Ser Lys Thr Ala Ser Gln Asn Tyr Lys Ile Pro
            485                 490                 495

Gln Gly Arg Asn Asn Ser Leu Leu His Tyr Glu Thr Arg Thr Thr Leu
        500                 505                 510

Asp Gly Arg Trp Ser Asn Phe Ala Pro Gly Thr Ala Met Ala Thr Ala
        515                 520                 525

Ala Asn Asp Ala Thr Asp Phe Ser Gln Ala Gln Leu Ile Phe Ala Gly
        530                 535                 540

Pro Asn Ile Thr Gly Asn Thr Thr Thr Asp Ala Asn Asn Leu Met Phe
545                 550                 555                 560

Thr Ser Glu Asp Glu Leu Arg Ala Thr Asn Pro Arg Asp Thr Asp Leu
                565                 570                 575

Phe Gly His Leu Ala Thr Asn Gln Gln Asn Ala Thr Thr Val Pro Thr
            580                 585                 590

Val Asp Asp Val Asp Gly Val Gly Val Tyr Pro Gly Met Val Trp Gln
        595                 600                 605

Asp Arg Asp Ile Tyr Tyr Gln Gly Pro Ile Trp Ala Lys Ile Pro His
        610                 615                 620

Thr Asp Gly His Phe His Pro Ser Pro Leu Ile Gly Gly Phe Gly Leu
625                 630                 635                 640
```

```
Lys Ser Pro Pro Pro Gln Ile Phe Ile Lys Asn Thr Pro Val Pro Ala
                645                 650                 655

Asn Pro Ala Thr Thr Phe Ser Pro Ala Arg Ile Asn Ser Phe Ile Thr
            660                 665                 670

Gln Tyr Ser Thr Gly Gln Val Ala Val Lys Ile Glu Trp Glu Ile Gln
        675                 680                 685

Lys Glu Arg Ser Lys Arg Trp Asn Pro Glu Val Gln Phe Thr Ser Asn
690                 695                 700

Tyr Gly Ala Gln Asp Ser Leu Leu Trp Ala Pro Asp Asn Ala Gly Ala
705                 710                 715                 720

Tyr Lys Glu Pro Arg Ala Ile Gly Ser Arg Tyr Leu Thr Asn His Leu
                725                 730                 735

<210> SEQ ID NO 195
<211> LENGTH: 724
<212> TYPE: PRT
<213> ORGANISM: adeno-associated virus 5

<400> SEQUENCE: 195

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285
```

```
Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
690                 695                 700
```

Ser Thr Gly Glu Tyr Arg Thr Thr Arg Pro Ile Gly Thr Arg Tyr Leu
705                 710                 715                 720

Thr Arg Pro Leu

<210> SEQ ID NO 196
<211> LENGTH: 534
<212> TYPE: PRT
<213> ORGANISM: goose parvovirus

<400> SEQUENCE: 196

Met Ala Glu Gly Gly Gly Ala Met Gly Asp Ser Ser Gly Gly Ala
1               5                   10                  15

Asp Gly Val Gly Asn Ala Ser Gly Asn Trp His Cys Asp Ser Gln Trp
                20                  25                  30

Met Gly Asn Thr Val Ile Thr Lys Thr Thr Arg Thr Trp Val Leu Pro
            35                  40                  45

Ser Tyr Asn Asn His Ile Tyr Lys Ala Ile Thr Ser Gly Thr Ser Gln
50                  55                  60

Asp Ala Asn Val Gln Tyr Ala Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn His Trp Gly Ile Arg Pro Lys Ser Leu Lys Phe Lys
                100                 105                 110

Ile Phe Asn Val Gln Val Lys Glu Val Thr Thr Gln Asp Gln Thr Lys
            115                 120                 125

Thr Ile Ala Asn Asn Leu Thr Ser Thr Ile Gln Val Phe Thr Asp Asp
130                 135                 140

Glu His Gln Leu Pro Tyr Val Leu Gly Ser Ala Thr Glu Gly Thr Met
145                 150                 155                 160

Pro Pro Phe Pro Ser Asp Val Tyr Ala Leu Pro Gln Tyr Gly Tyr Cys
                165                 170                 175

Thr Met His Thr Asn Gln Asn Gly Ala Arg Phe Asn Asp Arg Ser Ala
            180                 185                 190

Phe Tyr Cys Leu Glu Tyr Phe Pro Ser Gln Met Leu Arg Thr Gly Asn
            195                 200                 205

Asn Phe Glu Phe Thr Phe Asp Phe Glu Glu Val Pro Phe His Ser Met
210                 215                 220

Phe Ala His Ser Gln Asp Leu Asp Arg Leu Met Asn Pro Leu Val Asp
225                 230                 235                 240

Gln Tyr Leu Trp Asn Phe Asn Glu Val Asp Ser Ser Arg Asn Ala Gln
                245                 250                 255

Phe Lys Lys Ala Val Lys Gly Ala Tyr Gly Thr Met Gly Arg Asn Trp
            260                 265                 270

Leu Pro Gly Pro Lys Phe Leu Asp Gln Arg Val Arg Ala Tyr Thr Gly
            275                 280                 285

Gly Thr Asp Asn Tyr Ala Asn Trp Asn Ile Trp Ser Asn Gly Asn Lys
290                 295                 300

Val Asn Leu Lys Asp Arg Gln Tyr Leu Leu Gln Pro Gly Pro Val Ser
305                 310                 315                 320

Ala Thr Tyr Thr Glu Gly Glu Ala Ser Ser Leu Pro Ala Gln Asn Ile
                325                 330                 335

Leu Gly Ile Ala Lys Asp Pro Tyr Arg Ser Gly Ser Thr Thr Ala Gly
            340                 345                 350

```
Ile Ser Asp Ile Met Val Thr Glu Glu Gln Val Ala Pro Thr Asn
            355                 360                 365
Gly Val Gly Trp Lys Pro Tyr Gly Arg Thr Val Thr Asn Glu Gln Asn
370                 375                 380
Thr Thr Thr Ala Pro Thr Ser Ser Asp Leu Asp Val Leu Gly Ala Leu
385                 390                 395                 400
Pro Gly Met Val Trp Gln Asn Arg Asp Ile Tyr Leu Gln Gly Pro Ile
                405                 410                 415
Gly Ala Lys Ile Pro Lys Thr Asp Gly Lys Phe His Pro Ser Pro Asn
                420                 425                 430
Leu Gly Gly Phe Gly Leu His Asn Pro Pro Gln Val Phe Ile Lys
            435                 440                 445
Asn Thr Pro Val Pro Ala Asp Pro Pro Val Glu Tyr Val His Gln Lys
    450                 455                 460
Trp Asn Ser Tyr Ile Thr Gln Tyr Ser Thr Gly Gln Cys Thr Val Glu
465                 470                 475                 480
Met Val Trp Glu Leu Arg Lys Glu Asn Ser Lys Arg Trp Asn Pro Glu
                485                 490                 495
Ile Gln Phe Thr Ser Asn Phe Ser Asn Arg Thr Ser Ile Met Phe Ala
                500                 505                 510
Pro Asn Glu Thr Gly Gly Tyr Val Glu Asp Arg Leu Ile Gly Thr Arg
            515                 520                 525
Tyr Leu Thr Gln Asn Leu
        530

<210> SEQ ID NO 197
<211> LENGTH: 554
<212> TYPE: PRT
<213> ORGANISM: parvovirus B19

<400> SEQUENCE: 197

Met Thr Ser Val Asn Ser Ala Glu Ala Ser Thr Gly Ala Gly Gly Gly
1               5                   10                  15
Gly Ser Asn Pro Val Lys Ser Met Trp Ser Glu Gly Ala Thr Phe Ser
                20                  25                  30
Ala Asn Ser Val Thr Cys Thr Phe Ser Arg Gln Phe Leu Ile Pro Tyr
            35                  40                  45
Asp Pro Glu His His Tyr Lys Val Phe Ser Pro Ala Ala Ser Ser Cys
    50                  55                  60
His Asn Ala Ser Gly Lys Glu Ala Lys Val Cys Thr Ile Ser Pro Ile
65                  70                  75                  80
Met Gly Tyr Ser Thr Pro Trp Arg Tyr Leu Asp Phe Asn Ala Leu Asn
                85                  90                  95
Leu Phe Phe Ser Pro Leu Glu Phe Gln His Leu Ile Glu Asn Tyr Gly
                100                 105                 110
Ser Ile Ala Pro Asp Ala Leu Thr Val Thr Ile Ser Glu Ile Ala Val
            115                 120                 125
Lys Asp Val Thr Asp Lys Thr Gly Gly Gly Val Gln Val Thr Asp Ser
    130                 135                 140
Thr Thr Gly Arg Leu Cys Met Leu Val Asp His Glu Tyr Lys Tyr Pro
145                 150                 155                 160
Tyr Val Leu Gly Gln Gly Gln Asp Thr Leu Ala Pro Glu Leu Pro Ile
                165                 170                 175
Trp Val Tyr Phe Pro Pro Gln Tyr Ala Tyr Leu Thr Val Gly Asp Val
            180                 185                 190
```

```
Asn Thr Gln Gly Ile Ser Gly Asp Ser Lys Lys Leu Ala Ser Glu Glu
            195                 200                 205

Ser Ala Phe Tyr Val Leu Glu His Ser Ser Phe Gln Leu Leu Gly Thr
        210                 215                 220

Gly Gly Thr Ala Thr Met Ser Tyr Lys Phe Pro Pro Val Pro Pro Glu
225                 230                 235                 240

Asn Leu Glu Gly Cys Ser Gln His Phe Tyr Glu Met Tyr Asn Pro Leu
                245                 250                 255

Tyr Gly Ser Arg Leu Gly Val Pro Asp Thr Leu Gly Gly Asp Pro Lys
            260                 265                 270

Phe Arg Ser Leu Thr His Glu Asp His Ala Ile Gln Pro Gln Asn Phe
        275                 280                 285

Met Pro Gly Pro Leu Val Asn Ser Val Ser Thr Lys Glu Gly Asp Ser
    290                 295                 300

Phe Asn Thr Gly Ala Gly Lys Ala Leu Thr Gly Leu Ser Thr Gly Thr
305                 310                 315                 320

Ser Gln Asn Thr Arg Ile Ser Leu Arg Pro Gly Pro Val Ser Gln Pro
                325                 330                 335

Tyr His His Trp Asp Thr Asp Lys Tyr Val Thr Gly Ile Asn Ala Ile
            340                 345                 350

Ser His Gly Gln Thr Thr Tyr Gly Asn Ala Glu Asp Lys Glu Tyr Gln
        355                 360                 365

Gln Gly Val Gly Arg Phe Pro Asn Glu Lys Glu Gln Leu Lys Gln Leu
    370                 375                 380

Gln Gly Leu Asn Met His Thr Tyr Phe Pro Asn Lys Gly Thr Gln Gln
385                 390                 395                 400

Tyr Thr Asp Gln Ile Glu Arg Pro Leu Met Val Gly Ser Val Trp Asn
                405                 410                 415

Arg Arg Ala Leu His Tyr Glu Ser Gln Leu Trp Ser Lys Ile Pro Asn
            420                 425                 430

Leu Asp Asp Ser Phe Lys Thr Gln Phe Ala Ala Leu Gly Gly Trp Gly
        435                 440                 445

Leu His Gln Pro Pro Pro Gln Ile Phe Leu Lys Ile Leu Pro Gln Ser
    450                 455                 460

Gly Pro Ile Gly Ile Lys Ser Met Gly Ile Thr Thr Leu Val Gln
465                 470                 475                 480

Tyr Ala Val Gly Ile Met Thr Val Thr Met Thr Phe Lys Leu Gly Pro
                485                 490                 495

Arg Lys Ala Thr Gly Arg Trp Asn Pro Gln Pro Gly Val Tyr Pro Pro
            500                 505                 510

His Ala Ala Gly His Leu Pro Tyr Val Leu Tyr Asp Pro Thr Ala Thr
        515                 520                 525

Asp Ala Lys Gln His His Arg His Gly Tyr Glu Lys Pro Glu Glu Leu
    530                 535                 540

Trp Thr Ala Lys Ser Arg Val His Pro Leu
545                 550

<210> SEQ ID NO 198
<211> LENGTH: 587
<212> TYPE: PRT
<213> ORGANISM: minute virus of mice

<400> SEQUENCE: 198

Met Ser Asp Gly Thr Ser Gln Pro Asp Gly Gly Asn Ala Val His Ser
```

```
  1               5                   10                  15
Ala Ala Arg Val Glu Arg Ala Ala Asp Gly Pro Gly Gly Ser Gly Gly
                 20                  25                  30
Gly Gly Ser Gly Gly Gly Val Gly Val Ser Thr Gly Ser Tyr Asp
            35                  40                  45
Asn Gln Thr His Tyr Arg Phe Leu Gly Asp Gly Trp Val Glu Ile Thr
                50                  55                  60
Ala Leu Ala Thr Arg Leu Val His Leu Asn Met Pro Lys Ser Glu Asn
65                  70                  75                  80
Tyr Cys Arg Ile Arg Val His Asn Thr Thr Asp Thr Ser Val Lys Gly
                    85                  90                  95
Asn Met Ala Lys Asp Asp Ala His Glu Gln Ile Trp Thr Pro Trp Ser
                100                 105                 110
Leu Val Asp Ala Asn Ala Trp Gly Val Trp Leu Gln Pro Ser Asp Trp
                115                 120                 125
Gln Tyr Ile Cys Asn Thr Met Ser Gln Leu Asn Leu Val Ser Leu Asp
                130                 135                 140
Gln Glu Ile Phe Asn Val Val Leu Lys Thr Val Thr Glu Gln Asp Ser
145                 150                 155                 160
Gly Gly Gln Ala Ile Lys Ile Tyr Asn Asn Asp Leu Thr Ala Cys Met
                    165                 170                 175
Met Val Ala Val Asp Ser Asn Asn Ile Leu Pro Tyr Thr Pro Ala Ala
                180                 185                 190
Asn Ser Met Glu Thr Leu Gly Phe Tyr Pro Trp Lys Pro Thr Ile Ala
                195                 200                 205
Ser Pro Tyr Arg Tyr Tyr Phe Cys Val Asp Arg Asp Leu Ser Val Thr
                210                 215                 220
Tyr Glu Asn Gln Glu Gly Thr Ile Glu His Asn Val Met Gly Thr Pro
225                 230                 235                 240
Lys Gly Met Asn Ser Gln Phe Phe Thr Ile Glu Asn Thr Gln Gln Ile
                    245                 250                 255
Thr Leu Leu Arg Thr Gly Asp Glu Phe Ala Thr Gly Thr Tyr Tyr Phe
                260                 265                 270
Asp Thr Asn Pro Val Lys Leu Thr His Thr Trp Gln Thr Asn Arg Gln
                275                 280                 285
Leu Gly Gln Pro Leu Leu Ser Thr Phe Pro Glu Ala Asp Thr Asp
                290                 295                 300
Ala Gly Thr Leu Thr Ala Gln Gly Ser Arg His Gly Ala Thr Gln Met
305                 310                 315                 320
Glu Val Asn Trp Val Ser Glu Ala Ile Arg Thr Arg Pro Ala Gln Val
                    325                 330                 335
Gly Phe Cys Gln Pro His Asn Asp Phe Glu Ala Ser Arg Ala Gly Pro
                340                 345                 350
Phe Ala Ala Pro Lys Val Pro Ala Asp Val Thr Gln Gly Met Asp Arg
                355                 360                 365
Glu Ala Asn Gly Ser Val Arg Tyr Ser Tyr Gly Lys Gln His Gly Glu
                370                 375                 380
Asn Trp Ala Ala His Gly Pro Ala Pro Glu Arg Tyr Thr Trp Asp Glu
385                 390                 395                 400
Thr Asn Phe Gly Ser Gly Arg Asp Thr Arg Asp Gly Phe Ile Gln Ser
                    405                 410                 415
Ala Pro Leu Val Val Pro Pro Leu Asn Gly Ile Leu Thr Asn Ala
                420                 425                 430
```

Asn Pro Ile Gly Thr Lys Asn Asp Ile His Phe Ser Asn Val Phe Asn
            435                 440                 445

Ser Tyr Gly Pro Leu Thr Thr Phe Ser His Pro Ser Pro Val Tyr Pro
        450                 455                 460

Gln Gly Gln Ile Trp Asp Lys Glu Leu Asp Leu Glu His Lys Pro Arg
465                 470                 475                 480

Leu His Ile Thr Ala Pro Phe Val Cys Lys Asn Asn Ala Pro Gly Gln
                485                 490                 495

Met Leu Val Arg Leu Gly Pro Asn Leu Thr Asp Gln Tyr Asp Pro Asn
            500                 505                 510

Gly Ala Thr Leu Ser Arg Ile Val Thr Tyr Gly Thr Phe Phe Trp Lys
            515                 520                 525

Gly Lys Leu Thr Met Arg Ala Lys Leu Arg Ala Asn Thr Thr Trp Asn
            530                 535                 540

Pro Val Tyr Gln Val Ser Val Glu Asp Asn Gly Asn Ser Tyr Met Ser
545                 550                 555                 560

Val Thr Lys Trp Leu Pro Thr Ala Thr Gly Asn Met Gln Ser Val Pro
                565                 570                 575

Leu Ile Thr Arg Pro Val Ala Arg Asn Thr Tyr
            580                 585

<210> SEQ ID NO 199
<211> LENGTH: 584
<212> TYPE: PRT
<213> ORGANISM: feline panleukopenia virus

<400> SEQUENCE: 199

Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
            35                  40                  45

Thr Glu Phe Lys Phe Leu Glu Asn Gly Trp Val Glu Ile Thr Ala Asn
50                  55                  60

Ser Ser Arg Leu Val His Leu Asn Met Pro Glu Ser Glu Asn Tyr Lys
65                  70                  75                  80

Arg Val Val Val Asn Asn Met Asp Lys Thr Ala Val Lys Gly Asn Met
                85                  90                  95

Ala Leu Asp Asp Ile His Val Glu Ile Val Thr Pro Trp Ser Leu Val
            100                 105                 110

Asp Ala Asn Ala Trp Gly Val Trp Phe Asn Pro Gly Asp Trp Gln Leu
            115                 120                 125

Ile Val Asn Thr Met Ser Glu Leu His Leu Val Ser Phe Glu Gln Glu
130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
            195                 200                 205

Arg Tyr Tyr Phe Gln Trp Asp Arg Thr Leu Ile Pro Ser His Thr Gly

```
                210                 215                 220
Thr Ser Gly Thr Pro Thr Asn Val Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
                260                 265                 270

Cys Arg Leu Thr His Thr Trp Gln Thr Asn Arg Ala Leu Gly Leu Pro
                275                 280                 285

Pro Phe Leu Asn Ser Leu Pro Gln Ser Glu Gly Ala Thr Asn Phe Gly
                290                 295                 300

Asp Ile Gly Val Gln Gln Asp Lys Arg Arg Gly Val Thr Gln Met Gly
305                 310                 315                 320

Asn Thr Asp Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
                340                 345                 350

Phe Lys Thr Pro Ile Ala Ala Gly Arg Gly Gly Ala Gln Thr Asp Glu
                355                 360                 365

Asn Gln Ala Ala Asp Gly Asp Pro Arg Tyr Ala Phe Gly Arg Gln His
                370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Asn Asp Asn Val Leu Leu Pro
                420                 425                 430

Thr Asp Pro Ile Gly Gly Lys Thr Gly Ile Asn Tyr Thr Asn Ile Phe
                435                 440                 445

Asn Thr Tyr Gly Pro Leu Thr Ala Leu Asn Asn Val Pro Pro Val Tyr
                450                 455                 460

Pro Asn Gly Gln Ile Trp Asp Lys Glu Phe Asp Thr Asp Leu Lys Pro
465                 470                 475                 480

Arg Leu His Ile Asn Ala Pro Phe Val Cys Gln Asn Asn Cys Pro Gly
                485                 490                 495

Gln Leu Phe Val Lys Val Ala Pro Asn Leu Thr Asn Gln Tyr Asp Pro
                500                 505                 510

Asp Ala Ser Ala Asn Met Ser Arg Ile Val Thr Tyr Ser Asp Phe Trp
                515                 520                 525

Trp Lys Gly Lys Leu Val Phe Lys Ala Lys Leu Arg Ala Ser His Thr
                530                 535                 540

Trp Asn Pro Ile Gln Gln Met Ser Ile Asn Val Asp Asn Gln Phe Asn
545                 550                 555                 560

Tyr Val Pro Asn Asn Ile Gly Ala Met Lys Ile Val Tyr Glu Lys Ser
                565                 570                 575

Gln Leu Ala Pro Arg Lys Leu Tyr
                580

<210> SEQ ID NO 200
<211> LENGTH: 548
<212> TYPE: PRT
<213> ORGANISM: canine parvovirus

<400> SEQUENCE: 200
```

-continued

```
Gly Val Gly Ile Ser Thr Gly Thr Phe Asn Asn Gln Thr Glu Phe Lys
1               5                   10                  15

Phe Leu Glu Asn Gly Trp Val Glu Ile Thr Ala Asn Ser Ser Arg Leu
            20                  25                  30

Val His Leu Asn Met Pro Glu Ser Glu Asn Tyr Arg Arg Val Val Val
        35                  40                  45

Asn Asn Met Asp Lys Thr Ala Val Asn Gly Asn Met Ala Leu Asp Asp
50                  55                  60

Ile His Ala Gln Ile Val Thr Pro Trp Ser Leu Val Asp Ala Asn Ala
65                  70                  75                  80

Trp Gly Val Trp Phe Asn Pro Gly Asp Trp Gln Leu Ile Val Asn Thr
                85                  90                  95

Met Ser Glu Leu His Leu Val Ser Phe Glu Gln Glu Ile Phe Asn Val
            100                 105                 110

Val Leu Lys Thr Val Ser Glu Ser Ala Thr Gln Pro Pro Thr Lys Val
            115                 120                 125

Tyr Asn Asn Asp Leu Thr Ala Ser Leu Met Val Ala Leu Asp Ser Asn
        130                 135                 140

Asn Thr Met Pro Phe Thr Pro Ala Ala Met Arg Ser Glu Thr Leu Gly
145                 150                 155                 160

Phe Tyr Pro Trp Lys Pro Thr Ile Pro Thr Pro Trp Arg Tyr Tyr Phe
                165                 170                 175

Gln Trp Asp Arg Thr Leu Ile Pro Ser His Thr Gly Thr Ser Gly Thr
            180                 185                 190

Pro Thr Asn Ile Tyr His Gly Thr Asp Pro Asp Val Gln Phe Tyr
            195                 200                 205

Thr Ile Glu Asn Ser Val Pro Val His Leu Leu Arg Thr Gly Asp Glu
210                 215                 220

Phe Ala Thr Gly Thr Phe Phe Asp Cys Lys Pro Cys Arg Leu Thr
225                 230                 235                 240

His Thr Trp Gln Thr Asn Arg Ala Leu Gly Leu Pro Pro Phe Leu Asn
                245                 250                 255

Ser Leu Pro Gln Ser Glu Gly Ala Thr Asn Phe Gly Asp Ile Gly Val
            260                 265                 270

Gln Gln Asp Lys Arg Arg Gly Val Thr Gln Met Gly Asn Thr Asn Tyr
        275                 280                 285

Ile Thr Glu Ala Thr Ile Met Arg Pro Ala Glu Val Gly Tyr Ser Ala
        290                 295                 300

Pro Tyr Tyr Ser Phe Glu Ala Ser Thr Gln Gly Pro Phe Lys Thr Pro
305                 310                 315                 320

Ile Ala Ala Gly Arg Gly Gly Ala Gln Thr Asp Glu Asn Gln Ala Ala
                325                 330                 335

Asp Gly Asn Pro Arg Tyr Ala Phe Gly Arg Gln His Gly Gln Lys Thr
            340                 345                 350

Thr Thr Thr Gly Glu Thr Pro Glu Arg Phe Thr Tyr Ile Ala His Gln
            355                 360                 365

Asp Thr Gly Arg Tyr Pro Glu Gly Asp Trp Ile Gln Asn Ile Asn Phe
        370                 375                 380

Asn Leu Pro Val Thr Asn Asp Asn Val Leu Leu Pro Thr Asp Pro Ile
385                 390                 395                 400

Gly Gly Lys Thr Gly Ile Asn Tyr Thr Asn Ile Phe Asn Thr Tyr Gly
                405                 410                 415

Pro Leu Thr Ala Leu Asn Asn Val Pro Pro Val Tyr Pro Asn Gly Gln
```

```
                    420                 425                 430
Ile Trp Asp Lys Glu Phe Asp Thr Asp Leu Lys Pro Arg Leu His Val
            435                 440                 445

Asn Ala Pro Phe Val Cys Gln Asn Asn Cys Pro Gly Gln Leu Phe Val
    450                 455                 460

Lys Val Ala Pro Asn Leu Thr Asn Glu Tyr Asp Pro Asp Ala Ser Ala
465                 470                 475                 480

Asn Met Ser Arg Ile Val Thr Tyr Ser Asp Phe Trp Trp Lys Gly Lys
                485                 490                 495

Leu Val Phe Lys Ala Lys Leu Arg Ala Ser His Thr Trp Asn Pro Ile
            500                 505                 510

Gln Gln Met Ser Ile Asn Val Asp Asn Gln Phe Asn Tyr Val Pro Ser
        515                 520                 525

Asn Ile Gly Gly Met Lys Ile Val Tyr Glu Lys Ser Gln Leu Ala Pro
    530                 535                 540

Arg Lys Leu Tyr
545

<210> SEQ ID NO 201
<211> LENGTH: 10
<212> TYPE: PRT
<213> ORGANISM: Artificial Sequence
<220> FEATURE:
<223> OTHER INFORMATION: Synthetic Construct

<400> SEQUENCE: 201

Arg Thr Thr Asn Pro Val Ala Thr Glu Gln
1               5                   10

<210> SEQ ID NO 202
<211> LENGTH: 8
<212> TYPE: PRT
<213> ORGANISM: Artificial Sequence
<220> FEATURE:
<223> OTHER INFORMATION: Synthetic Construct

<400> SEQUENCE: 202

Ile Asn His Arg Gly Tyr Trp Val
1               5

<210> SEQ ID NO 203
<211> LENGTH: 9
<212> TYPE: PRT
<213> ORGANISM: Artificial Sequence
<220> FEATURE:
<223> OTHER INFORMATION: Synthetic Construct

<400> SEQUENCE: 203

Glu Lys Gln Arg Asn Gly Thr Leu Thr
1               5

<210> SEQ ID NO 204
<211> LENGTH: 11
<212> TYPE: PRT
<213> ORGANISM: Artificial Sequence
<220> FEATURE:
<223> OTHER INFORMATION: Synthetic Construct

<400> SEQUENCE: 204

Glu Asp Gly Gln Val Met Asp Val Asp Leu Ser
1               5                   10
```

<210> SEQ ID NO 205
<211> LENGTH: 17
<212> TYPE: PRT
<213> ORGANISM: Artificial Sequence
<220> FEATURE:
<223> OTHER INFORMATION: Synthetic Construct

<400> SEQUENCE: 205

Thr Tyr Gln Cys Arg Val Thr His Pro His Leu Pro Arg Ala Leu Met
1               5                   10                  15
Arg

<210> SEQ ID NO 206
<211> LENGTH: 14
<212> TYPE: PRT
<213> ORGANISM: Artificial Sequence
<220> FEATURE:
<223> OTHER INFORMATION: Synthetic Construct

<400> SEQUENCE: 206

Arg His Ser Thr Thr Gln Pro Arg Lys Thr Lys Gly Ser Gly
1               5                   10

<210> SEQ ID NO 207
<211> LENGTH: 13
<212> TYPE: PRT
<213> ORGANISM: Artificial Sequence
<220> FEATURE:
<223> OTHER INFORMATION: Synthetic Construct

<400> SEQUENCE: 207

Asp Ser Asn Pro Arg Gly Val Ser Ala Tyr Leu Ser Arg
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthetic Construct

<400> SEQUENCE: 208

Thr Ile Thr Cys Leu Val Val Asp Leu Ala Pro Ser Lys
1               5                   10

<210> SEQ ID NO 209
<211> LENGTH: 10
<212> TYPE: PRT
<213> ORGANISM: Artificial Sequence
<220> FEATURE:
<223> OTHER INFORMATION: Synthetic Construct

<400> SEQUENCE: 209

Lys Thr Lys Gly Ser Gly Phe Phe Val Phe
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Synthetic Construct

<400> SEQUENCE: 210

Thr His Pro His Leu Pro Arg Ala Leu Met Arg Ser
1               5                   10

<210> SEQ ID NO 211
<211> LENGTH: 23
<212> TYPE: PRT
<213> ORGANISM: Artificial Sequence
<220> FEATURE:
<223> OTHER INFORMATION: Synthetic Construct

<400> SEQUENCE: 211

Gly Glu Thr Tyr Gln Cys Arg Val Thr His Pro His Leu Pro Arg Ala
1               5                   10                  15

Leu Met Arg Ser Thr Thr Lys
            20

<210> SEQ ID NO 212
<211> LENGTH: 8
<212> TYPE: PRT
<213> ORGANISM: Artificial Sequence
<220> FEATURE:
<223> OTHER INFORMATION: Synthetic Construct

<400> SEQUENCE: 212

Leu Pro Arg Ala Leu Met Arg Ser
1               5

<210> SEQ ID NO 213
<211> LENGTH: 17
<212> TYPE: PRT
<213> ORGANISM: Artificial Sequence
<220> FEATURE:
<223> OTHER INFORMATION: Synthetic Construct

<400> SEQUENCE: 213

Pro Lys Thr Val Ser Asn Leu Thr Glu Ser Ser Ser Glu Ser Val Gln
1               5                   10                  15

Ser

<210> SEQ ID NO 214
<211> LENGTH: 13
<212> TYPE: PRT
<213> ORGANISM: Artificial Sequence
<220> FEATURE:
<223> OTHER INFORMATION: Synthetic Construct

<400> SEQUENCE: 214

Ser Leu Met Gly Asp Glu Phe Lys Ala Val Leu Glu Thr
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Synthetic Construct

<400> SEQUENCE: 215

Gln His Ser Val Ala Tyr Thr Phe Glu Glu Asp
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Synthetic Construct

<400> SEQUENCE: 216

Ile Asn Pro Glu Ile Ile Thr Arg Asp Gly
1               5                   10

<210> SEQ ID NO 217
<211> LENGTH: 15
<212> TYPE: PRT
<213> ORGANISM: Artificial Sequence
<220> FEATURE:
<223> OTHER INFORMATION: Synthetic Construct

<400> SEQUENCE: 217

Asp Ile Ser Leu Thr Gly Asp Pro Val Ile Thr Ala Ser Tyr Leu
1               5                   10                  15

<210> SEQ ID NO 218
<211> LENGTH: 12
<212> TYPE: PRT
<213> ORGANISM: Artificial Sequence
<220> FEATURE:
<223> OTHER INFORMATION: Synthetic Construct

<400> SEQUENCE: 218

Asp Ile Ser Leu Thr Gly Asp Pro Val Ile Thr Ala
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic Construct

<400> SEQUENCE: 219

Asp Gln Ser Ile Asp Phe Glu Ile Asp Ser Ala
1               5                   10

<210> SEQ ID NO 220
<211> LENGTH: 20
<212> TYPE: PRT
<213> ORGANISM: Artificial Sequence
<220> FEATURE:
<223> OTHER INFORMATION: Synthetic Construct

<400> SEQUENCE: 220

Lys Asn Val Ser Glu Asp Leu Pro Leu Pro Thr Phe Ser Pro Thr Leu
1               5                   10                  15

Leu Gly Asp Ser
            20

<210> SEQ ID NO 221
<211> LENGTH: 11
<212> TYPE: PRT
<213> ORGANISM: Artificial Sequence
<220> FEATURE:
<223> OTHER INFORMATION: Synthetic Construct

<400> SEQUENCE: 221

Lys Asn Val Ser Glu Asp Leu Pro Leu Pro Thr
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Synthetic Construct

```
<400> SEQUENCE: 222

Cys Asp Ser Gly Arg Val Arg Thr Asp Ala Pro Asp
1               5                   10

<210> SEQ ID NO 223
<211> LENGTH: 14
<212> TYPE: PRT
<213> ORGANISM: Artificial Sequence
<220> FEATURE:
<223> OTHER INFORMATION: Synthetic Construct

<400> SEQUENCE: 223

Phe Pro Glu His Leu Leu Val Asp Phe Leu Gln Ser Leu Ser
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Synthetic Construct

<400> SEQUENCE: 224

Gln Met Trp Ala Pro Gln Trp Gly Pro Asp
1               5                   10

<210> SEQ ID NO 225
<211> LENGTH: 20
<212> TYPE: PRT
<213> ORGANISM: Artificial Sequence
<220> FEATURE:
<223> OTHER INFORMATION: Synthetic Construct

<400> SEQUENCE: 225

Ser Ser Arg Thr Pro Ser Asp Lys Pro Val Ala His Val Val Ala Asn
1               5                   10                  15

Pro Gln Ala Glu
            20

<210> SEQ ID NO 226
<211> LENGTH: 16
<212> TYPE: PRT
<213> ORGANISM: Artificial Sequence
<220> FEATURE:
<223> OTHER INFORMATION: Synthetic Construct

<400> SEQUENCE: 226

Ser Arg Thr Pro Ser Asp Lys Pro Val Ala His Val Val Ala Asn Pro
1               5                   10                  15

<210> SEQ ID NO 227
<211> LENGTH: 9
<212> TYPE: PRT
<213> ORGANISM: Artificial Sequence
<220> FEATURE:
<223> OTHER INFORMATION: Synthetic Construct

<400> SEQUENCE: 227

Ser Ser Arg Thr Pro Ser Asp Lys Pro
1               5

<210> SEQ ID NO 228
<211> LENGTH: 14
<212> TYPE: PRT
<213> ORGANISM: Artificial Sequence
```

```
<220> FEATURE:
<223> OTHER INFORMATION: Synthetic Construct

<400> SEQUENCE: 228

Asn Ala Asp Gly Asn Val Asp Tyr His Met Asn Ser Val Pro
1               5                   10

<210> SEQ ID NO 229
<211> LENGTH: 11
<212> TYPE: PRT
<213> ORGANISM: Artificial Sequence
<220> FEATURE:
<223> OTHER INFORMATION: Synthetic Construct

<400> SEQUENCE: 229

Asp Gly Asn Val Asp Tyr His Met Asn Ser Val
1               5                   10

<210> SEQ ID NO 230
<211> LENGTH: 16
<212> TYPE: PRT
<213> ORGANISM: Artificial Sequence
<220> FEATURE:
<223> OTHER INFORMATION: Synthetic Construct

<400> SEQUENCE: 230

Arg Ser Phe Lys Glu Phe Leu Gln Ser Ser Leu Arg Ala Leu Arg Gln
1               5                   10                  15

<210> SEQ ID NO 231
<211> LENGTH: 11
<212> TYPE: PRT
<213> ORGANISM: Artificial Sequence
<220> FEATURE:
<223> OTHER INFORMATION: Synthetic Construct

<400> SEQUENCE: 231

Phe Lys Glu Phe Leu Gln Ser Ser Leu Arg Ala
1               5                   10

<210> SEQ ID NO 232
<211> LENGTH: 433
<212> TYPE: PRT
<213> ORGANISM: Macacus cynomolgus

<400> SEQUENCE: 232

Ser Val Phe Thr Ala Ser Ile Gln Ser Pro Phe Val Phe Pro Leu Ile
1               5                   10                  15

Pro Cys Cys Lys His Ile Ala Ser Asn Ala Thr Ser Val Thr Leu Gly
                20                  25                  30

Cys Leu Ala Thr Gly Tyr Phe Pro Glu Pro Val Met Val Thr Trp Asp
            35                  40                  45

Ala Gly Ser Leu Asn Arg Ser Thr Met Thr Leu Pro Ala Thr Thr Phe
        50                  55                  60

Thr Pro Ser Gly His Tyr Ala Thr Ile Ser Leu Leu Thr Val Ser Gly
65                  70                  75                  80

Ala Trp Ala Lys Glu Met Phe Thr Cys His Val Val His Thr Pro Ser
                85                  90                  95

Ser Ala Asp Lys Glu Val Asn Lys Thr Phe Gly Val Cys Ser Arg Asn
                100                 105                 110

Phe Thr Pro Pro Thr Val Lys Ile Leu Gln Ser Ser Cys Asp Asp Asp
            115                 120                 125
```

-continued

Gly His Phe Pro Pro Thr Ile Gln Leu Leu Cys Leu Ile Ser Gly Tyr
    130                 135                 140

Thr Pro Gly Ala Ile Asn Val Thr Trp Leu Glu Asn Gly Gln Val Met
145                 150                 155                 160

Lys Val Asn Ser Pro Thr Pro Ala Thr Gln Glu Gly Glu Leu Ala
                165                 170                 175

Ser Thr Gln Ser Glu Phe Thr Leu Ala Gln Lys His Trp Leu Ser Asp
                180                 185                 190

Arg Thr Tyr Thr Cys Gln Val Thr Tyr Gln Gly Thr Thr Tyr Asn Asp
            195                 200                 205

Ser Thr Lys Lys Cys Ala Asp Ser Asn Pro Arg Gly Val Ser Ala Tyr
        210                 215                 220

Leu Ser Arg Pro Ser Pro Phe Asp Leu Phe Ile Ser Lys Ser Pro Thr
225                 230                 235                 240

Ile Thr Cys Leu Val Val Asp Leu Ala Pro Ser Lys Glu Thr Val Asn
                245                 250                 255

Leu Thr Trp Ser Arg Ala Ser Gly Lys Pro Val Pro His Ile Pro Ala
                260                 265                 270

Thr Glu Lys Lys Gln Gln Arg Asn Gly Thr Leu Thr Val Thr Ser Ile
            275                 280                 285

Leu Pro Val Val Thr Gln Asp Trp Ile Glu Gly Glu Thr Tyr Gln Cys
290                 295                 300

Arg Val Thr His Pro His Leu Pro Arg Ala Leu Val Arg Ser Met Thr
305                 310                 315                 320

Lys Thr Ser Gly Pro Arg Ala Ala Pro Glu Val Tyr Val Phe Ala Thr
                325                 330                 335

Pro Glu Lys Leu Glu Ser Arg Asp Lys Arg Thr Leu Ala Cys Leu Ile
            340                 345                 350

Gln Asn Phe Met Pro Glu Asp Ile Ser Val Gln Trp Leu His Ser Asp
        355                 360                 365

Val Gln Leu Pro Asp Ala Arg His Ser Val Thr Gln Pro Arg Lys Thr
370                 375                 380

Lys Gly Ser Gly Phe Phe Val Phe Ser Arg Leu Glu Val Thr Lys Ala
385                 390                 395                 400

Glu Trp Glu Gln Lys Asp Glu Phe Ile Cys Arg Ala Val His Glu Ala
                405                 410                 415

Ala Ser Pro Ser Trp Ile Val Gln Gln Ala Val Ser Val Asn Pro Gly
            420                 425                 430

Lys

<210> SEQ ID NO 233
<211> LENGTH: 25
<212> TYPE: PRT
<213> ORGANISM: Artificial Sequence
<220> FEATURE:
<223> OTHER INFORMATION: Synthetic Construct

<400> SEQUENCE: 233

Cys Gly Glu Thr Tyr Gln Ser Arg Val Thr His Pro His Leu Pro Arg
1               5                   10                  15

Ala Leu Met Arg Ser Thr Thr Lys Cys
            20                  25

<210> SEQ ID NO 234
<211> LENGTH: 63
<212> TYPE: PRT

<213> ORGANISM: Artificial Sequence
<220> FEATURE:
<223> OTHER INFORMATION: Synthetic Construct

<400> SEQUENCE: 234

Thr Ala Lys Ser Lys Lys Phe Pro Ser Tyr Thr Ala Thr Tyr Gln Phe
1               5                   10                  15

Gly Gly Lys Lys Lys Ile Ile Thr Ile Thr Arg Ile Ile Thr Ile Ile
            20                  25                  30

Thr Thr Ile Asp Gly Gly Cys Gly Glu Thr Tyr Gln Ser Arg Val Thr
        35                  40                  45

His Pro His Leu Pro Arg Ala Leu Met Arg Ser Thr Thr Lys Cys
    50                  55                  60

<210> SEQ ID NO 235
<211> LENGTH: 23
<212> TYPE: PRT
<213> ORGANISM: Artificial
<220> FEATURE:
<223> OTHER INFORMATION: Peptide

<400> SEQUENCE: 235

Gly Glu Thr Tyr Gln Ser Arg Val Thr His Pro His Leu Pro Arg Ala
1               5                   10                  15

Leu Met Arg Ser Thr Thr Lys
            20

<210> SEQ ID NO 236
<211> LENGTH: 17
<212> TYPE: PRT
<213> ORGANISM: Artificial Sequence
<220> FEATURE:
<223> OTHER INFORMATION: Synthetic Construct

<400> SEQUENCE: 236

Ala Lys Ala Val Ser Asn Leu Thr Glu Ser Arg Ser Glu Ser Leu Gln
1               5                   10                  15

Ser

<210> SEQ ID NO 237
<211> LENGTH: 13
<212> TYPE: PRT
<213> ORGANISM: Artificial Sequence
<220> FEATURE:
<223> OTHER INFORMATION: Synthetic Construct

<400> SEQUENCE: 237

Ser Leu Thr Gly Asp Glu Phe Lys Lys Val Leu Glu Thr
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Synthetic Construct

<400> SEQUENCE: 238

Arg Glu Ala Val Ala Tyr Arg Phe Glu Glu Asp
1               5                   10

<210> SEQ ID NO 239
<211> LENGTH: 10
<212> TYPE: PRT

<213> ORGANISM: Artificial Sequence
<220> FEATURE:
<223> OTHER INFORMATION: Synthetic Construct

<400> SEQUENCE: 239

Ile Asn Pro Glu Ile Ile Thr Leu Asp Gly
1               5                   10

<210> SEQ ID NO 240
<211> LENGTH: 15
<212> TYPE: PRT
<213> ORGANISM: Artificial Sequence
<220> FEATURE:
<223> OTHER INFORMATION: Synthetic Construct

<400> SEQUENCE: 240

Asp Ile Ser Val Thr Gly Ala Pro Val Ile Thr Ala Thr Tyr Leu
1               5                   10                  15

<210> SEQ ID NO 241
<211> LENGTH: 12
<212> TYPE: PRT
<213> ORGANISM: Artificial Sequence
<220> FEATURE:
<223> OTHER INFORMATION: Synthetic Construct

<400> SEQUENCE: 241

Asp Ile Ser Val Thr Gly Ala Pro Val Ile Thr Ala
1               5                   10

<210> SEQ ID NO 242
<211> LENGTH: 11
<212> TYPE: PRT
<213> ORGANISM: Artificial Sequence
<220> FEATURE:
<223> OTHER INFORMATION: Synthetic Construct

<400> SEQUENCE: 242

Asp Gln Ser Val Asp Phe Glu Ile Asp Ser Ala
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct

<400> SEQUENCE: 243

Lys Asn Val Ser Glu Ala Phe Pro Leu Arg Ala
1               5                   10

<210> SEQ ID NO 244
<211> LENGTH: 76
<212> TYPE: DNA
<213> ORGANISM: Artificial Sequence
<220> FEATURE:
<223> OTHER INFORMATION: Synthetic Construct

<400> SEQUENCE: 244
ggccggcgga ggtgccaagg ccgtgagcaa cctaccgaga gcagaagcga gagcctgcag    60
agcgggggtg gcggtg                                                   76

<210> SEQ ID NO 245
<211> LENGTH: 77
<212> TYPE: DNA

```
<213> ORGANISM: Artificial Sequence
<220> FEATURE:
<223> OTHER INFORMATION: Synthetic Construct

<400> SEQUENCE: 245
cgcgcaccgc cacccccgct ctgcaggctc tcgcttctgc tctcggtcag gttgctcacg    60
gccttggcac ctccgcc                                                   77

<210> SEQ ID NO 246
<211> LENGTH: 65
<212> TYPE: DNA
<213> ORGANISM: Artificial Sequence
<220> FEATURE:
<223> OTHER INFORMATION: Synthetic Construct

<400> SEQUENCE: 246
ggccggcgga ggtagcctga ccggcgacga attcaagaag gtgctggaga ccggggtgg    60 cggtg                                                                65

<210> SEQ ID NO 247
<211> LENGTH: 65
<212> TYPE: DNA
<213> ORGANISM: Artificial Sequence
<220> FEATURE:
<223> OTHER INFORMATION: Synthetic Construct

<400> SEQUENCE: 247
cgcgcaccgc cacccccggt ctccagcacc ttcttgaatt cgtcgccggt caggctacct    60
ccgcc                                                                65

<210> SEQ ID NO 248
<211> LENGTH: 59
<212> TYPE: DNA
<213> ORGANISM: Artificial Sequence
<220> FEATURE:
<223> OTHER INFORMATION: Synthetic Construct

<400> SEQUENCE: 248
ggccggcgga ggtagagagg ccgtggccta cagattcgaa gaggacgggg gtggcggtg    59

<210> SEQ ID NO 249
<211> LENGTH: 59
<212> TYPE: DNA
<213> ORGANISM: Artificial Sequence
<220> FEATURE:
<223> OTHER INFORMATION: Synthetic Construct

<400> SEQUENCE: 249
cgcgcaccgc cacccccgtc ctcttcgaat ctgtaggcca cggcctctct acctccgcc    59

<210> SEQ ID NO 250
<211> LENGTH: 56
<212> TYPE: DNA
<213> ORGANISM: Artificial Sequence
<220> FEATURE:
<223> OTHER INFORMATION: Synthetic Construct

<400> SEQUENCE: 250
ggccggcgga ggtatcaacc ccgagatcat caccctggac ggcggggtg gcggtg         56

<210> SEQ ID NO 251
<211> LENGTH: 56
<212> TYPE: DNA
<213> ORGANISM: Artificial Sequence
```

<220> FEATURE:
<223> OTHER INFORMATION: Synthetic Construct

<400> SEQUENCE: 251
cgcgcaccgc caccccgcc gtccagggtg atgatctcgg ggttgatacc tccgcc      56

<210> SEQ ID NO 252
<211> LENGTH: 71
<212> TYPE: DNA
<213> ORGANISM: Artificial Sequence
<220> FEATURE:
<223> OTHER INFORMATION: Synthetic Construct

<400> SEQUENCE: 252
ggccggcgga ggtgacatca gcgtgaccgg tgcacccgtg atcaccgcca cctacctggg    60
gggtggcggt g       71

<210> SEQ ID NO 253
<211> LENGTH: 71
<212> TYPE: DNA
<213> ORGANISM: Artificial Sequence
<220> FEATURE:
<223> OTHER INFORMATION: Synthetic Construct

<400> SEQUENCE: 253
cgcgcaccgc caccccccag gtaggtggcg gtgatcacgg gtgcaccggt cacgctgatg    60
tcacctccgc c       71

<210> SEQ ID NO 254
<211> LENGTH: 62
<212> TYPE: DNA
<213> ORGANISM: Artificial Sequence
<220> FEATURE:
<223> OTHER INFORMATION: Synthetic Construct

<400> SEQUENCE: 254
ggccggcgga ggtgacatca gcgtgaccgg tgcacccgtg atcaccgccg ggggtggcgg    60
tg       62

<210> SEQ ID NO 255
<211> LENGTH: 62
<212> TYPE: DNA
<213> ORGANISM: Artificial Sequence
<220> FEATURE:
<223> OTHER INFORMATION: Synthetic Construct

<400> SEQUENCE: 255
cgcgcaccgc caccccggc ggtgatcacg ggtgcaccgg tcacgctgat gtcacctccg    60
cc       62

<210> SEQ ID NO 256
<211> LENGTH: 59
<212> TYPE: DNA
<213> ORGANISM: Artificial Sequence
<220> FEATURE:
<223> OTHER INFORMATION: Synthetic Construct

<400> SEQUENCE: 256
ggccggcgga ggtgaccaga gcgtggactt cgagatcgac agcgccgggg gtggcggtg    59

<210> SEQ ID NO 257
<211> LENGTH: 59
<212> TYPE: DNA

<213> ORGANISM: Artificial Sequence
<220> FEATURE:
<223> OTHER INFORMATION: Synthetic Construct

<400> SEQUENCE: 257
cgcgcaccgc cacccccggc gctgtcgatc tcgaagtcca cgctctggtc acctccgcc         59

<210> SEQ ID NO 258
<211> LENGTH: 59
<212> TYPE: DNA
<213> ORGANISM: Artificial Sequence
<220> FEATURE:
<223> OTHER INFORMATION: Synthetic Construct

<400> SEQUENCE: 258
ggccggcgga ggtaagaacg tgagcgaggc cttccctctg agagccgggg gtggcggtg         59

<210> SEQ ID NO 259
<211> LENGTH: 59
<212> TYPE: DNA
<213> ORGANISM: Artificial Sequence
<220> FEATURE:
<223> OTHER INFORMATION: Synthetic Construct

<400> SEQUENCE: 259
cgcgcaccgc cacccccggc tctcagaggg aaggcctcgc tcacgttctt acctccgcc         59

<210> SEQ ID NO 260
<211> LENGTH: 14
<212> TYPE: PRT
<213> ORGANISM: Artificial Sequence
<220> FEATURE:
<223> OTHER INFORMATION: Synthetic Construct

<400> SEQUENCE: 260

Phe Pro Lys His Leu Leu Val Asp Phe Leu Gln Ser Leu Ser
1               5                   10

<210> SEQ ID NO 261
<211> LENGTH: 20
<212> TYPE: PRT
<213> ORGANISM: Artificial Sequence
<220> FEATURE:
<223> OTHER INFORMATION: Synthetic Construct

<400> SEQUENCE: 261

Lys Asn Val Ser Glu Ala Phe Pro Leu Arg Ala Phe Pro Pro Gly Leu
1               5                   10                  15

Leu Gly Asp Ser
            20

<210> SEQ ID NO 262
<211> LENGTH: 76
<212> TYPE: DNA
<213> ORGANISM: Artificial Sequence
<220> FEATURE:
<223> OTHER INFORMATION: Synthetic Construct

<400> SEQUENCE: 262
ggccggcggt ggagccaagg ccgtgagcaa cctgaccgag agcagaagcg agagcctgca         60
gagcggtggc ggtgga                                                        76

<210> SEQ ID NO 263
<211> LENGTH: 76
<212> TYPE: DNA

```
<213> ORGANISM: Artificial Sequence
<220> FEATURE:
<223> OTHER INFORMATION: Synthetic Construct

<400> SEQUENCE: 263
cgcgtccacc gccaccgctc tgcaggctct cgcttctgct ctcggtcagg ttgctcacgg       60
ccttggctcc accgcc                                                      76

<210> SEQ ID NO 264
<211> LENGTH: 64
<212> TYPE: DNA
<213> ORGANISM: Artificial Sequence
<220> FEATURE:
<223> OTHER INFORMATION: Synthetic Construct

<400> SEQUENCE: 264
ggccggcggt ggaagcctga ccggcgacga attcaagaag gtgctggaga ccggtggcgg       60
tgga                                                                   64

<210> SEQ ID NO 265
<211> LENGTH: 64
<212> TYPE: DNA
<213> ORGANISM: Artificial Sequence
<220> FEATURE:
<223> OTHER INFORMATION: Synthetic Construct

<400> SEQUENCE: 265
cgcgtccacc gccaccggtc tccagcacct tcttgaattc gtcgccggtc aggcttccac       60
cgcc                                                                   64

<210> SEQ ID NO 266
<211> LENGTH: 58
<212> TYPE: DNA
<213> ORGANISM: Artificial Sequence
<220> FEATURE:
<223> OTHER INFORMATION: Synthetic Construct

<400> SEQUENCE: 266
ggccggcggt ggaagagagg ccgtggccta cagattcgaa gaggacggtg gcggtgga        58

<210> SEQ ID NO 267
<211> LENGTH: 58
<212> TYPE: DNA
<213> ORGANISM: Artificial Sequence
<220> FEATURE:
<223> OTHER INFORMATION: Synthetic Construct

<400> SEQUENCE: 267
cgcgtccacc gccaccgtcc tcttcgaatc tgtaggccac ggcctctctt ccaccgcc        58

<210> SEQ ID NO 268
<211> LENGTH: 55
<212> TYPE: DNA
<213> ORGANISM: Artificial Sequence
<220> FEATURE:
<223> OTHER INFORMATION: Synthetic Construct

<400> SEQUENCE: 268
ggccggcggt ggaatcaacc ccgagatcat caccctggac ggcggtggcg gtgga           55

<210> SEQ ID NO 269
<211> LENGTH: 55
<212> TYPE: DNA
<213> ORGANISM: Artificial Sequence
```

<220> FEATURE:
<223> OTHER INFORMATION: Synthetic Construct

<400> SEQUENCE: 269
cgcgtccacc gccaccgccg tccagggtga tgatctcggg gttgattcca ccgcc      55

<210> SEQ ID NO 270
<211> LENGTH: 70
<212> TYPE: DNA
<213> ORGANISM: Artificial Sequence
<220> FEATURE:
<223> OTHER INFORMATION: Synthetic Construct

<400> SEQUENCE: 270
ggccggcggt ggagacatca gcgtgaccgg tgcacccgtg atcaccgcca cctacctggg    60
tggcggtgga      70

<210> SEQ ID NO 271
<211> LENGTH: 70
<212> TYPE: DNA
<213> ORGANISM: Artificial Sequence
<220> FEATURE:
<223> OTHER INFORMATION: Synthetic Construct

<400> SEQUENCE: 271
cgcgtccacc gccacccagg taggtggcgg tgatcacggg tgcaccggtc acgctgatgt    60
ctccaccgcc      70

<210> SEQ ID NO 272
<211> LENGTH: 61
<212> TYPE: DNA
<213> ORGANISM: Artificial Sequence
<220> FEATURE:
<223> OTHER INFORMATION: Synthetic Construct

<400> SEQUENCE: 272
ggccggcggt ggagacatca gcgtgaccgg tgcacccgtg atcaccgccg gtggcggtgg    60
a      61

<210> SEQ ID NO 273
<211> LENGTH: 61
<212> TYPE: DNA
<213> ORGANISM: Artificial Sequence
<220> FEATURE:
<223> OTHER INFORMATION: Synthetic Construct

<400> SEQUENCE: 273
cgcgtccacc gccaccggcg gtgatcacgg gtgcaccggt cacgctgatg tctccaccgc    60
c      61

<210> SEQ ID NO 274
<211> LENGTH: 58
<212> TYPE: DNA
<213> ORGANISM: Artificial Sequence
<220> FEATURE:
<223> OTHER INFORMATION: Synthetic Construct

<400> SEQUENCE: 274
ggccggcggt ggagaccaga gcgtggactt cgagatcgac agcgccggtg gcggtgga      58

<210> SEQ ID NO 275
<211> LENGTH: 58
<212> TYPE: DNA

```
<213> ORGANISM: Artificial Sequence
<220> FEATURE:
<223> OTHER INFORMATION: Synthetic Construct

<400> SEQUENCE: 275
cgcgtccacc gccaccggcg ctgtcgatct cgaagtccac gctctggtct ccaccgcc        58

<210> SEQ ID NO 276
<211> LENGTH: 68
<212> TYPE: DNA
<213> ORGANISM: Artificial Sequence
<220> FEATURE:
<223> OTHER INFORMATION: Synthetic Construct

<400> SEQUENCE: 276
ggccggcgga ggtggtgaca gcaaccctag aggcgtgagc gcctacctga gcagagggg         60 tggcggtg                                                                68

<210> SEQ ID NO 277
<211> LENGTH: 68
<212> TYPE: DNA
<213> ORGANISM: Artificial Sequence
<220> FEATURE:
<223> OTHER INFORMATION: Synthetic Construct

<400> SEQUENCE: 277
cgcgcaccgc cacccctct gctcaggtag gcgctcacgc ctctagggtt gctgtcacca        60
cctccgcc                                                                68

<210> SEQ ID NO 278
<211> LENGTH: 62
<212> TYPE: DNA
<213> ORGANISM: Artificial Sequence
<220> FEATURE:
<223> OTHER INFORMATION: Synthetic Construct

<400> SEQUENCE: 278
ggccggcgga ggtacccacc cccacctgcc cagagccctg atgagaagcg ggggtggcgg        60
tg                                                                      62

<210> SEQ ID NO 279
<211> LENGTH: 62
<212> TYPE: DNA
<213> ORGANISM: Artificial Sequence
<220> FEATURE:
<223> OTHER INFORMATION: Synthetic Construct

<400> SEQUENCE: 279
cgcgcaccgc caccccgct tctcatcagg gctctgggca ggtggggtg ggtacctccg        60 cc                                                                      62

<210> SEQ ID NO 280
<211> LENGTH: 59
<212> TYPE: DNA
<213> ORGANISM: Artificial Sequence
<220> FEATURE:
<223> OTHER INFORMATION: Synthetic Construct

<400> SEQUENCE: 280
ggccggcgga ggtgaggacg gccaggtgat ggacgtggac ctgagcgggg gtggcggtg        59

<210> SEQ ID NO 281
<211> LENGTH: 59
```

```
<212> TYPE: DNA
<213> ORGANISM: Artificial Sequence
<220> FEATURE:
<223> OTHER INFORMATION: Synthetic Construct

<400> SEQUENCE: 281
cgcgcaccgc acccccgct caggtccacg tccatcacct ggccgtcctc acctccgcc        59

<210> SEQ ID NO 282
<211> LENGTH: 53
<212> TYPE: DNA
<213> ORGANISM: Artificial Sequence
<220> FEATURE:
<223> OTHER INFORMATION: Synthetic Construct

<400> SEQUENCE: 282
ggccggcgga ggtgagaagc agagaaacgg caccctgacc ggtggtggcg gtg            53

<210> SEQ ID NO 283
<211> LENGTH: 53
<212> TYPE: DNA
<213> ORGANISM: Artificial Sequence
<220> FEATURE:
<223> OTHER INFORMATION: Synthetic Construct

<400> SEQUENCE: 283
cgcgcaccgc caccaccggt cagggtgccg tttctctgct tctcacctcc gcc            53

<210> SEQ ID NO 284
<211> LENGTH: 53
<212> TYPE: DNA
<213> ORGANISM: Artificial Sequence
<220> FEATURE:
<223> OTHER INFORMATION: Synthetic Construct

<400> SEQUENCE: 284
ggccggcgga ggtggtctgc ccagagccct gatgagaagc gccggtggcg gtg            53

<210> SEQ ID NO 285
<211> LENGTH: 53
<212> TYPE: DNA
<213> ORGANISM: Artificial Sequence
<220> FEATURE:
<223> OTHER INFORMATION: Synthetic Construct

<400> SEQUENCE: 285
cgcgcaccgc caccggcgct tctcatcagg gctctgggca gaccacctcc gcc            53

<210> SEQ ID NO 286
<211> LENGTH: 20
<212> TYPE: PRT
<213> ORGANISM: Artificial Sequence
<220> FEATURE:
<223> OTHER INFORMATION: Synthetic Construct

<400> SEQUENCE: 286

Ser Ser Gln Asn Ser Ser Asp Lys Pro Val Ala His Val Val Ala Asn
1               5                   10                  15

His Gln Val Glu
            20

<210> SEQ ID NO 287
<211> LENGTH: 16
<212> TYPE: PRT
<213> ORGANISM: Artificial Sequence
<220> FEATURE:
```

```
<223> OTHER INFORMATION: Synthetic Construct

<400> SEQUENCE: 287

Ser Gln Asn Ser Ser Asp Lys Pro Val Ala His Val Val Ala Asn His
1               5                   10                  15

<210> SEQ ID NO 288
<211> LENGTH: 9
<212> TYPE: PRT
<213> ORGANISM: Artificial Sequence
<220> FEATURE:
<223> OTHER INFORMATION: Synthetic Construct

<400> SEQUENCE: 288

Ser Ser Gln Asn Ser Ser Asp Lys Pro
1               5

<210> SEQ ID NO 289
<211> LENGTH: 14
<212> TYPE: PRT
<213> ORGANISM: Artificial Sequence
<220> FEATURE:
<223> OTHER INFORMATION: Synthetic Construct

<400> SEQUENCE: 289

Asn Ala Glu Gly Lys Leu Asp His His Met Asn Ser Val Leu
1               5                   10

<210> SEQ ID NO 290
<211> LENGTH: 11
<212> TYPE: PRT
<213> ORGANISM: Artificial Sequence
<220> FEATURE:
<223> OTHER INFORMATION: Synthetic Construct

<400> SEQUENCE: 290

Glu Gly Lys Leu Asp His His Met Asn Ser Val
1               5                   10

<210> SEQ ID NO 291
<211> LENGTH: 16
<212> TYPE: PRT
<213> ORGANISM: Artificial Sequence
<220> FEATURE:
<223> OTHER INFORMATION: Synthetic Construct

<400> SEQUENCE: 291

Lys Ser Leu Glu Glu Phe Leu Lys Val Thr Leu Arg Ser Thr Arg Gln
1               5                   10                  15

<210> SEQ ID NO 292
<211> LENGTH: 11
<212> TYPE: PRT
<213> ORGANISM: Artificial Sequence
<220> FEATURE:
<223> OTHER INFORMATION: Synthetic Construct

<400> SEQUENCE: 292

Leu Glu Glu Phe Leu Lys Val Thr Leu Arg Ser
1               5                   10

<210> SEQ ID NO 293
<211> LENGTH: 86
<212> TYPE: DNA
<213> ORGANISM: Artificial Sequence
<220> FEATURE:
<223> OTHER INFORMATION: Synthetic Construct
```

<400> SEQUENCE: 293
ggccggcgga ggtagcagcc agaacagcag cgacaagccc gtggcccacg tggtggctaa      60
ccaccaggtg gagggggtg gcggtg                                           86

<210> SEQ ID NO 294
<211> LENGTH: 86
<212> TYPE: DNA
<213> ORGANISM: Artificial Sequence
<220> FEATURE:
<223> OTHER INFORMATION: Synthetic Construct

<400> SEQUENCE: 294
cgcgcaccgc cacccccctc cacctggtgg ttagccacca cgtgggccac gggcttgtcg      60
ctgctgttct ggctgctacc tccgcc                                          86

<210> SEQ ID NO 295
<211> LENGTH: 74
<212> TYPE: DNA
<213> ORGANISM: Artificial Sequence
<220> FEATURE:
<223> OTHER INFORMATION: Synthetic Construct

<400> SEQUENCE: 295
ggccggcgga ggtagccaga acagcagcga caagcccgtg gcccacgtgg tggctaacca      60 cggggggtggc ggtg                                                       74

<210> SEQ ID NO 296
<211> LENGTH: 74
<212> TYPE: DNA
<213> ORGANISM: Artificial Sequence
<220> FEATURE:
<223> OTHER INFORMATION: Synthetic Construct

<400> SEQUENCE: 296
cgcgcaccgc caccccgtg gttagccacc acgtgggcca cgggcttgtc gctgctgttc      60
tggctacctc cgcc                                                        74

<210> SEQ ID NO 297
<211> LENGTH: 53
<212> TYPE: DNA
<213> ORGANISM: Artificial Sequence
<220> FEATURE:
<223> OTHER INFORMATION: Synthetic Construct

<400> SEQUENCE: 297
ggccggcgga ggtagcagcc agaacagcag cgacaagccc gggggtggcg gtg             53

<210> SEQ ID NO 298
<211> LENGTH: 53
<212> TYPE: DNA
<213> ORGANISM: Artificial Sequence
<220> FEATURE:
<223> OTHER INFORMATION: Synthetic Construct

<400> SEQUENCE: 298
cgcgcaccgc caccccggg cttgtcgctg ctgttctggc tgctacctcc gcc              53

<210> SEQ ID NO 299
<211> LENGTH: 68
<212> TYPE: DNA
<213> ORGANISM: Artificial Sequence
<220> FEATURE:

<223> OTHER INFORMATION: Synthetic Construct

<400> SEQUENCE: 299
ggccggcgga ggtaacgccg agggcaagct tgaccaccac atgaacagcg tgctgggggg    60
tggcggtg                                                              68

<210> SEQ ID NO 300
<211> LENGTH: 68
<212> TYPE: DNA
<213> ORGANISM: Artificial Sequence
<220> FEATURE:
<223> OTHER INFORMATION: Synthetic Construct

<400> SEQUENCE: 300
cgcgcaccgc cacccccag cacgctgttc atgtggtggt caagcttgcc ctcggcgtta    60
cctccgcc                                                              68

<210> SEQ ID NO 301
<211> LENGTH: 59
<212> TYPE: DNA
<213> ORGANISM: Artificial Sequence
<220> FEATURE:
<223> OTHER INFORMATION: Synthetic Construct

<400> SEQUENCE: 301
ggccggcgga ggtgagggca agcttgacca ccacatgaac agcgtggggg gtggcggtg    59

<210> SEQ ID NO 302
<211> LENGTH: 59
<212> TYPE: DNA
<213> ORGANISM: Artificial Sequence
<220> FEATURE:
<223> OTHER INFORMATION: Synthetic Construct

<400> SEQUENCE: 302
cgcgcaccgc cacccccac gctgttcatg tggtggtcaa gcttgccctc acctccgcc      59

<210> SEQ ID NO 303
<211> LENGTH: 74
<212> TYPE: DNA
<213> ORGANISM: Artificial Sequence
<220> FEATURE:
<223> OTHER INFORMATION: Synthetic Construct

<400> SEQUENCE: 303
ggccggcgga ggtaagagcc tggaggaatt cctgaaggtg accctgagaa gcaccagaca    60 gggggggtggc ggtg                                                      74

<210> SEQ ID NO 304
<211> LENGTH: 74
<212> TYPE: DNA
<213> ORGANISM: Artificial Sequence
<220> FEATURE:
<223> OTHER INFORMATION: Synthetic Construct

<400> SEQUENCE: 304
cgcgcaccgc cacccccctg tctggtgctt ctcagggtca ccttcaggaa ttcctccagg    60
ctcttacctc cgcc                                                       74

<210> SEQ ID NO 305
<211> LENGTH: 59
<212> TYPE: DNA
<213> ORGANISM: Artificial Sequence
<220> FEATURE:
<223> OTHER INFORMATION: Synthetic Construct

<400> SEQUENCE: 305
ggccggcgga ggtctggagg aattcctgaa ggtgaccctg agaagcgggg gtggcggtg    59

<210> SEQ ID NO 306
<211> LENGTH: 59
<212> TYPE: DNA
<213> ORGANISM: Artificial Sequence
<220> FEATURE:
<223> OTHER INFORMATION: Synthetic Construct

<400> SEQUENCE: 306
cgcgcaccgc cacccccgct tctcagggtc accttcagga attcctccag acctccgcc    59

<210> SEQ ID NO 307
<211> LENGTH: 88
<212> TYPE: DNA
<213> ORGANISM: Artificial Sequence
<220> FEATURE:
<223> OTHER INFORMATION: Synthetic Construct

<400> SEQUENCE: 307
ggccgccggt ggaggcagca gccagaacag cagcgacaag cccgtggccc acgtggtggc    60
taaccaccag gtggagggcg gtggaggg                                       88

<210> SEQ ID NO 308
<211> LENGTH: 88
<212> TYPE: DNA
<213> ORGANISM: Artificial Sequence
<220> FEATURE:
<223> OTHER INFORMATION: Synthetic Construct

<400> SEQUENCE: 308
cgcgccctcc accgccctcc acctggtggt tagccaccac gtgggccacg ggcttgtcgc    60
tgctgttctg gctgctgcct ccaccggc                                       88

<210> SEQ ID NO 309
<211> LENGTH: 70
<212> TYPE: DNA
<213> ORGANISM: Artificial Sequence
<220> FEATURE:
<223> OTHER INFORMATION: Synthetic Construct

<400> SEQUENCE: 309
ggccgccggt ggaggcaacg ccagggcaa gcttgaccac cacatgaaca gcgtgctggg    60
cggtggaggg                                                           70

<210> SEQ ID NO 310
<211> LENGTH: 70
<212> TYPE: DNA
<213> ORGANISM: Artificial Sequence
<220> FEATURE:
<223> OTHER INFORMATION: Synthetic Construct

<400> SEQUENCE: 310
cgcgccctcc accgcccagc acgctgttca tgtggtggtc aagcttgccc tcggcgttgc    60
ctccaccggc                                                           70

<210> SEQ ID NO 311
<211> LENGTH: 61
<212> TYPE: DNA

<213> ORGANISM: Artificial Sequence
<220> FEATURE:
<223> OTHER INFORMATION: Synthetic Construct

<400> SEQUENCE: 311
ggccgccggt ggaggcctgg aggaattcct gaaggtgacc ctgagaagcg gcggtggagg    60
g                                                                   61

<210> SEQ ID NO 312
<211> LENGTH: 61
<212> TYPE: DNA
<213> ORGANISM: Artificial Sequence
<220> FEATURE:
<223> OTHER INFORMATION: Synthetic Construct

<400> SEQUENCE: 312
cgcgccctcc accgccgctt ctcagggtca ccttcaggaa ttcctccagg cctccaccgg    60
c                                                                   61

<210> SEQ ID NO 313
<211> LENGTH: 58
<212> TYPE: DNA
<213> ORGANISM: Artificial Sequence
<220> FEATURE:
<223> OTHER INFORMATION: Synthetic Construct

<400> SEQUENCE: 313
ggccgcagcc gcagtgaacc tgacctggag cagagcctcc ggcgcggcag ctgcagct     58

<210> SEQ ID NO 314
<211> LENGTH: 58
<212> TYPE: DNA
<213> ORGANISM: Artificial Sequence
<220> FEATURE:
<223> OTHER INFORMATION: Synthetic Construct

<400> SEQUENCE: 314
cgcgagctgc agctgccgcg ccggaggctc tgctccaggt caggttcact gcggctgc     58

<210> SEQ ID NO 315
<211> LENGTH: 73
<212> TYPE: DNA
<213> ORGANISM: Artificial Sequence
<220> FEATURE:
<223> OTHER INFORMATION: Synthetic Construct

<400> SEQUENCE: 315
ggccggcggt ggaggcggtg acagcaaccc tagaggcgtg agcgcctacc tgagcagagg    60
aggcggtgga ggg                                                      73

<210> SEQ ID NO 316
<211> LENGTH: 73
<212> TYPE: DNA
<213> ORGANISM: Artificial Sequence
<220> FEATURE:
<223> OTHER INFORMATION: Synthetic Construct

<400> SEQUENCE: 316
cgcgccctcc accgcctcct ctgctcaggt aggcgctcac gcctctaggg ttgctgtcac    60
cgcctccacc gcc                                                      73

<210> SEQ ID NO 317
<211> LENGTH: 70

```
<212> TYPE: DNA
<213> ORGANISM: Artificial Sequence
<220> FEATURE:
<223> OTHER INFORMATION: Synthetic Construct

<400> SEQUENCE: 317
ggccggcggt ggagacatca gcgtgaccgg tgcacccgtg atcaccgcca cctacctggg    60
tggcggtgga                                                          70

<210> SEQ ID NO 318
<211> LENGTH: 70
<212> TYPE: DNA
<213> ORGANISM: Artificial Sequence
<220> FEATURE:
<223> OTHER INFORMATION: Synthetic Construct

<400> SEQUENCE: 318
cgcgtccacc gccacccagg taggtggcgg tgatcacggg tgcaccggtc acgctgatgt    60
ctccaccgcc                                                          70

<210> SEQ ID NO 319
<211> LENGTH: 14
<212> TYPE: PRT
<213> ORGANISM: Artificial Sequence
<220> FEATURE:
<223> OTHER INFORMATION: Synthetic Construct

<400> SEQUENCE: 319

Cys Ser Leu Thr Gly Asp Glu Phe Lys Lys Val Leu Glu Thr
1               5                   10

<210> SEQ ID NO 320
<211> LENGTH: 12
<212> TYPE: PRT
<213> ORGANISM: Artificial Sequence
<220> FEATURE:
<223> OTHER INFORMATION: Synthetic Construct

<400> SEQUENCE: 320

Cys Arg Glu Ala Val Ala Tyr Arg Phe Glu Glu Asp
1               5                   10

<210> SEQ ID NO 321
<211> LENGTH: 11
<212> TYPE: PRT
<213> ORGANISM: Artificial Sequence
<220> FEATURE:
<223> OTHER INFORMATION: Synthetic Construct

<400> SEQUENCE: 321

Cys Ile Asn Pro Glu Ile Ile Thr Leu Asp Gly
1               5                   10

<210> SEQ ID NO 322
<211> LENGTH: 16
<212> TYPE: PRT
<213> ORGANISM: Artificial Sequence
<220> FEATURE:
<223> OTHER INFORMATION: Synthetic Construct

<400> SEQUENCE: 322

Cys Asp Ile Ser Val Thr Gly Ala Pro Val Ile Thr Ala Thr Tyr Leu
1               5                   10                  15

<210> SEQ ID NO 323
```

```
<211> LENGTH: 32
<212> TYPE: DNA
<213> ORGANISM: Artificial Sequence
<220> FEATURE:
<223> OTHER INFORMATION: Synthetic Construct

<400> SEQUENCE: 323
ggggaattca tgtcccaaag gcgcctccta cg                                      32

<210> SEQ ID NO 324
<211> LENGTH: 34
<212> TYPE: DNA
<213> ORGANISM: Artificial Sequence
<220> FEATURE:
<223> OTHER INFORMATION: Synthetic Construct

<400> SEQUENCE: 324
gggggatccc tagctcaggc tctggaggaa atcc                                    34

<210> SEQ ID NO 325
<211> LENGTH: 11
<212> TYPE: PRT
<213> ORGANISM: Artificial Sequence
<220> FEATURE:
<223> OTHER INFORMATION: Synthetic Construct

<400> SEQUENCE: 325

Val Asn Leu Thr Trp Ser Arg Ala Ser Gly Cys
1               5                   10

<210> SEQ ID NO 326
<211> LENGTH: 14
<212> TYPE: PRT
<213> ORGANISM: Artificial Sequence
<220> FEATURE:
<223> OTHER INFORMATION: Synthetic Construct

<400> SEQUENCE: 326

Cys Asp Ser Asn Pro Arg Gly Val Ser Ala Tyr Leu Ser Arg
1               5                   10

<210> SEQ ID NO 327
<211> LENGTH: 12
<212> TYPE: PRT
<213> ORGANISM: Artificial Sequence
<220> FEATURE:
<223> OTHER INFORMATION: Synthetic Construct

<400> SEQUENCE: 327

Cys Glu Asp Gly Gln Val Met Asp Val Asp Leu Ser
1               5                   10

<210> SEQ ID NO 328
<211> LENGTH: 10
<212> TYPE: PRT
<213> ORGANISM: Artificial Sequence
<220> FEATURE:
<223> OTHER INFORMATION: Synthetic Construct

<400> SEQUENCE: 328

Cys Glu Lys Gln Arg Asn Gly Thr Leu Thr
1               5                   10

<210> SEQ ID NO 329
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 329

Thr Gln Asn Asp Gly Thr Thr Thr Ile Ala
1               5                   10

<210> SEQ ID NO 330
<211> LENGTH: 15
<212> TYPE: PRT
<213> ORGANISM: Artificial Sequence
<220> FEATURE:
<223> OTHER INFORMATION: Synthetic Construct

<400> SEQUENCE: 330

Lys Glu Val Thr Gln Asn Asp Gly Thr Thr Thr Ile Ala Asn Asn
1               5                   10                  15

<210> SEQ ID NO 331
<211> LENGTH: 14
<212> TYPE: PRT
<213> ORGANISM: Artificial Sequence
<220> FEATURE:
<223> OTHER INFORMATION: Synthetic Construct

<400> SEQUENCE: 331

Met Val Pro Gln Tyr Gly Tyr Leu Thr Leu Asn Asn Gly Ser
1               5                   10

<210> SEQ ID NO 332
<211> LENGTH: 17
<212> TYPE: PRT
<213> ORGANISM: Artificial Sequence
<220> FEATURE:
<223> OTHER INFORMATION: Synthetic Construct

<400> SEQUENCE: 332

Glu Glu Glu Ile Arg Thr Thr Asn Pro Val Ala Thr Glu Gln Tyr Gly
1               5                   10                  15

Ser

<210> SEQ ID NO 333
<211> LENGTH: 10
<212> TYPE: PRT
<213> ORGANISM: Artificial Sequence
<220> FEATURE:
<223> OTHER INFORMATION: Synthetic Construct

<400> SEQUENCE: 333

Asn Lys Ser Val Asn Val Asp Phe Thr Val
1               5                   10

<210> SEQ ID NO 334
<211> LENGTH: 17
<212> TYPE: PRT
<213> ORGANISM: Artificial Sequence
<220> FEATURE:
<223> OTHER INFORMATION: Synthetic Construct

<400> SEQUENCE: 334

Ser Asn Tyr Asn Lys Ser Val Asn Val Asp Phe Thr Val Asp Thr Asn
1               5                   10                  15

Gly

<210> SEQ ID NO 335
```

<211> LENGTH: 49
<212> TYPE: DNA
<213> ORGANISM: Artificial Sequence
<220> FEATURE:
<223> OTHER INFORMATION: Synthetic Construct

<400> SEQUENCE: 335
ctacaaacaa atttccggcg cgccaggatc cggaagccaa tcaggagcc          49

<210> SEQ ID NO 336
<211> LENGTH: 49
<212> TYPE: DNA
<213> ORGANISM: Artificial Sequence
<220> FEATURE:
<223> OTHER INFORMATION: Synthetic Construct

<400> SEQUENCE: 336
ggctcctgat tggcttccgg atcctggcgc gccggaaatt tgtttgtag          49

<210> SEQ ID NO 337
<211> LENGTH: 51
<212> TYPE: DNA
<213> ORGANISM: Artificial Sequence
<220> FEATURE:
<223> OTHER INFORMATION: Synthetic Construct

<400> SEQUENCE: 337
gtcacgcaga atgacggtgg cgcgccagga tccggaacga cgacgattgc c       51

<210> SEQ ID NO 338
<211> LENGTH: 51
<212> TYPE: DNA
<213> ORGANISM: Artificial Sequence
<220> FEATURE:
<223> OTHER INFORMATION: Synthetic Construct

<400> SEQUENCE: 338
ggcaatcgtc gtcgttccgg atcctggcgc gccaccgtca ttctgcgtga c       51

<210> SEQ ID NO 339
<211> LENGTH: 55
<212> TYPE: DNA
<213> ORGANISM: Artificial Sequence
<220> FEATURE:
<223> OTHER INFORMATION: Synthetic Construct

<400> SEQUENCE: 339
cgatgaagaa aagttttttg gcgcgccagg atccggacct cagagcgggg ttctc   55

<210> SEQ ID NO 340
<211> LENGTH: 55
<212> TYPE: DNA
<213> ORGANISM: Artificial Sequence
<220> FEATURE:
<223> OTHER INFORMATION: Synthetic Construct

<400> SEQUENCE: 340
gagaaccccg ctctgaggtc cggatcctgg cgcgccaaaa aacttttctt catcg   55

<210> SEQ ID NO 341
<211> LENGTH: 55
<212> TYPE: DNA
<213> ORGANISM: Artificial Sequence
<220> FEATURE:
<223> OTHER INFORMATION: Primer

<400> SEQUENCE: 341
ccaatcccgt ggctacgggc gcgccaggat ccggagagca gtatggttct gtatc    55

<210> SEQ ID NO 342
<211> LENGTH: 55
<212> TYPE: DNA
<213> ORGANISM: Artificial Sequence
<220> FEATURE:
<223> OTHER INFORMATION: Synthetic Construct

<400> SEQUENCE: 342
gatacagaac catactgctc tccggatcct ggcgcgcccg tagccacggg attgg    55

<210> SEQ ID NO 343
<211> LENGTH: 53
<212> TYPE: DNA
<213> ORGANISM: Artificial Sequence
<220> FEATURE:
<223> OTHER INFORMATION: Synthetic Construct

<400> SEQUENCE: 343
ctacaacaag tctgttaatg gcgcgccagg atccggagtg gactttactg tgg    53

<210> SEQ ID NO 344
<211> LENGTH: 53
<212> TYPE: DNA
<213> ORGANISM: Artificial Sequence
<220> FEATURE:
<223> OTHER INFORMATION: Synthetic Construct

<400> SEQUENCE: 344
ccacagtaaa gtccactccg gatcctggcg cgccattaac agacttgttg tag    53

<210> SEQ ID NO 345
<211> LENGTH: 53
<212> TYPE: DNA
<213> ORGANISM: Artificial Sequence
<220> FEATURE:
<223> OTHER INFORMATION: Synthetic Construct

<400> SEQUENCE: 345
gacgtcttca tggtgccagg cgcgccagga tccggaaaca cgggagtca ggc    53

<210> SEQ ID NO 346
<211> LENGTH: 53
<212> TYPE: DNA
<213> ORGANISM: Artificial Sequence
<220> FEATURE:
<223> OTHER INFORMATION: Synthetic Construct

<400> SEQUENCE: 346
gcctgactcc cgttgtttcc ggatcctggc gcgcctggca ccatgaagac gtc    53

<210> SEQ ID NO 347
<211> LENGTH: 55
<212> TYPE: DNA
<213> ORGANISM: Artificial Sequence
<220> FEATURE:
<223> OTHER INFORMATION: Synthetic Construct

<400> SEQUENCE: 347
cattcaagtc aaagaggtcg gcgcgccagg atccggagcc aataaccta ccagc    55

<210> SEQ ID NO 348
<211> LENGTH: 55
<212> TYPE: DNA

```
<213> ORGANISM: Artificial Sequence
<220> FEATURE:
<223> OTHER INFORMATION: Synthetic Construct

<400> SEQUENCE: 348
gctggtaagg ttattggctc cggatcctgg cgcgccgacc tctttgactt gaatg        55

<210> SEQ ID NO 349
<211> LENGTH: 53
<212> TYPE: DNA
<213> ORGANISM: Artificial Sequence
<220> FEATURE:
<223> OTHER INFORMATION: Synthetic Construct

<400> SEQUENCE: 349
cagacgaaga ggaaatcggc gcgccaggat ccggatatgg ttctgtatct acc          53

<210> SEQ ID NO 350
<211> LENGTH: 53
<212> TYPE: DNA
<213> ORGANISM: Artificial Sequence
<220> FEATURE:
<223> OTHER INFORMATION: Synthetic Construct

<400> SEQUENCE: 350
ggtagataca gaaccatatc cggatcctgg cgcgccgatt tcctcttcgt ctg          53

<210> SEQ ID NO 351
<211> LENGTH: 55
<212> TYPE: DNA
<213> ORGANISM: Artificial Sequence
<220> FEATURE:
<223> OTHER INFORMATION: Synthetic Construct

<400> SEQUENCE: 351
ccaactacaa caagtctggc gcgccaggat ccggagacac taatggcgtg tattc        55

<210> SEQ ID NO 352
<211> LENGTH: 55
<212> TYPE: DNA
<213> ORGANISM: Artificial Sequence
<220> FEATURE:
<223> OTHER INFORMATION: Synthetic Construct

<400> SEQUENCE: 352
gaatacacgc cattagtgtc tccggatcct ggcgcgccag acttgttgta gttgg        55

<210> SEQ ID NO 353
<211> LENGTH: 53
<212> TYPE: DNA
<213> ORGANISM: Artificial Sequence
<220> FEATURE:
<223> OTHER INFORMATION: Synthetic Construct

<400> SEQUENCE: 353
cgcgggcgga tgcgacgccg gcagtgtgcg caccaatgca ccagacggtg gcg          53

<210> SEQ ID NO 354
<211> LENGTH: 53
<212> TYPE: DNA
<213> ORGANISM: Artificial Sequence
<220> FEATURE:
<223> OTHER INFORMATION: Synthetic Construct

<400> SEQUENCE: 354
ccggcgccac cgtctggtgc attggtgcgc acactgccgg cgtcgcatcc gcc          53
```

```
<210> SEQ ID NO 355
<211> LENGTH: 20
<212> TYPE: PRT
<213> ORGANISM: Artificial Sequence
<220> FEATURE:
<223> OTHER INFORMATION: Synthetic Construct

<400> SEQUENCE: 355

Gly Ala Gly Gly Cys Asp Ala Gly Ser Val Arg Thr Asn Ala Pro Asp
1               5                   10                  15

Gly Gly Ala Gly
            20

<210> SEQ ID NO 356
<211> LENGTH: 16
<212> TYPE: PRT
<213> ORGANISM: Artificial Sequence
<220> FEATURE:
<223> OTHER INFORMATION: Synthetic Construct

<400> SEQUENCE: 356

His Tyr Ala Ala Ala Gln Trp Asp Phe Gly Asn Thr Met Cys Gln Leu
1               5                   10                  15

<210> SEQ ID NO 357
<211> LENGTH: 13
<212> TYPE: PRT
<213> ORGANISM: Artificial Sequence
<220> FEATURE:
<223> OTHER INFORMATION: Synthetic Construct

<400> SEQUENCE: 357

Tyr Ala Ala Gln Trp Asp Phe Gly Asn Thr Met Cys Gln
1               5                   10

<210> SEQ ID NO 358
<211> LENGTH: 10
<212> TYPE: PRT
<213> ORGANISM: Artificial Sequence
<220> FEATURE:
<223> OTHER INFORMATION: Synthetic Construct

<400> SEQUENCE: 358

Arg Ser Gln Lys Glu Gly Leu His Tyr Thr
1               5                   10
```